US011951165B2

(12) United States Patent
Fairman et al.

(10) Patent No.: US 11,951,165 B2
(45) Date of Patent: *Apr. 9, 2024

(54) CONJUGATED VACCINE CARRIER PROTEINS

(71) Applicant: Vaxcyte, Inc., San Carlos, CA (US)

(72) Inventors: Jeffery C. Fairman, Mountain View, CA (US); Jon H. Heinrichs, Doylestown, PA (US); Wei Chan, San Francisco, CA (US)

(73) Assignee: Vaxcyte, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/459,303

(22) Filed: Jul. 1, 2019

(65) Prior Publication Data

US 2020/0054739 A1 Feb. 20, 2020

Related U.S. Application Data

(63) Continuation-in-part of application No. 15/859,251, filed on Dec. 29, 2017.

(60) Provisional application No. 62/693,978, filed on Jul. 4, 2018, provisional application No. 62/693,981, filed on Jul. 4, 2018, provisional application No. 62/591,160, filed on Nov. 27, 2017, provisional application No. 62/568,201, filed on Oct. 4, 2017, provisional application No. 62/530,803, filed on Jul. 10, 2017, provisional application No. 62/441,115, filed on Dec. 30, 2016.

(51) Int. Cl.

| *A61K 39/385* | (2006.01) |
| *A61K 39/09* | (2006.01) |
| *A61P 31/04* | (2006.01) |
| *C07K 14/00* | (2006.01) |
| *C07K 14/285* | (2006.01) |
| *C07K 14/33* | (2006.01) |
| *C07K 14/34* | (2006.01) |
| *A61K 38/00* | (2006.01) |
| *A61K 39/00* | (2006.01) |

(52) U.S. Cl.
CPC .......... *A61K 39/385* (2013.01); *A61K 39/092* (2013.01); *A61P 31/04* (2018.01); *C07K 14/001* (2013.01); *C07K 14/285* (2013.01); *C07K 14/33* (2013.01); *C07K 14/34* (2013.01); *A61K 38/00* (2013.01); *A61K 2039/6037* (2013.01); *A61K 2039/627* (2013.01); *A61K 2039/70* (2013.01)

(58) Field of Classification Search
None
See application file for complete search history.

(56) References Cited

U.S. PATENT DOCUMENTS

| 4,902,506 A | 2/1990 | Anderson et al. |
| 5,360,897 A | 11/1994 | Anderson et al. |
| 5,565,204 A | 10/1996 | Kuo et al. |
| 5,614,382 A | 3/1997 | Metcalf |
| 5,623,057 A | 4/1997 | Marburg et al. |
| 5,785,973 A | 7/1998 | Bixler et al. |
| 6,329,512 B1 | 12/2001 | Yang et al. |
| 6,548,276 B2 | 4/2003 | Swartz et al. |
| 6,855,321 B1 | 2/2005 | Rappuoli et al. |
| 6,927,042 B2 | 8/2005 | Schultz et al. |
| 6,994,986 B2 | 2/2006 | Swartz et al. |
| 7,018,637 B2 | 3/2006 | Chong et al. |
| 7,041,479 B2 | 5/2006 | Swartz et al. |
| 7,129,333 B2 | 10/2006 | Schultz et al. |
| 7,217,791 B2 | 5/2007 | Chen et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,560,535 B2 | 7/2009 | Schultz et al. |
| 7,709,001 B2 | 5/2010 | Hausdorff et al. |
| 7,718,791 B2 | 5/2010 | Bahler et al. |
| 7,825,226 B2 | 11/2010 | Schultz et al. |
| 7,867,498 B2 | 1/2011 | Rappuoli et al. |
| 7,871,794 B2 | 1/2011 | Knapp et al. |
| 7,935,787 B2 | 5/2011 | Khandke et al. |
| 7,955,605 B2 | 6/2011 | Prasad |
| 8,030,074 B2 | 10/2011 | Schultz et al. |
| 8,114,648 B2 | 2/2012 | Schultz et al. |
| 8,183,010 B2 | 5/2012 | Swartz et al. |

(Continued)

FOREIGN PATENT DOCUMENTS

| CN | 101374548 A | 2/2009 |
| CN | 102716480 A | 10/2012 |

(Continued)

OTHER PUBLICATIONS

NCBI CRM197 (GeneBank: AMV91693.1) Jan. 11, 2016. https://www.ncbi.nlm.nih.gov/protein/AMV91693.1 (Year: 2016).*
Hosaka et al. Arg-X-Lys/Arg-Arg motif as a signal for precursor cleavage catalyzed by furin within the constitutive secretory pathway. J Biol Chem. 1991; 266(19):12127-30. (Year: 2014).*
Zimmerman et al. Production of Site-Specific Antibody-Drug Conjugates Using Optimized Non-Natural Amino Acids in a Cell-Free Expression System. Bioconjugate Chem. 2014, 25, 351-361. (Year: 2014).*
Moginger, U. et al. Cross Reactive Material 197 glycoconjugate vaccines contain privileged conjugation sites. Sci. Rep. 6, 20488; doi: 10.1038/srep20488 (2016). (Year: 2016).*

(Continued)

*Primary Examiner* — Aradhana Sasan
*Assistant Examiner* — Jia-Hai Lee
(74) *Attorney, Agent, or Firm* — Cooley LLP

(57) ABSTRACT

Methods for the production of immunogenic compositions containing a non-natural amino acid are disclosed. The non-natural amino acid can be a site for attachment of antigens, such as bacterial capsular polysaccharides, to make immunogenic conjugates. Bio-orthogonal attachment chemistry incorporated into the non-natural amino acids allows for more efficient and potent antigen presentation to the immune system, simplified purification, and more well-defined structure of these semi-synthetic immunogens.

4 Claims, 8 Drawing Sheets

Specification includes a Sequence Listing.

(56) References Cited

U.S. PATENT DOCUMENTS

| | | |
|---|---|---|
| 8,192,746 B2 | 6/2012 | Caulfield et al. |
| 8,298,759 B2 | 10/2012 | Voloshin et al. |
| 8,329,184 B2 | 12/2012 | Biemans et al. |
| 8,357,529 B2 | 1/2013 | Swartz et al. |
| 8,481,054 B2 | 7/2013 | Nahm et al. |
| 8,492,115 B2 | 7/2013 | Swartz et al. |
| 8,551,527 B2 | 10/2013 | Chouvenc et al. |
| 8,562,999 B2 | 10/2013 | Khandke et al. |
| 8,603,484 B2 | 12/2013 | Prasad |
| 8,642,042 B2 | 2/2014 | Mekalanos |
| 8,652,480 B2 | 2/2014 | Yuan et al. |
| 8,715,958 B2 | 5/2014 | Goerke et al. |
| 8,753,645 B2 | 6/2014 | Biemans et al. |
| 8,753,649 B2 | 6/2014 | Lee et al. |
| 8,758,764 B2 | 6/2014 | Masignani et al. |
| 8,778,631 B2 | 7/2014 | Voloshin et al. |
| 8,795,689 B2 | 8/2014 | Crinean |
| 8,808,707 B1 | 8/2014 | Siber et al. |
| 8,895,024 B2 | 11/2014 | Hausdorff et al. |
| 8,895,724 B2 | 11/2014 | Hausdorff et al. |
| 8,912,322 B2 | 12/2014 | Popik et al. |
| 8,999,697 B2 | 4/2015 | Yuan et al. |
| 9,040,253 B2 | 5/2015 | Roy et al. |
| 9,095,567 B2 | 8/2015 | Khandke et al. |
| 9,175,033 B2 | 11/2015 | Lee |
| 9,265,839 B2 | 2/2016 | Biemans et al. |
| 9,265,840 B2 | 2/2016 | Biemans et al. |
| 9,315,468 B2 | 4/2016 | Boon et al. |
| 9,358,284 B2 | 6/2016 | Saul et al. |
| 9,399,060 B2 | 7/2016 | Hausdorff et al. |
| 9,410,170 B2 | 8/2016 | Calhoun et al. |
| 9,422,345 B2 | 8/2016 | Blais et al. |
| 9,474,795 B2 | 10/2016 | Lee et al. |
| 9,480,736 B2 | 11/2016 | Hausdorff et al. |
| 9,492,559 B2 | 11/2016 | Emini et al. |
| 9,493,517 B2 | 11/2016 | Costantino et al. |
| 9,649,372 B2 | 5/2017 | Harper et al. |
| 9,650,621 B2 | 5/2017 | Thanos et al. |
| 9,669,084 B2 | 6/2017 | Siber et al. |
| 9,675,681 B2 | 6/2017 | Yuan et al. |
| 9,682,934 B2 | 6/2017 | Stafford et al. |
| 9,682,984 B2 | 6/2017 | Bonde-Larsen et al. |
| 9,778,266 B2 | 10/2017 | Nahm et al. |
| 9,840,493 B2 | 12/2017 | Yang et al. |
| 9,938,516 B2 | 4/2018 | Zimmerman et al. |
| 9,981,035 B2 | 5/2018 | Hausdorff et al. |
| 9,981,045 B2 | 5/2018 | Prasad |
| 9,988,619 B2 | 6/2018 | Zimmerman et al. |
| 9,994,527 B2 | 6/2018 | Stafford et al. |
| 10,034,949 B2 | 7/2018 | Shin et al. |
| 10,112,900 B2 | 10/2018 | Stafford et al. |
| 10,124,050 B2 | 11/2018 | Watson et al. |
| 10,137,088 B2 | 11/2018 | Zale et al. |
| 10,179,909 B2 | 1/2019 | Zimmerman et al. |
| 10,190,145 B2 | 1/2019 | Yam et al. |
| 10,316,322 B2 | 6/2019 | Groff et al. |
| 10,597,664 B2 | 3/2020 | Oganesyan et al. |
| 2004/0102388 A1 | 5/2004 | High et al. |
| 2004/0202668 A1 | 10/2004 | Boutriau et al. |
| 2006/0228380 A1 | 10/2006 | Hausdorff et al. |
| 2006/0228381 A1 | 10/2006 | Bahler et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2008/0102498 A1 | 5/2008 | Bahler et al. |
| 2009/0117148 A1 | 5/2009 | Constantino |
| 2009/0162394 A1 | 6/2009 | Biemans et al. |
| 2009/0269370 A1 | 10/2009 | Cohen et al. |
| 2010/0034847 A1 | 2/2010 | Borkowski et al. |
| 2012/0321658 A1 | 12/2012 | Biemans et al. |
| 2013/0189300 A1 | 7/2013 | Costantino et al. |
| 2013/0273098 A1 | 10/2013 | Blue et al. |
| 2013/0344103 A1 | 12/2013 | Biemans et al. |
| 2014/0066598 A1* | 3/2014 | Stafford .................. A61P 37/02 530/387.1 |
| 2014/0154286 A1 | 6/2014 | Malley et al. |
| 2015/0017187 A1 | 1/2015 | Thanos et al. |
| 2015/0017192 A1 | 1/2015 | Usera et al. |
| 2015/0190520 A1 | 7/2015 | Shin et al. |
| 2015/0216996 A1 | 8/2015 | Gu et al. |
| 2016/0101187 A1 | 4/2016 | Berti et al. |
| 2016/0251336 A1 | 9/2016 | Yang et al. |
| 2016/0257945 A1 | 9/2016 | Zimmerman et al. |
| 2016/0257946 A1 | 9/2016 | Zimmerman et al. |
| 2016/0324948 A1 | 11/2016 | Gu et al. |
| 2016/0324949 A1 | 11/2016 | Han et al. |
| 2016/0370376 A1 | 12/2016 | Polukhtin et al. |
| 2016/0375118 A1 | 12/2016 | Park et al. |
| 2017/0002012 A1 | 1/2017 | Van Delft et al. |
| 2017/0007713 A1 | 1/2017 | Gu et al. |
| 2017/0008858 A1 | 1/2017 | Van Delft et al. |
| 2017/0021006 A1 | 1/2017 | Watson et al. |
| 2017/0143821 A1 | 5/2017 | Porro |
| 2017/0196962 A1 | 7/2017 | Niz et al. |
| 2017/0224802 A1 | 8/2017 | Crinean |
| 2017/0224804 A1 | 8/2017 | Gu et al. |
| 2017/0252423 A1 | 9/2017 | Siber et al. |
| 2017/0267637 A1 | 9/2017 | Stafford et al. |
| 2017/0283469 A1 | 10/2017 | Thanos et al. |
| 2018/0000922 A1 | 1/2018 | Cooper et al. |
| 2018/0002732 A1 | 1/2018 | Chandler et al. |
| 2018/0051065 A1 | 2/2018 | Yin |
| 2018/0086734 A1 | 3/2018 | Yang et al. |
| 2018/0099039 A1 | 4/2018 | Emini et al. |
| 2018/0136224 A1 | 5/2018 | Nahm et al. |
| 2018/0147288 A1 | 5/2018 | Robinson et al. |
| 2018/0161445 A1 | 6/2018 | Dhere et al. |
| 2018/0207262 A1 | 7/2018 | Biemans et al. |
| 2018/0250390 A1 | 9/2018 | Hausdorff et al. |
| 2018/0303923 A1 | 10/2018 | Bertaud et al. |
| 2018/0333484 A1 | 11/2018 | Fairman et al. |
| 2019/0000952 A1 | 1/2019 | Lin et al. |
| 2019/0047958 A1 | 2/2019 | Stafford et al. |
| 2019/0070282 A1 | 3/2019 | Watson et al. |
| 2019/0070283 A1 | 3/2019 | Han et al. |
| 2019/0070287 A1 | 3/2019 | Fanger et al. |
| 2019/0161781 A1 | 5/2019 | Yam et al. |
| 2019/0248841 A1 | 8/2019 | Faridmoayer et al. |
| 2020/0054739 A1 | 2/2020 | Fairman et al. |
| 2020/0113993 A1 | 4/2020 | Forrest et al. |

FOREIGN PATENT DOCUMENTS

| | | | |
|---|---|---|---|
| CN | 102807621 A | | 12/2012 |
| CN | 102861326 A | * | 1/2013 ........... A61K 39/095 |
| CN | 104080479 A | | 10/2014 |
| CN | 106102770 A | | 11/2016 |
| EP | 0 071 515 A1 | | 2/1983 |
| EP | 0 245 045 A2 | | 11/1987 |
| EP | 0 375 778 A1 | | 7/1990 |
| EP | 1 601 689 B1 | | 11/2007 |
| EP | 1 791 860 B1 | | 4/2008 |
| EP | 1 861 420 B1 | | 11/2009 |
| EP | 1 976 697 B1 | | 6/2011 |
| EP | 1 896 065 B1 | | 7/2011 |
| EP | 2 044 194 B1 | | 10/2011 |
| EP | 2 382 986 A2 | | 11/2011 |
| EP | 2 402 025 A2 | | 1/2012 |
| EP | 2 094 298 B1 | | 2/2012 |
| EP | 1 868 645 B1 | | 3/2012 |
| EP | 2 086 582 B1 | | 11/2012 |
| EP | 2 417 983 B1 | | 6/2013 |
| EP | 2 676 679 A2 | | 12/2013 |
| EP | 2 322 631 B1 | | 11/2014 |
| EP | 2 815 762 A2 | | 12/2014 |
| EP | 2 099 487 A1 | | 6/2015 |
| EP | 2 544 708 B1 | | 6/2015 |
| EP | 2 932 979 A1 | | 10/2015 |
| EP | 2 932 980 A1 | | 10/2015 |
| EP | 2 094 304 B1 | | 11/2015 |
| EP | 3 009 146 A1 | | 4/2016 |
| EP | 3 020 411 A1 | | 5/2016 |
| EP | 2 865 392 B1 | | 11/2016 |
| EP | 3 096 785 A2 | | 11/2016 |

(56) References Cited

FOREIGN PATENT DOCUMENTS

| | | |
|---|---|---|
| EP | 3 096 786 A2 | 11/2016 |
| EP | 2 129 693 B1 | 12/2016 |
| EP | 2 351 578 B1 | 1/2017 |
| EP | 2 726 494 B1 | 1/2017 |
| EP | 3 130 348 A1 | 2/2017 |
| EP | 3 004 062 B1 | 7/2017 |
| EP | 2 796 546 B1 | 8/2017 |
| EP | 3 269 385 A1 | 1/2018 |
| EP | 3 269 386 A1 | 1/2018 |
| EP | 2 716 661 B1 | 3/2018 |
| EP | 3 296 741 A1 | 3/2018 |
| EP | 2 950 815 B1 | 4/2018 |
| EP | 3 302 542 A1 | 4/2018 |
| EP | 3 311 836 A1 | 4/2018 |
| EP | 2 907 525 B1 | 5/2018 |
| EP | 3 325 008 A1 | 5/2018 |
| EP | 2 436 700 B1 | 6/2018 |
| EP | 3 377 098 A1 | 9/2018 |
| EP | 3 055 321 B1 | 10/2018 |
| EP | 3 017 827 B1 | 11/2018 |
| EP | 3 406 635 A1 | 11/2018 |
| EP | 3 436 061 A2 | 2/2019 |
| EP | 3 470 080 A1 | 4/2019 |
| EP | 3 170 837 B1 | 8/2019 |
| EP | 2 945 641 B1 | 1/2020 |
| JP | 2001-190665 A | 7/2001 |
| JP | 2009-520761 A | 5/2009 |
| JP | 2011-212183 A | 10/2011 |
| JP | 2012-521403 A | 9/2012 |
| JP | 2014-518061 A | 7/2014 |
| JP | 2015-501329 A | 1/2015 |
| JP | 2015-529208 A | 10/2015 |
| JP | 2016-155835 A | 9/2016 |
| JP | 2017-504661 A | 2/2017 |
| JP | 2020-504760 A | 7/2018 |
| JP | 2019-513821 A | 5/2019 |
| WO | WO-89/06974 A2 | 8/1989 |
| WO | WO-89/06974 A3 | 8/1989 |
| WO | WO-94/09115 A1 | 4/1994 |
| WO | WO-98/51339 A1 | 11/1998 |
| WO | WO-02/40497 A1 | 5/2002 |
| WO | WO-03/007985 A2 | 1/2003 |
| WO | WO-03/007985 A3 | 1/2003 |
| WO | WO-2004/043376 A2 | 5/2004 |
| WO | WO-2004/043376 A3 | 5/2004 |
| WO | WO-2004/067030 A2 | 8/2004 |
| WO | WO-2004/067030 A3 | 8/2004 |
| WO | WO-2004/067574 A1 | 8/2004 |
| WO | WO-2005/033148 A1 | 4/2005 |
| WO | WO-2005/105141 A2 | 11/2005 |
| WO | WO-2005/105141 A3 | 11/2005 |
| WO | WO-2006/000920 A2 | 1/2006 |
| WO | WO-2006/000920 A3 | 1/2006 |
| WO | WO-2006/110352 A2 | 10/2006 |
| WO | WO-2006/110352 A3 | 10/2006 |
| WO | WO-2006/110381 A1 | 10/2006 |
| WO | WO-2008/045852 A2 | 4/2008 |
| WO | WO-2008/045852 A3 | 4/2008 |
| WO | WO-2008/079653 A1 | 7/2008 |
| WO | WO-2008/079732 A2 | 7/2008 |
| WO | WO-2008/079732 A3 | 7/2008 |
| WO | WO-2008/081014 A2 | 7/2008 |
| WO | WO-2008/081014 A3 | 7/2008 |
| WO | WO-2008/118752 A2 | 10/2008 |
| WO | WO-2008/118752 A3 | 10/2008 |
| WO | WO-2008/143709 A2 | 11/2008 |
| WO | WO-2008/143709 A3 | 11/2008 |
| WO | WO-2009/000824 A2 | 12/2008 |
| WO | WO-2009/000824 A3 | 12/2008 |
| WO | WO-2009/000825 A2 | 12/2008 |
| WO | WO-2009/000825 A3 | 12/2008 |
| WO | WO-2009/106085 A1 | 9/2009 |
| WO | WO-2008/079732 A3 | 7/2010 |
| WO | WO-2010/080484 A1 | 7/2010 |
| WO | WO-2010/080486 A2 | 7/2010 |
| WO | WO-2010/150230 A1 | 12/2010 |
| WO | WO2010150230 A1 * | 12/2010 ............ C07K 14/34 |
| WO | WO-2011/110241 A1 | 9/2011 |
| WO | WO-2011/110531 A2 | 9/2011 |
| WO | WO-2011/110531 A3 | 9/2011 |
| WO | WO-2008/079732 A3 | 12/2011 |
| WO | WO-2011/151760 A2 | 12/2011 |
| WO | WO-2012/121973 A1 | 9/2012 |
| WO | WO-2013/009564 A1 | 1/2013 |
| WO | WO-2013/068949 A1 | 5/2013 |
| WO | WO-2014/036492 A1 | 3/2014 |
| WO | WO-2014/102265 A1 | 7/2014 |
| WO | WO-2014/111344 A1 | 7/2014 |
| WO | WO-2015/054658 A1 | 4/2015 |
| WO | WO-2015/110940 A2 | 7/2015 |
| WO | WO-2015/110940 A3 | 7/2015 |
| WO | WO-2015/110941 A2 | 7/2015 |
| WO | WO-2015/110941 A3 | 7/2015 |
| WO | WO-2015/117093 A1 | 8/2015 |
| WO | WO-2016/020413 A1 | 2/2016 |
| WO | WO-2016/113644 A1 | 7/2016 |
| WO | WO-2016/207905 A2 | 12/2016 |
| WO | WO-2016/207905 A3 | 12/2016 |
| WO | WO-2017/067962 A1 | 4/2017 |
| WO | WO-2017/173415 A2 | 10/2017 |
| WO | WO-2017/173415 A3 | 10/2017 |
| WO | WO-2018/064444 A1 | 4/2018 |
| WO | WO-2018/126229 A9 | 7/2018 |
| WO | WO-2018/134693 A1 | 7/2018 |
| WO | WO-2018/144438 A1 | 8/2018 |
| WO | WO-2018/147641 A1 | 8/2018 |
| WO | WO-2018/156465 A1 | 8/2018 |
| WO | WO-2018/156467 A1 | 8/2018 |
| WO | WO-2018/156468 A1 | 8/2018 |
| WO | WO-2018/156491 A1 | 8/2018 |
| WO | WO-2018/206635 A1 | 11/2018 |
| WO | WO-2019/050813 A1 | 3/2019 |
| WO | WO-2019/050814 A1 | 3/2019 |
| WO | WO-2019/050815 A1 | 3/2019 |
| WO | WO-2019/050816 A1 | 3/2019 |
| WO | WO-2019/050818 A1 | 3/2019 |
| WO | WO-2019/070994 A1 | 4/2019 |
| WO | WO-2019/139692 A2 | 7/2019 |
| WO | WO-2019/139692 A3 | 7/2019 |
| WO | WO-2019/152921 A1 | 8/2019 |
| WO | WO-2019/152925 A1 | 8/2019 |
| WO | WO-2019/212842 A1 | 11/2019 |
| WO | WO-2019/212846 A1 | 11/2019 |
| WO | WO-2019/220304 A1 | 11/2019 |

OTHER PUBLICATIONS

Leonard et al. Antigen processing of the heptavalent pneumococcal conjugate vaccine carrier protein CRM(197) differs depending on the serotype of the attached polysaccharide. Infect Immun. Jul. 2003;71(7):4186-9. (Year: 2003).*
CAS REGISTRYSM: Exact and pattern searching of protein sequences. STN 2008. (Year: 2008).*
Izidoro et al. A study of human furin specificity using synthetic peptides derived from natural substrates, and effects of potassium ions. Arch Biochem Biophys. Jul. 15, 2009; 487(2): 105-114. (Year: 2009).*
Zarei et al. Hib Vaccines: Past, Present, and Future Perspectives. Journal of Immunology Research. vol. 2016, Article ID 7203587, 18 pages. (Year: 2016).*
Dagan, R. et al. (2010). "Glycoconjugate vaccines and immune interference: A review," Vaccine 28:5513-5523.
GenBank Accession AMV91693. (2016). Toxin CRM 197 [synthetic construct], located at https://www.ncbi.nlm.nih.gov/protein/AMV91693.1?report=genbank&log$=protalign&blast_rank=1&RID=NGAS5FVZ016[Sep. 8, 2020, 2 total pages.
Gruber, W.C. et al. (2012). "Development and clinical evaluation of Prevnar 13, a 13-valent pneumococcal CRM197 conjugate vaccine," Annals of the New York Academy of Sciences 1263:15-26.
Park, I.H. et al. (2008). "Differential effects of pneumococcal vaccines against serotypes 6A and 6C," The Journal of Infectious Diseases 198:1818-1822.

(56) References Cited

OTHER PUBLICATIONS

Pollabauer, E.M. et al. (2009). "The influence of carrier protein on the immunogenicity of simultaneously administered conjugate vaccines in infants," Vaccine 27:1674-1679.
Kapoor, N. et al. (2018). "Malaria derived glycosylphosphatidylinositol anchor enhances anti-Pfs25 functional antibodies that block malaria transmission," Biochem. 57:516-519.
International Search Report dated Dec. 20, 2019, for PCT Application No. PCT/US2019/040131, filed on Jul. 1, 2019, 13 pages.
Leonard, E.G. et al. (2003). "Antigen processing of the heptavalent pneumococcal conjugate vaccine carrier protein CRM(197) differs depending on the serotype of the attached polysaccharide," Infect Immun 71(7):4186-4189.
Li, J. et al. (2016). "Epigenetic switch driven by DNA inversions dictates phase variation in Streptococcus pneumonia," PLOS Pathogens 12:e1005762, 36 total pages.
Lim, S. et al. (2016). "Bioconjugation of therapeutic proteins and enzymes using the expanded set of genetically encoded amino acids," Crit. Rev. in Biotechnol. 36:803-815.
Manso, A.S. et al. (2014). "A random six-phase switch regulates pneumococcal virulence via global epigenetic changes," Nat. Comm. 5:5055, 9 total pages.
Pillai, S. et al. (1995). "Immunogenicity of genetically engineered glutathione S-transferase fusion proteins containing a T-cell epitope from diphtheria toxin," Infect Immun 63:1535-40.
Written Opinion of the International Searching Authority dated Dec. 20, 2019, for PCT Application No. PCT/US2019/040131, filed on Jul. 1, 2019, 19 pages.
Adamo, R. et al. (2013). Synthetically defined glycoprotein vaccines: Current status and future directions, Chem. Sci. 4:2995-3008.
Andrews, N.J. et al. (2014). "Serotype-specific effectiveness and correlates of protection for the 13-valent pneumococcal conjugate vaccine: a postlicensure indirect cohort study," Lancet Infect Dis. 14:839-846.
Astronomo, R.D. et al. (2010). Carbohydrate vaccines: developing sweet solutions to sticky situations? Nature Reviews. 9:308-324.
Avci, F.Y. et al. (2013). "Carbohydrates and T cells: A sweet twosome," Seminars in Immunology. 25:146-151.
Bain, J.D. et al. (1989). "Biosynthetic site-specific incorporation of a non-natural amino acid into a polypeptide," J. Am. Chem. Soc. 111:8013-8014.
Baraldo et al. (2004). "N19 polyepitope as a carrier for enhanced immunogenicity and protective efficacy of meningococcal conjugate vaccines," Infect. Immun. 72:4884-4887.
Bardotti, A. et al. (2008). "Physicochemical characterization of glycoconjugate vaccines for prevention of meningococcal diseases," Vaccine 26:2284-2296.
Barrett, D.J. (1985). "Human immune responses to polysaccharide antigens: an analysis of bacterial polysaccharide vaccines in infants," Adv Pediatr. 32: 139-158.
Baskin, J.M. et al. (2007). "Copper-free click chemistry for dynamic in vivo imaging," PNAS. 104:16793-16797.
Bazewicz, C.G. et al. (2013). "Sensitive, site-specific, and stable vibrational probe of local protein environments: 4-azidomethyl-L-phenylalanine," J. Phys. Chem. B. 117:8987-8993.
Beatty, K.E. et al. (2006). "Fluorescence visualization of newly synthesized proteins in mammalian cells," Angew. Chem. Int. Ed. 45:7364-7367.
Beatty, K.E. et al. (2005). "Selective dye-labeling of newly synthesized proteins in bacterial cells," J. Am. Chem. Soc. 127:14150-14151.
Beißbarth, T. et al. (2005). "A systematic approach for comprehensive T-cell epitope discovery using peptide libraries," Bioinformatics 21(Suppl 1):i29-i37.
Berkowitz, B. et al. (1972). "Evidence for active immunity to morphine in mice," Science 178:1290-1292.
Bonten, M. et al. (2014). Community Acquired Pneumonia Immunization Trial in Adults (CAPiTA). Abstract No. 0541. 9th International Symposium on Pneumococci and Pneumococcal disease.

Broker, M. et al. (2011). "Biochemical and biological characteristics of cross-reacting material 197 CRM197, a non-toxic mutant of diphtheria toxin: use as a conjugation protein in vaccines and other potential clinical applications," Biologicals 39:195-204.
Broker, M. et al. (2017). "Polysaccharide conjugate vaccine protein carriers as a "neglected valency"—Potential and limitations," Vaccine 35:3286-3294.
Buttery, J.P. et al. (2005). "Immunogenicity and safety of a combination pneumococcal-meningococcal vaccine in infants: a randomized controlled trial," JAMA 293:1751-1758.
Calix, J.J. et al. (2012). "Biochemical, genetic, and serological characterization of two capsule subtypes among Streptococcus pneumoniae Serotype 20 strains: discovery of a new pneumococcal serotype," J. Biol. Chem. 287:27885-94.
Chang, J.Y. et al. (1998). "Unique chemical reactivity of His-21 of CRM197, a mutated diphtheria toxin," J. FEBS Lett. 427:362-366.
Chin, J.W. (2014). "Expanding and reprogramming the genetic code of cells and animals," Annu. Rev. Biochem. 83:379-408.
Chong, S. (2014). "Overview of cell-free protein synthesis: historic landmarks, commercial systems, and expanding applications," Curr. Protoc. Mol. Biol. 108:16.30.1-11.
Costantino, P. et al. (2011). "The design of semi-synthetic and synthetic glycoconjugate vaccines," Expert Opin. Drug Disc. 6:1045-1066.
Coutinho, A. et al. (1973). "B cell mitogenic properties of thymus-independent antigens," Nature New Biol. 245: 12-14.
Crotti, S. et al. (2014). "Defined conjugation of glycans to the lysines of CRM197 guided by their reactivity mapping," Chembiochem. 15:836-843.
Dagan, R. et al. (1998). "Reduced response to multiple vaccines sharing common protein epitopes that are administered simultaneously to infants," Infect Immun. 66:2093-2098.
De Benedetto, G. (2015/2016). "Characterization of polysaccharide-based vaccines against invasive nontyphoidal Salmonella disease (INTS)," Universita Degli Studi Di Trieste, 174 total pages.
Declaration of Ron Dagan, MD, EPO Opposition to Wyeth LLC, EP 1868645 (Pfizer submission May 4, 2015).
de Graaf, A.J. et al. (2009). "Nonnatural amino acids for site-specific protein conjugation," Bioconjugate Chem. 20:1281-1295.
DeLisi, C. et al. (1985). "T-cell antigenic sites tend to be amphipathic structures," PNAS 82:7048-7052.
De Velasco, E.A. et al. (1995). "Synthetic peptides representing t-cell epitopes act as carriers in pneumococcal polysaccharide conjugate vaccines," Infection & Immunity 65:961-968.
Desai, D.V. et al. (2014). "T-cell epitope prediction methods: an overview," Methods Mol. Biol. 1184:333-364.
Diethelm-Okita, B.M. et al. (1997). "Epitope repertoire of human CD4+ T cells on tetanus toxin: identification of immunodominant sequence segments," J. Infect. Dis. 175:382-391.
Diethelm-Okita, B.M. et al. (2000). "Universal epitopes for human CD4+ cells on tetanus and diphtheria toxins," J. Infect. Dis. 181:1001-1009.
Ederwine, J. et al. (1992). "Analysis of gene expression in single live neurons," PNAS 89:3010-3014.
Endo, Y. et al. (2006). "Cell-free expression systems for eukaryotic protein production,"Curr Opin Biotechnol. 17:373-380.
Falugi, F. et al. (2001). "Rationally designed strings of promiscuous CD4(+) T cell epitopes provide help to Haemophilus influenzae type b oligosaccharide: a model for new conjugate vaccines," Eur. J. Immunol. 31:3816-3824.
Feikin, D. et al. (2013). "Serotype-specific changes in Invasive Pneumococcal Disease after pneumoccocal conjugate vaccine introduction: A pooled analysis of multiple sites," Serotype Replacement Study Group. PLoS Med. 10:e1001517.
Frasch, Preparation of bacterial polysaccharide-protein conjugates: Analytical and manufacturing challenges, Vaccine 27, 6468-70 (2009).
Fridman, A. et al. (2012). "An efficient T-cell epitope discovery strategy using in silico prediction and the iTopia assay platform," Oncoimmunol. 1:1258-1270.
Geno, K.A. et al. (2015). "Pneumococcal Capsules and Their Types: Past, Present, and Future," Clin. Microbiol. Rev. 28:871-899.

(56) References Cited

OTHER PUBLICATIONS

Glesby, M.J. et al. (2015). "Immunogenicity and Safety of 13-Valent Pneumococcal Conjugate Vaccine in HIV-Infected Adults Previously Vaccinated With Pneumococcal Polysaccharide Vaccine," J. Infect. Dis. 212:18-27.
Goetsch, L. et al. (2003). "Identification of B- and T-cell epitopes of BB, a carrier protein derived from the G protein of *Streptococcus* strain G148," Clin. Diagn. Lab. Immunol. 10:125-132.
Gonzalez, D. et al. (2003). "Immunization with Porphyromonas gingivalis capsular polysaccharide prevents P. gingivalis-elicited oral bone loss in a murine model," Infect. Immun. 71:2283-2287.
Goffin, P. et al. (2017). "High-yield production of recombinant CRM197, a non toxic mutant of diphtheria toxin, in the periplasm of *Escherichia coli*," Biotechnol. J. 12:1700168, 11 total pages.
Goldblatt, D. (2000). "Editorial Review: Conjugate Vaccines," Clin Exp Immunol. 119:1-3.
Grayson, E.J. et al. (2011). "A coordinated synthesis and conjugation strategy for the preparation of homogeneous glycocojugate vaccine candidates," 50:4127-4132.
Guttormsen, H.K. et al. (1999). "Cognate stimulatory B-Cell-T-Cell interactions are critical for T-cell help recruited by glycoconjugate vaccines," Infect Immun. 67:6375-6384.
Hatsukami, D.K. et al. (2005). "Safety and immunogenicity of a nicotine conjugate vaccine in current smokers." 78:456-467.
Heckler, T.G. et al. (1984). "T4 RNA ligase mediated preparation of novel "chemically misacylated" tRNAPheS," Biochem. 23:1468-1473.
Henikoff, S. et al. (1992). "Amino acid substitution matrices from protein blocks," PNAS 89:10915.
Henrichsen, J. (1995). "Six newly recognized types of *Streptococcus pneumoniae*," J. Clin. Microbiol. 33:2759-2762.
Hermans, J.P.G. et al. (1988). "Synthesis of two analogues of a fragment of the complex polysaccharide C substance from *Streptococcus pneumonia* type 1," Recl. Trav. Chim. Pays-Bas. 107:600-606.
Hovijitra, N.T. et al. (2009). "Cell-free synthesis of functional aquaporin Z in synthetic liposomes," Biotechnol Bioeng. 104:40-49.
Howard, J.G. et al. (1971). "Studies on immunological paralysis. V. The influence of molecular weight on the immunogenicity, tolerogenicity and antibody-neutralizing activity of the 3 pneumococcal polysaccharide," 21:535-545.
Hu, Q.Y. et al. (2016). "Towards the next generation of biomedicines by site-selective conjugation," Chem Soc. Rev. 45:1691-1719.
Hua, C.Z. et al. (2016). "Serum Concentrations of Antibodies against Outer Membrane Protein P6, Protein D, and T- and B-Cell Combined Antigenic Epitopes of Nontypeable Haemophilus influenzae in Children and Adults of Different Ages," Clin. Vaccine Immunol. 23:155-161.
Hutchins, B.M. et al. (2011). "Selective formation of covalent protein heterodymers with an unnatural amino acid," Chemical Biology 18:299-303.
Huang, N. et al. (2015). "Liver X receptors contribute to periodontal pathogen-elicited inflammation and oral bone loss," Mol. Oral Microbiol. 30:438-450.
Institut Merieux (1980). Brevet Belge 80:26320, FR2 495 939, (With English abstract).
International Search Report dated Jul. 3, 2018, for PCT Application No. PCT/US2017/069129, filed on Dec. 29, 2017, 8 pages.
Jermutus, L. et al. (1998). "Recent advances in producing and selecting functional proteins by using cell-free translation," Curr Opin Biotechnol. 9:534-548.
Jewett, M.C. et al. (2004). "Rapid expression and purification of 100 nmol quantities of active proteinusing cell-free protein synthesis," Biotechnol Prog. 20:102-109.
Jewett, M.C. et al. (2002). "Prokaryotic systems for in vitro expression," Weiner MP, Lu Q, editors. Gene cloning and expression technologies. Westborough, MA: Eaton Publishing. pp. 391-411.
Jin, Z. et al. (2007). "Haemophilus influenzae type a infection and its prevention," Infect. Immun. 75:2650-2654.

Jones, C. (2005). "Vaccines based on the cell surface carbohydrates of pathogenic bacteria," Anals of the Bras. Academy of Sciences 77:293-324.
Jones, C. et al. (2002). "Use and validation of NMR assays for the identity and O-acetyl content of capsular polysaccharides from Neisseria meningitidis used in vaccine manufacture," J. Pharm. Biomed. Analysis 30:1233-1247.
Kabat, E.A. et al. (1958). "The effect of variation in molecular weight on the antigenicity of dextran in man," Arch. Biochem. Biophys. 78:306-318.
Kalin, M. (1998). "Pneumococcal serotypes and their clinical relevance," Thorax 53:159-162.
Kim, J.O. et al. (1999). "Relationship between cell surface carbohydrates and intrastrain variation on Opsonophagocytosis of *Streptococcus pneumonia*," Infection and Immunity 67:2327-2333.
Kim, C.H et al. (2013). "Protein conjugation with genetically encoded unnatural amino acids," Current Opinion in Chemical Biology 17:412-419.
Kosten, T.R. et al. (2002). "Human therapeutic cocaine vaccine: safety and immunogenicity," Vaccine 20:1196-1204.
Kuberan, B. et al. (2000). "Carbohydrate based vaccines," Curr. Org. Chem. 4:653-677.
LaFerriere, C.A. et al. (1997). "The synthesis of *Streptococcus pneumoniae* polysaccharide-tetanus toxoid conjugates and the effect of chain length on immunogenicity," Vaccine 15:179.
Lagos, R. et al. (2009). "Immunology of combining CRM(197) conjugates for *Streptococcus pneumoniae*, Neisseria meningitis and Haemophilus influenzae in Chilean infants," Vaccine 27:2299-2305.
Laine, M.L. et al. (1996). "Novel polysaccharide capsular serotypes ion Porphyromonas gingivalis," J. Periodontal Res. 31:278-284.
Lee, C.J. (2002). "Quality control of polyvalent pneumococcal polysaccharide-protein conjugate vaccine by nephelometry," Biologicals 30:97-103.
Lees et al. (2008). Conjugation Chemistry, Chap. 11, Pneumococcal Vaccines: The Impact of Conjugate Vaccine, pp. 163-174.
Lees, A. et al. (1996). "Activation of soluble polysaccharides with 1-cyano-4-dimethylaminopyridinium tetrafluoroborate for use in protein-polysaccharide conjugate vaccines and immunological reagents," Vaccine 14:190-198.
Lei, Q.P. et al. (2000). "Quantification of free polysaccharide in meningococcal polysaccharide-diphtheria toxoid conjugate vaccines," Dev. Biol. 103:259-264.
Lemercinier et al. (1996). "Full 1H NMR assignment and detailed O-acetylation patterns of capsular polysaccharides from Neisseria meningitidis used in vaccine production," Carb. Res. 296:83-96.
Lu, Y. et al. (2013). "*Escherichia coli*-based cell free production of flagellin and ordered flagellin display on virus-like particles," Biotechnol Bioeng 110:2073-2085.
Lu, Y. et al. (2014). "Production and stabilization of the trimeric influenza hemagglutinin stem domain for potentially broadly protective influenza vaccines," PNAS. 111:125-130.
Maciel, M., Jr. et al. (2008). "Comprehensive analysis of T cell epitope discovery strategies using 17DD yellow fever virus structural proteins and BALB/c (H2d) mice model," Virol. 378:105-117.
Maza, J.C. et al. (2015). "Synthesis and Incorporation of Unnatural Amino Acids To Probe and Optimize Protein Binconjugations" Binconjugate Chem 26:1884-1889.
Micoli, F. et al. (2018). "Protein carriers for glycoconjugate vaccines: History, selection criteria, characterization and new trends," Molecules 23:1451.
Miyataki, N. et al. (1993). "Removal of N-terminal formyl groups and deblocking of pyrrolidone carboxylic acid of proteins with anhydrous hydrazine vapor," Eur. J. Biochem. 212:785-789.
Moginger, U. et al. (2016). "Cross reactive material 197 glycoconjugate vaccines contain privileged conjugation sites," Sci. Reports 6:20488.
Musher, D. et al. (1990). "Pneumococcal Polysaccharide Vaccine in Young Adults and Older Bronchitics: Determination of IgG Responses by ELISA and the Effect of Adsorption of Serum with Non-Type-Specific Cell Wall Polysaccharide," Infect Dis. 161:728-735.
Nguyen, D.P. et al. (2009). "Genetic encoding and labeling of aliphatic azides and alkynes in recombinant proteins via a pyrrolysyl-tRNA Synthetase/tRNA(CUA) pair and click chemistry," JACS 131:8720-8721.

(56) References Cited

OTHER PUBLICATIONS

Noren, C.J. et al. (1989). "A general method for site-specific incorporation of unnatural amino acids into proteins," Science 244:182-188.
Nwe, K. et al. (2009). Growing applications of "Click chemistry" for bioconjugation in contemporary biomedical research, Cancer Biotherapy and Radiopharmaceuticals. 24:289-302.
O'Brien, K.L. et al. (2007). "Predictors of pneumococcal conjugate vaccine immunogenicity among infants and toddlers in an American Indian PnCRM197 efficacy trial," J Infect Dis. 196:104-114.
Orr, N. et al. (1999). "Expression and immunogenicity of a mutant diphtheria toxin molecule, CRM(197), and its fragments in *Salmonella typhi* vaccine strain CVD 908-htrA," Infect. Immunol. 67:4290-4294.
Pantosti, A. et al. (1991). "Immunochemical characterization of two surface polysaccharides of Bacteroides fragilis," Infect. Immunol. 59:2075-2082.
Patel, K.G. et al. (2011). "Surface functionalization of virus-like particles by direct conjugation using azide-alkyne click chemistry," Bioconjug Chem. 22:376-387.
Pecetta, S. et al. (2016). "Evaluation of the non-toxic mutant of the diphtheria toxin K51E/E148K as carrier protein for meningococcal vaccines," Vaccine 34:1405-1411.
Peltola, H. et al. (1977). "Haemophilus influenzae type b capsular polysaccharide vaccine in children: a double-blind field study of 100,000 vaccinees 3 months to 5 years of age in Finland,"Pediatrics 60:730-737.
Pobre, K. et al. (2014). "Carrier priming or suppression: understanding carrier priming enhancement of anti-polysaccharide antibody response to conjugate vaccines," Vaccine 32:1423-1430.
Poolman et al. (Feb. 2011), "Impact of the Conjugation Method on the Immunogenicity of *Streptococcus pneumoniae* Serotype 19F Polysaccharide Conjugate Vaccines," Clinical and Vaccine Immunology, pp. 327-336.
Powell & Newman (1995). Vaccine Design, Chaps. 8 and 9. ISBN: 030644867X.
Presolski, S.I. et al. (2011). "Copper-catalyzed azide-alkyne click chemistry for bioconjugation," Curr. Protoc. Chem. Biol. 3:153-162.
Prevnar 13 Package Insert (2017). 43 total pages.
Prevnar 13 VRBPAC Briefing Document Nov. 18, 2009, 248 total pages.
Quast, R.B. et al. (2015). "Cotranslational incorporation of non-standard amino acids using cell-free protein synthesis," FEBS Letters 589:1703-1712.
Raju, R. et al. (1995). "Epitopes for human CD4+ cells on diphtheria toxin: Structural features of sequence segments forming epitopes recognized by most subjects," Eur J Immunol 25:3207-3214.
Reece, J.C. et al. (1993). "Mapping the major human T helper epitopes of Tetanus toxin,"IJ. Immunol. 151:6175-6184.
Richter, S.S. et al. (2013). "Pneumococcal serotypes before and after introduction of conjugate vaccines. United States, 1999-2011(1)," Emerg Infect Dis. 19:1074-1083.
Safari et al. (2012). The future of synthetic carbohydrate vaccines: Immunological studies on *Streptococcus pneumoniae* type 14, Chapter 24, pp. 617-634.
Schneerson, R. et al. (1980). "Preparation, characterization, and immunogenicity of Haemophilus influenzae type b polysaccharide-protein conjugates," J Exp Med. 152:361-376.
Schifferle, R.E. et al. (1989). "Characterization of a polysaccharide anigen from Bacteroides gingivalis," J. Immunol. 143:3035-3042.
Shimizu, Y. et al. (2006). "Cell-free translation systems of protein engineering," FEBS Journal 273:4133-4140.
Schultz, P.G. et al. (2010). "Adding new chemistries to the genetic code," Annu. Rev. Biochem. 79:413-444.
Skinner, J, et al. (2011). "Pre-clinical evaluation of a 15-valent pneumococcal conjugate vaccine (PCV15-CRM197) in an infant-rhesus monkey immunogenicity model," Vaccine. 29:8870-8876.

Sletten, E.M. et al. (2011). "From mechanism to mouse: a tale of two bioorthogonal reactions," Acc. Chem. Res. 44:666-676.
Sobanjo, A. et al. (2015). "Safety, Tolerability and Immunogenicity of 15-valent Pneumococcal Conjugate Vaccine in Toddlers Previously Vaccinated With 7-valent Pneumococcal Conjugate Vaccine," Pediatr Infect Dis J. 34:186-194.
Spirin, A.S. et al. (1988). "A continuous cell-free translation system capable of producing polypeptides in high yield," Science. 242:1162-1164.
Tomczyk, S et al. (2014). Use of 13-valent pneumococcal conjugate vaccine and 23-valent pneumococcal polysaccharide vaccine among adults aged ≥65 years: recommendations of the Advisory Committee on Immunization Practices (ACIP). Centers for Disease Control and Prevention (CDC). MMWR Morb Mortal Wkly Rep. 63: 822-825.
Tontini, M. et al. (2016). "Preclinical studies on new proteins as carrier for glycoconjugate vaccines," Vaccine 34:4235-4242.
Trotter, C. et al. (2004). "Effectiveness of meningococcal serogroup C conjugate vaccine 4 years after Introduction," The Lancet 364:24-30.
Turner, A.E.B. et al. (2017). "Novel polysaccharide-protein conjugates provide an immunogenic 13-valent pneumococcal conjugate vaccine for *S. pneumonia*," Synth. And Systems Biotechnol. 2:49-58.
Van Gelder, R.N et al. (1990). "Amplified RNA synthesized from limited quantities of heterogeneous CDNA," PNAS 87:1663-1667.
Van Winkelhoff, A.J. et al. (1993). "K-antigens in porphyromonas gingivalis are associated with Virulence," Oral Microbiol. Immunol. 8:259-265.
Wang, Q. et al. (2009). "Expanding the genetic code for biological studies," Chem. and Biol., Current Biology, London, GB, 16(3):323-336.
Wang, L. et al. (2001). "Expanding the genetic code of *Escherichia coli*," Science 292:498-500.
Weiser, J.N. et al. (1999). "Effect of intrastrain variation in the amount of capsular polysaccharide on genetic transformation of *Streptococcus pneumonia*: Implications for virulence studies of encapsulated strains," Infection and Immunity 67:3690-3692.
Weiser, J.N. et al. (1994). "Phase variation in Pneumococcal opacity: Relationship between colonial morphology and nasopharyngeal colonization," Infection and Immunity 62:2582-2589.
Wessels, M.R. et al. (1998). "Structural properties of group B streptococcal type III polysaccharide conjugate vaccines that influence immunogenicity and efficacy," Infect. Immun. 66:2186-2192.
WHO Technical Report Series, Annex 4, No. 927, 2005, 3 total pages.
Wiertz et al. (1992). "Identification of T cell epitopes occurring in a meningococcal class 1 outer membrane protein using overlapping peptides assembled with simultaneous multiple peptide Synthesis," J. Exp. Med. 176:79-88.
Wizemann, T.M. et al. (2001). "Use of a whole genome approach to identify vaccine molecules affording protection against *Streptococcus pneumoniae* infection," Infect. Immun. 69:1593-1598.
Written Opinion of the International Searching Authority dated Jul. 3, 2018, for PCT Application No. PCT/US2017/069129, filed on Dec. 29, 2017, 8 pages.
Wu, D. et al. (2013). "Development of pneumococcal polysaccharide conjugate vaccine with long spacer arm," Vaccine 31:5623-5626.
Wyeth Grounds of Appeal, EPO Opposition to Wyeth LLC, EP 1868645 (Pfizer submission May 4, 2015).
Young, T.S. et al. (2010). "Beyond the canonical 20 amino acids: Expanding the genetic lexicon," J. Biol. Chem. 285:11039-11044.
Yu, J. et al. (2011). "Development of an automated and multiplexed serotyping assay for *Streptococcus pneumonia*," Clin. Vacc. Immunol. 18:1900-1907.
Zangwill, K.M. et al. (2003). "Safety and immunogenicity of a heptavalent pneumococcal conjugate vaccine in infants," Vaccine. 21:1894-1900.
Zawada, J.F. et al. (2011). "Microscale to manufacturing scale-up of cell free cytokine production—A new approach for shortening protein production development timeliness," Biotechnol. Bioeng. 108:1570-1578.

(56) References Cited

OTHER PUBLICATIONS

Zhang, X. et al. (2013). "Applications of azide-based bioorthogonal click," Chemistry in Glycobiology 18:7145-7159.

Zhu, J. et al. (2009). "Synthetic carbohydrate-based anticancer vaccines: The memorial Sloan-Kettering experience," Expert Rev. Vaccines 10:1399-1413.

Zimmerman, E.S. et al. (2014). "Production of site-specific antibody-drug conjugates using optimized non-natural amino acids in a cell-free expression system," Bioconjugate Chem. 25:351-361.

Zubay, G. (1973). "In vitro synthesis of protein in microbial systems," Annu Rev Genet. 7:267-287.

Nahn, M.H. et al. (2016). "Protocol for opsonophagocytic killing assay for antibodies against Group B Streptococcus (UAB GBS OPA)," Version B.04, Mar. 2016, located at https://www.vaccine.uab.edu/uploads/mdocs/UAB-GBS-OPA.pdf, 24 total pages.

Nahn, M.H. et al. (2014). "Protocol for multiplexed opsonophagocytic killing assay (UAB-MOPA) for antibodies against Streptococcus pneumoniae," Version E.02, Dec. 2014, located athttps://www.vaccine.uab.edu/uploads/mdocs/UAB-MOPA.pdf, 43 total pages.

Avci, F. et al. (2019). Glycoconjugates: What it would take to master these three well-known yet little-understood immunogens for vaccine development, mSphere 4:e00520-19, 8 total pages.

Gamblin, D. et al. (2009). Glycoprotein synthesis: An update, Chem. Rev. 109:131-163.

Ogawa T. (1994). "The potential protective immune responses to synthetic peptides containing conserved epitopes of Porphyromonas gingivalis fimbrial protein," J Med Microbial. 41:349-358.

Selva, L. et al. (2012). "Rapid and easy identification of capsular serotypes of Streptococcus pneumoniae by use of fragment analysis by automated fluorescence-based capillary electrophoresis," J Clin Microbial. 50:3451-3457.

Behrens, C. et al. (2021). "Development of a Next Generation 30+ Valent Pneumococcal Conjugate Vaccine (VAX-XP) Using Site-Specific Carrier Protein Conjugation," Vaxcyte, Inc. Poster, 1 total page.

Durando et al. (2013). "Experience with pneumococcal polysaccharide conjugate vaccine (conjugated to CRM197 carrier protein) in children and adults," Clin. Microbiol. Infect. 19(suppl. 1):1-9.

Fairman, J. et al. (2021). "Non-clinical immunological comparison of a Next-Generation 24-valent pneumococcal conjugate vaccine (VAX-24) using site-specific carrier protein conjugation to the current standard of care (PCV13 and PPV23)," Vaccine 39:3197-3206.

Hurley, D. et al. (2019). Safety, tolerability, & immunogenicity of a 20-Valent Pneumococcal Conjugate Vaccine (PCV20) in adults 60-64 years of age, Presented at 29th European Congress of Clinical Microbiology & Infectious Disease, Apr. 13-16, 2019, Amsterdam.

Jones, L.H. (2015). "Recent advances in the molecular design of synthetic vaccines," Nature chemistry 7: 952-960.

Ladhani, S.N. et al. (2018). "Rapid increase in non-vaccine serotypes causing invasive pneumococcal disease in England and Wales, 2000-17: a prospective national observational cohort study," Lancet Infect. Dis. 18:441-451.

Moore, M.R. et al. (2015). "Effect of use of 13-valent pneumococcal conjugate vaccine in children on invasive pneumococcal disease in children and adults in the USA: analysis of multisite, population-based surveillance," Lancet Infect. Dis. 15:301-309.

Non-Final Office Action dated Jul. 19, 2021, for U.S. Appl. No. 15/859,251, filed Dec. 29, 2017, 20 pages.

Stefanetti, G. et al. (2015). "Click Chemistry Applied to the Synthesis of Salmonella Typhimurium O-Antigen Glycoconjugate Vaccine on Solid Phase with Sugar Recycling," Bioconjugate Chemistry 26:2507-2513.

Yeh, S.H. et al. (2010). "Immunogenicity and safety of 13-valent pneumococcal conjugate vaccine in infants and toddlers," Pediatrics 126:e493-e505.

Final Office Action dated Jan. 7, 2022, for U.S. Appl. No. 15/859,251, filed Dec. 29, 2017, 24 pages.

ClinicalTrials.Gov (2018). Trial to Evaluate the Safety and Immunogenicity of a Multivalent Pneumococcal Vaccine in Healthy Infants, ClinicalTrials.Gov Identifier NCT03512288, 39 total pages.

Non-Final Office Action dated Sep. 8, 2022, for U.S. Appl. No. 15/859,251, filed Dec. 29, 2017, 23 pages.

Prevnar 20 Package Insert (2021). 18 total pages.

Prevnar 20 BLA Clinical Review Memorandum (Jun. 8, 2021). STN: 125731/0, 117 total pages.

Vaxcyte, Inc. (2022). VAX-24 Phase 1/2 Proof-of-Concept Study Topline Results, located at https://www.sec.gov/Archives/edgar/data/1649094/000119312522267147/d413834dex992.htm, 35 total pages.

Vaxcyte, Inc. (2022). Vaxcyte Reports Positive Topline Data from Phase 1/2 Proof-of-Concept Study of its 24-Valent Pneumococcal Conjugate Vaccine Candidate Being Investigated for the Prevention of Invasive Pneumococcal Disease in Adults Aged 18-64—Press Release, located at https://investors.vaxcyte.com/news-releases/news-release-details/vaxcyte-reports-positive-topline-data-phase-12-proof-concept, 3 total pages.

Duowei, Y. et al. (Jul. 31, 2007). Molecular Biology, Nanjing Normal University Press, p. 149, 7 total pages (with English translation).

Final Office Action dated Feb. 28, 2023, for U.S. Appl. No. 15/859,251, filed Dec. 29, 2017, 27 pages.

Guo, Q. et al. (2014). "Genetic diversity of fluoroquinolone-nonsusceptible Streptococcus pneumoniae clinical isolates and the first identification of serotype 20B in China," Eur. J. Clin. Microbial. Infect. Dis. 33:465-470.

Nakayama, K. (1994). "Kex2-like endoproteases involved in processing of precursors for bioactive peptides and proteins," Biophysics 34(3):124-130 (pp. 30-36), 9 total pages (with English Translation).

Notice of Allowance dated Jan. 18, 2024, for U.S. Appl. No. 15/859,251, filed Dec. 29, 2017, 9 pages.

\* cited by examiner

CONJUGATED VACCINE CARRIER PROTEINS

CROSS-REFERENCE TO RELATED APPLICATIONS

This application is a continuation-in-part of U.S. Ser. No. 15/859,251, filed Dec. 29, 2017, which claims priority under 35 U.S.C. § 119(e)(1) to provisional U.S. patent applications 62/441,115 (filed Dec. 30, 2016), 62/530,803 (filed Jul. 10, 2017), 62/568,201 (filed Oct. 4, 2017), and 62/591,160 (filed Nov. 27, 2017). This application also claims priority under 35 U.S.C. § 119(e)(1) to provisional U.S. patent applications 62/693,978, and 62/693,981, all filed Jul. 4, 2018. The complete contents of all of the aforementioned patent applications are hereby incorporated by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: STRO_006_00US_SeqList_ST25.txt, date recorded: Jul. 1, 2019, file size ~47 kilobytes).

BACKGROUND OF THE INVENTION

Vaccines based on isolated antigenic macromolecules (e.g. the first-generation meningococcus, pneumococcus, and *Haemophilus* polysaccharide vaccines) represented significant improvements over earlier vaccine formulations based around live attenuated or inactivated organism vaccines.

Purified macromolecules are significantly easier to manufacture, have an improved safety profile, and can generate a more productive specific immune response (e.g. they can be directed against an antigen that is more conserved or is important for pathogenesis). Moreover, they offer a simplified template for vaccine production, where an immune response can be directed against a specific site or a specific organism simply by providing the proper immunogen. Not every macromolecule antigen, however, generates a strong immune response. Many lipids, polysaccharides, and certain protein antigens (and most small molecules) generate immune responses that are inherently weak, transient, and/or ineffective in certain patient populations (e.g., infants and the elderly). These weak immune responses are thought to result from antigen structures that primarily activate B-cells, or otherwise fail to activate T-cell dependent pathways that are involved in immunological memory and antibody maturation.

In protein carrier-antigen conjugate vaccines the immune response to a "weak" antigen can be amplified by conjugation to a known carrier polypeptide antigen such as diphtheria toxoid, tetanus toxoid, *H. influenzae* protein D, or CRM197. Conjugate vaccines based on bacterial oligo and polysaccharide antigens have played an important role in preventing infectious diseases caused by virulent pathogens such as *H. influenzae, Streptococcus pneumoniae*, and *Neisseria meningitidis*. While conjugate vaccines can have better performance than vaccines based on the same unconjugated antigen, there remains a need to improve conjugate vaccine technology. The conjugation methods used for current vaccines have inherent limitations on the ability to optimize conjugate structure and consistency, improve the strength and breadth of the immune response, and the efficiency of commercial scale production. For example, there is a need to produce multivalent conjugate vaccines because bacteria like *S. pneumoniae* have dozens of clinically relevant serotypes, each requiring different polysaccharide antigens. Despite the need for higher valency vaccines for *S. pneumonia*, the broadest spectrum vaccine that has been approved covers only thirteen of the clinically relevant *S. pneumonia* serotypes. The field has been particularly concerned with carrier-induced suppression as the valency of these conventional vaccines is increased.

It is an object of the inventions herein to provide vaccine carriers, methods of making conjugates, conjugate vaccines and methods of vaccination which address one or more of the limitations of conventional conjugate vaccine technology.

SUMMARY OF THE INVENTION

The present disclosure is directed to methods, compositions, and techniques that provide a new class of conjugated vaccines which addresses many of the limitations in the field. These new vaccines are based around carrier proteins which contain non-natural amino acids at pre-selected sites, which allows for the optimization of conjugate structure and immunological properties. These carriers and the conjugates made therefrom can be used to make vaccines that have more efficient and potent immunogenicity, even at a high valency heretofore unobtainable (e.g., >20). Furthermore, these new conjugated vaccines can be made efficiently at commercial scale with a high degree of consistency compared to conventional conjugated vaccines.

In some embodiments, the present disclosure provides a carrier protein for use in a protein-conjugate vaccine, where the carrier protein comprises (a) at least two non-natural amino acid residues (nnAArs) at nn sites where each nnAAr (i) comprises a reactive group that provides site-specific conjugation of an antigen to the carrier protein, and (ii) was introduced site-specifically during synthesis of the carrier protein; (b) wherein nn is an integer selected from the group consisting of ≥2, ≥3, ≥4, 3, 4, 5, 6, 3-9, 4-8, and 4-6; and (c) at least 1 T-cell activating epitope that has not been inactivated by the presence of an nnAA residue. In certain embodiments, the carrier protein comprises at least one T-cell activating epitope from a protein selected from the group consisting of *Corynebacterium diphtheriae* toxin, *Clostridium tetani* tetanospasmin (also known as tetanus toxin), *Haemophilus influenzae* protein D (PD, HiD), outer membrane protein complex of serogroup B meningococcus (OMPC) and CRM197.

In certain embodiments, the reactive group comprises a bio-orthogonal reactive moiety, such as an azide, phosphine, alkyne, alkene, or 1,2,4,5-tetrazine.

In some embodiments, the at least two nnAArs of the carrier protein (a) correspond to a non-natural amino acid (nnAA) having the structure of formula XII

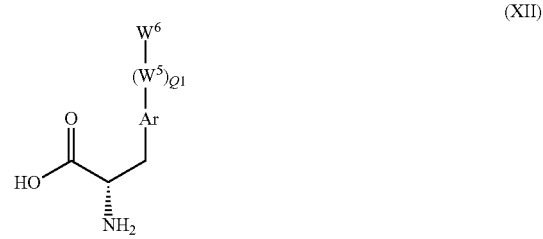

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

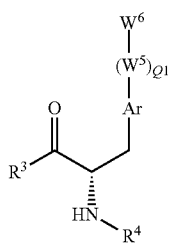

(XIII)

in which $R^3$ is OH or an amino acid residue of the carrier protein, and $R^4$ is H or an amino acid residue of the carrier protein; (b) correspond to an nnAA according to (a) wherein $W^6$ is azido and Ar is phenylene; (c) correspond to an nnAA according to (b) wherein Ar contains a nitrogen heteroatom and optionally at least one additional heteroatom selected from N, O, and S; (d) correspond to an nnAA according to (b) wherein Q1 is 1 and $W^5$ is lower alkylene; (e) are a 2,3-disubstituted propanoic acid bearing an amino substituent at the 2-position and an azido-containing substituent, a 1,2,4,5-tetrazinyl substituent, or an ethynyl-containing substituent at the 3-position; (f) correspond to an nnAA according to (e) wherein the 2,3-disubstituted propanoic acid has an azido-containing substituent at the 3-position; or (g) are selected from 2-amino-3-(4-azidophenyl) propanoic acid (pAF), 2-amino-3-(4 (azidomethyl)phenyl) propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl)phenyl) propanoic acid, or any combination thereof.

In some embodiments, the carrier protein comprises at least 80% sequence identity to SEQ ID NO:1 or SEQ ID NO:11.

The invention additionally provides protein-antigen conjugates comprising the carrier protein and an antigen wherein the antigen has been site-specifically conjugated to a reactive group of nnAAs in the unconjugated carrier protein through a chemical handle introduced into the antigen. In some embodiments, the chemical handle is introduced into the antigen by a linker molecule. In some embodiments, the site-specific conjugation is the product of strain-promoted azide-alkyne cycloaddition between the chemical handle of the unconjugated antigen and the reactive group of the unconjugated carrier protein where the chemical handle comprises a cyclooctyne group and the reactive group comprises an azide group. In some embodiments, the protein-antigen conjugate has a molecular weight of at least 900 kDa.

In some embodiments, the antigen is a bacterial antigen. In some embodiments, the antigen is a viral antigen. Bacterial antigens include bacterial polysaccharides selected from the group consisting of capsular polysaccharides from Streptococcus pneumoniae, capsular polysaccharides from Streptococcus pyogenes, group-A-strep cell wall polysaccharides from Streptococcus pyogenes, capsular polysaccharides of Streptococcus agalactiae, capsular polysaccharides of Haemophilus influenzae, capsular polysaccharides of Neisseria meningitidis, and capsular polysaccharides from Porphyromonas gingivalis. In some embodiments, the antigen is a capsular polysaccharide of a Streptococcus pneumoniae serotype selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48. In some embodiments, the ratio (weight by weight) of polysaccharide to carrier protein (PS:PC) in the conjugate is (i) at least 1.0, or (ii) between 1.5 and 4.0.

Also provided are immunogenic compositions comprising at least 2 protein-antigen conjugates according to the invention and at least one excipient suitable for parenteral administration wherein the at least 2 protein-antigen conjugates comprise multiple antigens and the antigen of each of the at least 2 protein-antigen conjugates is distinct from the antigens of the other at least 2 protein-antigen conjugates. In some embodiments, the immunogenic composition comprises at least 4, 11, 14, 15, 16, 20, 21, or 24 of the at least 2 protein-antigen conjugates. In some embodiments, the distinct antigens are capsular polysaccharides from Streptococcus pneumoniae and the ratio of Streptococcus pneumoniae capsular polysaccharides to carrier protein is from about 1.0 to about 4.0.

Iimmunogenic compositions may include wherein the capsular polysaccharides from Streptococcus pneumoniae are independently selected from capsular polysaccharides of Streptococcus pneumoniae serotypes selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A and 48.

In some embodiments, the capsular polysaccharides from Streptococcus pneumoniae are independently selected from capsular polysaccharides of Streptococcus pneumoniae serotypes selected from:
 a) a first group consisting of serotypes 1, 2, 3, 4, 5, 6A, 6B, 7F, 8, 9V, 9N, 10A, 11A, 13, 14, 16, 17F, 18C, 19A, 19F, 20, 22F, 23F, 24F, 31, and 33F;
 b) a second group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
 c) a third group consisting of serotypes 1, 2, 3, 4, 5, 6A, 6B, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48;
 d) a fourth group consisting of serotypes 3, 4, 18C, and 11A;
 e) a fifth group consisting of serotypes 3, 7F and 10A;

f) a sixth group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F; or g) a seventh group consisting of serotypes 6C, 7C, 13, 15A, 15C, 16, 16F, 23A, 23B, 24F, 31, 34, 35B, 33F, 35F, 37 and 38.

In other embodiments, the distinct antigens comprise capsular polysaccharides from:

a) 2 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

b) 14 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

c) 15 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

d) 20 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

e) 21 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

f) 24 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

g) 25 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;

h) 4 or more different *Neisseria meningitidis* serogroups selected from the group consisting of serogroups A, C, W135, X, and Y; or i) 2 or more different *Porphyromonas gingivalis* serotypes selected from the group consisting of serotypes K1, K2, K3, K4, K5, and K6.

The invention also provides a multivalent immunogenic composition comprising carrier protein-antigen conjugates wherein:

(a) the carrier protein-antigen conjugates comprise at least 14 distinct carrier protein-antigen conjugates wherein the antigens are capsular polysaccharides of *Streptococcus pneumoniae*;

(b) the at least 14 distinct carrier protein-antigen conjugates each comprise a capsular polysaccharide from a different serotype of *Streptococcus pneumoniae* wherein: (i) 13 of the distinct carrier protein-antigen conjugates comprise a capsular polysaccharide from *Streptococcus pneumoniae* serotypes 1, 3, 4, 5, 6A, 6B, 7F, 9V, 14, 18C, 19A, 19F and 23F; and (ii) at least one distinct carrier protein-antigen conjugate wherein the antigen is a capsular polysaccharide from *Streptococcus pneumoniae* serotype selected from the group consisting of serotypes 2, 6C, 8, 9N, 10A, 12F, 15A, 15B, 15C, 16F, 17F, 20 (e.g., 20A, 20B), 22F, 23A, 23B, 24F, 24B, 31, 33F, 34, 35B, 35F and 38;

(c) the carrier protein in each of the at least 14 distinct carrier protein-antigen conjugates comprises: (i) at least 3 (e.g., at least 4, or 4-6) non-natural amino acid residues (nnAArs); at nn sites, wherein nn i is an integer selected from the group consisting of ≥3, ≥4 and 4-6; and (ii) at least one T-cell activating epitopes not comprising the at least 3 nnAAs;

(d) the *Streptococcus pneumoniae* capsular polysaccharides of the at least 14 distinct carrier protein-antigen conjugates are conjugated to the nnAAs; and (e) the overall (weight by weight) ratio of polysaccharides to carrier protein (PS:PC) in the multivalent immunogenic composition is at least 1.1.

In some embodiments, the invention provides an improved method of making a conjugate vaccine comprising multiple distinct carrier protein-antigen conjugates, where each distinct carrier protein-antigen conjugate comprises a distinct antigen that is different from the antigens in the other distinct carrier protein-antigen conjugates, and the improvement comprises using an enhanced carrier protein as the carrier protein in at least one of the distinct carrier-protein conjugates wherein the enhanced carrier protein is a carrier protein that:

a) was made by cell-free protein synthesis;

b) comprises at least 2 non-natural amino acid residues (nnAArs) at nn sites wherein each said nnAAr (i) comprises a reactive group that provides site-specific conjugation of an antigen to the carrier protein, and (ii) was introduced site-specifically during synthesis of the carrier protein;

c) wherein nn is an integer selected from the group consisting of ≥2, ≥3, ≥4, 3, 4, 5, 6, 3-9, 4-8, and 4-6; and d) at least 1 T-cell activating epitope that has not been inactivated by the presence of an nnAA residue.

Also provided is a method for producing a carrier protein of the invention by cell-free protein synthesis, where the method comprises:

a) providing a nucleic acid encoding the carrier protein, wherein the nucleic acid comprises a plurality of suppression codons encoding the site of the nnAAs;

b) creating a reaction mixture by combining the nucleic acid with a cell-free bacterial extract comprising canonical amino acids, the nnAAs, a tRNA complementary to the suppression codons and specific for the nnAAs, and an aminoacyl-tRNA synthetase; and c) incubating the reaction mixture of b) under conditions sufficient to selectively incorporate the non-natural amino acid in the carrier protein at the site corresponding to each suppression codon.

Additionally provided is a method of making an immunogenic composition comprising combining at least 2 enhanced protein-antigen conjugates with at least one excipient suitable for parenteral administration, wherein the at least 2 enhanced protein-antigen conjugates are protein-antigen conjugates of the invention, and further wherein the antigen of each of the enhanced protein-antigen conjugates is distinct from the antigens of the other enhanced protein-antigen conjugates.

The invention also provides methods of using the present carrier proteins, conjugates, and immunogenic compositions. In some embodiments, a method is provided for eliciting an immunoprotective response in a subject comprising administering to the subject a conjugate as provided herein. In some embodiments, a method is provided for eliciting an immunoprotective response in a subject comprising administering to the subject an immunogenic composition as provided herein.

Additionally provided is a method of making a protein-antigen conjugate of the invention, where the method is selected from a cyanylation or a periodate method, the antigen is a saccharide and the cyanylation method comprises (a) functionalizing the saccharide with a chemical handle capable of participating in a click chemistry reaction with a bio-orthogonal reactive moiety coupled to a nnAA residue in the carrier protein by (i) providing the saccharide as a solution in an aqueous buffer having a pH in the range of 7 to 11; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the chemical handle coupled to a primary amino group under conditions that couple the chemical handle to the cyanate-substituted saccharide thereby providing an activated saccharide antigen; the periodate method comprises the steps of: (b) oxidizing a solution of the saccharide in an aqueous medium by adding a periodate reagent to the solution, thereby providing an aldehyde-bearing saccharide; (c) purifying the aldehyde-bearing saccharide; (d) dissolving the aldehyde-bearing saccharide in an aqueous buffer having a pH in the range of 5.5 to 5.9; and (e) in a reductive amination reaction, contacting the dissolved aldehyde-bearing saccharide of step (d) with an activating reagent comprising the chemical handle coupled to a primary amino group, followed by admixture with sodium cyanoborohydride for a time period effective to couple the chemical handle to the cyanate-substituted saccharide, thereby providing an activated saccharide antigen; and combining the activated saccharide antigen of step (a) or step (e) with the carrier protein comprising at least one nnAA bearing the bio-orthogonal reactive moiety, such that a click chemistry reaction between the chemical handle and the bio-orthogonal reactive moiety results in a conjugate of the saccharide and the carrier protein.

Also provided are methods of eliciting an immunoprotective response to an antigen in a subject in need thereof using any of the conjugates and composition described herein.

BRIEF DESCRIPTION OF THE DRAWINGS

The features and advantages of the embodiments described herein are further explained by reference to the following detailed description and accompanying drawings that sets forth illustrative embodiments.

In FIG. 2A the ladder shows from top to bottom 10, 15, 20, 25, 37, 50, 75, 100, 150, and 250 kDa. In FIG. 2B the fluorescent markers are at 25 and 75 kDa. Lanes are as follows: L=ladder; W=wild-type; C=C-terminus TAG; then lanes 1-12 have TAG to replace Lys at positions 11, 25, 34, 38, 40, 52, 60, 77, 83, 91, 96 and 103 respectively.

DETAILED DESCRIPTION OF THE INVENTION

I. Overview

Figure 1:
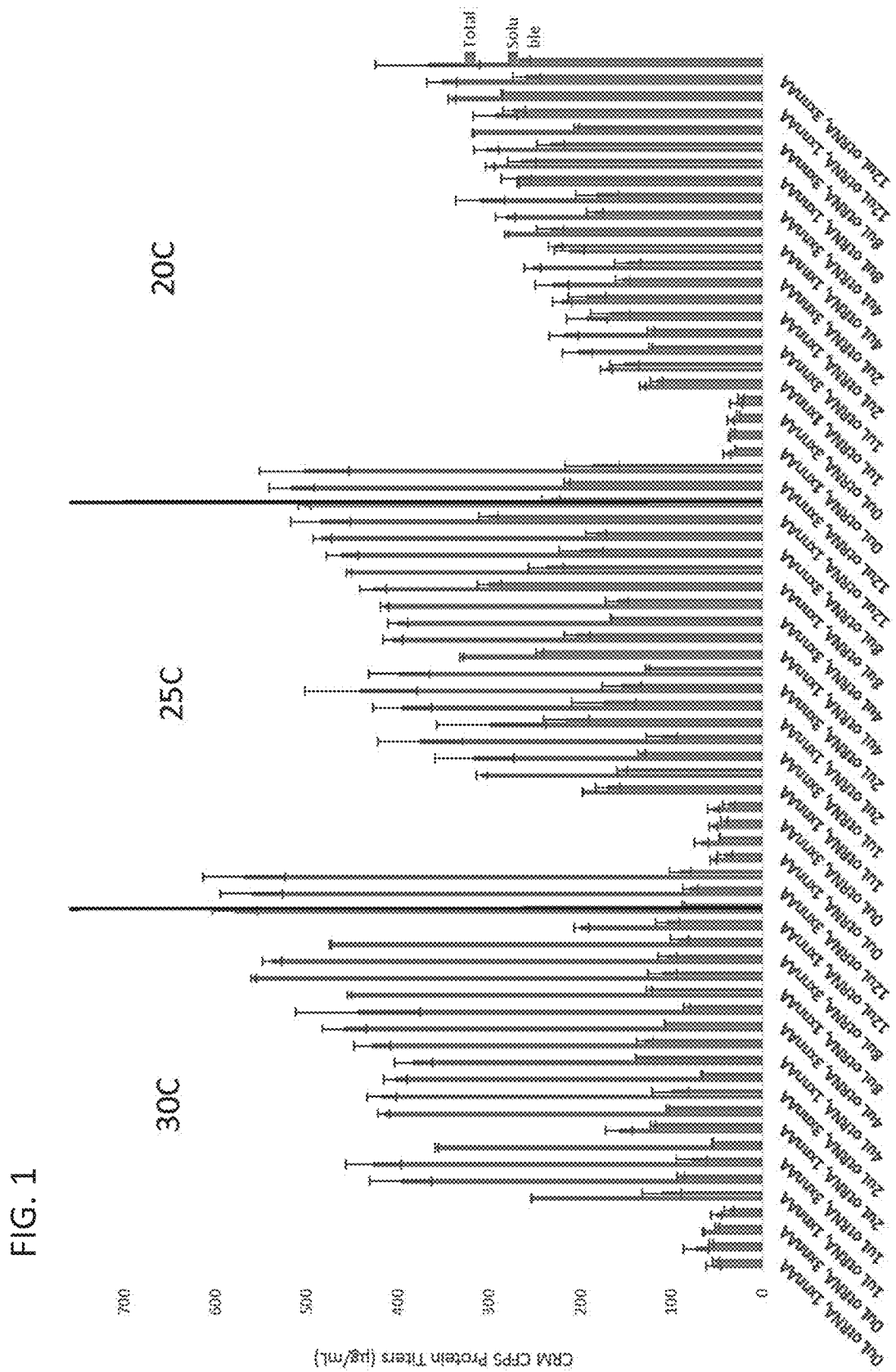
FIG. 1. shows the yield of a 6 nnAA-containing eCRM produced at 30, 25, or 20 degrees Celsius in CFPS reactions optionally supplemented with increasing amounts of tRNA (otRNA) or nnAA/aaRS synthetase (nnAA). Two bars are shown in each column, representing both total and soluble yield.

The current methods and building blocks used for protein-conjugate vaccine production hamper the wider application of conjugate vaccines for disease treatment and prevention. First, relatively few strong protein antigens are chemically resistant, nontoxic, and scalable enough to be used as carriers in conjugate vaccines. Second, the oxidation/reduction chemistry generally used for conjugate vaccine production makes it difficult to preserve epitopes on the carrier and antigen needed for maximum immunogenicity. Third, the relatively low efficiency of these oxidation/reduction reactions complicates quality control and purification, especially at commercial scale.

Recombinant protein production allows the optimization of antigenicity and nontoxicity of carrier proteins, but the existing carrier proteins are difficult to produce in recombinant cells and wholly engineered proteins are difficult to produce in high yields. Gentler conjugation reactions minimize the denaturation/obstruction of carrier and antigen epitopes, but the lower efficiency of these reactions results in less loading of the antigen on the carrier protein and more complicated purification schemes. Importantly, relatively lower antigen to carrier results in a higher likelihood of immune "interference" by antibody responses to the carrier protein itself, or the recognized phenomenon of carrier-induced epitopic suppression.

Thus, a need has been identified for strategies and reagents that allow the combination of these technologies to produce higher-immunogenicity, more easily manufactured conjugate vaccines. Accordingly, described herein are, inter alia, (1) polypeptides, including enhanced carrier proteins, comprising non-natural amino acids; (2) antigens that are suitable to conjugate to polypeptides, including enhanced carrier proteins, comprising non-natural amino acids; (3) polypeptide-antigen conjugates of (1) and (2), including antigens conjugated to enhanced carrier proteins comprising non-natural amino acids; (4) vaccine compositions comprising the foregoing; and (5) methods of making and using the foregoing.

The term "suppression codon" refers to a nucleotide triplet that is introduced into a polynucleotide at a predetermined location and is recognized by a specific tRNA that can recognize a stop codon (e.g., an amber, ochre or opal stop codon) and allows translation to read through the codon to produce the protein, thereby suppressing the stop codon.

A "non-natural amino acid" (nnAA) refers to an amino acid that is not one of the 20 common amino acids or pyrolysine or selenocysteine; other terms that are used synonymously with the term "non-natural amino acid" are "non-naturally encoded amino acid," "unnatural amino acid," "non-naturally occurring amino acid," and variously hyphenated and non-hyphenated versions thereof. Non-natural amino acids with bio-orthogonal reactive chemical side chains are able to be used as a chemical "handle" to conjugate various payloads to discrete sites in a protein.

The term "sequence identity" or "percent identity" in the context of two or more nucleic acids or polypeptide sequences, refers to two or more sequences that are the same or have a specified percentage of amino acid residues or nucleotides that are the same, when compared and aligned for maximum correspondence over a comparison window, as measured using a sequence comparison algorithm (e.g., BLASTP for amino acid sequences). For purposes of this document, the percent identity is determined over the full-length sequence, such as the reference sequence set forth in SEQ ID NO:1 or SEQ ID NO:11. The method for calculating the sequence identity as provided herein is the BLASTP program having its defaults set at a wordlength (W) of 3, an expectation (E) of 10, and the BLOSUM62 scoring matrix (see, e.g., Henikoff & Henikoff, 1989, *Proc Natl Acad Sci USA* 89:10915). See e.g., the BLAST alignment tool available on the WWW at blast.ncbi.nlm.nih.gov/Blast.cgi or elsewhere.

The term "antigen" refers to any molecule or a linear molecular fragment that is able to be recognized by the highly variable antigen receptors (B-cell receptors, T-cell receptors, or both) of the adaptive immune system. Non-limiting examples of antigens include polysaccharides or glycans (e.g., bacterial capsular polysaccharides), polynucleotides, polyamino acids, lipids, and small molecules (e.g., haptens, drugs of abuse).

The term "T-cell activating epitope" refers to a structural unit of molecular structure which is capable of inducing T-cell immunity. The function of carrier proteins which include T-cell activating epitopes is well known and documented for conjugates. Without wishing to be bound by theory, a T-cell activating epitope in the carrier protein enables the covalently-attached antigen to be processed by antigen-presenting cells and presented to $CD4^{+ve}$ T cells to induce immunological memory against the antigen.

The term "B-cell epitope" refers generally to those features of a macromolecular structure which are capable of inducing a B cell response. In contrast to a T-cell epitope, a B-cell epitope need not comprise a peptide, since processing by antigen-presenting cells and loading onto the peptide-binding cleft of MHC is not required for B-cell activation.

As used herein, "carrier protein" refers to a non-toxic or detoxified polypeptide containing a T-cell activating epitope which is able to be attached to an antigen (e.g., a polysaccharide) to enhance the humoral response to the conjugated antigen in a subject. The term includes any of the bacterial proteins used as epitope carriers in FDA-approved vaccines. In some embodiments, the carrier protein is *Corynebacterium diphtheriae* toxin, *Clostridium tetani* tetanospasmin, *Haemophilus influenzae* protein D (PD, HiD), outer membrane protein complex of serogroup B meningococcus (OMPC), CRM197, or malaria ookinete specific surface protein Pfs25. In certain embodiments, the carrier protein is BB, derived from the G protein of *Streptococcus* strain G148. A "native carrier protein" has only naturally occurring amino acids. An "enhanced carrier protein" has at least one non-natural amino acid replaced for a naturally occurring amino acid in the carrier protein. The terms "carrier protein" and "carrier polypeptide" are used interchangeably herein.

As used herein, the term "immunogenic polypeptide" refers to a polypeptide comprising at least one T-cell activating epitope, wherein the T-cell epitope is derived from a protein capable of inducing immunologic memory in animals.

The term "eCRM" or "enhanced CRM" as used interchangeably herein refers to a modified version of the G52E codon variant of diphtheria toxin, wherein at least one of the natural amino acid residues is substituted for a non-natural amino acid and the polypeptide retains at least one T-cell activating epitope.

As used herein, the terms "modified," "replaced," "enhanced," and "substituted" are considered synonymous when used to describe residues of a polypeptide, and in all cases refer to the replacement of a non-natural amino acid for a naturally occurring amino acid within a polypeptide chain.

As used herein, the term "T-independent antigen" refers to an antigen that induces the features of B-cell mediated immunity, or which does not induce processes associated with helper T-cell mediated immunity such as isotype switching or immunologic memory.

The term "polysaccharide" as used herein, is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and optionally from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosaccharides typically have from about 6, 7, 8, 9, or 10 repeating units to about 15, 20, 25, 30, or 35 to about 40 or 45 repeating units.

As used herein, the term "glycan" refers to any linear or branched polymer consisting of monosaccharide (e.g. glucose) residues joined to each other by glycosidic linkages. Examples of glycans include glycogen, starch, hyaluronic acid, and cellulose. Other examples of "glycans" include bacterial capsular polysaccharides.

As used herein, the term "molecular weight" of a polysaccharide or of a carrier protein-polysaccharide conjugate refers to molecular weight calculated by size exclusion chromatography (SEC) combined with multiangle laser light scattering (MALS).

The term "lower alkyl" as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties. See also US-2014/0066598. The term "lower alkylene" refers to an alkylene radical of a lower alkyl.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

The compounds of the various embodiments disclosed herein, or their pharmaceutically acceptable salts that contain one or more asymmetric centers and give rise to enantiomers, diastereomers, and other stereoisomeric forms that are defined, in terms of absolute stereochemistry, as (R) or (S), or as (D) or (L) for amino acids. The present disclosure is meant to include all such isomers, as well as their racemic and optically pure forms. The nnAA used herein are generally α-amino acids with a chiral center at the α-carbon, and they are preferably (L) isomers.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). Except as described below, all bonds are identified in the chemical structure diagrams herein, except for all bonds on some carbon atoms, which are assumed to be bonded to sufficient hydrogen atoms to complete the valency.

The present invention provides, in part, immunogenic conjugates and methods for the preparation of immunogenic conjugates, wherein the methods comprise activating an antigen and then coupling the activated antigen to a polypeptide carrier (also referred to herein as a "carrier protein") as explained herein. Immunogenic conjugates provided herein thus comprise a carrier polypeptide that is covalently linked to an antigen. This linking can convert a T-cell independent immunogen (such as a saccharide) into a T-cell dependent immunogen, thereby enhancing the immune response that is elicited (particularly in children). The conjugates prepared using the present methods contain covalent linkages that are formed between an antigen and a non-natural amino acid (nnAA) residue within the carrier polypeptide. These nnAA residues can provide functional groups which facilitate reactivity with an antigen of interest.

Typically, a single carrier polypeptide will be linked to multiple antigen molecules. The antigens can have a single linking group per molecule (e.g. the reducing terminus of a saccharide) for attaching to a carrier polypeptide, or can have multiple linking groups (e.g. multiple aldehyde or cyanate ester groups). Where an antigen molecule has multiple linking groups this generally leads to the formation of high molecular weight cross-linked or lattice conjugates, involving links between multiple carrier polypeptides via the antigens. Cross-linked conjugates may be advantageous (particularly for pneumococcus), and thus antigens with multiple linking groups can confer advantages.

Covalent linkages are formed between the antigen and a nnAA residue within the carrier polypeptide. Preferably the antigen is not conjugated to a lysine residue in the carrier polypeptide; more preferably, the antigen is not conjugated to a natural amino acid residue in the carrier polypeptide.

II. General Methods

Unless defined otherwise, all technical and scientific terms used herein have the commonly understood meaning. Practitioners are particularly directed to Green & Sambrook (eds.) *Molecular Cloning: A Laboratory Manual*, 4th ed., Cold Spring Harbor Laboratory Press, Cold Spring Harbor, N.Y. (2012), and Ausubel, F. M., et al., *Current Protocols in Molecular Biology* (Supplement 99), John Wiley & Sons, New York (2012), and Plotkin, S. A., Orenstein, W. A., & Offit, P. A., Vaccines, 6 ed, Elsevier, London (2013), which are incorporated herein by reference, for definitions and terms. Standard methods also appear in Bindereif, Schon, & Westhof (2005) *Handbook of RNA Biochemistry*, Wiley-VCH, Weinheim, Germany which describes detailed methods for RNA manipulation and analysis, and is incorporated herein by reference. Examples of appropriate molecular techniques for generating recombinant nucleic acids, and instructions of many cloning exercises are found in Green & Sambrook (Id.); Ausubel, F. M., et al., (Id.); Berger & Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990), which are incorporated by reference herein. Examples of appropriate bio-organic techniques for activating and derivatizing biomolecules with chemical handles, and instructions to design such syntheses are found in Hermanson, G. T, *Bioconjugate Techniques*, $2^{nd}$ ed., Elsevier, London (2008). For examples of techniques and components necessary for parenteral administration of biomolecules described herein, practitioners are directed to Remington, Essentials of Pharmaceutics, Pharmaceutical Press, London (2012). Methods for protein purification, chromatography, electrophoresis, centrifugation, and crystallization are described in Coligan et al. (2000) *Current Protocols in Protein Science*, Vol. 1, John Wiley and Sons, Inc., New York. Methods for cell-free synthesis are described in Spirin & Swartz (2008) *Cell free Protein Synthesis*, Wiley-VCH, Weinheim, Germany. Methods for incorporation of non-natural amino acids into proteins using cell-free synthesis are described in Shimizu et al. (2006) *FEBS Journal*, 273, 4133-4140 and also in Chong (2014) *Curr Protoc Mol Biol.* 108:16.30.1-11.

PCR amplification methods are described, for example, in Innis et al., PCR Protocols: A Guide to Methods and Applications, Academic Press Inc. San Diego, Calif., 1990 and Domingues (ed.) *PCR: Methods and Protocols* ISBN 1493970593 (2017). An amplification reaction typically includes the DNA that is to be amplified, a thermostable DNA polymerase, two oligonucleotide primers, deoxynucleotide triphosphates (dNTPs), reaction buffer and magnesium. Typically, a desirable number of thermal cycles is between 1 and 25. Methods for primer design and optimization of PCR conditions are found in molecular biology texts such as Ausubel et al., *Short Protocols in Molecular Biology*, 5th Edition, Wiley, 2002, and Innis et al., *PCR Protocols*, Academic Press, 1990. Computer programs are useful in the design of primers with the required specificity and optimal amplification properties (e.g., Oligo Version 5.0 (National Biosciences)). In some embodiments, the PCR primers additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers also contain an RNA polymerase promoter site, such as T7 or SP6, to allow for subsequent in vitro transcription. Methods for in vitro transcription are found in sources such as Van Gelder et al., *Proc. Natl. Acad. Sci. U.S.A.* 87:1663-1667, 1990; Eberwine et al., *Proc. Natl. Acad. Sci. U.S.A.* 89:3010 3014, 1992.

The molecular weight of a polysaccharide or of a carrier protein-polysaccharide conjugate is measured by size exclusion chromatography (SEC) combined with multiangle laser light scattering (MALS). The SEC MALS-UV-RI setup consists of an Agilent HPLC 1100 (including degasser, quaternary pump, temperature-controlled auto-sampler, temperature controlled column compartment and UV-VIS diode array detector) in line with a DAWN-HELEOS multiangle laser light scattering detector and Optilab T-rEX differential refractive interferometer (Wyatt Technology, Santa Barbara, CA) for the detection of eluting species. The following series of columns is attached to this system: TSKgel Guard PWXL 6.0 mm ID×4.0 cm long, 12 µm particle; TSKgel 6000 PWXL 7.8 mm ID×30 cm long, 13 µm particle; and a TSKgel 3000 PWXL 7.8 mm II)×30 cm long, 7 µm particle. The column compartment is set to 25° C. and the sample compartment is set to 4° C. A mobile phase consisting of 0.2 µm filtered 1×PBS with 5% v/v acetonitrile is used at a 0.5 mL/min flow rate. Samples are injected within a concentration range of 0.2-1.5 mg/mL polysaccharide and the injected volume is adjusted to yield a total injected mass of 30-40 µg. Agilent Open Lab software is used to control the HPLC, and Wyatt Astra 7 software is used for data collection and analysis. The technique reveals the distribution of absolute molecular weights for conjugates in a sample, and results for a population are expressed as an average value.

In some embodiments, *S. pneumoniae* isolated capsular polysaccharides are obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In other embodiments, *S. pneumoniae* isolated capsular polysaccharides are obtained from a commercial source (e.g., ATCC).

III. Immunogenic Polypeptides Useful as Carrier Proteins

III.A. Polypeptides Comprising at Least One nnAA Residue

III.A.1. Overview of nnAA-Containing Polypeptides

Described herein are polypeptides comprising at least one nnAA residue, wherein nnAA residues are defined and discussed in detail in Section III.A.2, infra. In general, suitable polypeptides are biologically active peptides, such as those inducing a T-cell immune response in mammals, particularly humans, as well as domesticated animals, such as cattle, horses, sheep, dogs and cats; in general, any polypeptide that contains a T-cell epitope can be used as a carrier protein. The T-cell epitope can bind to MHC class II and interact with T-cell receptors on the surface of CD4+ T-cells, thereby enhancing antibody responses against antigens or haptens conjugated thereto (see, e.g., Costantino et al. 2011, *Expert Opin Drug Discov* 6:1045-66). Micoli et al. (2018) *Molecules* 23:1451 reviews various carrier polypeptides and criteria for their selection. Tontini et al. (2016) *Vaccine* 34:4235-42 discuss pre-clinical studies of 28 carrier polypeptides, including tests of their ability to induce antibodies against saccharide antigens. Polyepitope carrier polypeptides containing multiple broadly-reactive (i.e. immunogenic in the context of most human MHC class II molecules) human CD4+ T-cell epitopes from various pathogen-derived antigens have been designed e.g. the N19 and other polypeptides as disclosed by Falugi et al. (2001) *Eur J Immunol* 31:3816-24, Baraldo et al. (2004) *Infect Immun* 72:4884-7, and U.S. Pat. Nos. 6,855,321 and 7,867,498. The ability to design these polyepitope carriers demonstrates the ability of those skilled in the art to identify suitable T cell epitopes from diverse sources and also to use them to design effective carrier polypeptides. See also patent application US2016/0101187A1. T-cell epitopes found within known carriers (e.g. Tt, PD, CRM197) can be used. Various detoxified bacterial toxins have been successfully used as carriers e.g. Tt, Dt, the *P. aeruginosa* exotoxin, the *C. difficile* A and B toxins, etc. Many different carrier polypeptides have been used for pneumococcal saccharides, e.g., CRM197 in Prevnar™, PD, Tt and Dt in Synflorix™, and various peptides in Velasco et al. (1995) *Infect Immun* 63:961-8. Within other approved vaccines it is known to use diphtheria toxoid (chemically treated toxin from *Corynebacterium diphtheriae*; 'Dt'), tetanus toxoid (chemically treated tetanospasmin toxin from *Clostridium tetani*; 'Tt'), protein D from *Haemophilus influenzae* ('PD' or 'HiD'), the outer membrane protein complex of serogroup B meningococcus ('OMPC'), and the CRM197 mutant *C. diphtheriae* toxin. The invention can use any of these numerous carrier polypeptides as starting points to design carrier proteins according to the present invention, modifying them to include at least one nnAA.

One exemplary carrier polypeptide upon which to base the carriers of the present invention is CRM197. CRM197 is well-known in the art (e.g. see Broker et al. 2011 *Biologicals* 39:195-204) and has the following amino acid sequence (SEQ ID NO:11), where the underlined residue (Glu-52) differs from the natural diphtheria toxin, whereby the substitution of Gly→Glu leads to the loss of toxic enzymatic activity in the protein:

```
                                          (SEQ ID NO: 11)
GADDVVDSSKSFVMENFSSYHGTKPGYVDSIQKGIQKPKSGTQGNYDD

DWKEFYSTDNKYDAAGYSVDNENPLSGKAGGVVKVTYPGLTKVLALKV

DNAETIKKELGLSLTEPLMEQVGTEEFIKRFGDGASRVVLSLPFAEGS

SSVEYINNWEQAKALSVELEINFETRGKRGQDAMYEYMAQACAGNRVR

RSVGSSLSCINLDWDVIRDKTKTKIESLKEHGPIKNKMSESPNKTVSE

EKAKQYLEEFHQTALEHPELSELKTVTGTNPVFAGANYAAWAVNVAQV

IDSETADNLEKTTAALSILPGIGSVMGIADGAVHHNTEEIVAQSIALS

SLMVAQAIPLVGELVDIGFAAYNFVESIINLFQVVHNSYNRPAYSPGH

KTQPFLHDGYAVSWNTVEDSIIRTGFQGESGHDIKITAENTPLPIAGV

LLPTIPGKLDVNKSKTHISVNGRKIRMRCRAIDGDVTFCRPKSPVYVG

NGVHANLHVAFHRSSSEKIHSNEISSDSIGVLGYQKTVDHTKVNSKLS

LFFEIKS.
```

The invention does not use CRM197. Instead of using CRM197 comprising SEQ ID NO:11, a modified amino acid sequence is used which contains at least one nnAA. These new carrier polypeptides are described infra. Modified CRM197 may also include, for example, an N-terminal methionine (e.g., such as in SEQ ID NO:1, below) or other modifications described herein.

```
                                          (SEQ ID NO: 1)
MGADDVVDSSKSFVMENFSSYHGTKPGYVDSIQKGIQKPKSGTQGNYD

DDWKEFYSTDNKYDAAGYSVDNENPLSGKAGGVVKVTYPGLTKVLALK

VDNAETIKKELGLSLTEPLMEQVGTEEFIKRFGDGASRVVLSLPFAEG
```

```
SSSVEYINNWEQAKALSVELEINFETRGKRGQDAMYEYMAQACAGNRV

RRSVGSSLSCINLDWDVIRDKTKTKIESLKEHGPIKNKMSESPNKTVS

EEKAKQYLEEFHQTALEHPELSELKTVTGTNPVFAGANYAAWAVNVAQ

VIDSETADNLEKTTAALSILPGIGSVMGIADGAVHHNTEEIVAQSIAL

SSLMVAQAIPLVGELVDIGFAAYNFVESIINLFQVVHNSYNRPAYSPG

HKTQPFLHDGYAVSWNTVEDSIIRTGFQGESGHDIKITAENTPLPIAG

VLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSKL

SLFFEIKS
```

Aside from CRM197, other detoxified mutant forms of diphtheria toxin can be used as a starting point for the design of new carriers. For instance, a non-toxic K51E/E148K double mutant has also been used as a carrier polypeptide in conjugates (Pecetta et al. 2016 *Vaccine* 34:1405-11) and nnAA residues can be incorporated into the sequence of this double mutant in the same way as in CRM197.

Another carrier polypeptide of interest is PD from *H. influenzae*, which naturally has the following amino acid sequence (SEQ ID NO:8):

(SEQ ID NO: 8)

CSSHSSNMANTQMKSDKIIIAHRGASGYLPEHTLESKALAFAQQADYL

EQDLAMTKDGRLVVIHDHFLDGLTDVAKKFPHRHRKDGRYYVIDFTLK

EIQSLEMTENFETKDGKQAQVYPNRFPLWKSHFRIHTFEDEIEFIQGL

EKSTGKKVGIYPEIKAPWFHHQNGKDIAAETLKVLKKYGYDKKTDMVY

LQTFDFNELKRIKTELLPQMGMDLKLVQLIAYTDWKETQEKDPKGYWV

NYNYDWMFKPGAMAEVVKYADGVGPGWYMLVNKEESKPDNIVYTPLVK

ELAQYNVEVHPYTVRKDALPEFFTDVNQMYDALLNKSGATGVFTDFPD

TGVEFLKGIK

Rather than using native PD, a modified amino acid sequence is used which contains at least one nnAA. For instance, one or more Lys residues within SEQ ID NO:8 can be replaced with a nnAA. There are 36 Lys residues within SEQ ID NO:8, so several can be replaced by nnAA and then used for conjugation. T-cell epitope prediction and recognition for PD has been reported by Hua et al. (2016) *Clin Vaccine Immunol* 23:155-61.

An additional carrier polypeptide of interest is Tt from *C. tetani*, which naturally has the amino acid sequence SEQ ID NO:15. Rather than using native Tt, a modified amino acid sequence is used which contains at least one nnAA. For instance, one or more Lys residues within SEQ ID NO:15 can be replaced with a nnAA. There are 109 Lys residues within SEQ ID NO:15, so several can be replaced by nnAA and then used for conjugation. The polypeptide should also be detoxified prior to use as a carrier e.g. by formaldehyde or glutaraldehyde treatment. The polypeptide will typically be cleaved between residues 457-458, with the two fragments being held together by a disulfide bond between residues 439 & 467.

(SEQ ID NO: 15)

MPITINNFRYSDPVNNDTIIMMEPPYCKGLDIYYKAFKITDRIWIVPE

RYEFGTKPEDFNPPSSLIEGASEYYDPNYLRTDSDKDRFLQTMVKLFN

RIKNNVAGEALLDKIINAIPYLGNSYSLLDKFDTNSNSVSFNLLEQDP

SGATTKSAMLTNLIIFGPGPVLNKNEVRGIVLRVDNKNYFPCRDGFGS

IMQMAFCPEYVPTFDNVIENITSLTIGKSKYFQDPALLLMHELIHVLH

GLYGMQVSSHEIIPSKQEIYMQHTYPISAEELFTFGGQDANLISIDIK

NDLYEKTLNDYKAIANKLSQVTSCNDPNIDIDSYKQIYQQKYQFDKDS

NGQYIVNEDKFQILYNSIMYGFTEIELGKKFNIKTRLSYFSMNHDPVK

IPNLLDDTIYNDTEGFNIESKDLKSEYKGQNMRVNTNAFRNVDGSGLV

SKLIGLCKKIIPPTNIRENLYNRTASLTDLGGELCIKIKNEDLTFIAE

KNSFSEEPFQDEIVSYNTKNKPLNFNYSLDKIIVDYNLQSKITLPNDR

TTPVTKGIPYAPEYKSNAASTIEIHNIDDNTIYQYLYAQKSPTTLQRI

TMTNSVDDALINSTKIYSYFPSVISKVNQGAQGILFLQWVRDIIDDFT

NESSQKTTIDKISDVSTIVPYIGPALNIVKQGYEGNFIGALETTGVVL

LLEYIPEITLPVIAALSIAESSTQKEKIIKTIDNFLEKRYEKWIEVYK

LVKAKWLGTVNTQFQKRSYQMYRSLEYQVDAIKKIIDYEYKIYSGPDK

EQIADEINNLKNKLEEKANKAMININIFMRESSRSFLVNQMINEAKKQ

LLEFDTQSKNILMQYIKANSKFIGITELKKLESKINKVFSTPIPFSYS

KNLDCWVDNEEDIDVILKKSTILNLDINNDIISDISGFNSSVITYPDA

QLVPGINGKAIHLVNNESSEVIVHKAMDIEYNDMFNNFTVSFWLRVPK

VSASHLEQYGTNEYSIISSMKKHSLSIGSGWSVSLKGNNLIWTLKDSA

GEVRQITFRDLPDKFNAYLANKWVFITITNDRLSSANLYINGVLMGSA

EITGLGAIREDNNITLKLDRCNNNNQYVSIDKFRIFCKALNPKEIEKL

YTSYLSITFLRDFWGNPLRYDTEYYLIPVASSSKDVQLKNITDYMYLT

NAPSYTNGKLNIYYRRLYNGLKFIIKRYTPNNEIDSFVKSGDFIKLYV

SHIVGYPKDGNAFNNLDRILRVGYNAPGIPLYKKMEAVKLRDLKTYSV

QLKLYDDKNASLGLVGTHNGQIGNDPNRDILIASNWYFNHLKDKILGC

DWYFVPTDEGWTND

More generally, any polypeptide including a T-cell epitope can be used as a carrier polypeptide. The T-cell epitope can bind to MHC class II and interact with T-cell receptors on the surface of CD4+ T-cells, thereby enhancing antibody responses against antigens or haptens conjugated thereto (e.g. see Costantino et al. 2011, *Expert Opin Drug Discov* 6:1045-66). Micoli et al. (2018) *Molecules* 23, 1451 reviews various carrier polypeptides and criteria for their selection. Tontini et al. (2016) *Vaccine* 34:4235-42 discuss pre-clinical studies of 28 carrier polypeptides, including tests of their ability to induce antibodies against saccharide antigens. Polyepitope carrier polypeptides containing multiple broadly-reactive (i.e. immunogenic in the context of most human MHC class II molecules) human CD4+ T-cell epitopes from various pathogen-derived antigens have been designed e.g. the N19 and other polypeptides as disclosed by Falugi et al. (2001) *Eur J Immunol* 31:3816-24, Baraldo et al. (2004) *Infect Immun* 72:4884-7, and U.S. Pat. No. 6,855,321 & 7,867,498. See also patent application US2016-0101187. T cell epitopes found within known carriers (e.g.

Tt, PD, CRM197) can be used. Various detoxified bacterial toxins have been successfully used as carriers e.g. Tt, Dt, the *P. aeruginosa* exotoxin, the *C. difficile* A & B toxins, etc. Many different carrier polypeptides have been used for pneumococcal saccharides e.g. CRM197 in Prevnar™, PD, Tt and Dt in Synflorix™, and various peptides in Velasco et al. (1995) *Infect Immun* 63:961-8. The invention can use any of these numerous carrier polypeptides as starting points to design carrier proteins according to the present invention, modifying them to include at least one nnAA, to enhance the immunogenicity of antigens of interest.

The nnAA-containing carrier polypeptides to be used with the invention can be prepared using the techniques disclosed in section III.C., below. Exemplary carriers contain nnAAs outside of at least one T-cell epitope of the carrier. If the T-cell epitope regions for a carrier are unknown then one can identify the epitopes using standard techniques e.g. see Reece et al. (1993) IJ Immunol 151:6175-84, Beissbarth et al. (2005) *Bioinformatics* 21 Suppl 1: i29-37, Maciel Jr et al. (2008) *Virol* 378:105-17, Fridman et al. (2012) *Oncoimmunol* 1:1258-70, etc. (including empirical and/or predictive approaches). It is also possible to confirm that any particular modification of a carrier polypeptide's sequence does not eliminate the desired T-cell response to a conjugated antigen, such as the saccharides herein. An exemplary group of carriers do not contain any modification, including insertion or substitution of a nnAA, within a T-cell epitope. Another exemplary group of carriers do not contain any modification, including insertion or substitution of a nnAA, within multiple T-cell epitopes. Yet another exemplary group of carriers do not contain any modification, including insertion or substitution of a nnAA, within any T-cell epitope.

In some embodiments, the polypeptide is an immunogenic polypeptide. In some embodiments, the nnAA residue is substituted for a native residue of a specified polypeptide. In other embodiments, the nnAA residue is incorporated by insertion, or by C-terminal or N-terminal extension. In further embodiments, the polypeptide comprises at least 1, at least 2, at least 3, at least 4, at least 5, at least 6, at least 7, at least 8, or at least 9 nnAA residues. In certain embodiments, the polypeptide comprises 1, 2, 3, 4, 5, 6, 7, 8, or 9 nnAA residues. Some carriers contain as least 2, at least 3, at least 4, at least 5, or at least 6 nnAAs. Certain carriers may also have a maximum of 10, 9, 8, 7 or 6 nnAAs. In some embodiments carrier polypeptides with fewer than 10 nnAA residues are may be utilized. Exemplary ranges of nnAAs in a carrier polypeptide include 2-10, 2-9, 2-8, 2-7, 2-6, 3-10, 3-9, 3-8, 3-7, 3-6, 4-10, 4-9, 4-8, 4-7, and 4-6 nnAAs, with 2-9 nnAAs, e.g., 4-6 nnAAs.

The carrier polypeptide may comprise two or more nnAA residues that are chemically distinct, i.e., the two or more nnAA residues comprise at least two different non-natural amino acids, such as those identified herein. The polypeptide may comprise a T-cell activating epitope of a carrier protein, and may be conjugated to an antigen, such as through an nnAA within the polypeptide structure, where the antigen may be a T-cell independent antigen such as a hapten, a bacterial capsular polysaccharide, a bacterial lipopolysaccharide, or a tumor-derived glycan (for example, the antigen may comprise a bacterial non-capsular polysaccharide such as an exopolysaccharide, e.g. the *S. aureus* exopolysaccharide). In some embodiments, the nnAA are not in a T-cell activating epitope of the carrier polypeptide.

Conveniently, in some embodiments, the nnAA can be substituted for a lysine residue in the native polypeptide. For instance, in a modified CRM197 the substitution can occur at one or more of positions K24, K33, K37, K39, K212, K214, K227, K244, K264, K385, K522 and K526 in SEQ ID NO:11 or 12. An exemplary modified CRM may include substitution of a nnAA (e.g. pAMF) at each of K33, K212, K244, K264, K385, and K526 (and in some embodiments at no other positions) according to the number of SEQ ID NO:11 or 12.

Substitutions to incorporate nnAA are not limited to lysine positions, however, and it is also possible to substitute other amino acids with a nnAA e.g. Phe, Asp, Asn, Glu, Gln, Arg, Ser, and/or Thr.

Ideally, the carrier proteins described herein have a solubility of at least 50 mg/L (e.g., at least 100 mg/L, at least 150 mg/L, at least 200 mg/L, or at least 250 mg/L) when expressed in a cell-free protein synthesis system.

Where a carrier protein described herein includes more than one nnAA residue, some embodiments include only a single species of nnAA (e.g., the only nnAA in the carrier is pAMF). This permits the same conjugation chemistry to be used simultaneously at each nnAA. If it is desired to attach two different antigens to a single carrier molecule, this can be achieved by using different nnAA species within a single carrier and conjugating each antigen to a different nnAA; conjugation to a single species of nnAA in a carrier may be preferred for ease of production. Moreover, where a composition includes multiple different conjugates (e.g., different pneumococcal serotypes) it is sometimes advantageous that each conjugate includes the same single species of nnAA. Furthermore, where a composition includes multiple different conjugates (e.g., different pneumococcal serotypes) it is may be advantageous that each conjugate includes the same carrier protein.

In certain embodiments, the disclosure provides a polynucleotide encoding the polypeptides described herein. In certain embodiments, the disclosure provides for an expression vector comprising the polynucleotide encoding the polypeptide described herein. In certain embodiments, the disclosure provides for a host cell comprising the expression vector.

III.A.2. Non-Natural Amino Acids

As mentioned herein, conjugates used herein may include covalent linkages between an antigen and a functional group within a nnAA residue in the carrier polypeptide. The side chains of nnAA residues can provide reactive functional groups which are useful for conjugating antigens to discrete sites in the carrier polypeptide.

In general terms, the nnAA can be any non-natural amino acid that can be incorporated into a polypeptide during translation but is not one of the 20 common amino acids. A nnAA can be incorporated into a polypeptide by converting a tRNA molecule such that its codon incorporates the nnAA rather than the natural cognate amino acid. One technique for achieving this involves using a "suppression codon" i.e. a nucleotide triplet that is introduced into a coding sequence at a desired position and is recognized by a specific tRNA that can recognize a natural stop codon (e.g., an amber, ochre or opal stop codon) but allows translation to continue, with incorporation of the nnAA (thereby suppressing the natural stop codon).

The nnAA residue can be any of the nnAA residues described herein, or any other that has been identified as compatible with cell-based or cell-free protein synthesis (see, e.g., Schultz et al. (2010) *Annu Rev Biochem.* 79:413-44, particularly at pp. 418-420; and Chin et al. (2014) *Annu Rev Biochem.* 83:5.1-5.30, which are hereby incorporated by reference). As described earlier, the nnAA is an amino acid that is not one of the 20 common amino acids or pyrolysine or selenocysteine.

Examples of non-natural amino acids that can be used in conjunction with the invention include, without limitation: a non-natural analog of a tyrosine amino acid; a non-natural analog of a glutamine amino acid; a non-natural analog of a phenylalanine amino acid; a non-natural analog of a serine amino acid; a non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino-substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analog containing amino acid; a glycosylated or carbohydrate modified amino acid; a keto-containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar-substituted amino acid, e.g., a sugar-substituted serine or the like; a carbon-linked sugar-containing amino acid; a redox-active amino acid; an α-hydroxy acid; a thioacid-containing amino acid; an α,α-disubstituted amino acid; a β-amino acid; a cyclic amino acid other than proline, etc.

Exemplary nnAA for use as described herein are those which can be incorporated during translation (in a cellular or a cell-free system) with a side chain that provides a functional group which is not found in the side chain of any of the 20 naturally occurring amino acids (e.g., azido). Various techniques for incorporating such amino acids into polypeptides are known e.g. see Young & Schultz (2010) *J Biol Chem* 285:11039-44, Maza et al. (2015) *Bioconjugate Chem.* 26:1884-9, and Zimmerman et al. (2014) *Bioconjugate Chem.* 25:351-61. Additionally, described herein are methods whereby nnAA residues can be incorporated into carrier polypeptides e.g. using cell-free expression mixtures, orthogonal tRNA/aminoacyl-tRNA synthetase pairs specific for the nnAA, suppression codons, etc. See also U.S. Patent Publication No. U52017/0267637, which is also incorporated by reference in its entirety.

The nnAA can include a chemical group suitable for a "click" chemistry reaction with a corresponding group on an antigen of interest or hapten. Suitable chemical groups for "click" chemistry include, but are not limited to, azido (—N$_3$), alkyne (—C≡C—), alkene (—C=C—), 1,2,4,5-tetrazine

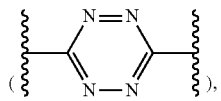

and phosphine groups.

The nnAA can be any of 2-amino-3-(4-azidophenyl) propanoic acid (para-azido-L-phenylalanine or pAF), 2-amino-3-(4-(azidomethyl)phenyl)propanoic acid (para-azidomethyl-L-phenylalanine or pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, or 2-amino-5-azidopentanoic acid.

In some embodiments, the present disclosure provides a polypeptide comprising at least one nnAA replaced for a naturally occurring amino acid within the polypeptide according to SEQ ID NO:1, wherein the at least one nnAA is replaced for K25, K34, K38, K40, K213, K215, K228, K245, K265, K386, K523, or K527 of SEQ ID NO:1, wherein, in some embodiments, the nnAA comprises a linking moiety. In some embodiments, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In some embodiments, K265 of SEQ ID NO:1 is replaced. In some embodiments, K386 of SEQ ID NO:1 is replaced. In some embodiments, K265 and K386 of SEQ ID NO:1 are replaced. In some embodiments, the polypeptide comprises at least 2, at least 3, at least 4, at least 5, at least 6, at least 7, at least 8, or at least 9 nnAAs. In some embodiments, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

An exemplary nnAA for use herein is pAMF:

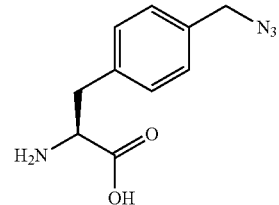 [SMILES: [N-]=[N+]=NCc1ccc(C[C@H](N)C(=O)O)cc1]

pAMF provides very favorable reaction kinetics for producing conjugates (e.g. much faster than using pAF when reacting with an alkyne-containing carbohydrate antigen in a SPAAC method).

The nnAA can be a 2,3-disubstituted propanoic acid bearing: an amino substituent at the 2-position; and an azido-containing substituent, a 1,2,4,5-tetrazinyl-containing substituent, or an ethynyl-containing substituent at the 3-position. In some embodiments, the substituent at the 3-position is an azido-containing substituent, particularly an azido-containing substituent comprising a terminal azido group bound to the carbon atom at the 3-position through a linking group. For example, the linking group may comprise an arylene moiety that is optionally substituted and optionally heteroatom-containing. For instance, the linking group may comprise a 5- or 6-membered arylene moiety containing 0 to 4 heteroatoms and 0 to 4 non-hydrogen ring substituents.

The nnAA can have the structure of formula (XII):

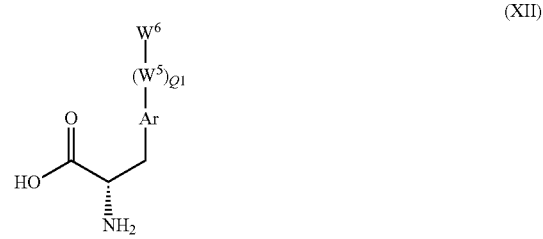

(XII)

wherein: Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl It will be appreciated that the corresponding nnAA residue in a polypeptide has the structure of formula (XIII)

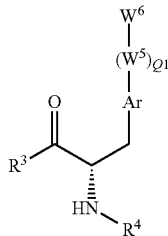

(XIII)

in which $R^3$ is OH or an amino acid residue of the carrier protein, and $R^4$ is H or an amino acid residue of the carrier protein.

In some embodiments, "Ar" in formulae (XII) and (XIII) does not contain any heteroatoms, in which case a preferred linker is an unsubstituted phenylene group (i.e. Ar is —$C_6H_4$—). In other embodiments, Ar contains a nitrogen heteroatom and at least one additional heteroatom selected from N, O, and S. Exemplary nitrogen heterocycles are described infra and Ar may be e.g. a pyridine or a pyridazine. In a certain embodiments, Q1 is 1, $W^5$ is lower alkylene, and $W^6$ is azido.

III.A.3. Azido-Containing Amino Acids

In some embodiments, the nnAA residue comprises an azido-containing nnAA, such as an azido-containing nnAA of formula (I):

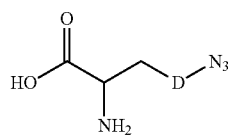

(I)

wherein: D is —Ar—$W_3$— or —$W_1$—$Y_1$—C(O)—$Y_2$—$W_2$—; each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; Ar is

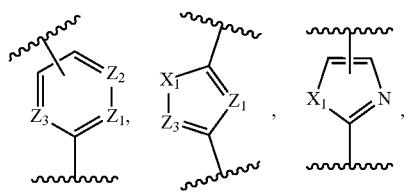

-continued

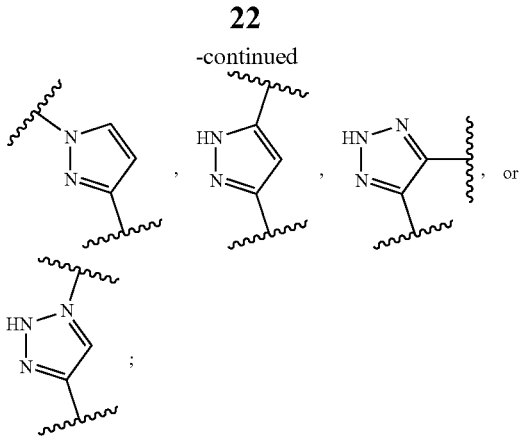

and one of $Z_1$, $Z_2$, and $Z_3$ is —N— and the others of $Z_1$, $Z_2$, and $Z_3$ are independently —CH—.

In other embodiments, the nnAA residue comprises an azido-containing amino acid of formula (II):

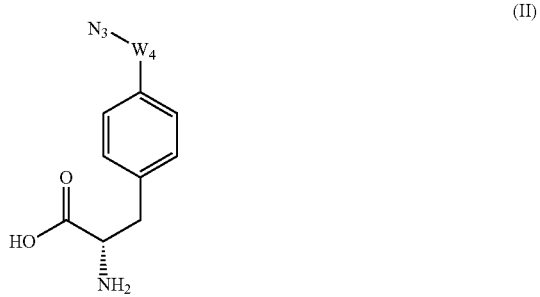

(II)

wherein $W_4$ is $C_1$-$C_{10}$ alkylene.

In some embodiments, the nnAA residue may comprise an azido-containing amino acid selected from the group consisting of 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, or 2-amino-3-(4-(azidomethyl)phenyl)propanoic acid, and any combination thereof. In a further embodiment, the nnAA residue comprises 2-amino-3-(4-(azidomethyl)phenyl)propanoic acid (pAMF). pAMF provides very favorable reaction kinetics for producing conjugates (e.g., much faster than using pAF when reacting with an alkyne-containing carbohydrate antigen in a SPAAC method).

Preparation of azido-containing amino acids according to formulae (I) and (II) is described, for example, in U.S. Patent Publication No. US 2014/0066598 A1 to Stafford et al., particularly in paragraphs [0331]-[0333], which are incorporated by reference herein. The Stafford et al. synthesis involves replacement of hydroxyl groups with chloride using thionyl chloride, followed by nucleophilic displacement of the chloride with azide. Suitable aryl side-chain containing amino acids are also available commercially.

III.A.4. 1,2,4,5-Tetrazinyl-Containing Amino Acids

In some embodiments, the non-natural amino acid residue comprises a 1,2,4,5-tetrazine containing nnAA. In particular embodiments, the non-natural amino acid comprises a 1,2,4,5-tetrazine containing nnAA of formula (III):

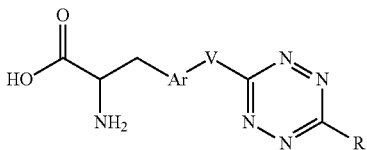

(III)

wherein: Ar is

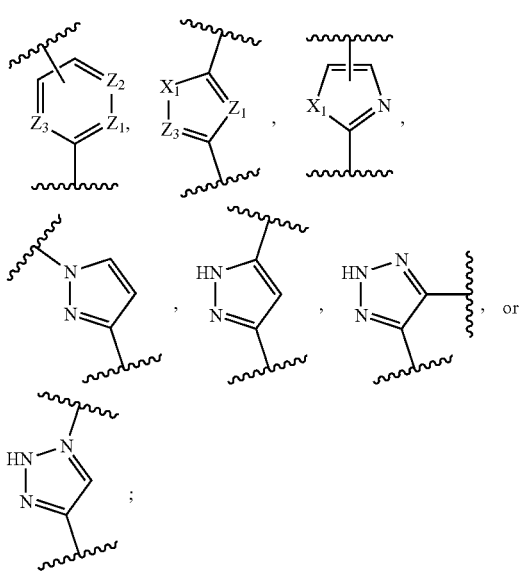

V is a single bond, lower alkylene, or —W$_1$-W$_2$-; one of W$_1$ and W$_2$ is absent or lower alkylene, and the other is —NH—, —O—, or —S—; each one of Z$_1$, Z$_2$, and Z$_3$ is independently —CH— or —N—; and X$_1$ is independently —NH—, —O—, or —S—; and R is lower alkyl,
and, optionally, when Ar is

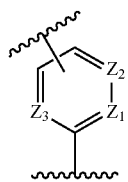

and V is —NH—, then one of Z$_1$, Z$_2$, and Z$_3$ is —N— provided the non-natural amino acid is not:

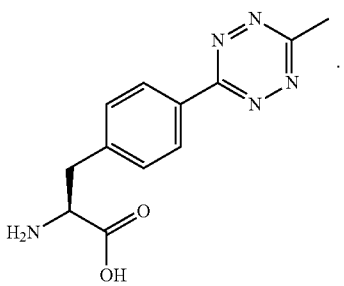 [SMILES: Cc1nnc(-c2ccc(C[C@H](N)C(=O)O)cc2)nn1]

Preparation of 1,2,4,5-tetrazine-containing amino acids according to formula (III) is known in the art and described, for example, in U.S. Patent Publication No. US 2016/0251336 A1 to Yang et al., particularly at paragraphs [0341]-[0377], which are incorporated by reference herein. The process involves Negishi coupling of an amino/carboxyl protected derivative of (R)-2-amino-3-iodopropanoic acid with an aminopyridyl bromide to introduce the aromatic group Ar, followed by reaction with a methylthio-1,2,4,5-tetrazine derivative to introduce the tetrazine moiety into the amino acid.

III.A.5. Alkyne-Containing Amino Acids

In some embodiments, the nnAA residue comprises an alkyne-containing nnAA, such as a propargyl group. A variety of propargyl-containing amino acids and syntheses thereof are found in Beatty et al. (2006) *Angew. Chem. Int. Ed.* 45: 7364-7; Beatty et al. (2005) *J. Am. Chem. Soc.* 127: 14150-1; Nguyen et al. (2009) *J Am Chem Soc.* 131: 8720-1. Such propargyl-containing amino acids are suitable for incorporation as nnAAs into proteins using cell-based systems. In some embodiments, the nnAA residue comprises a propargyl-containing nnAA selected from the group consisting of homopropargylglycine, ethynylphenylalanine, and N6-[(2-propynyloxy)carbonyl]-L-lysine.

As noted earlier, the nnAA are generally α-amino acids with a chiral center at the α-carbon, and they are preferably L-stereoisomers.

III.B. Modified Carrier Proteins

As noted herein, useful carrier polypeptides contain a T-cell epitope, and an exemplary carrier polypeptide upon which to base the modified carriers of the present invention is CRM197.

In one aspect, the polypeptide comprising at least one nnAA residue is a modified version of a native carrier protein (e.g., referred to as an "enhanced" or "eCRM" for an enhanced CRM197), or a polypeptide comprising one or a plurality of T-cell activating epitopes of a native carrier protein. Carrier proteins suitable for such modifications include, but are not limited to, proteins used in conjugate vaccines such as *Corynebacterium diphtheriae* toxin, *Clostridium tetani* tetanospasmin, *Haemophilus influenzae* protein D (PD, HiD), the outer membrane protein complex of serogroup B meningococcus (OMPC), and CRM197, and ovalbumin.

The amino acid sequences of many native carrier proteins are publicly available, as are the nucleic acid sequences of the DNA encoding them. Native carrier proteins and other unmodified carrier proteins have limitations, including nondiscriminate antigen conjugation to any surface-exposed amino acid. As a result, the T-cell activating epitopes are often sites where antigen conjugation occurs. In certain embodiments of the present disclosure, the immunogenic polypeptide is a carrier protein modified by the inclusion of at least one nnAA residue for use as a site of conjugation. As discussed above, the nnAA can be substituted for a native residue or added to the polypeptide by appending before, appending after, or inserting within the sequence of the polypeptide. The use of non-natural amino acids, as described herein, allows the selective placement of non-natural amino acids for conjugation and as a result the T-cell activating epitopes of the enhanced carrier protein can be avoided in antigen conjugation. As also described herein, a number (e.g., 2-9) of nnAA may replace naturally occurring amino acids within a polypeptide sequence.

Table I shows the amino acid and nucleic acid sequences (SEQ ID NOs: 1 & 2) of an exemplary modified carrier protein: CRM197. Those of skill in the art will recognize the addition of a N-terminal methionine to the amino acid sequence of conventional CRM197 produced by fermentation of *C. diphtheriae*, and the resulting addition of 1 to the conventional amino acid residue position numbering. The methionine is present because of the inclusion of a start codon in the cell-free protein synthesis method which was used to produce these carriers a described herein. In some aspects, the enhanced carrier protein comprising the nnAA residues has at least 80% sequence identity, at least 85% sequence identity, at least 90% sequence identity, or at least 95% sequence identity to a homologous native or non-toxic carrier protein used in a conjugate vaccine.

Carrier proteins having significant sequence identity to SEQ ID NO:11 (native CRM197), i.e., at least 80% sequence identity, at least 85% sequence identity, at least 90% sequence identity, or at least 95% sequence identity include other mutant diphtheria toxin proteins, such as the non-toxic K51E/E148K double mutant which has also been used as a carrier protein in conjugates (Pecetta et al. 2016 Vaccine 34:1405-11). In all of these variants of SEQ ID NO:11 the natural toxicity of wild-type diphtheria toxin is absent (via the G52E mutation in CRM197, or the K51E/E148K mutations of Pecetta et al. (where residue numbers are according to the native CRM197 sequence e.g. SEQ ID NO:11).

```
                                              (SEQ ID NO: 11)
GADDVVDSSKSFVMENFSSYHGTKPGYVDSIQKGIQKPKSGTQGNYDD
DWKEFYSIDNKYDAAGYSVDNENPLSGKAGGVVKVTYPGLIKVLALKV
DNAETIKKELGLSLTEPLMEQVGTEEFIKRFGDGASRVVLSLPFAEGS
SSVEYINNWEQAKALSVELEINFETRGKRGQDAMYEYMAQACAGNRVR
RSVGSSLSCINLDWDVIRDKIKTKIESLKEHGPIKNKMSESPNKTVSE
EKAKQYLEEFHQTALEHPELSELKTVIGINPVFAGANYAAWAVNVAQV
IDSETADNLEKTTAALSILPGIGSVMGIADGAVHHNTEEIVAQSIALS
SLMVAQAIPLVGELVDIGFAAYNFVESIINLFQVVHNSYNRPAYSPGH
KTQPFLHDGYAVSWNTVEDSIIRTGFQGESGHDIKITAENTPLPIAGV
LLPTIPGKLDVNKSKTHISVNGRKIRMRCRAIDGDVTFCRPKSPVYVG
NGVHANLHVAFHRSSSEKIHSNEISSDSIGVLGYQKTVDHTKVNSKLS
LFFEIKS
```

Table I also shows the amino acid sequence of protein D (SEQ ID NO:8) from *H. influenzae*. The enhanced carrier protein comprising nnAA residues may have at least 80% sequence identity to SEQ ID NO:8. At least one Lys residue in SEQ ID NO:8 can be replaced by a nnAA. There are 36 Lys residues within SEQ ID NO:8 so several can be replaced by nnAA and then used for conjugation.

Where sequence identity is determined relative to diphtheria or tetanus toxin, it should be determined relative to the processed heavy chain sequence e.g. relative to amino acids 226-567 of P00588-1, or to amino acids 458-1315 of P04958-1 (UniProt sequences).

In some embodiments, the enhanced carrier protein comprising the nnAA residues comprises less than the full native sequence of the carrier protein, and instead comprises at least one or a plurality of T-cell activating epitopes from *Corynebacterium diphtheriae* toxin, *Clostridium tetani* tetanospasmin, *Haemophilus influenzae* protein D (PD, HiD), outer membrane protein complex of serogroup B *meningococcus* (OMPC), CRM197, Pfs25, or another suitable native or non-toxic carrier protein. In some embodiments, the toxicity of the enhanced carrier protein is limited by treatment with paraformaldehyde (or by treatment with formaldehyde or glutaraldehyde) followed by a quenching agent. In some embodiments the enhanced carrier protein comprising the nnAA residues is a polypeptide comprising a plurality of T-cell activating epitopes of native CRM197 (SEQ ID NO:11).

TABLE I

| | |
|---|---|
| Amino acid | >4AE1_B<br>MGADDVVDSSKSFVMENFSSYHGTKPGYVDSIQKGIQKPKSGTQGNYDDDWKEFYS<br>TDNKYDAAGYSVDNENPLSGKAGGVVKVTYPGLTKVLALKVDNAETIKKELGLSLT<br>EPLMEQVGTEEFIKRFGDGASRVVLSLPFAEGSSSVEYINNWEQAKALSVELEINF<br>ETRGKRGQDAMYEYMAQACAGNRVRRSVGSSLSCINLDWDVIRDKTKTKIESLKEH<br>GPIKNKMSESPNKTVSEEKAKQYLEEFHQTALEHPELSELKTVTGTNPVFAGANYA<br>AWAVNVAQVIDSETADNLEKTTAALSILPGIGSVMGIADGAVHHNTEEIVAQSIAL<br>SSLMVAQAIPLVGELVDIGFAAYNFVESIINLFQVVHNSYNRPAYSPGHKTQPFLH<br>DGYAVSWNTVEDSIIRTGFQGESGHDIKITAENTPLPIAGVLLPTIPGKLDVNKSK<br>THISVNGRKIRMRCRAIDGDVTFCRPKSPVYVGNGVHANLHVAFHRSSSEKIHSNE<br>ISSDSIGVLGYQKTVDHTKVNSKLSLFFEIKS (SEQ ID NO: 1) |
| Nucleic acid | >KU521393.1 Synthetic construct clone pUC57-CRM197 toxin<br>CRM197 (CRM197) gene, complete cds<br>ATGGGCGCAGACGATGTTGTGGACTCAAGTAAATCATTTGTCATGGAAAACTTCTC<br>CTCATATCACGGCACGAAACCGGGCTACGTTGATAGCATTCAGAAAGGTATCCAAA<br>AACCGAAATCTGGCACGCAGGGTAACTACGATGACGATTGGAAAGAATTCTACAGC<br>ACCGACAACAAATATGATGCGGCCGGTTACTCAGTCGACAACGAAAATCCGCTGTC<br>GGGCAAAGCCGGCGGTGTGGTTAAAGTGACGTATCCGGGCCTGACCAAAGTCCTGG<br>CCCTGAAAGTGGATAATGCAGAAACCATCAAAAAAGAACTGGGTCTGAGCCTGACG<br>GAACCGCTGATGGAACAGGTTGGCACCGAAGAATTTATCAAACGCTTCGGCGATGG<br>TGCCAGTCGTGTCGTGCTGTCCCTGCCGTTCGCAGAAGGTAGCTCTAGTGTGGAAT<br>ATATTAACAATTGGGAACAAGCGAAAGCCCTGTCCGTTGAACTGGAAATCAACTTT<br>GAAACCCGCGGCAAACGTGGTCAGGATGCGATGTATGAATACATGGCACAAGCTTG<br>CGCGGGTAATCGCGTTCGTCGCAGCGTCGGCTCCTCACTGTCTTGTATCAACCTGG<br>ACTGGGATGTTATCCGTGATAAAACCAAAACGAAAATCGAAAGTCTGAAAGAACAT<br>GGCCCGATCAAAAACAAAATGAGCGAATCTCCGAATAAAACGGTGTCCGAAGAAAA<br>AGCTAAACAGTATCTGGAAGAATTCCACCAAACCGCACTGGAACATCCGGAACTGT<br>CAGAACTGAAAACCGTGACGGGTACCAACCCGGTTTTTGCCGGCGCAAATTACGCA<br>GCTTGGGCTGTGAACGTTGCGCAAGTGATTGACTCGGAAACGGCCGATAATCTGGA<br>AAAAACCACGGCGGCCCTGAGTATTCTGCCGGGCATCGGTTCCGTTATGGGTATTG |

TABLE I-continued

```
CCGACGGCGCAGTCCATCACAACACCGAAGAAATTGTGGCCCAGTCTATCGCACTG
TCGAGCCTGATGGTTGCTCAAGCGATTCCGCTGGTTGGCGAACTGGTTGATATCGG
CTTTGCAGCTTACAACTTCGTGGAAAGTATTATCAACCTGTTTCAGGTTGTCCACA
ACTCATATAATCGCCCGGCCTACTCGCCGGGTCACAAAACCCAACCGTTCCTGCAT
GACGGCTACGCGGTTAGCTGGAATACGGTCGAAGATTCTATTATCCGTACCGGCTT
TCAGGGTGAATCTGGCCACGACATTAAAATCACGGCTGAAAACACCCCGCTGCCGA
TTGCAGGTGTTCTGCTGCCGACGATCCCGGGTAAACTGGATGTTAACAAATCAAAA
ACCCATATCTCGGTCAACGGTCGCAAAATTCGTATGCGCTGCCGTGCGATCGACGG
CGATGTGACCTTCTGTCGTCCGAAAAGCCCGGTCTATGTGGGCAACGGTGTCCATG
CTAATCTGCACGTGGCGTTTCATCGCTCTAGTTCCGAAAAAATCCATAGTAACGAA
ATCTCATCGGATTCCATTGGTGTGCTGGGCTACCAGAAAACCGTGGACCATACCAA
AGTGAATAGCAAACTGAGCCTGTTCTTCGAAATCAAATCGTAA (SEQ ID NO: 2)
```

Amino acid
```
>AAA24998.1 Haemophilus influenzae protein D
CSSHSSNMANTQMKSDKIIIAHRGASGYLPEHTLESKALAFAQQADYLEQDLAMTK
DGRLVVIHDHFLDGLTDVAKKFPHRHRKDGRYYVIDFTLKEIQSLEMTENFETKDG
KQAQVYPNRFPLWKSHFRIHTFEDEIEFIQGLEKSTGKKVGIYPEIKAPWFHHQNG
KDIAAETLKVLKKYGYDKKTDMVYLQTFDFNELKRIKTELLPQMGMDLKLVQLIAY
TDWKETQEKDPKGYWVNYNYDWMFKPGAMAEVVKYADGVGPGWYMLVNKEESKPDN
IVYTPLVKELAQYNVEVHPYTVRKDALPEFFTDVNQMYDALLNKSGATGVFTDFPD
TGVEFLKGIK (SEQ ID NO: 8)
```

CRM197 ("cross-reacting material 197"; also known as "CRM197") is a non-toxic mutant of diphtheria toxin which is used in many approved glycoconjugate vaccines (e.g. see Broker et al. (2011) *Biologicals* 39:195-204). Exemplary carrier proteins for use with the invention comprise an amino acid sequence which has at least 90% sequence identity to SEQ ID NOs:1 or 11. For instance, the carrier protein can comprise the amino acid sequence SEQ ID NOs:1 or 11 except for the presence of one or more nnAA (which may be inserted within SEQ ID NOs:1 or 11 or may be substituted for one or more amino acid residues within SEQ ID NOs:1 or 11 e.g. substituted for Lys and/or Phe).

In some embodiments, at least one Lys and/or at least one Phe residue in SEQ ID NOs:1 or 11 is substituted by a nnAA residue. It may be preferred to substitute more than one residue in SEQ ID NOs:1 or 11 with a nnAA and, in some embodiments, only one species of residue in SEQ ID NOs:1 or 11 is substituted by a nnAA e.g. only Lys residues are substituted. Where more than one residue in SEQ ID NOs:1 or 11 is substituted with a nnAA it may be advantageous that the same nnAA is used at each position e.g. pAMF at each substitution position.

Carrier proteins with from 2-9 nnAA residues within SEQ ID NOs:1 or 11 may be useful, for example with from 4-9, 4-8, or 4-6 nnAA residues e.g. 4, 5 or 6 nnAA residues. This may permit more extensive attachment of antigens to the carrier than using a single nnAA, thereby increasing the antigen:carrier ratio, while avoiding excessive disruption of the native sequence and structure, which can result in insolubility.

Studies of CRM197 have identified T-cell epitopes within residues P272-D291, V322-G384, and Q412-I458 (according to SEQ ID NO:1 numbering). Exemplary modified CRM avoid introducing nnAA within these regions of SEQ ID NOs:1 or 11. These regions include F274, F356, F361, F369, K420, K441, K446, K448, and K457 (numbered according to SEQ ID NO:1), so these are the Phe and Lys residues which are less preferred for nnAA substitution in CRM197 or a modified CRM. Exemplary Lys residues for substitution by a nnAA in SEQ ID NO:11 are K24, K33, K37, K39, K212, K214, K227, K244, K264, K385, K522 and K526. Other useful Lys residues for substitution by a nnAA are K10, K37, K82, K103, K104, K125, K157, K172, K221, K236, K242, K474, and K499 (SEQ ID NO:11). Useful Lys residues for substitution by a nnAA in SEQ ID NO:1 are K25, K34, K38, K40, K213, K215, K228, K245, K265, K386, K523, or K527. Other useful Lys residues for substitution by a nnAA are K11, K38, K83, K104, K105, K126, K158, K173, K222, K237, K243, K475, and K499. Useful Phe residues for substitution by a nnAA are F13, F54, F124, F128, F141, F168, F251, F390, F531, or F532 (of SEQ ID NO:1).

Structural studies of CRM197 reveal two general 3D regions: the first region runs from the N-terminus to Asn-374; and the second region runs from Ser-375 to the C-terminus. Exemplary carriers used with the invention include at least one nnAA in the first region and at least one nnAA in the second region e.g. at least two nnAA in each region, or at least 3 nnAA in each region. This may permit conjugated antigens to be spatially separated when attached to the carrier. A carrier with 3 nnAA in the first region and 3 nnAA in the second region is useful.

The first region contains 27 Lys residues, and the second region contains 12 Lys residues. Thus one or more (e.g. 3) Lys residues within the N-terminal 374 amino acids and one or more (e.g. 3) Lys residues within the C-terminal 162 amino acids of SEQ ID NO:1 can be substituted with a nnAA e.g. within pAMF.

Exemplary embodiments of nnAA-containing carriers based on CRM197 have the amino acid sequence of SEQ ID NO:11 in which one or more of residues K24, K33, K37, K39, K212, K214, K227, K244, K264, K385, K522 and/or K526 is/are replaced by a nnAA. Exemplary embodiments of nnAA-containing carriers based on N-terminally modified CRM197 have the amino acid sequence of SEQ ID NO:1 in which one or more of residues K25, K34, K38, K40, K213, K215, K228, K245, K265, K386, K523, and/or K527 is/are replaced by a nnAA. One such sequence is SEQ ID NO:9, in which each X represents a nnAA (preferably the same nnAA, such as pAMF):

(SEQ ID NO: 9)
MGADDVVDSSKSFVMENFSSYHGTKPGYVDSIQXGIQKPKSGTQGNYD

DDWKEFYSTDNKYDAAGYSVDNENPLSGKAGGVVKVTYPGLTKVLALK

VDNAETIKKELGLSLTEPLMEQVGTEEFIKRFGDGASRVVLSLPFAEG

SSSVEYINNWEQAKALSVELEINFETRGKRGQDAMYEYMAQACAGNRV

RRSVGSSLSCINLDWDVIRDXTKTKIESLKEHGPIKNKMSESPNKTVS

-continued
EEKA<u>X</u>QYLEEFHQTALEHPELSEL<u>X</u>TVTGTNPVFAGANYAAWAVNVAQ

VIDSETADNLEKTTAALSILPGIGSVMGIADGAVHHNTEEIVAQSIAL

SSLMVAQAIPLVGELVDIGFAAYNFVESIINLFQVVHNSYNRPAYSPG

H<u>X</u>TQPFLHDGYAVSWNTVEDSIIRTGFQGESGHDIKITAENTPLPIAG

VLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNS<u>X</u>L

SLFFEIKS

This carrier protein has been found to be very well-expressed in a cell-free protein synthesis system, while retaining good solubility and providing good immunogenic responses when conjugated to pneumococcal capsular polysaccharides.

The invention also provides herein compositions including multiple different conjugates (e.g. different pneumococcal serotypes) in which each conjugate includes a carrier protein having amino acid sequence SEQ ID NO:9 (for example, in which each X residue is the same nnAA, preferably pAMF).

SEQ ID NO:1 has a N-terminal methionine (which will typically be formylated) that is not present in wild-type CRM197 (SEQ ID NO:11) but is included for initiating translation without requiring the whole native leader sequence. In some embodiments the carrier protein used herein lacks a N-terminal methionine e.g. the N-terminus methionine of SEQ ID NO:1 or SEQ ID NO:9 may be absent. In some embodiments a carrier protein based on CRM197 includes no natural amino acids (and more preferably no amino acids) upstream of the N-terminus of SEQ ID NO: 1 or downstream of the C-terminus of SEQ ID NO: 1.

These nnAA-containing enhanced CRM197 carrier proteins are particularly useful for conjugating to pneumococcal capsular polysaccharides. These conjugates can be combined to form multivalent compositions as discussed elsewhere herein.

The invention also provides a protein for preparing an immunogenic polysaccharide-protein conjugate, wherein the protein has an amino acid sequence which has at least 80% sequence identity to SEQ ID NO:1 (e.g. at least 85%, at least 90%, or at least 95%) and includes at least one nnAA, wherein the protein has a N-terminal methionine. The invention also provides an immunogenic polysaccharide-protein conjugate prepared by conjugating a polysaccharide to at least one nnAA in the protein.

The invention also provides a protein for preparing an immunogenic polysaccharide-protein conjugate, wherein the protein comprises the amino acid sequence SEQ ID NO:1 except that at least one (e.g. 2-9) lysine residues is a nnAA. The nnAA is ideally an azido-containing nnAA (such as pAMF), a 1,2,4,5-tetrazinyl-containing nnAA, or an alkenyl-containing nnAA. The invention also provides a conjugate comprising such a protein conjugated to a polysaccharide antigen via at least one of its nnAA.

The invention also provides an immunogenic polysaccharide-protein conjugate, wherein the protein is a modified CRM197 having a N-terminal methionine.

The nnAA-containing modified CRM197-based carriers are typically present in monomeric form when used for preparing conjugates, rather than being associated with other modified CRM197-based carrier subunits to form modified CRM197-based multimers.

III.B.1. Modified CRM197 Carrier Polypeptides

As mentioned herein, the carrier polypeptides of interest herein are modified forms of CRM197. Thus carrier polypeptides for use with the invention may comprise an amino acid sequence that has at least 80% sequence identity (e.g. ≥85%, ≥90%, ≥95%, ≥96%, ≥97%, or preferably ≥98%) to SEQ ID NOs: 1 or 11. For instance, the carrier polypeptide can comprise the amino acid sequence SEQ ID NOs: 1 or 11 except for the presence of up to 10 nnAA, as discussed above.

SEQ ID NOs: 1 and 11 include an Arg-Arg dipeptide sequence at positions 192-193 according to SEQ ID NO:11 or 193-914 according to SEQ ID NO:1. This sequence can be subject to proteolytic cleavage in some circumstances. If desired, this site can be modified to prevent cleavage and improve yield. Thus in some embodiments a modified CRM197 carrier polypeptide used herein is free from an Arg-Arg dipeptide sequence. For instance, Arg-192 and/or Arg-193 of SEQ ID NO: 11 (or Arg-193 and/or Arg-194 of SEQ ID NO:1) can be deleted or can be substituted with a different amino acid. Thus a useful carrier polypeptide may comprise an amino acid sequence which (i) has at least 80% (e.g. ≥85%, ≥90%, ≥95%, ≥96%, ≥97%, or preferably ≥98%) sequence identity to SEQ ID NO:1 or 11; (ii) is free from an Arg-Arg dipeptide sequence; and (iii) includes at least one (e.g. at least 2, and preferably more, as discussed above) nnAA residue.

One such amino acid sequence is SEQ ID NO:12, which differs from SEQ ID NO: 11 by having an Arg→Asn substitution at position 193:

(SEQ ID NO: 12)
GADDVVDSSKSFVMENFSSYHGTKPGYVDSIQKGIQKPKSGTQGNYDD

DWKEFYSTDNKYDAAGYSVDNENPLSGKAGGVVKVTYPGLTKVLALKV

DNAETIKKELGLSLTEPLMEQVGTEEFIKRFGDGASRVVLSLPFAEGS

SSVEYINNWEQAKALSVELEINFETRGKRGQDAMYEYMAQACAGNRVR

<u>N</u>SVGSSLSCINLDWDVIRDKTKTKIESLKEHGPIKNKMSESPNKTVSE

EKAKQYLEEFHQTALEHPELSELKTVTGTNPVFAGANYAAWAVNVAQV

IDSETADNLEKTTAALSILPGIGSVMGIADGAVHHNTEEIVAQSIALS

SLMVAQAIPLVGELVDIGFAAYNFVESIINLFQVVHNSYNRPAYSPGH

KTQPFLHDGYAVSWNTVEDSIIRTGFQGESGHDIKITAENTPLPIAGV

LLPTIPGKLDVNKSKTHISVNGRKIRMRCRAIDGDVTFCRPKSPVYVG

NGVHANLHVAFHRSSSEKIHSNEISSDSIGVLGYQKTVDHTKVNSKLS

LFFEIKS

Any embodiment described herein, by reference to SEQ ID NO: 11 can be put into effect using SEQ ID NO:12 instead.

Another such amino acid sequence is SEQ ID NO: 13, which differs from SEQ ID NO: 1 by having an Arg→Asn substitution at position 194:

(SEQ ID NO: 13)
MGADDVVDSSKSFVMENFSSYHGTKPGYVDSIQKGIQKPKSGTQGNYD

DDWKEFYSTDNKYDAAGYSVDNENPLSGKAGGVVKVTYPGLTKVLALK

VDNAETIKKELGLSLTEPLMEQVGTEEFIKRFGDGASRVVLSLPFAEG

-continued
SSSVEYINNWEQAKALSVELEINFETRGKRGQDAMYEYMAQACAGNRV

R<u>N</u>SVGSSLSCINLDWDVIRDKTKTKIESLKEHGPIKNKMSESPNKTVS

EEKAKQYLEEFHQTALEHPELSELKTVTGTNPVFAGANYAAWAVNVAQ

VIDSETADNLEKTTAALSILPGIGSVMGIADGAVHHNTEEIVAQSIAL

SSLMVAQAIPLVGELVDIGFAAYNFVESIINLFQVVHNSYNRPAYSPG

HKTQPFLHDGYAVSWNTVEDSIIRTGFQGESGHDIKITAENTPLPIAG

VLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSKL

SLFFEIKS

Any embodiment described herein, by reference to SEQ ID NO:1 can be put into effect using SEQ ID NO:13 instead.

Thus we provide a carrier polypeptide comprising amino acid sequence SEQ ID NO: 12, wherein SEQ ID NO:12 has been modified to include from 1-10 (e.g. from 3-9 or from 2-8, or from 2-6, or from 3-6, or from 4-6) nnAA residues. These nnAA residue modifications can be incorporated into SEQ ID NO:12 as insertions and/or substitutions (e.g. 6 Lys→nnAA substitutions (e.g., pAMF) at positions K33, K212, K244, K264, K385, K526). In certain variations, Asn-193 of SEQ ID NO:12 is not substituted by a nnAA. This carrier polypeptide can be used to prepare immunogenic conjugates (e.g. of saccharide antigens) via the nnAA residue(s) therein.

Thus we also provide a carrier polypeptide comprising amino acid sequence SEQ ID NO:13, wherein SEQ ID NO:13 has been modified to include from 1-10 (e.g. from 3-9 or from 2-8, or from 2-6, or from 3-6, or from 4-6) nnAA residues. These nnAA residue modifications can be incorporated into SEQ ID NO: 13 as insertions and/or substitutions (e.g. SEQ ID NO:14, which includes 6 Lys→nnAA substitutions e.g., pAMF). In certain variations, Asn-194 of SEQ ID NO:13 is not substituted by a nnAA. This carrier polypeptide can be used to prepare immunogenic conjugates (e.g. of saccharide antigens) via the nnAA residue(s) therein.

In some embodiments these carrier polypeptides include amino acid sequences upstream and/or downstream of SEQ ID NO: 11 or 12. Thus, for instance, they can include a methionine residue upstream of the N-terminus amino acid residue of SEQ ID NO:11 or 12. This methionine residue may be formylated. A methionine residue is not present at this position in wild-type CRM197 but it can be included herein for initiating translation (e.g. in a cell-free polypeptide synthesis system) without requiring the whole native leader sequence. In some embodiments a carrier polypeptide includes (i) no amino acids upstream of the N-terminus of SEQ ID NO: 11 or 12, except for an optional methionine, and (ii) no amino acids downstream of the C-terminus of SEQ ID NO: 11 or 12.

In some embodiments these carrier polypeptides include amino acid sequences upstream and/or downstream of SEQ ID NO: 1 or 13. In some embodiments a carrier polypeptide includes (i) no amino acids upstream of the N-terminus of SEQ ID NO: 1 or 13, except for an optional methionine, and (ii) no amino acids downstream of the C-terminus of SEQ ID NO: 1 or 13.

In certain embodiments, at least one Lys residue in SEQ ID NO:11 or 12 is substituted by a nnAA residue. In some embodiments, it is useful to substitute more than one residue in SEQ ID NO:11 or 12 with a nnAA and, in some embodiments, only one species of residue in SEQ ID NO:11 is substituted by a nnAA e.g. only Lys residues are substituted. Where more than one residue in SEQ ID NO:11 is substituted for a nnAA it may be preferred that the same nnAA is used at each position e.g. pAMF at each substitution position. As noted above, in some embodiments residues other than Lys are substituted.

In certain embodiments, at least one Lys residue in SEQ ID NO:1 or 13 is substituted by a nnAA residue. It can be useful to substitute more than one residue in SEQ ID NO:1 or 13 with a nnAA and, in some embodiments, only one species of residue in SEQ ID NO:1 is substituted by a nnAA e.g. only Lys residues are substituted. Where more than one residue in SEQ ID NO:1 is substituted for a nnAA it may be preferred that the same nnAA is used at each position e.g. pAMF at each substitution position. As noted above, in some embodiments residues other than Lys are substituted.

Carrier polypeptides comprising amino acid sequence SEQ ID NO: 11 or 12 with from 2-9 substitutions by nnAA residues (e.g. Lys→nnAA substitutions, such as Lys→pAMF) are provided, and for example with from 2-8, 2-6, 3-8, 3-6, 4-9, 4-8, or 4-6 nnAA substitutions e.g. 4, 5 or 6 nnAA residues. Carrier polypeptides comprising amino acid sequence SEQ ID NO: 1 or 13 with from 2-9 substitutions by nnAA residues (e.g. Lys→nnAA substitutions, preferably Lys→pAMF) are provided, and for example with from 2-8, 2-6, 3-8, 3-6, 4-9, 4-8, or 4-6 nnAA substitutions e.g. 4, 5 or 6 nnAA residues. This permits more extensive attachment of antigens to the carrier than using a single nnAA, thereby increasing the antigen:carrier ratio, while avoiding excessive disruption of the native sequence and structure, which can result in insolubility.

The two general 3D regions evidenced by the structural studies of CRM197 mentioned earlier herein may be within SEQ ID NO:11 or 12, wherein, again, the first region runs from the N-terminus to Asn-373, and the second region runs from Ser-374 to the C-terminus.

Exemplary embodiments of nnAA-containing carriers based on CRM197 have the amino acid sequence of SEQ ID NO:11 or SEQ ID NO: 12 in which one or more of residues K24, K33, K37, K39, K212, K214, K227, K264, K385, K522 and K526 is/are replaced by a nnAA (such as pAMF). For example, K33, K212, K244, K264, K385, K526 are replaced by a nnAA. For example, in which each nnAA is same nnAA, such as pAMF).

Additional exemplary embodiments of nnAA-containing carriers based on CRM197 have the amino acid sequence of SEQ ID NO:1 or SEQ ID NO: 13 in which one or more of residues K25, K343, K38, K40, K213, K215, K228, K265, K386, K523 and K527 is/are replaced by a nnAA (such as pAMF). For example, K343, K213, K245, K265, K386, K527 are replaced by a nnAA. One such sequence is SEQ ID NO:9, in which each X represents a nnAA (preferably the same nnAA, such as pAMF).

Another such sequence is SEQ ID NO:14, containing the above-mentioned Arg-Asn substitution and in which each X represents a nnAA (preferably the same nnAA, such as pAMF):

(SEQ ID NO: 14)
MGADDVVDSSKSFVMENFSSYHGTKPGYVDSIQ<u>X</u>GIQKPKSGTQGNYD

DDWKEFYSTDNKYDAAGYSVDNENPLSGKAGGVVKVTYPGLTKVLALK

VDNAETIKKELGLSLTEPLMEQVGTEEFIKRFGDGASRVVLSLPFAEG

SSSVEYINNWEQAKALSVELEINFETRGKRGQDAMYEYMAQACAGNRV

-continued

RNSVGSSLSCINLDWDVIRDXTKTKIESLKEHGPIKNKMSESPNKTVS

EEKAXQYLEEFHQTALEHPELSELXTVTGTNPVFAGANYAAWAVNVAQ

VIDSETADNLEKTTAALSILPGIGSVMGIADGAVHHNTEEIVAQSIAL

SSLMVAQAIPLVGELVDIGFAAYNFVESIINLFQVVHNSYNRPAYSPG

HXTQPFLHDGYAVSWNTVEDSIIRTGFQGESGHDIKITAENTPLPIAG

VLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSXL

SLFFEIKS

SEQ ID NOs: 9 and 14 can be very well-expressed in a cell-free protein synthesis system, while retaining good solubility and providing good immunogenic responses when conjugated to pneumococcal capsular saccharides. SEQ ID NO:14 lacks the native Arg-Arg dipeptide linkage.

A polypeptide consisting of SEQ ID NO:14, in which each X is pAMF, is an exemplary carrier polypeptide for use with the invention.

Several amino acid residues which may be suitable for nnAA substitution (e.g. Lys-24, Lys-33, Lys-37, Lys-39, Lys-212, Lys-214, Lys-227, Lys-244, Lys-264, Lys-385, Lys-522, Lys-526, Phe-12, Phe-53, Phe-123, Phe-127, Phe-140, Phe-167, Phe-250, Phe-389, Phe-530, or Phe-531, numbered according to SEQ ID NO: 11 herein). Other residues which can be substituted are: Asp-211; Asp-295; Asp-352; Asp-392; Asp-465; Asp-467; Asp-507; Asp-519; Asn-296; Asn-359; Asn-399; Asn-481; Asn-486; Asn-502; Asn-524; Glu-240; Glu-248; Glu-249; Glu-256; Glu-259; Glu-292; Glu-362; Gln-252; Gln-287; Lys-212; Lys-218; Lys-221; Lys-229; Lys-236; Lys-264; Lys-299; Lys-385; Lys-456; Lys-474; Lys-498; Lys-516; Lys-522; Lys-534; Arg-377; Arg-407; Arg-455; Arg-460; Arg-462; Arg-472; Arg-493; Ser-198; Ser-200; Ser-231; Ser-233; Ser-239; Ser-261; Ser-374; Ser-381; Ser-297; Ser-397; Ser-451; Ser-475; Ser-494; Ser-495; Ser-496; Ser-501; Ser-505; Thr-253; Thr-265; Thr-267; Thr-269; Thr-293; Thr-386; Thr-400; Thr-408; Thr-469; and/or Thr-517 (numbered according to SEQ ID NO:11).

We also provide a polypeptide comprising an amino acid sequence which (i) has at least 80% (e.g. ≥85%, ≥90%, ≥95%, ≥96%, ≥97%, or preferably ≥98%) sequence identity to SEQ ID NO: 1 or 11; (ii) is free from an Arg-Arg dipeptide sequence; and (iii) includes at least one nnAA residue; and wherein the polypeptide has a N-terminus methionine and/or is in monomeric form. We also provide a polypeptide comprising an amino acid sequence which (i) has at least 80% (e.g. ≥85%, ≥90%, ≥95%, ≥96%, ≥97%, or preferably ≥98%) sequence identity to SEQ ID NO: 1; (ii) is free from an Arg-Arg dipeptide sequence; and (iii) includes at least one nnAA residue; and wherein the polypeptide has a N-terminal methionine and/or is in monomeric form.

These modified CRM197-derived carrier polypeptides can be used in the same manner for conjugation as CRM197 has been used in the prior art (e.g. see Broker et al. 2011 supra, WO2015/117093, etc.), but with the improvement of permitting site-specific conjugation via the nnAA residue(s). They will generally be used in monomeric form, rather than being associated with other CRM197 or CRM197-derived subunits to form polypeptide multimers. Similarly, they will generally include at least one disulfide bridge e.g. between Cys-186 & Cys-201 (numbered according to SEQ ID NO: 11) and, optionally, between Cys-461 & Cys-471.

Also provided is an immunogenic conjugate comprising any of these various carrier polypeptides conjugated to a saccharide antigen via at least one of its nnAA. The carrier polypeptides are particularly useful for conjugating to pneumococcal capsular saccharides via the nnAA residue(s) therein. Immunogenic conjugates prepared in this way can be combined to form multivalent compositions as discussed elsewhere herein.

The invention additionally provides an immunogenic conjugate comprising a carrier polypeptide and a saccharide antigen, wherein (i) the carrier polypeptide has amino acid sequence SEQ ID NO:14 e.g. where each X is pAMF; and (ii) the saccharide antigen is covalently bonded to the carrier polypeptide via at least one nnAA residue within SEQ II) NO:14. Also provided is a multivalent pharmaceutical composition comprising two or much such immunogenic conjugates.

The invention additionally provides a pharmaceutical composition including multiple different conjugates (e.g. different pneumococcal serotypes) in which each conjugate includes a carrier polypeptide having amino acid sequence SEQ ID NO:14.

Additionally provided is an immunogenic conjugate comprising a carrier polypeptide and a saccharide antigen, wherein (i) the carrier polypeptide has amino acid sequence SEQ ID NO:14; (ii) the saccharide antigen is covalently bonded to the carrier polypeptide via at least one nnAA residue within SEQ ID NO:14; and (iiia) the saccharide antigen is a capsular saccharide from any of pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F or (iiib) the saccharide antigen is a capsular saccharide from any of pneumococcal serotypes 1, 2, 3, 4, 5, 6A, 6B, 6C, 7F, 8, 9N, 9V, 10A, 11A, 12F, 14, 15A, 15B, 16F, 17F, 18C, 19A, 19F, 20, 22F, 23A, 23B, 23F, 31, 33F, and 35B. In some embodiments, the serotype 20 saccharide is 20A, 20B or a mixture thereof.

These individual conjugates can be combined to make multivalent pharmaceutical compositions of the invention.

We also provide a polynucleotide encoding a carrier polypeptide described herein. In certain embodiments, the disclosure provides for an expression vector comprising the polynucleotide. In certain embodiments, the disclosure provides for a host cell comprising the expression vector.

III.C. Carrier Protein Production Methods

III.C.1. General Methods for Polypeptide Production:

The enhanced carrier protein is produced by any method described for production of polypeptides. Methods suitable for production of polypeptides include, but are not limited to, solid phase chemical peptide synthesis, cell-based recombinant protein expression (in *E. coli* or a native host), and cell-free protein expression, and any combination thereof (e.g. expressed protein ligation using a combination of synthetic and recombinant peptide components).

In some embodiments of the enhanced carrier protein production method, the nnAA-bearing enhanced carrier protein is produced by a method that comprises "codon reassignment". In one variation of this embodiment, nnAAs that are close structural analogs of the 20 canonical amino acids (e.g. homoallylglycine, fluorinated leucine, azidohomoalanine) are used. The nnAA is loaded onto its corresponding tRNA using wild-type aminoacyl-tRNA synthetases, and the nnAA completely replaces one of the 20 canonical amino acids specified in a template DNA sequence. To prevent interference from the native amino acid, this generally requires use of a bacterial expression strain that is auxotrophic for the native amino acid being replaced. This strategy is amino acid rather than residue-specific, since all AA residues of a certain type are replaced with the nnAA.

In certain embodiments of the enhanced carrier protein production method, the nnAA-bearing enhanced carrier protein is produced by a strategy that comprises "nonsense suppression". In this approach the non-natural amino acid is specified in a template DNA sequence by a rare or "nonsense" codon that does not ordinarily specify an amino acid in nature. One variation of the nonsense suppression approach has been pioneered by Schultz (Noren et al. *Science*. 1989(244):182-188.) and Chamberlin (Bain et al. *J Am Chem Soc*. 1989(111):8013-8014), and involves the use of the rare stop codon TAG (the "amber" codon; UAG in the RNA code) along with its tRNA and its corresponding aminoacyl-tRNA synthetase (aaRS) to incorporate nnAAs into a polypeptide in a site-specific manner.

In some embodiments, the "nonsense suppression" approach involves isolating a tRNA/aaRS pair, modifying the tRNA at the anti-codon loop to recognize an orthogonal codon (e.g. the amber codon TAG, the opal codon TGA, or another codon or base sequence not commonly used to specify amino acids in translation), and modifying the aaRS to prefer the nnAA over the aminoacyl-tRNAs native amino acid. In some variations of this embodiment, the tRNA/aminoacyl-tRNA synthetase pair is from the same organism as the translation machinery used for polypeptide synthesis. In other embodiments, the tRNA/aminoacyl-tRNA synthetase pair is from a different species as the translation machinery used for polypeptide synthesis. Methods to modify the tRNA anticodon loop and aaRS active site have been described, as are examples of engineered orthogonal tRNA/aaRS pairs.

In certain embodiments of the "nonsense suppression" approach, production of the enhanced carrier protein does not involve the use of an engineered aminoacyl-tRNA synthetase. In this embodiment an orthogonal tRNA alone is isolated and modified at the anti-codon loop to recognize an orthogonal codon (e.g. the amber codon TAG, or another codon or base sequence not commonly used to specify amino acids in translation). The orthogonal engineered tRNA is then acylated in vitro by a suitable chemical method (e.g., the method of Heckler et al. *Biochemistry*. 1984 Mar. 27; 23(7):1468-73. which involves the use of T4 RNA ligase and mutant tRNAPhe), and supplemented in a cell-free protein synthesis extract. Because this embodiment uses chemically acylated tRNAs, it is only compatible with protein synthesis methods that are cell-free.

III.C.2. Cell-Free Protein Synthesis:

A particularly useful technique for producing nnAA-containing carrier proteins use cell-free protein synthesis. Several cell-free protein expression techniques are known in the art and various nnAA can be incorporated in this way (e.g. see Table 1 of Quast et al. (2015) *FEES Letters* 589:1703-12) while avoiding potential cytotoxic effects of nnAA. In some embodiments, the enhanced carrier protein is produced by cell-free extract-based protein synthesis. In some embodiments, the cell-free extract comprises an extract of rabbit reticulocytes, wheat germ, or *E. coli*. In further embodiments, the cell-free extract is supplemented with amino acids, energy sources, energy regenerating systems, or cation cofactors, and any combination thereof. In some embodiments, the extract comprises exogenously supplemented mutant tRNA or mutant aaRS (aminoacyl tRNA synthetase), and any combination thereof. In some embodiments the extract comprises lysates from *E. coli* strains genetically encoding mutant tRNA or mutant aaRS, and any combination thereof. In some embodiments the *E. coli* strains used for lysates are RF-1 attenuated strains. Compatible cell-free protein synthesis systems have been described for the insertion of formulas I, II, and III into recombinant polypeptides (e.g., U.S. Pat. No. 8,715,958B2, US20160257946A1, and US 20160257945A1).

In one example U.S. Pat. No. 8,715,958B2 demonstrates a regenerating cell-free *E. coli* based system whereby the tRNA$^{Tyr}$/Tyrosine-synthetase pair from *Methanococcus jannaschii* (Wang et al. (2001) *Science* 292(5516):498-500) is used to introduce the non-natural amino acid p-azido-L-phenylalanine (pAF) into recombinant chloramphenicol acetyltransferase (CAT), GM-CSF, and TetA. Using this system, the tRNA/synthetase pair is either supplemented into the extract, or transformed into bacteria used to make the extract.

In another example, US20160257946A1 demonstrates: (a) how the *Methanococcus jannaschii* Tyrosine-synthetase above is adapted using mutagenesis so that it preferentially loads p-azidomethyl-L-phenylalanine (pAMF) onto an amber-recognizing tRNA, and (b) how a cell-free synthesis system comprising the modified synthetase/tRNA pair is used to selectively incorporate pAMF into antibodies such as trastuzumab.

In a further example, US20160257945A1 demonstrates: (a) how the *Methanococcus jannaschii* Tyrosine-synthetase above is adapted using mutagenesis so that it preferentially loads (S)-2-amino-3-(5-((6-methyl-1,2,4,5-tetrazin-3-ylamino)methyl)pyridin-2-yl)propanoic acid (a pyridyl tetrazine amino acid derivative) onto an amber-recognizing tRNA, and (b) how a cell-free synthesis system comprising the modified synthetase/tRNA pair is used to selectively incorporate (S)-2-amino-3-(5-((6-methyl-1,2,4,5-tetrazin-3-ylamino)methyl)pyridin-2-yl)propanoic acid into recombinant GFP.

In a further embodiment, the disclosure provides for methods of producing polypeptides in a cell-free extract containing two or more non-natural amino acids. In this embodiment the polypeptides also have biological activity comparable to the native protein. In other embodiments the polypeptides have improved or enhanced biological activity comparable to the native protein.

One optionally determines the specific activity of a protein in a composition by determining the level of activity in a functional assay, quantitating the amount of protein present in a non functional assay (e.g. immunostaining, ELISA, quantitation on coomassie or silver stained gel, etc.) and determining the ratio of biologically active protein or non-aggregated protein to total protein. Generally, the specific activity as thus defined will be at least about 5% that of the native protein, usually at least about 10% that of the native protein, and optionally is about 20%, about 40%, about 60% or greater.

In some embodiments, the methods of producing the nnAA-containing polypeptides involve altering the concentrations of nnAA-specific tRNA, nnAA-specific synthetase, nnAA itself, or translation temperature, and any combination thereof. Such conditions optionally allow for fewer translational errors, improved rate of incorporation of the nnAA, improved activity of chaperones necessary for protein folding with incorporation of the nnAA, decreased activity of cellular factors that interfere with nnAA incorporation, or any combination of the aforementioned mechanisms.

In some embodiments of the enhanced polypeptide production methods, nnAA-specific tRNA concentration is increased to a concentration above about 20 µM, leading to an increased fraction of soluble or active polypeptide. In further variations of this embodiment the tRNA concentration is increased while the nnAA concentration is kept below about 2 mM and the nnAA synthetase is maintained below about 5 µM.

In some embodiments of the enhanced polypeptide production methods, the translation mix incubation temperature is between 20 degrees and 30 degrees Celsius, about 20 degrees Celsius, or below 20 degrees Celsius. In some variations, these temperature modifications are independently combined with modifications to the nnAA-specific tRNA concentrations, nnAA concentrations, or nnAA synthetase concentrations described in the preceding paragraph.

III.D. Sequence Variants

The improved carrier proteins of the present disclosure comprise one or more nnAA substituted at any position within the polypeptide as long as the immunogenic function of one or more T-cell epitopes of the polypeptide is preserved. When basing the improved carrier protein on a known carrier it is usually useful to substitute some or all of the nnAAs for existing naturally occurring amino acids in the known carrier to minimize the chance of adversely affecting the carrier's properties. It is appreciated, however, that nnAAs may be inserted internally or at a terminus as additions to the starting carrier sequence. In some embodiments the at least one nnAA in the improved carrier protein (e.g., eCRM) is not present within one or more regions of the protein that comprise a T-cell epitope. In certain embodiments, no nnAA in the enhanced immunogenic polypeptide is present within one or more regions of the protein that comprise a T-cell epitope.

In some embodiments, the nnAA residue is substituted for one or more of the twenty naturally-encoded amino acids, including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some other embodiments the nnAA residue is substituted for one or more of a specific class of natural amino acid residue, such as aliphatic, aromatic, acidic, basic, hydroxylic, sulfur-containing, or amidic (containing amide group). In some cases, only one specific amino acid (e.g., lysine) is substituted for a nnAA within the polypeptide at one or more positions. In other cases, two or more different amino acids (e.g., lysine, phenylalanine, etc.) are substituted for a nnAA within the polypeptide at two or more positions. Polypeptides in which only a single species of amino acid is substituted for a nnAA may be advantageous e.g. in which only Lys residues are substituted.

In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of a carrier protein. In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of a carrier protein. In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of SEQ ID NO:1 or SEQ ID NO:11.

In further aspects the nnAA is substituted for one or more amino acid residues within a carrier protein. The specific amino acid residue that is selected to create single- or multiple-substituted nnAA variants described herein is optionally determined by dividing the protein into subdomains and choosing for substitution a single amino acid or sets of amino acid residues that do not sterically obstruct each other (e.g. such that there is a multi-angstrom distance between the substitution sites). Division of CRM197 into two structural regions is discussed below.

In some embodiments, the nnAA is substituted for a charged amino acid residue. Thus a nnAA can be substituted for an aspartate, glutamate, lysine, arginine or histidine amino acid residue. In some embodiments, the nnAA is substituted for a negatively-charged amino acid residue e.g. for an aspartate or glutamate residue. In some embodiments, the nnAA is substituted for a positively-charged amino acid residue e.g. for a lysine, arginine or histidine residue.

In some embodiments, the nnAA is substituted for one or more lysine residues within an immunogenic polypeptide. For example, an enhanced version of SEQ ID NO: 11 is generated by substituting an nnAA for lysine in the following manner: 1) one residue from the group consisting of K24, K33, K37, and K39; 2) one residue selected from the group consisting of K212 and K214; and 3) 2 to 4 residues selected from the group consisting of K227, K244, K264, K385, K522, and K526. In yet further embodiments the one or more of a specific class of natural amino acid residue substituted is selected from the group consisting of K24, K33, K37, K39, K212, K214, K227, K244, K264, K385, K522 and K526, and any combination thereof of SEQ ID NO: 1. In other embodiments, the nnAA substitution in SEQ ID NO:11 is selected from one or more of K24, K33, K37, K39, K212, K214, K227, K244, K264, K385, K522 and K526. In some embodiments the nnAA substitution comprises six residues consisting of K24, K214, K227, K264, K385, and K522 of SEQ ID NO:11. In some embodiments, the nnAA substitution in SEQ ID NO:11 comprises K264. In other embodiments, the nnAA substitution in SEQ ID NO:11 comprises K385. In certain embodiments, the nnAA substitutions in SEQ ID NO:11 comprise K264 and K385. For example, an enhanced version of SEQ ID NO: 1 may also be generated by substituting an nnAA for lysine in the following manner: 1) one residue from the group consisting of K25, K34, K38, and K40; 2) one residue selected from the group consisting of K213 and K215; and 3) 2 to 4 residues selected from the group consisting of K228, K245, K265, K386, K523, and K527. In yet further embodiments the one or more of a specific class of natural amino acid residue substituted is selected from the group consisting of K25, K34, K38, K40, K213, K215, K228, K265, K386, K523 and K527, and any combination thereof of SEQ ID NO: 1. In other embodiments, the nnAA substitution in SEQ ID NO:1 is selected from one or more of K25, K34, K38, K40, K213, K215, K228, K245, K265, K386, K523, and K527. In one embodiment the nnAA substitution comprises six residues consisting of K25, K215, K228, K265, K386, and K523 of SEQ ID NO:1. In some embodiments, the nnAA substitution in SEQ ID NO:1 comprises K265. In other embodiments, the nnAA substitution in SEQ ID NO:1 comprises K386. In another embodiment, the nnAA substitutions in SEQ ID NO:1 comprise K265 and K386. In a further embodiment, the nnAA is substituted for a phenylalanine. Exemplary phenylalanines for substitution include F13, F54, F124, F128, F141, F168, F251, F390, F531, or F532 of SEQ ID NO:1. Because of their proximity, it is generally advantageous to not substitute at both F531 and F532.

The binding epitopes for human CD4+ cells on diphtheria toxin that are recognized by most subjects tested encompass residues 271-290, 321-340, 331-350, 351-370, 411-430, or 431-450 (see, Raju et al. (1995) *Eur J Immunol.* 25(12): 3207-14). Therefore, in some embodiments the one or more nnAA substituted is not within residues 270-289, 320-339, 330-349, 350-360, 410-429, and/or 430-449 of SEQ ID NO:11. In some embodiments, the one or more nnAA substituted is not within residues 330-349 of SEQ ID NO:1. In certain embodiments, the one or more nnAA substituted is not within residues 320-339 of SEQ ID NO:1. In certain embodiments, the one or more nnAA substituted is not within residues 432-449 of SEQ ID NO:11. Also, in some embodiments the one or more nnAA substituted is not within residues 271-290, 321-340, 331-350, 351-370, 411-430, and/or 431-450 of SEQ ID NO:1. In some embodiments, the one or more nnAA substituted is not within residues 331-350 of SEQ ID NO:1. In other embodiments, the one or more nnAA substituted is not within residues 321-340 of SEQ ID NO:1. In yet other embodiments, the one or more nnAA substituted is not within residues 431-450 of SEQ ID NO:1.

The binding epitopes for human CD4+ cells on tetanus toxin that are recognized by all subjects tested encompass heavy chain residues H176-195, IDKISDVS-TIVPYIGPALNI [SEQ ID NO:3], and H491-510, NNFTVSFWLRVPKVSASHLE [SEQ ID NO:4] (see, Diethelm-Okita et al., *J Infect Dis.* 1997 February; 175(2): 382-91). Thus, in some embodiments the one or more nnAA substituted is not within residues 176-195 and/or 491-510 of the heavy chain peptide component of the tetanus toxin precursor protein. In certain embodiments, the one or more nnAA substituted is not within residues 176-195 of the heavy chain peptide component of the tetanus toxin precursor protein. In yet certain embodiments, the one or more nnAA substituted is not within residues 491-510 of the heavy chain peptide component of the tetanus toxin precursor protein.

The binding epitopes for human CD4+ cells on *Neisseria meningitidis* outer membrane protein (OMP or PorA) that are recognized by most subjects tested encompass immunodominant T-cell epitopes, which are mostly located outside the variable regions and are conserved among different meningococcal (and gonococcal) strains, e.g., corresponding to conserved putative trans-membrane regions of OMP (Wiertz et al. *J Exp Med.* 1992; 176(1): 79-88). Thus, in some embodiments the one or more nnAA substituted is not within a conserved region of OMP.

The binding epitopes for human CD4+ cells on BB, a carrier protein derived from the G protein of *Streptococcus* strain G148, that are recognized by most subjects tested encompass amino acids 25-40 (VSDYYKNLINNAKTVE [SEQ ID NO:5]), 63-78 (DGLSDFLKSQTPAEDT [SEQ ID NO:6]), and 74-89 (AEDTVKSIELAEAKVL [SEQ ID NO:7]) in the BB sequence (Goetsch et al., *Clin Diagn Lab Immunol.* 2003 January; 10(1):125-32). Thus, in some embodiments the one or more nnAA substituted is not within residues 25-40, 63-78, and/or 74-89 of the BB sequence.

In some embodiments the immunogenic polypeptide comprising at least one non-natural amino acid residue further comprises at least one antigen. In some embodiments the immunogenic polypeptide comprising at least one non-natural amino acid is an enhanced carrier protein and further comprises at least one antigen. In some embodiments the immunogenic polypeptide comprising at least one non-natural amino acid is an enhanced carrier protein and further comprises at least one antigen.

III.E T-Cell Epitopes

The T-cell epitopes of a carrier protein are optionally determined by any of the known methods. As an aid in designing improved carrier proteins of the present disclosure, T-cell binding epitopes in proteins are predicted using algorithms that take into account various factors, such as amphipathicity profiles of proteins, sequence motifs, quantitative matrices (QM), artificial neural networks (ANN), support vector machines (SVM), quantitative structure activity relationship (QSAR) and molecular docking simulations, etc. (see, Desai et al. *Methods Mol Biol.* 2014; 1184:333-64). For example, the T-cell binding epitopes in diphtheria toxin/CRM have been predicted using the DeLisi & Berzofsky algorithm (see, Bixler et al. WO89/06974 and *PNAS* 82:7848, 1985). Predicted T-cell epitopes can be experimentally confirmed. For example, the T-cell epitopes of an immunogenic polypeptide of interest can be experimentally determined by synthesizing partially overlapping peptide fragments corresponding to the complete sequence of the immunogenic polypeptide (or predicted regions) and performing proliferation assays of CD4+ cell lines (e.g., peripheral blood mononuclear cells (PBMC)) in the presence of each fragment. This general approach has been employed to map the T-cell epitopes in diphtheria toxin (Raju et al., *Eur J Immunol.* 1995 December; 25(12):3207-14), tetanus toxin (Diethelm-Okita et al., *J Infect Dis.* 1997 February; 175(2):382-91), *Neisseria meningitidis* outer membrane protein (OMP) (*J Exp Med.* 1992 Jul. 1; 176(1): 79-88), and BB, a carrier protein derived from the G protein of *Streptococcus* strain G148 (Goetsch et al., *Clin Diagn Lab Immunol.* 2003 January; 10(1):125-32). One can also directly screen the improved carrier proteins of the present disclosure for CD4+ cell proliferation and/or a cytokine response to establish the presence of a T-cell epitope that has not been inactivated by the presence of one or more nnAAs.

IV. Methods of Conjugate Production

Briefly, the conjugation scheme generally involves cell-free synthesis of the selected polypeptide (e.g., CRM197 or a modified version thereof) followed by activation of the polysaccharide to enable conjugation to the polypeptide, and, finally, conjugation. A mechanical sizing step may be used to reduce the average fragment size of the polysaccharide antigen as will be explained in detail infra.

IV.A. The Polypeptide

In some embodiments, the disclosure provides for a method for synthesis of a polypeptide comprising an nnAA in a cell-free expression mixture maintained at a temperature between about 10 degrees Celsius and about 30 degrees Celsius. In certain embodiments, the temperature is above about 20 degrees Celsius. In certain embodiments, the temperature is below about 20 degrees Celsius. In certain embodiments, the temperature is between about 14 degrees Celsius and about 18 degrees Celsius. In certain embodiments, the polypeptide is encoded by a nucleic acid comprising a suppression codon. In certain embodiments, the cell-free expression mixture comprises an orthogonal tRNA/aminoacyl-tRNA synthetase pair specific for the nnAA. In certain embodiments, the tRNA concentration is at least 20 µM. In certain embodiments, the nnAA concentration is less than about 2 mM and the concentration of the aminoacyl-tRNA synthetase is less than about 5 µM. In certain embodiments, the method comprises conjugating the polypeptide to an active moiety. In certain embodiments, the active moiety is selected from the group consisting of a hapten, a bacterial antigen, a viral antigen, a tumor-derived glycan, a peptide toxin, a macrolide, a polyether, and any combination thereof. In certain embodiments, the polypeptide is selected from the group consisting of a growth hormone, a clotting factor, a plasma protein, an interleukin, a T-cell receptor extracellular domain, a growth factor extracellular domain, a bacterial antigen, a viral antigen, and any combination thereof. In certain embodiments, the expression mixture comprises a cellular extract of E co/i, wheat germ, or rabbit reticulocyte. In certain embodiments, the expression mixture comprises at least 30% cellular extract. In certain embodiments, the polypeptide comprises at least 2, at least 3, at least 4, at least 5, at least 6, at least 7, at least 8, or at least 9 nnAAs. In certain embodiments, the nnAA is selected from the group consisting of 2-amino-3-(4-azidophenyl) propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, 2-amino-3-(4-(azidomethyl)phenyl)propanoic acid, and any combination thereof. In certain embodiments, the polypeptide produced comprises both a soluble and an insoluble fraction, wherein the ratio of the soluble fraction to the insoluble fraction is at least 40% (w/w). In certain embodiments, the polypeptide produced comprises both a soluble and an insoluble fraction, wherein the ratio of the soluble fraction to the insoluble fraction is at least 60% (w/w). In some embodiments, the polypeptide produced by cell-free expression comprises at least 2, at least 3, at least 4, at least 5, at least 6, at least 7, at least 8, or at least 9 nnAAs and the ratio of the soluble fraction to the insoluble fraction is at least at least 20% (w/w), at least 30% (w/w), at least 40% (w/w), at least 50% (w/w), 60% (w/w), at least 70% (w/w), at least 80% (w/w), at least 90% (w/w).

IV.B. Antigens:

Described herein are immunogenic antigens that are optionally further derivatized with a chemical handle to facilitate attachment to an enhanced carrier protein. In some embodiments, the antigens are any purified natural, synthetic, or recombinantly produced macromolecule or fragment thereof. Examples include, but are not limited to lipids, polysaccharides, nucleic acids, or polypeptides, and any combination thereof (e.g. glycoproteins, glycolipoproteins, glycolipids). For instance, the glycolipid optionally is glycophosphatidylinositol. In certain embodiments, the antigen is a T-independent or T-activating antigen (usually a weak T-activating antigen) selected from the group consisting of a bacterial polysaccharide, a bacterial lipopolysaccharide, a tumor-derived glycan, or a hapten.

An antigen comprising a polysaccharide is optionally an oligosaccharide. Oligosaccharides have a low number of repeat units, e.g., 5-15 repeat units, and are typically derived synthetically or by hydrolysis of higher molecular weight polysaccharides.

The antigen comprising a polysaccharide generally has a molecular weight of between about 10 kDa and about 10,000 kDa. In other such embodiments, the polysaccharide has a molecular weight of between 50 kDa and 10,000 kDa. In further such embodiments, the polysaccharide has a molecular weight of between 50 kDa and 10,000 kDa; between 50 kDa and 9,500 kDa; between 50 kDa and 9,000 kDa; between 50 kDa and 8,500 kDa; between 50 kDa and 8,000 kDa; between 50 kDa and 7,500 kDa; between 50 kDa and 7,000 kDa; between 50 kDa and 6,500 kDa; between 50 kDa and 6,000 kDa; between 50 kDa and 5,500 kDa; between 50 kDa and 5,000 kDa; between 50 kDa and 4,500 kDa; between 50 kDa and 4,000 kDa; between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; 100 kDa and 10,000 kDa; between 100 kDa and 9,500 kDa; between 100 kDa and 9,000 kDa; between 100 kDa and 8,500 kDa; between 100 kDa and 8,000 kDa; between 100 kDa and 7,500 kDa; between 100 kDa and 7,000 kDa; between 100 kDa and 6,500 kDa; between 100 kDa and 6,000 kDa; between 100 kDa and 5,500 kDa; between 100 kDa and 5,000 kDa; between 100 kDa and 4,500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; 200 kDa and 10,000 kDa; between 200 kDa and 9,500 kDa; between 200 kDa and 9,000 kDa; between 200 kDa and 8,500 kDa; between 200 kDa and 8,000 kDa; between 200 kDa and 7,500 kDa; between 200 kDa and 7,000 kDa; between 200 kDa and 6,500 kDa; between 200 kDa and 6,000 kDa; between 200 kDa and 5,500 kDa; between 200 kDa and 5,000 kDa; between 200 kDa and 4,500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

In some embodiments, an antigen comprising a polysaccharide has a molecular weight of between about 50 kDa and about 1,400 kDa, such as between about 500 kDa and about 3,000 kDa.

Accordingly, various antigens can be included within the present immunogenic conjugates. Typically, the antigen is a saccharide, where the term "saccharide" includes polysaccharides having 50 or more repeat units, and oligosaccharides having fewer than 50 repeating units. Typically, polysaccharides have from about 50, 55, 60, 65, 70, 75, 80, 85, 90, or 95 repeating units to about 2,000 (sometimes more) repeating units, and optionally from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosaccharides typically have from about 6, 7, 8, 9, or 10 repeating units to about 15, 20, 25, 30, or 35 to about 40 or 45 repeating units.

Useful saccharides for incorporation into immunogenic conjugates include those found in bacteria. These can be non-capsular saccharides (such as an exopolysaccharide e.g. the *S. aureus* exopolysaccharide) but are preferably bacterial capsular saccharides.

Bacterial capsular saccharides are high molecular weight saccharides found in the capsule of Gram-positive or Gram-negative bacteria and they can be used as vaccine antigens. Such capsular saccharides are generally prepared from whole cell lysates or culture supernatant of the corresponding bacterium via processes that involve diafiltration, protein removal, ethanol precipitation, nucleic acid removal, and freeze drying. Bacterial saccharides used with the invention can be intact as found in the bacteria, or can be fragments obtained from intact saccharides e.g. obtained by hydrolysis of saccharides purified from the bacteria.

Saccharide antigens of particular interest include, but are not limited to, those identified below: capsular saccharides of *S. pneumoniae*; saccharides of *Streptococcus pyogenes*; capsular saccharides of *Streptococcus agalactiae*; capsular saccharides of *Haemophilus influenzae*; capsular saccharides of *Neisseria meningitidis*; capsular saccharides of

*Porphyromonas gingivalis*; capsular saccharides of *Salmonella typhi*; saccharides of *Staphylococcus aureas*; surface saccharides of *Clostridium difficile*; glucans; tumor-derived glycans; and haptens.

IV.B.1. Bacterially Derived and Synthetic Polysaccharides

In some embodiments, an antigen comprising a polysaccharide comprises a bacterially derived or synthetic polysaccharide, such as a capsular polysaccharide. Such capsular polysaccharides are high molecular mass polymers of gram-positive or gram-negative bacteria that function to protect the microorganisms against immune responses, and as such represent appealing vaccine targets when the goal is production of neutralizing antibodies. Such capsular polysaccharides are generally prepared from whole cell lysates or culture supernatant of the corresponding bacterium via processes that involve diafiltration, protein removal, ethanol precipitation, nucleic acid removal, and freeze drying. Examples include, but are not limited to, the Merieux protocol (Institut Merieux (1980) Brevet Belge 80:26320) and the Yavordios protocol (Yavordios et al. EP0071515A1 (1983)).

IV.B.2. Capsular Polysaccharides of *S. pneumoniae*

Exemplary antigens for use with the invention are capsular saccharides from *Streptococcus pneumoniae*. *S. pneumoniae* is an encapsulated Gram-positive bacterium that can cause pneumonia, bacteremia, and meningitis. There are at least 90 distinct documented serotypes of *S. pneumoniae* (see e.g. Kalin, M. *Thorax* 1998; 53:159-162) which bear capsular saccharides with serotype-specific repeating unit structures. As will be understood by those in the field, it has been proposed that *S. pneumoniae* serotype 20 is actually made up of two closely related serotypes, the capsular polysaccharides of which are largely cross-protecting (Calix et al. 2012 *J Biol Chem* 287:27885-94). Thus, as would be further appreciated by those of skill in the art, serotype 20 refers to a saccharide that would have previously been classified in the field as serotype 20, and could therefore structurally be either 20A or 20B (from a strain which would have previously been classified in the field as serotype 20, but could genotypically be either 20A or 20B) as disclosed by Calix et al. For example, the strain used to produce serotype 20 polysaccharide in Pneumovax™ (Merck) is now believed to be serotype 20A. In some instances, 20A may be utilized. In other instances, 20B may be utilized. Prevalence in a target population could be a basis for selecting between these serotypes. Nevertheless, because of strains classified as 20, 20A and 20B are serologically similar, they are largely cross-protective in a vaccine and the choice among strain may not be critical. Note that as pointed out earlier, reference to serotype 20 herein may include reference to 20A, 20B, other sub-types within the serotype 20 family, or a combination of any of the foregoing.

The antigen used with the invention can be a capsular saccharide from any of *S. pneumoniae* serotypes 1, 2, 3, 4, 5, 6A, 6B, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, or 48 (Henrichsen *J Clin Microbiol* 1995; 33:2759-2762). However, only a subset of these serotypes are commonly responsible for bacterial infection of clinical significance, so the antigen can be a capsular saccharide from any of *S. pneumoniae* serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. Serotypes 6C, 7C, 15A, 15C, 16F, 20A, 20B, 23A, 23B, 24B, 31, 34, 35B, 35F, 37 and 38 have also become of clinical concern, so the antigen can be a capsular saccharide from one of these *S. pneumoniae* serotypes.

Where the invention uses conjugates from different pneumococcal serotypes, it may be advantageous to include saccharides from at least 14 different *S. pneumoniae* serotypes (e.g. from 15, 16, 17, 18, 19, 20, 21, 22, 23, 24, 25, or more) Where a composition includes 14 or more serotypes, these may include the 13 serotypes 1, 3, 4, 5, 6A, 6B, 7F, 9V, 14, 18C, 19A, 19F, and 23F. In addition to these 13 *S. pneumoniae* serotypes a compositions may include one or more of serotypes 2, 8, 9N, 10A, 11A, 12F, 15B, 17F, 20, 22F, and/or 33F. Alternatively, in addition to the above 13 serotypes, a composition may include one or more *S. pneumoniae* serotypes 2, 6C, 8, 9N, 10A, 12F, 15A, 15B, 15C, 16F, 17F, 20, 22F, 23A, 23B, 24F, 24B, 31, 33F, 34, 35B, 35F and 38. A useful combination of 15 or more (e.g., 16 or more) serotypes includes each of *S. pneumoniae* serotypes 1, 3, 4, 5, 6A, 6B, 7F, 9V, 14, 18C, 19A, 19F, 22F, 23F and 33F, and may also include serotype 8. A useful combination of 20 or more (e.g. 21 or more) *S. pneumoniae* serotypes includes each of serotypes 1, 3, 4, 5, 6A, 6B, 7F, 8, 9V, 10A, 11A, 12F, 14, 15B, 18C, 19A, 19F, 22F, 23F and 33F. A useful combination of 24 or more serotypes includes each of *S. pneumoniae* serotypes 1, 2, 3, 4, 5, 6A, 6B, 7F, 8, 9V, 9N, 10A, 11A, 12F, 14, 15B, 17F, 18C, 19A, 19F, 20, 22F, 23F and 33F. A useful combination of 32 or more serotypes includes each of *S. pneumoniae* serotypes 1, 2, 3, 4, 5, 6A, 6B, 6C, 7F, 8, 9N, 9V, 10A, 11A, 12F, 14, 15A, 15B, 16F, 17F, 18C, 19A, 19F, 20, 22F, 23A, 23B, 23F, 31, 33F, and 35B.

The structures of common pneumococcal serotype capsular saccharide repeating units are described in Jones et al. (Jones C et al. *An Acad Bras Ciênc.* 2005 June; 77(2):293-324):

Type 1
[→3)-D-AAT-α-Galp-(1→4)-α-D-GalpA(2/3OAc)-(1→3)-α-D-GalpA-(1→]
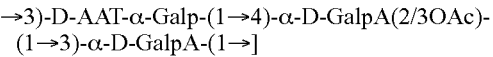

Type 2
[→4)-β-D-Glcp-(1→3)-[α-D-GlcpA-(1→6)-α-D-Glcp-(1→2)]-α-L-Rhap-(1→3)-α-L-Rhap-(1→3)β-L-Rhap-(1→]
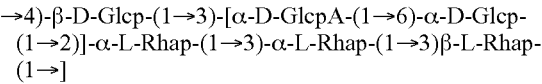

Type 3
[→3)-β-D-GlcA-(1→4)-β-D-Glcp-(1→]
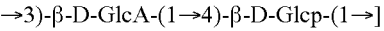

Type 4
[→3)-β-D-ManpNAc-(1→3)-α-L-FucpNAc-(1→3)-α-D-GalpNAc-(1→4)-α-D-Galp2,3(S)Py-(1→]
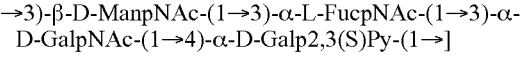

Type 5
[→4)-β-D-Glcp-(1→4)-[α-L-PnepNAc-(1→2)-β-D-GlcpA-(1→3)]-α-L-FucpNAc-(1→3)-β-D-Sugp-(1→]
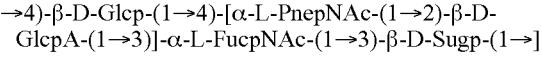

Type 6B
[→2)-α-D-Galp-(1→3)-α-D-Glcp-(1→3)-α-L-Rhap-(1→4)-D-Rib-ol-(5→P→]
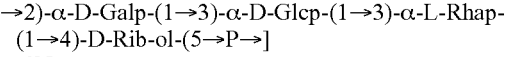

Type 9N
[→4)-α-D-GlcpA-(1→6)-α-D-Glcp-(1→3)-β-D-ManpNAc-(1→4)-β-D-Glcp-(1→4)-α-D-GlcpNAc-(1→]
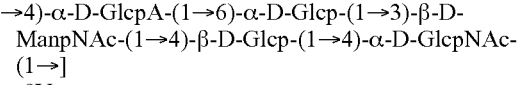

Type 9V
[→4)-α-D-GlcpA(2/3OAc)-(1→3)-α-D-Galp-(1→6)-β-D-ManpNAc(4/6OAc)-(1→4)-β-D-Glcp-(1→4)-α-D-Glcp-(1→]
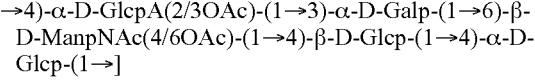

Type 12F
[→4)-[α-D-Galp-(1→3)]α-L-FucpNAc-(1→3)-β-D-GlcNAc-(1→4)-[α-D-Glc-(1→2)-α-D-Glc-(1→3)]-β-D-ManNAcA-(→]
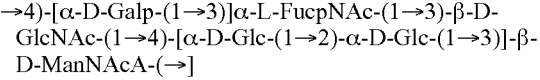

Type 14
[→4)-β-D-Glcp-(1→6)-[β-D-Galp-(1→4)]-β-D-GlcpNAc-(1→3)-β-D-Galp-(1→]

Type 18C
[→4)-β-D-Glcp-(1→4)-[α-D-Glcp(6OAc) (1→2)][Gro-(1→P→3)]-β-D-Galp-(1→4)-α-D-Glcp-(1→3)-β-L-Rhap-(1→]

Type 19F
[→4)-β-D-ManpNAc-(1→4)-α-D-Glcp-(1→2)-α-L-Rhap-(1→P→]

Type 23F
[→4)-β-D-Glcp-(1→4)-[α-L-Rhap-(1→2)]-[Gro-(2→P→3)]-β-D-Galp-(1→4)-β-L-Rhap-(1→]

A more extensive discussion of the saccharides is found in Geno et al. (2015) *Clin. Microbiol. Rev.* 28:871-99, in which Table 1 shows the structures for 97 known serotypes. This table also discloses the proportion of saccharide residues which are acetylated when acetylation is not complete.

The capsular saccharide can be O-acetylated. In some embodiments, the capsular saccharide from serotype 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, or from 1, 2, 3, 4, 5, 6A, 6B, 6C, 7F, 8, 9N, 9V, 10A, 11A, 12F, 14, 15A, 15B, 16F, 17F, 18C, 19A, 19F, 20, 22F, 23A, 23B, 23F, 31, 33F, and 35B, comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is greater than 10%, greater than 20%, greater than 30%, greater than 40%, greater than 50%, greater than 60%, greater than 70%, greater than 80%, greater than 90%, or about 100%. The degree of O-acetylation of the saccharide can determined by proton NMR (see for example Lemercinier & Jones (1996) *Carbohydrate Research* 296:83-96; Jones et al. (2002) *J. Pharmaceutical and Biomedical Analysis* 30:1233-1247). Normally the saccharide used to prepare a conjugate will retain at least 50% (e.g. 75%, or even 100%) of the O-acetylation levels seen in the starting capsular saccharide purified from a bacterium.

The *S. pneumoniae* capsular saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). As an alternative, they may be obtained from a commercial source (e.g., ATCC) or synthetically produced.

A pneumococcal capsular saccharide antigen used with the invention can usefully have a molecular weight between 10 kDa and 4,000 kDa e.g. between 50 kDa and 3,000 kDa, or between 100 kDa and 2,000 kDa. For instance, the molecular weight can be between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Further details and guidance with respect to molecular weights are available in appendix B.

The capsular saccharide is optionally chemically modified relative to the capsular saccharide found in nature. For example, the saccharide is optionally de-O-acetylated (partially or fully), de-N-acetylated (partially or fully), N-propionated (partially or fully), etc. De-acetylation optionally occurs before, during or after activation, derivatization, or conjugation, but typically occurs before conjugation.

Some embodiments of the invention involve the use of two or more different conjugates. In relation to pneumococcal capsular saccharide conjugates, this means (when using a single type of carrier polypeptide for each conjugate) that each 'different' conjugate has a saccharide from a different pneumococcal serotype.

IV.B.3. Polysaccharides of *S. pyogenes*

The antigen can be a saccharide from *S. pyogenes*. *S. pyogenes* is a gram-positive bacterium (also known as group A *streptococcus* or 'GAS') responsible for a wide array of infections in humans, including pharyngitis, tonsillitis, scarlet fever, cellulitis, erysipelas, rheumatic fever, post-streptococcal glomerulonephritis, necrotizing fasciitis, myonecrosis and lymphangitis. In some embodiments, the polysaccharide is the capsular polysaccharide of *S. pyogenes*, which is composed of hyaluronic acid, a high molecular weight polymer where the repeating unit has the structure:

[→4)-β-D-GlcUAp-(143)-β-D-GlcpNAc-(→]

which appears to be invariant between *S. pyogenes* serotypes.

In some embodiments, the capsular polysaccharide from *S. pyogenes* has a molecular weight of between 10 kDa and 4,000 kDa, for example between 50 kDa and 4,000 kDa; between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

In certain embodiments, the polysaccharide is a non-capsular polysaccharide from *S. pyogenes*. Non-capsular polysaccharides include the group-A-strep cell wall polysaccharide, which comprises a backbone of poly-L-rhamnopyranosyl units connected by alternating α-L (1→3) and α-L-(1→2) linkages, to which N-acetyl-β-D-glucosamine residues are attached at the 3-position of the rhamnose backbone.

In an embodiment, the group-A-strep cell wall polysaccharide from *S. pyogenes* has a molecular weight of between 10 kDa and 4,000 kDa. In other such embodiments, the polysaccharide has a molecular weight of between 50 kDa and 4,000 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

IV.B.4. Capsular Polysaccharides of *Streptococcus agalactiae*

The antigen can be a capsular polysaccharide derived from *S. agalactiae* (Group B *Streptococcus* or GBS), a gram-positive bacterium commonly commensal with mammals that causes septicemia, pneumonia, and meningitis in immunologically vulnerable humans and bovine mastitis in dairy cows. There are at least 10 *S. agalactiae* serotypes with distinct capsular polysaccharide repeating units (Ia, Ib, II-IX), but only a few serotypes are commonly responsible for disease. These include serotypes Ia, Ib, II, III, and V, and conjugates of capsular polysaccharides from these serotypes can be prepared. The structures for the capsular polysaccharide repeating units of common *S. agalactiae* serotypes have been determined and are:

Type Ia

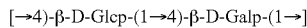

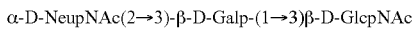

Type Ib

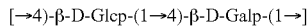

Type II

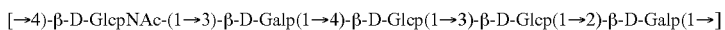

Type III

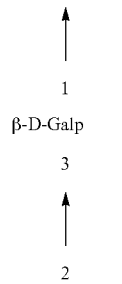

Type V

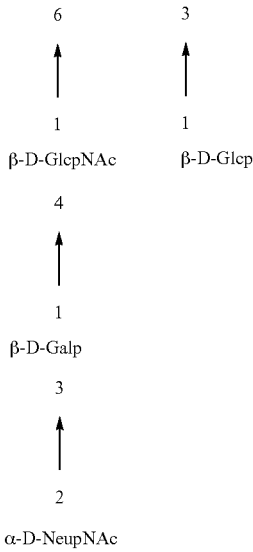

IV.B.5. Capsular Polysaccharides of *Haemophilus* Influenzae

In some embodiments, the antigen comprising a polysaccharide comprises a capsular polysaccharide derived from *H. influenzae*. *H. influenzae* is a gram-negative, anaerobic pathogenic bacterium responsible for a wide range of localized and invasive infections including pneumonia, bacteremia, meningitis, epiglottitis, cellulitis and infectious arthritis. There are at least 6 serotypes of *H. influenzae* with distinct capsular polysaccharide chemical structures (types a-f). However, only type a and type b are considered "high-virulence" strains of *H. influenzae*, and the bulk of childhood infections are thought to be caused by type b (Jin et al. *Infect. Immun.* June 2007 vol. 75 no. 6 2650-2654), which is thus the preferred type of *H. influenzae* polysaccharide for use with the invention. The structure of the repeating unit of the type b capsular polysaccharide has been determined and is:

[→3)-β-D-Ribf-(1→1)-D-Ribitol-(5→OPO$_3^-$→].

IV.B.6. Capsular Polysaccharides of *Neisseria meningitidis*:

In some embodiments, the antigen comprising a polysaccharide comprises a capsular polysaccharide derived from *N. meningitidis*. *N. meningitidis* is a gram negative bacterium that is a major causative agent of meningitis and meningococcal septic infection. There are at least 13 serogroups of *N. meningitidis* with distinct capsular polysaccharide chemical structures (serogroups A, B, C, E-29, H, I, K, L, W-135, X, Y, Z, and Z' (29E)). However, only six serogroups (A, B, C, W-135, X, Y) are thought to cause life-threatening disease. The structures of the repeating unit of the capsular polysaccharide for the five main life threatening serogroups of interest for conjugate preparation have been determined and are:

Type A
[→6)-α-D-ManpNAc(3/4OAc)-(1→OPO3→]
Type C
[→9)-α-D-Neup5Ac(7/8OAc)-(2→]
Type W-135
[→6)-α-D-Galp-(1→4)-α-D-Neup5Ac(9OAc)-α-(2→]
Type X
[→4)-α-D-GlcpNAc-(1→OPO$_3$→]
Type Y
[→6)-α-D-Glcp-(1→4)-α-D-Neup5Ac(9OAc)-α-(2→]

IV.B.7. Capsular Polysaccharides of *Porphyromonas gingivalis*:

In certain embodiments, the antigen is a capsular polysaccharide derived from one of the six serotypes of *Porphyromonas gingivalis* (e.g., K1, K2, K3, K4, K5 and/or K6). See Van Winkelhoff et al. (1993) *Oral Microbiol. Immunol.* 8:259-265; and Laine et al. (1996) *J. Periodontal Res.* 31: 278-84.

IV.B.8. Capsular Polysaccharides of *Salmonella typhi*

In certain embodiments, the antigen is a Vi polysaccharide. Vi is the capsular polysaccharide of *Salmonella typhi* (previously classified as a species itself, but now referred to as the *typhi* serovar of *S. enterica*). Vi may also be found in other serovars of *Salmonella* (such as *S. enterica* serovar *paratyphi* C or serovar *dublin*) and in other bacteria, such as *Citrobacter* (e.g. *C. freundii* and *C. youngae*). The Vi polysaccharide is a linear homopolymer of a hexosaminuronic acid, α1,4-N-acetylgalactos-aminouronic acid, which is 60-90% acetylated at the C-3 position. The O-acetyl substitution on Vi is a factor in its ability to elicit a protective immune response. The immunogenicity of Vi is closely related to its degree of O-acetylation. Partial de-O-acetylation can slightly increase immunogenicity; complete de-O-acetylation eliminates the immunogenicity of Vi. The Vi polysaccharide used in the present invention may be chemically modified relative to the capsular polysaccharide as found in nature. For example, the Vi polysaccharide may be partially de-O-acetylated, de-N-acetylated (partially or fully), N-propionated (partially or fully), etc. De-acetylation may occur before, during or after conjugation, but preferably occurs before conjugation. The effect of de-acetylation etc. can be assessed by routine assays.

IV.B.9. Saccharides of *Staphylococcus aureus*

In certain embodiments, the antigen is a polysaccharide from *S. aureus*. The polysaccharide can be the exopolysaccharide of *S. aureus*, which is a poly-N-acetylglucosamine (PNAG), or the capsular polysaccharide of *S. aureus*, which can be e.g. type 5, type 8 or type 336.

IV.B.10. Surface Polysaccharides of *Clostridium difficile*

In certain embodiments, the antigen is a surface glycan from *C. difficile*, such as PS-I or PS-II.

IV.B.11. Glucans

In certain embodiments, the antigen is a glucan containing β-1,3-linkages and/or β-1,6-linkages. These conjugated glucans can be useful for raising an anti-fungal immune response, for example against *Candida albicans*. Glucans are glucose-containing polysaccharides found inter alia in fungal cell walls. β-glucans include one or more β-linkages between glucose subunits. A glucan used in accordance with the invention includes β-linkages, and may contain only β-linkages (i.e. no α linkages). The glucan may comprise one or more β-1,3-linkages and/or one or more β-1,6-linkages. It may also comprise one or more β-1,2-linkages and/or β-1, 4-linkages, but normally its only βlinkages will be β-1,3-linkages and/or β-1,6-linkages. The glucan may be branched or linear. The glucan may be a fungal glucan. A 'fungal glucan' will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis*, *Trichophyton verrucosum*, *Blastomyces dermatidis*, *Cryptococcus neoformans*, *Histoplasma capsulatum*, *Saccharomyces cerevisiae*, *Paracoccidioides brasiliensis*, or *Pythiumn insidiosum*. There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. In some embodiments the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia bicyclis* laminarin, but as high as 7:1 in *Laminaria digititata* laminarin. Thus the glucan used with the invention may have a β(1-3):β(1-6) ratio of between 1.5:1 and 7.5:1 e.g. about 2:1, 3:1, 4:1, 5:1, 6:1 or 7:1. In other embodiments, the glucan has exclusively or mainly β-1,3 linkages, as seen in curdlan. Thus the glucan may be made solely of β-1,3-linked glucose residues (e.g. linear β-D-glucopyranoses with exclusively 1,3 linkages). Optionally, though, the glucan may include monosaccharide residues that are not β-1,3-linked glucose residues e.g. it may include β-1,6-linked glucose residues. The ratio of β1,3-linked glucose residues to these other residues should be at least 8:1 (e.g. ≥9:1, ≥10:1, ≥11:1, ≥12:1, ≥13:1, ≥14:1, ≥15:1, ≥16:1, ≥17:1, ≥18:1, ≥19:1, ≥20:1, ≥25:1, ≥30:1, ≥35:1, ≥40:1, ≥45:1, ≥50:1, ≥75:1, ≥100:1, etc.).

IV.B.12. Tumor-Derived Glycans

In some embodiments, an antigen comprising a polysaccharide comprises a developmentally-inappropriate cell-surface glycan characteristic of tumor cells. Danishefsky (reviewed in Zhu et al. *Expert Rev Vaccines*. 2009(10):1399-1413) among others have discovered that certain oligosaccharide motifs (stage-specific embryonic antigens, SSEAs) are originally expressed on cell surfaces during embryogenesis and "reactivated" in adult tumors. As these are short polysaccharides, they are primarily accessed via chemical synthesis (reviewed in Zhu above). Among these oligosaccharides, the most clearly associated with carcinogenesis (e.g. prostate and breast cancer) are Globo-H, Le$^y$, STn, TF, and Tn.

IV.B.13. Haptens

In some embodiments, an antigen comprises a hapten: a non-polymeric synthetic moiety of molecular weight less than 1,000 Da. The application of haptens in therapeutic protein conjugates is of haptens that mimic drugs of abuse, e.g., nicotine or cocaine (see, e.g., Berkowitz & Spector. *Science*. 1972(178):1290-1292 for morphine; Kosten et al. *Vaccine*. 2002(20):1196-1204 for cocaine; and Hatsukami et al. *Clin Pharmacol Ther*. 2005(78):456-467). The conjugation of otherwise poorly-immunogenic small molecules to immunogenic polypeptides allows for drug specific antibodies to be raised, which sequester abusive drugs away from the central nervous system.

Antigens often do not intrinsically contain functional groups that are suitable or ideal for conjugation. Thus an antigen might need to be functionalized prior to its conjugation to the nnAA. Further details of such functionalization are given below.

IV.C. Activation and Conjugation Via Chemical Handle: Overview

Conjugation involves formation of a covalent linkage between the nnAA residue and the antigen. This requires a reactive functional group in both the nnAA and the antigen. A nnAA for the carrier polypeptide will generally be chosen because it already has a suitable functional group (e.g. the azido group of pAMF), but antigens often do not intrinsically contain functional groups that are suitable or ideal for conjugation. Thus an antigen might need to be functionalized prior to its conjugation to the nnAA.

Detailed technical information about conjugation can be found in *Bioconjugate Techniques* (Greg T Hermanson, 3rd edition, 2013). Methods for functionalizing antigens and conjugating the functionalized antigens to nnAA are also described infra. As noted above, useful nnAA include a functional group (e.g. an azido group) which is suitable for a "click" chemistry reaction with a functional group on the antigen. Thus a functionalized antigen ideally includes a group suitable for such "click" reactions.

In general terms, conjugation thus takes place by a process comprising 3 steps: (a) activating the antigen; (b) optionally derivatizing the activated antigen (e.g. with a linker or nucleophilic group) to introduce a reactive functional group not normally present in the antigen; and (c) conjugating the antigen to the carrier polypeptide via a group introduced in step (a) or, if present, step (b). In some embodiments step (a) includes a first step of removing a blocking group on the antigen, such that certain functional groups (e.g. hydroxyls, amines, thiols) are more accessible to activation. Sometimes the steps (a)-(c) can occur essentially simultaneously (e.g. where a reactive moiety such as N-hydroxysuccinimide is added to the antigen), but in other embodiments two or more of steps (a)-(c) are discrete, with optional purification between steps.

As noted above, cross-linked conjugates are advantageous, so it is also useful to introduce multiple reactive functional groups per antigen molecule. For instance, multiple aldehyde or cyanate ester groups can be introduced when activating a saccharide molecule. These groups can then be derivatized e.g. to introduce a reactive cyclooctyne which can then react with azido groups in in the nnAA.

An antigen can be activated using various chemistries, detailed in Section IV.D. Initially, the antigen is functionalized with a reactive moiety, i.e., a "first chemical handle," that is capable of participating in a click chemistry reaction with a bio-orthogonal reactive moiety, i.e., a "second chemical handle," on a second reactant. For example, the first chemical handle can be reacted with the activated antigen (e.g. DBCO-NH$_2$ or DBCO-PEG$_4$-NH$_2$) and then the antigen-chemical handle moiety is reacted with a second chemical handle (e.g., azido on pAMF) on the modified carrier protein to form a protein-antigen conjugate as described in greater detail herein. Antigen activation in this manner is carried out within the context of a two-part method for conjugate preparation. The method involves a first, activation step in which a saccharide antigen is covalently modified with a selected reagent or reagents to provide a plurality of first functional groups on the saccharide, the functional groups serving as a "first chemical handle." The activated saccharide so provided is then covalently conjugated to the carrier polypeptide having a plurality of second functional groups each associated with an nnAA and serving as a "second chemical handle," where the covalent coupling between the saccharide and the polypeptide occurs by reaction of the first chemical handle with the second chemical handle.

Suitable chemical groups for "click" chemistry include, but are not limited to, azido (—N$_3$), alkyne (C≡C), a phosphine (e.g. —P(Ph)$_2$), alkene (C=C) and 1,2,4,5-tetrazine

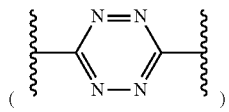

groups.

The first chemical handle is introduced via a general process comprising three steps: (a) activating the antigen; (b) optionally reacting the antigen with a linker or nucleophilic group to introduce reactivity not normally present in the antigen; and (c) conjugating the antigen to the chemical handle. In some embodiments, two or more of steps (a)-(c) are simultaneous, as in the case where a chemical handle is modified by the addition of a reactive moiety such as N-hydroxysuccinimide. In some embodiments two or more of steps (a)-(c) are discrete, with optional purification of the antigen between steps. In some embodiments step (a) additionally comprises a step to remove a blocking group on the antigen, such that certain functional groups (e.g. hydroxyls, amines, thiols) are more accessible to activation.

The chemical handle is optionally introduced at varying locations with respect to the antigen. In some embodiments, the chemical handle is introduced at a terminus (e.g. reducing and non-reducing ends of a polysaccharide, the N- and C-termini of a polypeptide, or the end of the acyl chain of a glyceride). In some embodiments the chemical handle is introduced at an internal location (e.g. an internal amino acid of a polypeptide, or an internal hydroxyl, amine, or activated hydroxyl of a polysaccharide). In some embodiments the chemical handle is introduced at one or more termini in addition to an internal location. The particular method of activation used for the antigen will affect the locations activated for conjugation, and hence the ultimate location of the conjugated chemical handle on the antigen. It is useful to introduce multiple chemical handles into an antigen such that it can achieve multiple linkages with carriers.

In certain embodiments, a method for conjugating a polypeptide to an antigen via chemical handles is as follows. An antigen is activated to incorporate at least one first chemical handle therein, where the first chemical handle is capable of conjugating to a second chemical handle of an nnAA in the polypeptide. The activated antigen is combined with a polypeptide containing at least one nnAA bearing the second handle under conditions in which the first and second chemical handles react to form an antigen-polypeptide conjugate. The reaction thus enabled is a non-catalytic covalent bioconjugation reaction. The reactive sites on the antigen that serve as the "first chemical handle" are preferably alkynyl groups, where the alkynyl groups may be incorporated in a molecular context that increases reactivity. For instance, the alkynyl groups may be incorporated into a ring, e.g., a cyclooctynyl ring, such as a diaryl-strained cyclooctyne. Useful reactive sites in the polypeptide, i.e., the "second chemical handle" provided by the nnAA residues, are azido groups. As known in the art, the reaction in this case is a [3+2] cycloaddition referred to in the art as "strain-promoted azide-alkyne cycloaddition" (SPAAC), discussed in further detail infra.

As will be explained in further detail infra, the activated antigen can be conjugated to a nnAA directly, but usually the activated group is derivatized to introduce a functional group that shows better reactivity towards the nnAA's functional group. For instance, an alkynyl group can be introduced. A bifunctional reagent with an amino group and an alkyne group can react with an aldehyde group that has been introduced into an antigen (e.g. via reductive amination) thereby leaving a pendant alkyne which can react with a nnAA. For instance, bifunctional reagents including amino and DBCO functional groups can be used.

IV.D. Antigen Activation

Prior to functionalization of a saccharide antigen to provide an activated antigen capable of conjugation to a carrier polypeptide, the antigen may be subject to a process that reduces molecular weight. The process may be a mechanical sizing step, in which case the polysaccharide is subjected to shearing forces (as may accomplished using a high shear homogenizer or the like), and/or the process may involve treatment with heat or mild acid. Ideally, the molecular weight of the antigen following this initial treatment will approximate, within 25-30%, the native molecular weight of the corresponding serotype. One example of a mechanical sizing method involves use of a PandaPLUS 2000 homogenizer (available from GEA Niro Soavi) at a pressure in the range of about 200 psi to about 25,000 psi and a heat exchanger temperature setting in the range in of about 4° C. to 12° C. (e.g., 8° C. to 12° C.), with a polysaccharide concentration of about 1 g/L to about 4 g/L and a temperature range during processing of about 8° C. to 15° C.

The selected antigen can be activated using any suitable method, including, without limitation: periodate oxidation (e.g. to oxidize hydroxyl groups on adjacent carbon atoms to give reactive aldehyde groups, for instance as disclosed in WO2011/110531); unmasking of an intrinsic aldehyde (e.g. a reducing terminus of a polysaccharide); cyanylation using, e.g., 1-cyano-4-dimethylaminopyridinium tetrafluoroborate (CDAP) activation; and hydroxyl activation with 1,1'-carbonyldiimidazole (CDI) followed by nucleophilic addition. Further chemical strategies for saccharide derivatization are described in Hermanson (Hermanson, Greg. *Bioconjugate Techniques* (2008)). Activation can also involve the use of p-nitrophenylcyanate, N-cyanotriethylammonium tetrafluoroborate, active esters, carbodiimides, hydrazides, norborane, p-nitrobenzoic acid, N-hydroxysuccinimide, S-NHS, EDC, TSTU, etc.

Periodate oxidation and CDAP cyanylation are two useful activation techniques. Periodate oxidation has been shown to be useful for activating, inter alia, pneumococcal serotypes 1, 2, 3, 7F, 8, 9N, and 11A. CDAP cyanylation has been shown to be useful for activating, inter alia, pneumococcal serotypes 3, 7F, and 10A.

The invention additionally provides an antigen (in particular a polysaccharide antigen as disclosed herein, such as a pneumococcal capsular polysaccharide antigen) which is activated according to any of the chemistry discussed below e.g. the product of reacting the antigen with one or more the DBCO and DIFO groups discussed below.

IV.D.1. Periodate Activation:

One technique for activating saccharide antigens herein involves treatment with a periodate reagent followed by reductive deamination, with the activated antigen so provided then available for conjugation to an appropriately functionalized polypeptide carrier. Periodate activation is thus a two-step method, with an initial periodate oxidation reaction followed by purification of the oxidation product and then a second reaction involving reductive amination as will be explained infra. Periodate oxidation, as is understood in the field, involves the cleavage of adjacent hydroxyl groups, i.e., hydroxyl groups in the form of a "vicinal" diol in which two adjacent carbon atoms are each substituted with a hydroxyl group. Periodate cleavage of such a diol results in the breakage of the carbon-carbon bond and formation of an aldehyde moiety at each carbon atom, e.g., a —$CH_2(OH)$—$CH_2(OH)$— motif is converted upon periodate oxidation to —C(CO)H at each carbon atom. Periodate activation thus activates carbohydrate sugar residues bearing adjacent hydroxyl moieties; periodate can also be used to activate amino acids containing the 2-amino alcohol moiety, i.e., N-terminal threonine or serine residues. As the aldehyde moiety has a long half-life, antigens activated by this method are optionally chromatographically purified and/or lyophilized after activation.

For periodate oxidation of antigens: (a) antigens are dissolved in a solution, e.g., in water or an aqueous buffer; (b) a source of periodate is added to the antigen from a concentrated stock solution to form an oxidation mixture; (c) the reaction mixture is incubated; and (d) (optional) excess periodate is removed.

Deionized water or a suitable buffered solution is optionally used for the oxidation reaction. In some embodiments, the solution in step (a) is deionized water. In some embodiments, the solution in step (a) comprises an effective amount of a buffer with a pKa around physiological pH. In some embodiments, the solution in step (a) comprises an effective amount of a buffer with a pKa around physiological pH. Step (a) may be provided as a solution in an aqueous buffer, e.g., having a pH in the range of 5.1 to 5.9 (e.g., 5.2-5.9, 5.3-5.7, 5.4-5.6, 5.4-5.9). In some embodiments, the buffer does not comprise an amine group. Examples of amine-free buffers include, but are not limited to acetate, formate, and phosphate. In some embodiments, an amine buffer is employed in step (a). Suitable amine buffers generally comprise a combination of a tertiary amine or an N-heterocyclic compound with a weak acid (e.g., pyridine and acetic acid; pyridine and formic acid; N-ethylmorpholine and acetic acid; trimethylamine and carbonic acid; triethanolamine and phosphoric acid; etc.), or they can be a zwitterionic amine buffer such as 4-(2-hydroxyethyl)-1-piperazineethanesulfonic acid (HEPES), 2-(N-morpholino)ethanesulfonic acid (MES), or 3-[4-(2-hydroxyethyl)piperazin-1-yl]propane-1-sulfonic acid (HEPPS).

The periodate source in step (b) is optionally selected from any periodate source with appropriate stability in aqueous solution. Examples of periodate sources include, but are not limited to, sodium periodate, potassium periodate, tetrabutylammonium (meta)periodate, barium periodate, sodium hydrogen periodate, sodium (para)periodate, and tetraethylammonium (meta)periodate.

In some embodiments, the level of periodate addition and reaction conditions are adjusted to convert all available diols on a polysaccharide to aldehydes. For example, large excesses of sodium periodate (>1000× excess with respect to the molar concentration of polysaccharide, or a 10 mM solution of sodium periodate) in combination with incubation at room temperature favor total conversion of diols to aldehydes.

In some embodiments, the level of periodate addition and reaction conditions are adjusted to introduce a low amount of oxidation/aldehyde formation into the polysaccharide chain. Less than stoichiometric amounts of sodium periodate (e.g. <1.0 equivalents) in the oxidation reaction favor low amounts of polysaccharide chain oxidation. For example, a bacterial saccharide is activated by 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate (see WO2011/110531). In certain embodiments, 0.4 molar equivalent of periodate is added to a pH 6.0 solution containing a pneumococcal capsular polysaccharide and incubated for 17 hrs at 25° C. (see WO2011/110531).

In some embodiments, the relative amount of periodate reagent added into the saccharide antigen solution is typically, although not necessarily, in the range of 0.1 equivalents to 0.5 equivalents of periodate, with "equivalents" being relative to individual saccharide units (i.e., saccharide "monomer" units in a polysaccharide). Reaction conditions for periodate oxidation of a saccharide antigen can vary, but in certain embodiments are as follows: a reaction pH in the range of 5 to 7, such as 5 to 6 or 5.4 to 5.9, e.g., 5.4; a reaction temperature in the range of 4° C. to 25° C.; a reaction time in the range of 2 to 30 hours, e.g., 2 to 24 hours, 14 to 30 hours, 14 to 24 hours, 18 to 30 hours, 18 to 24 hours, 24 hours, and the like; and polysaccharide-aldehyde (PS-aldehyde) purification carried out using dialysis, size exclusion chromatography (SEC), ultrafiltration/diafiltration (UF/DF), or the like. The PS-aldehyde is maintained in an aqueous buffer throughout the activation process, typically a buffer having a concentration in the range of about 25 mM to about 150 mM, such as about 50 mM to about 110 mM, including 50 mM and 110 mM (e.g., 110 mM for serotypes 6B and 23F and 50 mM for other periodate-activatable serotypes), and is not "isolated" from aqueous buffer at any point during the activation reactions.

Periodate treatment can also be used as a way to decrease the molecular weight of polysaccharides that have a interchain glycerol phosphate linkage as periodate tends to cleave such linkages. If the purpose of the periodate treatment is both sizing and activation, larger amounts of the periodate reagent can be used.

Following purification of the PS-aldehyde intermediate, the PS-aldehyde is dissolved in an aqueous buffer, typically maintained at a pH in the range of 5 to 7, such as 5 to 6.7, 5 to 6.5, 5.5 to 6.9, 5.5 to 6.7, 5.5 to 5.9, or 5.7.

The second step of periodate activation, reductive amination, is carried out by adding to the PS-aldehyde solution an activating reagent in the form of a reactive moiety coupled to a primary amino group, followed by admixture with sodium cyanoborohydride, for a time period effective to transfer the reactive moiety to the cyanate-substituted saccharide, thereby providing an activated saccharide antigen. In some embodiments, 2 to 12 equivalents of the cyanoborohydride are used; in other embodiments, 4 to 12, 6 to 12, or 8 to 12 equivalents are used. The reactive moiety is one that is capable of participating in a click chemistry reaction with a second, bio-orthogonal reactive moiety at nnAA residues on the polypeptide carrier, as will be discussed below. The reaction temperature for reductive amination can vary, as can reaction time, but typical reaction temperatures are in the range of about 20° C. to about 25° C., and typical reaction times are in the range of about 6 to 48 hours, e.g., 24 hours.

One example of a useful activating reagent is a dibenzylcyclooctyne (DBCO) derivative having the structure (I).

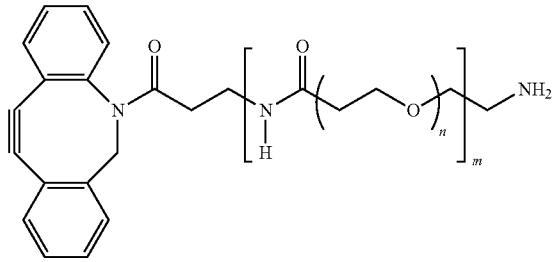

(I)

wherein m is zero or 1 and n is an integer in the range of 2 to 12. In some embodiments, m is 1 and n is an integer in the range of 2 to 12, e.g., 2 to 8, 2 to 6, 2 to 4, or 4. In certain embodiments, m is zero. The reactive moiety in this case is the alkyne functionality in the eight-membered ring, the reactivity of which is enhanced by the strain imposed by the adjacent phenyl rings. The amount of the DBCO derivative used in the reaction is usually in the range of 1 to 3 equivalents, e.g., at least 2 equivalents, such as 2 equivalents or 3 equivalents, again relative to the individual saccharide units, with the DBCO dissolved in a suitable solvent such as DMSO. The amount of sodium cyanoborohydride employed is typically in the range of 2.0 to 12.0 equivalents, again relative to the saccharide units. In some embodiments, the amount of sodium cyanoborohydride is in the range of in the range of 8.0 to 12.0 equivalents, as this excess can increase the "degree of the activation reaction," or "DBCO %," (i.e., the mol amount of DBCO incorporated per mole of polysaccharide repeating unit). The reaction is allowed to proceed, with stirring, for 6 to 48 hours at a reaction temperature typically in the range of 20° C. to 25° C., with the DBCO-derivatized antigen then purified using any conventional technique, e.g., dialysis, SEC, UF/DF, or the like.

In some embodiments, a periodate activation method is provided that can be used across a plurality of antigen serotypes to provide a target DBCO %, wherein the only variable that may need to be adjusted for a specific serotype is the relative amount of periodate used per polysaccharide unit, i.e., periodate molar equivalents. "DBCO %" refers to one measure of the yield of the activation reaction and is defined the amount of DBCO derivative that reacts with the saccharide relative to the total DBCO derivative employed. Other variables can be kept constant regardless of the specific serotype undergoing activation, i.e., reaction pH, activation time, reaction temperature, molar equivalents of DBCO, and overall reaction time. These standardized conditions provide a target DBCO %, typically in the range of 3% to 15%, e.g., 3% to 5%, 5% to 15%, 5% to 7%, such as 3% to 10%, e.g., 3% to 5%, 5% to 10%, 5% to 7%, and the like.

Exemplary reaction conditions that are generally useful for all periodate-activatable serotypes (e.g., serotypes 5, 6A, 6B, 7F, 12F, 14, 20. and 23F; see Table 2, infra) are set forth in Table 1:

TABLE 1

| Aspect of procedure | Specification/value |
|---|---|
| Polysaccharide sizing (mechanical, chemical, thermal) | Optional |
| Periodate activation reaction | |
| Polysaccharide concentration | 1 to 5 mg/mL (e.g., 2 mg/mL) |
| $NaIO_4$ molar equivalents | 0.1 to 0.5 |
| Periodate reaction buffer | Acetate or other |
| Periodate reaction buffer concentration | 25 mM to 150 mM (e.g., 50 mM to 110 mM) |
| Periodate buffer pH | 5 to 7 (e.g., 5.4 to 5.9) |
| Periodate reaction temperature | 4° C. to 25° C. |
| Periodate reaction time | 2 to 30 hours (e.g., 14 to 30 hours) |
| Reductive amination reaction | |
| Oxidized polysaccharide concentration | 1 to 5 mg/mL (e.g., 2-3 mg/mL) |
| Activating reagent | DBCO-amine or DBCO-[PEG]$_n$-amine |
| Reductive amination buffer pH | 5.5 to 6.9 (e.g., 5.5 to 5.9) |
| $NaCNBH_3$ molar equivalents | 2 to 12 |
| Reductive amination reaction temperature | 20° C. to 25° C. |
| Reductive amination reaction time | 6 to 48 hours (e.g., 24 hours) |

Representative standardized conditions in this embodiment involve the following:
  (a) after an optional sizing step, carried out mechanically, thermally or chemically as described above, providing the saccharide antigen as a solution in an aqueous buffer, e.g., a phosphate buffer, having a pH in the range of 5.4 to 5.9;
  (b) oxidizing the saccharide antigen with an effective oxidizing amount of a periodate reagent, e.g., sodium periodate, thereby providing an aldehyde-bearing saccharide, where the amount of periodate reagent may vary with antigen serotype;
  (c) purifying the aldehyde-bearing saccharide;
  (d) in a reductive amination reaction, contacting the aldehyde-bearing saccharide with an activating reagent comprising the reactive moiety coupled to a primary amino group, followed by admixture with 8 to 12 equivalents of sodium cyanoborohydride for a time period in the range of 6 to 48 hours, e.g., 14 to 30 hours, 14 to 24 hours, or 24 hours, such as 18 to 30 hours, e.g., 18 to 24 hours or 24 hours, during which the reactive moiety is transferred to the cyanate-substituted saccharide, thereby providing an activated saccharide antigen.

Alternative conditions in this embodiment involve the following:
  (a) after an optional sizing step, providing the saccharide antigen as a solution in an aqueous buffer, e.g., an acetate buffer (e.g., about 110 mM-120 mM), having a pH of about 5.4;
  (b) oxidizing the saccharide antigen with an effective oxidizing amount of a periodate reagent, e.g., sodium periodate, thereby providing an aldehyde-bearing saccharide, where the amount of periodate reagent may vary with antigen serotype;
  (c) purifying the aldehyde-bearing saccharide;
  (d) in a reductive amination reaction, contacting the aldehyde-bearing saccharide with an activating reagent comprising the reactive moiety coupled to a primary amino group, followed by admixture with 8 to 12 equivalents of sodium cyanoborohydride for a time period in the range of 6 to 48 hours, e.g., 14 to 30 hours, 14 to 24 hours or 24 hours, such as 18 to 30 hours, e.g., 18 to 24 hours or 24 hours, during which the reactive moiety is transferred to the aldehyde-bearing saccharide, thereby providing an activated saccharide antigen.

In some embodiments, a capping step follows reductive amination in order to cap unreacted aldehyde moieties on the polysaccharide; in other embodiments, capping is optional, e.g., when reductive amination is carried out using a higher ratio of the cyanoborohydride reagent to saccharide units. See Section IV.E.1, infra.

In some embodiments, fewer than 0.001%, 0.01%, 0.1%, 0.5%, 1%, 2%, 5%, 10%, 30% or 50% of the vicinal diols of a bacterial saccharide become oxidized during periodate activation (see WO2011/110531) e.g. between 5-10%. Low reaction temperatures also favor lower amounts of polysaccharide chain oxidation. In some embodiments low periodate concentrations (<0.1 eq) are combined with reactions overnight at 4° C. to minimize polysaccharide chain oxidation of particular capsular polysaccharides, such as *S. pneumoniae* 19F.

In some embodiments, the level of periodate addition and reaction conditions are adjusted to direct cleavage to selective sugars a polysaccharide chain. For example, 1 mM NaIO$_4$ at 4 degrees Celsius is used in the literature to selectively oxidize sialic acid residues at carbons 7, 8, or 9, while 10 mM NaIO$_4$ at room temperature is used to oxidize a wide variety of sugar residues, including sialic acid, galactose, and mannose residues.

For oxidation of N-terminal serine or methionine residues in protein antigens, milder oxidation conditions (low periodate concentrations and reaction times) are generally used, to avoid oxidative damage to internal side chains of the antigens. In an embodiment, step (b) comprises adding sodium periodate to a final concentration of 2.5 mM and step (c) comprises incubating the reaction mixture at 25 degrees Celsius for 3 minutes.

Because excess unreacted periodate can cause higher than desirable oxidation levels or damage to immunogenic moieties in the antigen, excess periodate is optionally removed in step (d). For large antigens (>10 kDa), excess periodate, in some embodiments, is removed by size exclusion, dialysis, or diafiltration against water or buffer solution using a medium with a suitable molecular weight cutoff or exclusion limit. For small antigens where size-based purification is inconvenient (short peptides or oligosaccharides), and removal of periodate in step (d) comprises adding a quenching agent. Excess periodate is optionally quenched by the addition of glycerol (10% (v/v)), the addition of a molar excess of sodium sulfite, or the addition of a molar excess of N-acetylmethionine.

In some embodiments, a polysaccharide or protein antigen is deprotected to increase accessibility of hydroxyl or amine groups for periodate activation. In some embodiments, O-acetyl or N-acetyl groups on polysaccharides are removed to increase reactivity of adjacent hydroxyls to periodate. For polysaccharide antigens, de-O-acetylation or de-N-acetylation is optionally accomplished by incubation in a mild acid (e.g. low concentration HCl) or alkaline (e.g. sodium bicarbonate) solution, followed by optional heating and adjustment back to physiological pH. In some embodiments, mild acid treatment (<0.1M HCl or <0.2M AcOH), followed by heating and neutralization is used to partially hydrolyze ("size") polysaccharides of high molecular weight. In some embodiments, mild acid treatment (e.g. <0.1M HCl or <0.2M AcOH), followed by heating (45-95° C.) and neutralization (to pH 5.5-6.0) is used to simultaneously partially hydrolyze ("size") polysaccharides of high molecular weight and deprotect the polysaccharide. In some embodiments, serotypes 3, 4, 18C, and 11A are treated by such an acid/heating/neutralization process to deprotect the polysaccharide, size the polysaccharide, or both. In some embodiments, *S. pneumoniae* serotype 3 polysaccharide is treated with 0.18M acetic acid, followed by heating at 85° C. for 1 hour. In some embodiments, *S. pneumoniae* serotype 4 polysaccharide is treated with 0.01M HCl followed by heating at 45° C. for 1 hour. In some embodiments, *S. pneumoniae* 18C polysaccharide is treated with 0.18M acetic acid, followed by heating at 95° C. for 40 minutes. In some embodiments, *S. pneumoniae* serotype 11A polysaccharide is treated by 0.18M acetic acid, followed by heating at 80° C. for 1 hour.

In certain embodiments, N-formyl groups on purified proteins are removed/amine groups are de-formylated by treatment with a formyl-L-methionyl peptide amidohydrolase in deionized water or a physiological pH buffered solution. In yet certain embodiments, N-formyl groups on purified proteins are removed by treatment of lyophilized protein with anhydrous hydrazine vapor at −5° C. (Miyataki et al. *Eur. J. Biochem.* 212, 785-789 (1993)).

Periodate activation is a useful technique used to activate *Streptococcus pneumoniae* serotypes 5, 6A, 6B, 7F, 12F, 14, 20, and 23F; see Table 2, infra.

IV.D.2. CDAP Activation

In certain embodiments, a different method is used to activate the saccharide antigen in preparation for conjugation. In this embodiment, the antigen is also functionalized with a reactive moiety capable of participating in a click chemistry reaction with a bio-orthogonal reactive moiety on the polypeptide carrier, but functionalization is carried out by cyanylating the antigen with a cyanylating reagent to provide cyanate (—O—C≡N) group in place of hydroxyl groups, and thereafter, in a "one pot" reaction, contacting the cyanylated antigen (PS—O—C≡N) with an activating reagent as was done in periodate activation. The activating reagent again comprises the reactive moiety coupled to a primary amino group, and may be a DBCO derivative as discussed in the preceding section.

In some embodiments, the saccharide antigen is provided at the outset in any suitable solvent (e.g., an aqueous solution, an organic solvent such as DMSO or acetonitrile, or an organic solvent mixture), preferably an aqueous buffer, typically having a pH in the range of 7 to 11, e.g., greater than 7 and up to 11, such as 8.5 to 10, 8.5. to 9.5, or 8.5 to 9.0, or 8.9, or 9.0. Starting with the antigen in an alkaline buffer solution obviates the need for pH adjustment during the reactions (i.e., during or after cyanylation and prior to conjugation to a polypeptide carrier). Other useful reaction conditions are as follows: addition of the DBCO derivative 3 to 13 minutes after contacting the antigen with the cyanylation reagent; and a DBCO:cyanylated PS ratio achieved by using 0.25 equivalents to 3.0 equivalents, e.g., 0.25 to 2.0 equivalents, including 0.25 to 1.5 equivalents, 0.25 to 1.25 equivalents, 1.0 equivalent, and 2.0 equivalents, of DBCO.

In certain embodiments, a CDAP activation method is provided that can be used across a plurality of antigen serotypes to provide a target DBCO %, wherein the only variable that may need to be adjusted for a specific serotype is the relative amount of CDAP used per polysaccharide unit, i.e., CDAP molar equivalents. Other variables can be kept constant regardless of the specific serotype undergoing activation, i.e., reaction pH, activation time, reaction temperature, and molar equivalents of DBCO. These standardized conditions provide a target DBCO %, typically in the range of 3% to 10%, e.g., 3% to 5%, 5% to 10%, 5% to 7%, and the like.

Representative standardized conditions in this embodiment are as follows:
  (a) providing the saccharide antigen as a solution in an aqueous buffer having a pH in the range of 7 to 11, e.g., 8.5 to 10;
  (b) cyanylating hydroxyl groups on the saccharide antigen with an effective cyanylating amount of CDAP to provide a cyanate-substituted saccharide, where the effective cyanylating amount of CDAP may vary with antigen serotype;
  (c) allowing the cyanylation reaction to proceed for 3 to 13 minutes;
  (d) thereafter contacting the cyanate-substituted saccharide with 0.25 equivalents to 2.0 equivalents, e.g., 0.25 to 1.5 equivalents, such as 1.0 equivalent, of a dibenzylcyclooctyne (DBCO) derivative having the structure of formula (I) wherein m is zero, or m is 1 and n is an integer in the range of 2 to 12, e.g., 2 to 8, such as 4, thereby transferring the DBCO moiety to the cyanate-substituted saccharide.

In other embodiments, supra- or sub-stoichiometric (with respect to polysaccharide) amounts of CDAP are used for activation, e.g., about 0.1 to about 3 eq, about 0.2 to about 0.8 eq CDAP is used for activation of a polysaccharide. In some embodiments, S. pneumoniae serotype 3 capsular polysaccharide is activated using 2.0 eq CDAP. In certain embodiments, S. pneumoniae serotype 10A capsular polysaccharide is activated using 0.8 eq CDAP.

In some embodiments, the addition of a buffering agent dramatically increases the efficiency of CDAP activation, e.g., about 1 to about 4 eq of TEA (relative to the polysaccharide). In some embodiments, about 1 to about 4 eq TEA is used as a buffering agent for a CDAP activation reaction involving S. pneumoniae serotype 7F polysaccharide. In some embodiments, 2.5 eq of TEA is used as a buffering agent. In some embodiments, 2.5 eq TEA is used as a buffering agent for a CDAP activation reaction involving S. pneumoniae serotype 7F polysaccharide. In other embodiments, the buffering agent is sodium borate, sodium carbonate, or sodium hydroxide, or any combination thereof. In some embodiments, the buffering agent has a pKa of between about 8.0 to about 11.0 or the buffering agent is used to adjust the pH of the reaction solution to between about 8.0 to about 11.0. In some embodiments, the buffering agent has a pKa of between about 9.0 to about 9.5 or the buffering agent is used to adjust the pH of the reaction solution to between about 9.0 to about 9.5. In some embodiments, sodium hydroxide adjustment of pH to 9.5 is used for a CDAP activation reaction involving S. pneumoniae serotype 3 polysaccharide. In some embodiments, sodium hydroxide adjustment of pH to 9.5 is used for a CDAP activation reaction involving S. pneumoniae serotype 10A polysaccharide.

CDAP activation is useful technique used to activate Streptococcus pneumoniae serotypes 1, 2, 3, 4, 5, 8, 9N, 9V, 10A, 11A, 15B, 17F, 18C, 19A, 19F, 22F, and 33F (note that serotype 5 can be readily activated effectively using either periodate or CDAP chemistry).

Exemplary activation technique(s) for various pneumococcal serotypes are set forth in Table 2 (where serotype 20 includes 20A and 20B):

TABLE 2

| Serotype | Exemplary Activation Chemistry |
|---|---|
| 1 | CDAP |
| 2 | CDAP |
| 3 | CDAP |
| 4 | CDAP |
| 5 | Periodate/CDAP |
| 6A | Periodate |
| 6B | Periodate |
| 7F | Periodate |
| 8 | CDAP |
| 9N | CDAP |
| 9V | CDAP |
| 10A | CDAP |
| 11A | CDAP |
| 12F | Periodate |
| 14 | Periodate |
| 15B | CDAP |
| 17F | CDAP |
| 18C | CDAP |
| 19A | CDAP |
| 19F | CDAP |
| 20 | Periodate |
| 22F | CDAP |
| 23F | Periodate |
| 33F | CDAP |

IV.D.3. Carbonyldiimidazole (CDI)/Carbonylditriazole (CDT) Activation:

In some embodiments the antigen is activated with carbonyldiimidazole (CDI) or carbonylditriazole (CDT). CDI and CDT, like CDAP, are capable of activating hydroxyl groups on an antigen to form a transient reactive moiety; in this case it is an unstable carbamate

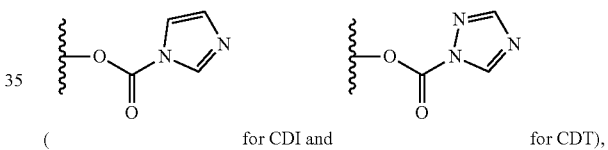

( for CDI and for CDT), which is then optionally reacted with an amine or thiol on a chemical handle or linker to form a carbamate or carbonothioate linkage. The activation should be performed in a dry organic solvent. In some embodiments, CDI/CDT activation is performed in anhydrous dimethylsulfoxide (DMSO). In some embodiments, CDI/CDT activation is performed by adding a molar excess of CDI/CDT with respect to the antigen. In other embodiments, CDI/CDT activation is performed by adding a molar amount of CDI/CDT approximately equal to the molar amount of the antigen.

IV.D.4. No Chemical Activation

In some embodiments, endogenous amines or other nucleophilic moieties (e.g. a primary amine) either naturally present or the result of a deprotection step (e.g. as discussed above) are used to conjugate a given polysaccharide to a chemical handle or carrier protein. Such nucleophilic moieties can be conveniently reacted with a variety of common electrophilic conjugation reagents like succinate derivatives (e.g. N-hydroxysuccinimide (NHS) or sulfo-NHS esters). In such embodiments, it is sometimes advantageous to treat with a periodate protocol as in (i) to promote degradation of antigenic contaminants like S. pneumoniae C-polysaccharide. In this embodiment, periodate treatment is followed by a vast excess of sodium borohydride to quench any chemically introduced aldehyde groups. In some embodiments, S. pneumoniae serotype 1 polysaccharide is treated with between about 0.05 to about 0.25 eq of sodium periodate at room temperature for between about 12 to about 14 hours, followed by treatment with between about 5 eq to about 15 eq of sodium borohydride. In some embodiments, *S. pneumoniae* serotype 1 polysaccharide is treated with 0.15 eq of sodium periodate at room temperature for 18 hours, followed by treatment with 10 eq of sodium borohydride.

IV.E. Conjugation to Chemical Handle

In some embodiments, the antigen is conjugated to the chemical handle using any chemical method compatible with the activation methods described above ("Activation of antigens"). Such methods include, but are not limited to, Schiff-base formation with synthetic antigen aldehydes followed by reductive amination, hydrazone formation, oxime formation, direct nucleophilic addition, and Schiff-base formation with native antigen aldehydes followed by reductive amination. In some embodiments, the absolute polysaccharide concentration in a conjugation reaction with a chemical handle is important to minimize aggregation or cross-reactivity of the polysaccharide. In some embodiments, the absolute polysaccharide/antigen concentration in a conjugation reaction with DBCO (a dibenzocyclo-octyne) or a DBCO derivative is important for polysaccharides activated with periodate or CDAP, as described above. In other embodiments, the polysaccharide concentration in a DBCO/DBCO-derivative conjugation reaction is less than 2, less than 5, less than 7, less than 10, less than 15, less than 17.5, or less than 20 µmol/mL. In some embodiments, the polysaccharide concentration in a DBCO/DBCO-derivative conjugation reaction is about 1.5 to about 17.5 µmol/mL.

IV.E.1. Reactions with Periodate-Activated Antigen

In some embodiments the chemical handle is conjugated to a polypeptide or polysaccharide antigen activated as described above using the periodate methodology. Prior to conjugation of the chemical handle to the antigen, unreacted aldehyde moieties remaining on the activated antigen can be capped using conventional aldehyde capping chemistry (e.g., treatment with sodium borohydride, glutamic acid, or the like). Aldehyde capping is optional, however, insofar as unreacted aldehydes on the polysaccharide following periodate activation can be capped to a sufficient degree during reductive amination, particularly when higher equivalents of the cyanoborohydride reagent are used, e.g., 6 to 12 equivalents, or 8 to 12 equivalents.

In these embodiments a chemical handle comprising a functional group that forms a stable or semi-stable adduct with aldehydes is combined with the periodate activated antigen, followed by optional reduction to convert semi-stable adducts to stable adducts (see, e.g., WO2014/111344; Wu et al. *Vaccine* 31(2013): 5623-2626; Hermanson, G. T., *Bioconjugate Techniques, Second Edition*, 2008). In some variations of these embodiments, the chemical handle is added at a large molar excess with respect to the aldehyde groups on the activated antigen, such that all the aldehydes are consumed in the chemical handle/antigen conjugation reaction. In other variations of these embodiments, the chemical handle is added at a lower molar ratio with respect to the aldehydes groups on the activated antigen, and excess unreacted aldehydes on the activated antigen are consumed by further reaction with an excess of an inexpensive aldehyde-reactive nucleophile (e.g. ethanolamine), or by treatment with a reducing agent strong enough to reduce aldehydes to hydroxyl groups (e.g. $NaBH_4$).

In certain embodiments, as alluded to in the preceding section, the chemical handle is conjugated to the antigen by Schiff-base formation with synthetic antigen aldehydes followed by reductive amination. This embodiment results in an end-product that has secondary amine linkage between the chemical handle and the antigen: a direct N—C bond between the amine of the chemical handle and a carbon atom on antigen. In this embodiment the chemical handle comprises an amine. In this embodiment the conjugation method comprises: combining the amine-containing handle with periodate-activated antigen in DI water or buffered solution containing DMSO; incubating to form a Schiff base; reducing the Schiff base to a secondary amine using sodium cyanoborohydride ($NaBH_3CN$); and optionally quenching unreacted aldehydes with $NaBH_4$. In some embodiments of this method the chemical handle and antigen are combined at or near 1:1 stoichiometry. In some embodiments of this method the chemical handle and antigen are combined with a molar excess of chemical handle. In some embodiments of this method, the chemical handle and antigen are combined with a molar excess of antigen. In some embodiments sodium cyanoborohydride is substituted for another reducing agent with similar selectivity for reducing C=N bonds such as sodium triacetoxyborohydride.

The chemical handle can be conjugated to the antigen via hydrazone formation. In this embodiment the chemical handle comprises a hydrazide (—C(=O)—NH—$NH_2$) group. This embodiment results in an end product that has a hydrazone (—C(=O)—NH—N=C—) or N'-alkyl hydrazide (—C(=O)—NH—NH—C—) linkage between the chemical handle and the antigen carbon. In this embodiment, the conjugation method comprises: combining a molar excess of the hydrazide-containing chemical handle with the antigen in a solution pH 6.0-8.5 and incubating to form a hydrazone (—C(=O)—NH—N=C—). In some further embodiments of this method, sodium cyanoborohydride or sodium triacetoxyborohydride is included in the reaction mixture to reduce the N=C bond, which produces an N'-alkyl hydrazide (—C(=O)—NH—NH—C—).

In some embodiments, the chemical handle is conjugated to the antigen by oxime formation. In this embodiment the chemical handle comprises an aminooxy (—O—Nib) group. This embodiment results in an end product that has an oxime (—O—N=C—) linkage between the chemical handle and an antigen carbon. In this embodiment, the conjugation method comprises: combining a molar excess of the aminooxy-containing chemical handle with the antigen in a solution pH 6.0-8.5 and incubating to form an oxime linkage (—O—N=C—). In some further embodiments of this method, sodium cyanoborohydride or sodium triacetoxyborohydride is included in the reaction mixture to reduce the N=C bond and improve stability; this produces an N'-alkyl hydroxylamine linkage (—O—N—C—).

IV.E2. Reactions with CDAP-Activated Antigen:

In some embodiments the chemical handle is conjugated to a polypeptide or polysaccharide antigen activated as described above ("CDAP activation") with CDAP. In these embodiments, a transient cyanato (—OCN) group produced via CDAP activation is further reacted with an amine-containing chemical handle to produce a carbamimidate linkage (—NH—C(=NH)—O—) between the chemical handle and an antigen carbon.

For CDAP conjugation of chemical handles, hydroxyl groups on the antigen are activated as described above ("CDAP activation"), and a chemical handle comprising an amine is additionally added to the activation mixture. Because the cyanato group is labile, the chemical handle is generally added shortly (within minutes) after activation of the antigen. In some embodiments, the antigen is added 2.5 minutes after CDAP is introduced. In some embodiments, a large molar excess of the amine-containing chemical handle with respect to activated hydroxyl groups on the antigen is added. In other embodiments, the chemical handle is added at a concentration closer to 1:1 molar ratio with respect to the activated hydroxyl groups on the antigen, and excess unreacted cyanato groups are exhausted by addition of an excess of an inexpensive amine (e.g. ethanolamine or hexanediamine).

IV.E.3. Reactions with CDI/CDT-Activated Antigens:

In some embodiments the chemical handle is conjugated to a polypeptide or polysaccharide antigen activated as described above ("Carbonyldiimidazole (CDI)/carbonylditriazole (CDT) activation") with CDI/CDT. In these embodiments, an unstable carbamate produced by CDI/CDT activation of antigen hydroxyl groups

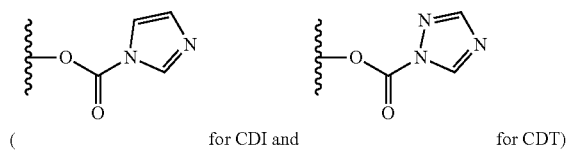

( for CDI and    for CDT)

is further reacted with a primary amine to produce a stable carbamate (—NH—C(=O)—O—) linkage or primary thiol to produce a stable carbonothioate (—S—C(=O)—O—) linkage between the chemical handle and an antigen carbon. In some embodiments, a large molar excess of the amine/thiol-containing chemical handle with respect to activated hydroxyl groups on the antigen is added. In other embodiments, the chemical handle is added at a concentration closer to 1:1 molar ratio with respect to the activated hydroxyl groups on the antigen. In yet further embodiments, residual CDI/CDT in the reaction is further inactivated by treatment with sodium tetraborate.

IV.E.4. Reactions with Non-Activated Antigens:

In some embodiments the chemical handle is conjugated to an endogenous amine or other nucleophilic moiety (e.g. a primary amine) either naturally present or the result of a deprotection step from a polypeptide or polysaccharide antigen as described above. In some embodiments of this, an electrophilic group (e.g. an NHS or sulfo-NHS ester) on a chemical handle is reacted with a primary amine group on the antigen to produce an amide linkage (—C(=O)—NH—) between the chemical handle and the antigen amine. In certain embodiments, a carboxylic acid group on a chemical handle is reacted with a primary amine group on the antigen in the presence of standard peptide coupling reagents and conditions to produce an amide linkage between the chemical handle and the antigen amine.

IV.E5. Alkyne-Containing Handles:

In some embodiments the chemical handle comprises a moiety that allows for a "click" chemistry reaction with a corresponding group on nnAA residue of a polypeptide. One such moiety is an alkyne group, which is capable of reacting with a nnAA residue comprising an azido group. In the simplest embodiment, this is a propargyl group, such that an alkyne group on an antigen comprises a structure of formula IV:

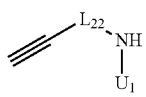

wherein:
$L_{22}$ is $C_1$-$C_{10}$ alkyl; and
$U_1$ is at least one moiety of an antigen.

In other embodiments an alkyne group on an antigen comprises a structure of formula Na:

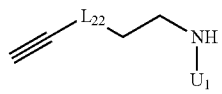

wherein:
$L_{22}$ is —(CH$_2$CH$_2$O)$_{1-10}$—; and
$U_1$ is at least one moiety of an antigen.

In some embodiments the alkyne group further comprises additional features that accelerate or facilitate the reaction of the alkyne with an azido group. An example of one such feature is an 8-membered ring structure (e.g., cyclo-octyne), such that an alkyne group on an antigen further comprises a DIFO or DBCO group. In some embodiments, an alkyne group on an antigen comprises a structure of formula V, formula VI, or VIa:

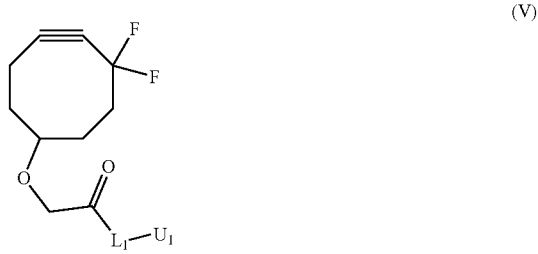
(V)

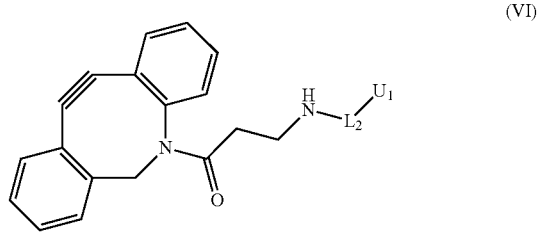
(VI)

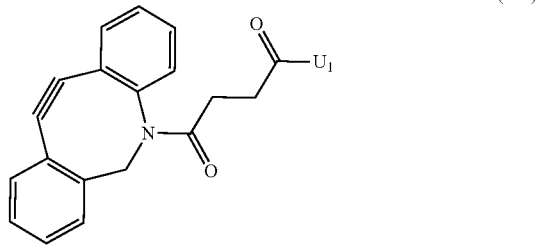
(VIa)

wherein:
$L_1$ is independently a bond, —NH—, —O—, —S—, —NH($L_{12}$)—, —O($L_{12}$)—, or —S($L_{12}$)—;
$L_2$ is independently a bond, —C(=O)—, —S(=O)$_2$—, —C(=O)$L_{12}$-, —S(=O)$_2 L_{12}$;
$L_{12}$ is independently $L_{22}$ or $L_{22}$NH—
$L_{22}$ is independently $C_{1-10}$ alkyl or —(CH$_2$CH$_2$O)$_{1-10}$—; and
$U_1$ is independently at least one moiety of an antigen.

In some embodiments, structures of formula V and VIa are conveniently formed from an antigen comprising a nucleophilic group (e.g. a primary amine) and the NHS or sulfo-NHS ester of the corresponding DIFO or DBCO carboxylic acids of structures V and VIa. In some embodiments structures of formula VI are conveniently formed from an activated antigen, and a DBCO derivative such as DBCO-NH$_2$ or DBCO-PEGn-NH$_2$. In some embodiments, DBCO-PEGn-NH$_2$ is DBCO-PEG$_4$-NH$_2$.

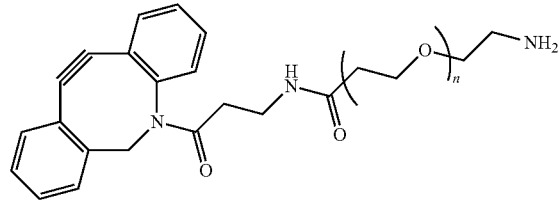

DBCO-PEGn-NH$_2$

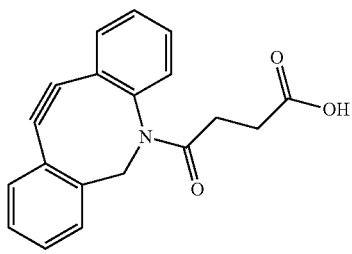

DBCO carboxylic acid

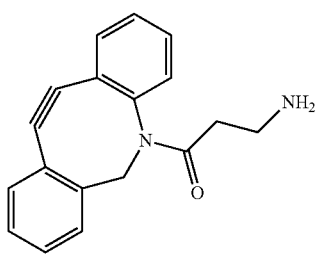

DBCO NH$_2$

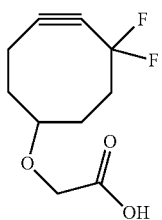

DIFO carboxylic acid

The value of 'n' in 'PEGn' represents the number of oxyethylene repeat units e.g. in the structure shown above, or within formula VII, formula VIIb, formula XI, or moiety 'A', or within the poly(alkyloxy) of L$_{22}$. The value of n is in the range 1-20 e.g. within 2-18, 3-16, or 4-14. Thus n can be, for example, any of 4, 5, 11, 12 or 13.

In some embodiments of formulas IV, V, or VI, the moiety of U$_1$ is at least one polyol of a polysaccharide. In some embodiments the moiety of U$_1$ is at least one polyol of a lipopolysaccharide. In some embodiments the moiety of U$_1$ is at least one amino acid of an antigenic polypeptide.

In further embodiments, an antigen comprising an alkyne comprises a structure of formula VII or VIIa:

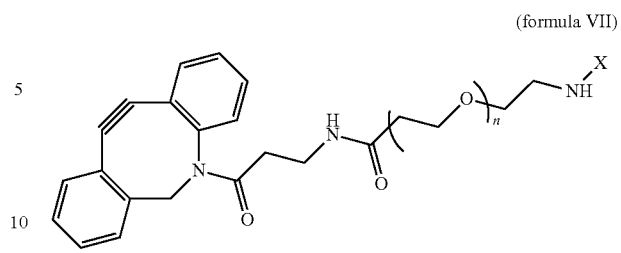
(formula VII)

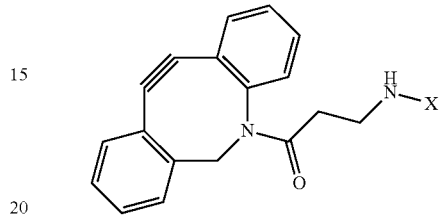
(formula VIIa)

wherein:

X is independently at least one polyol of a polysaccharide; and n is at least 1.

Where a group (e.g. X, Y or U$_1$) is described as being a polyol, this can refer to a chemical attachment to a polyol within the polysaccharide (e.g. to a monosaccharide within the polysaccharide, which monosaccharide is a polyol). The attachment itself can be to any suitable functional group (e.g. to an aldehyde, which may arise from oxidation of a vicinal diol).

In further embodiments, an antigen comprising an alkyne comprises a structure of formula VIIb or VIIc

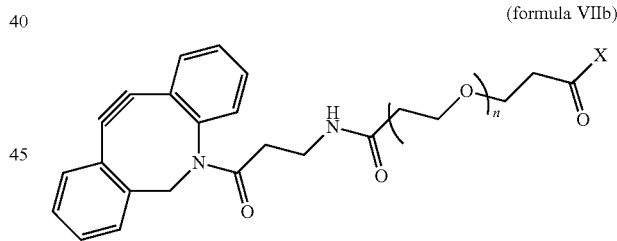
(formula VIIb)

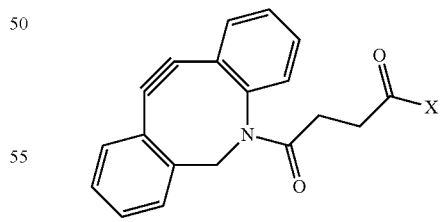
(formula VIIc)

wherein:

X is independently an amine of at least one aminosugar of a polysaccharide; and n is at least 1.

In some embodiments, an antigen comprising an alkyne comprises a polysaccharide according to (A-X)$_z$—Y, wherein:

A is

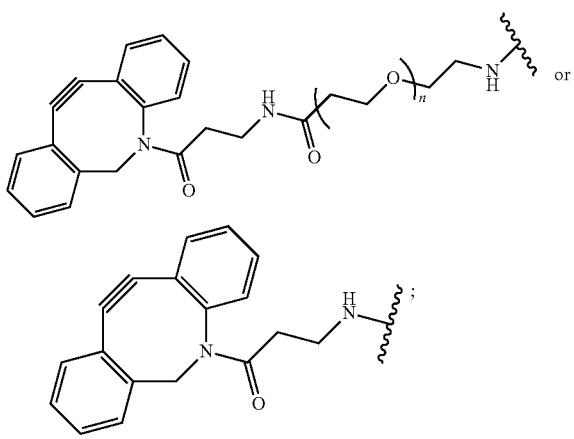 or

 ;

X is independently at least one polyol;
Y is independently at least one polyol of a polysaccharide;
n is at least 1; and
z is greater than 1.

In some embodiments, an antigen comprises a polysaccharide which further comprises a DBCO group, with at least 1.5%, at least, 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% (w/w) covalently attached DBCO. In some embodiments, the antigen comprises greater than about 1.5% (w/w) DBCO. In some embodiments, the antigen comprises greater than 3% (w/w) DBCO. In some embodiments the antigen comprises at most 20% at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, at most 3.5%, at most 3.0%, at most 2.5%, at most 2.0%, or at most about 1.7% (w/w) covalently attached DBCO. In some embodiments the antigen comprises less than 20% (w/w) covalently attached DBCO. In other embodiments the antigen comprises less than 10% (w/w) covalently attached DBCO. In some embodiments the antigen comprises between about 1.5 and 20%, 3% and 20%, 3% and 18%, 3% and 16%, 3% and 14%, 3% and 12%, 3% and 10%, 3% and 8%, 3% and 6%, or 3% and 4%, or 1.5 and 9% (w/w) covalently attached DBCO.

In some embodiments, an antigen comprises a polysaccharide which further comprises a DBCO group comprises at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% DBCO molecules per 100 polysaccharide repeating units. In some embodiments, the antigen comprises greater than 3% DBCO molecules per polysaccharide 100 repeating units. In some embodiments the antigen comprises at most 20% at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, or at most 3.5% covalently attached DBCO molecules per 100 polysaccharide repeating units. In some embodiments the antigen comprises less than 20% covalently attached DBCO per polysaccharide repeating unit. In other embodiments the antigen comprises less than 10% covalently attached DBCO molecules per 100 polysaccharide repeating units. In some embodiments the antigen comprises between about 3% and 20%, 3% and 18%, 3% and 16%, 3% and 14%, 3% and 12%, 3% and 10%, 3% and 8%, 3% and 6%, or 3% and 4% covalently attached DBCO molecules per 100 polysaccharide repeating units.

IV.E.6. Azido-Containing Handles:

In some embodiments the chemical handle comprises a moiety that allows for a "click" chemistry reaction with a corresponding group on nnAA residue of a polypeptide. One such moiety is an azido group, which is capable of reacting with a nnAA residue comprising an alkyne group or a phosphine on a polypeptide. In some embodiments, an azido group on an antigen comprises a structure of formula VIII:

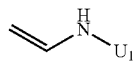 (VIII)

wherein $L_{22}$ is a bond, alkyl, or poly(alkyloxy), and $U_1$ is independently at least one moiety of an antigen.

IV.E.7. Alkene-Containing Handles:

In some embodiments the chemical handle comprises a moiety that allows for a "click" chemistry reaction with a corresponding group on nnAA residue of a polypeptide. One such moiety is an alkene group, which is capable of reacting with a nnAA residue comprising an 1,2,4,5-tetrazine group. In the simplest embodiments, this is a vinyl group. In one such embodiment, an alkene group on an antigen comprises a structure of formula IX:

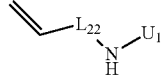

wherein:
$U_1$ is independently at least one moiety of an antigen

In other embodiments, an alkene group on an antigen comprises a structure of formula IXa:

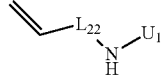

wherein:
$L_{22}$ is $C_{1-10}$ alkyl or $-(CH_2CH_2O)_{1-10}-$; and
$U_1$ is independently at least one moiety of an antigen.

IV.E.8. Representative Method of Producing a Glycoconjugate with an Azide Containing Chemical Handle:

In a representative embodiment, a method for producing a glycoconjugate in which the chemical handle is an azide group, provided by 4-azidomethylphenylalanine (pAMF) as the nnAA, comprises: (a) providing a nucleic acid encoding a carrier protein, wherein the nucleic acid comprises a suppression codon; (b) creating a reaction mixture by combining the nucleic acid with a cell-free bacterial extract comprising 4-azidomethylphenylalanine (pAMF), a tRNA complementary to the suppression codon, and an aminoacyl-tRNA synthetase; (c) incubating the reaction mixture of (b) under conditions sufficient to selectively incorporate pAMF at a site corresponding to the suppression codon in the carrier protein; and (d) conjugating the pAMF to a polysaccharide by a [2+3] cycloaddition. In certain embodiments, the [2+3] cycloaddition comprises the reaction between an azide and an alkyne group. In certain embodiments, step (c) comprises incubating the reaction mixture at less than 20 degrees Celsius. In certain embodiments, the method additionally comprises purifying the carrier protein immediately after (c). In certain embodiments, the suppression codon is selectively substituted at codon 25, 34, 38, 40, 213, 215, 228, 245, 265, 386, 523, or 527 of SEQ ID NO:2. In certain embodiments, the reaction mixture in (b) further comprises biological components necessary for protein synthesis. In certain embodiments, the tRNA in (b) is capable of being charged with pAMF. In certain embodiments, the aminoacyl-tRNA synthetase in (b) preferentially aminoacylates the tRNA with pAMF compared to the 20 natural amino acids. In certain embodiments, the alkyne group comprises a DBCO moiety conjugated to the polysaccharide. In certain embodiments, the polysaccharide is a capsular polysaccharide of *Streptococcus pneumoniae, Neisseria meningitidis, Haemophilus influenzae, Streptococcus pyogenes*, or *Streptococcus agalactiae*. In certain embodiments, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, or any combination thereof. In certain embodiments, the antigen is a capsular polysaccharide derived from one of the six serotypes of *Porphyromonas gingivalis* (e.g., K1, K2, K3, K4, K5 and/or K6). In certain embodiments, the disclosure provides a glycoconjugate prepared by a process comprising steps (a)-(d). In certain embodiments, the pAMF is conjugated to the polysaccharide to generate a conjugate of formula X, Xa, XI, or XIa. In some embodiments, the disclosure provides for a vaccine comprising the glycoconjugate prepared by steps (a)-(d).

V. Polypeptide-Antigen Conjugates and Preparation Thereof

Described herein are polypeptide-antigen conjugates that can be formed between an immunogenic polypeptide as described above and an antigen as described above.

In some embodiments the polypeptide-antigen conjugates comprise an enhanced carrier protein and an antigen, wherein the antigen is linked to an nnAA in the enhanced carrier protein. In some embodiments, the antigen is not linked to a natural amino acid of an immunogenic polypeptide. In certain embodiments, the antigen is not linked to a lysine within an immunogenic polypeptide. For example, the antigen is not linked to a lysine in SEQ ID NOs:1 or 11. In certain embodiments, the antigen is only linked to one or more nnAAs of an immunogenic polypeptide. The one or more nnAA is optionally located at the N-terminus, the C-terminus, or anywhere in between the N- and C-terminal ends of an immunogenic polypeptide. In some cases, the antigen is only linked to one or more pAMFs in an immunogenic polypeptide. For example, the antigen is only linked to one or more pAMFs in SEQ ID NOs:1 or 11.

In certain embodiments, at least one antigen is linked to an amino acid located outside a T-cell epitope of an immunogenic polypeptide. In certain embodiments, no antigen is linked to an amino acid located within a T-cell epitope of an immunogenic polypeptide.

The amino acids selected for conjugation within an immunogenic polypeptide optionally comprises one or more surface-accessible residues based on the crystal structure (or other 3D structure, such as a NMR structure) of the polypeptide. Additionally or alternatively, a comprehensive replacement of natural amino acids for nnAAs is performed on an immunogenic polypeptide followed by conjugation, to assess the utility of specific sites on the polypeptide for conjugation.

In some embodiments, the antigen is conjugated to the enhanced carrier protein indirectly (e.g. by first combining the enhanced carrier protein or antigen with a reactive linker, and then combining the enhanced carrier protein-linker or antigen-linker adduct with an antigen or enhanced carrier protein, respectively). In certain embodiments, the antigen is conjugated to the enhanced carrier protein directly (e.g. by combining two components comprising the enhanced carrier protein and antigen together in one reaction). Where a conjugate includes a linker, any suitable group can be used. For example, a conjugate can include a linker selected from adipic acid, adipic acid dihydrazide (ADH), β-propionamido, nitrophenyl-ethylamine, haloacyl halides, glycosidic linkages, 6-aminocaproic acid, N-succinimidyl-3-(2-pyridyldithio)-propionate (SPDP), $C_4$ to $C_{12}$ moieties, etc. Linkers resulting from the DBCO and DIFO groups discussed above can also be used e.g. including the residue of a diarylcyclooctyne moiety, such as diarylcyclooctene. The linker will generally be attached to an antigen for conjugation, rather than being attached to a carrier.

Because the antigen-polypeptide conjugates can form large cross-linked complexes, it may not be possible with available analytical methods to directly measure or determine the exact location of some or all conjugations and other physical features. It is understood, however, that such locations or physical features may be reliably inferred from the design of a synthetic scheme, its expected product, and analytical results consistent with that expectation.

In some embodiments, the conjugate comprises a polypeptide and an antigen, wherein the polypeptide is a carrier protein comprising at least one T-cell activating epitope and at least one nnAA, preferably at least two nnAA, wherein the antigen is conjugated to the at least one nnAA. In some embodiments, the at least one nnAA is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the conjugate comprises a polypeptide and an antigen, wherein the polypeptide is a carrier protein comprising at least one T-cell activating epitope and at least one an nnAA residue, wherein the antigen is conjugated to the nnAA and further wherein the nnAA residue corresponds to an amino acid having the structure of formula XII

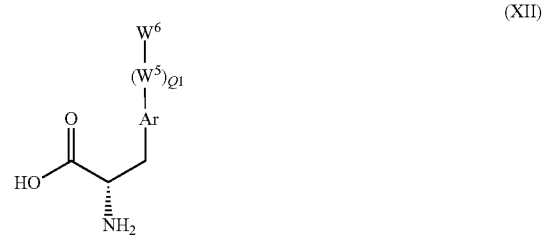

wherein:
Ar comprises a 5-membered or 6-membered aromatic ring optionally containing at least one heteroatom;

$W^5$ is selected from $C_1$-$C_{10}$ alkylene, —NH—, —O— and —S—;

Q1 is zero or 1; and $W^6$ is selected from azido, 1,2,4,5-tetrazinyl optionally C-substituted with a lower alkyl group, and ethynyl, such that the nnAA residue in the polypeptide has the structure of formula XIII

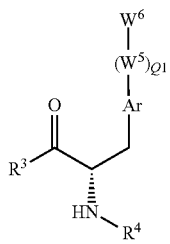

(XIII)

in which $R^3$ is OH or an amino acid residue of the carrier protein, and $R^4$ is H or an amino acid residue of the carrier protein V.A. Antigen Polypeptide Conjugation Reaction As noted previously, the activated antigen can be conjugated to a nnAA directly, but usually the activated group is derivatized to introduce a functional group which shows better reactivity towards the nnAA's functional group. As one example, an alkynyl group can be introduced; a bifunctional reagent with an amino group and an alkyne group can react with an aldehyde group that has been introduced into an antigen, e.g., via reductive amination, thereby leaving a pendant alkyne that can react with a nnAA. For instance, bifunctional reagents including amino and DBCO functional groups can be used.

In some embodiments, the nnAA reacts with an alkynyl group in the antigen (e.g. a propargyl group). An alkyne group in an antigen is ideal for reacting with an azido group in a nnAA e.g. using the reactions known in the art as copper-catalyzed azide-alkyne cycloaddition (CuAAC), ruthenium-catalyzed azide-alkyne cycloaddition (RuAAC), or Huisgen azide-alkyne 1,3-dipolar cycloaddition. The alkynyl group may have a molecular context that increases its reactivity e.g. it can be within a ring. For instance, the alkyne can be within a cyclooctyne ring (optionally including a heteroatom), such as a diaryl-strained cyclooctyne ring (e.g. DBCO). This reaction can be a [3+2]cycloaddition referred to in the art as strain-promoted azide-alkyne cycloaddition (SPAAC). DIFO- and DBCO-based reagents are readily available for these reactions. Alkyne-containing rings useful in SPAAC reactions include difluorinated cyclooctyne (DIFO) and dibenzocyclooctynes. These are available with pendant functional groups for linking to activated antigens (e.g. with a pendant amino for linking to an aldehyde or a cyanate ester), for instance using any of the following reagents:

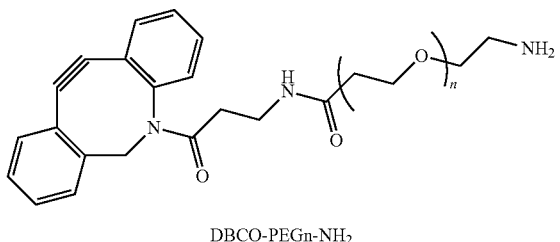

DBCO-PEGn-NH$_2$

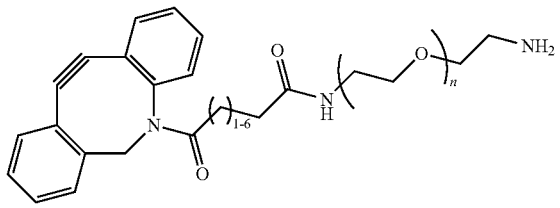

DBCO-PEGn-NH$_2$

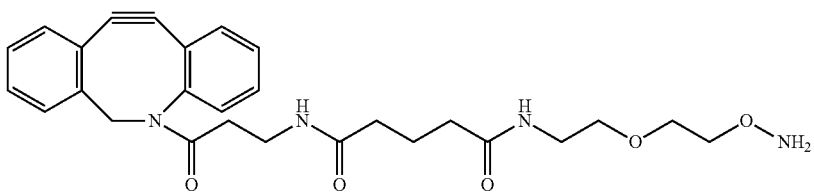

-continued

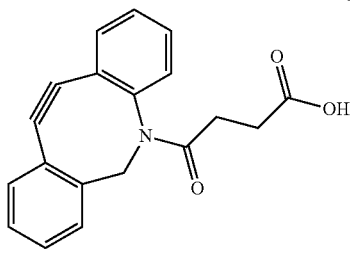
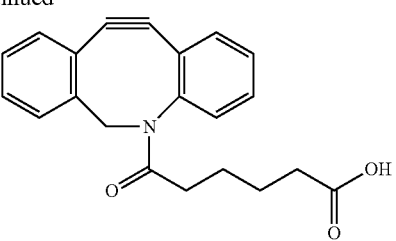

DBCO carboxylic acids

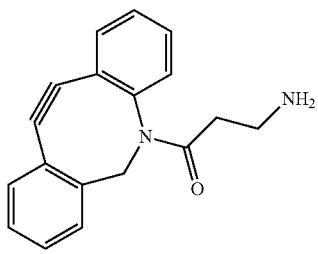

DBCO-NH₂

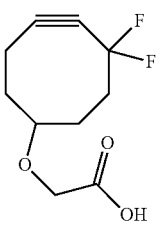

DIFO carboxylic acid

The value of 'n' in 'PEGn' represents the number of oxyethylene repeat units. The value of n is in the range 1-20 e.g. within 2-18, 3-16, or 4-14. Thus n can be, for example, any of 4, 5, 11, 12 or 13.

Other click chemistry reactions which can be used for conjugation of an antigen and a nnAA include, but are not limited to, tetrazine-alkene ligation and Staudinger ligation between a phosphine and an azide.

CuAAC: In some embodiments, the antigen is conjugated to the enhanced carrier protein by copper(I)-catalyzed alkyne-azide cycloaddition (CuAAC). In one variation of this embodiment, the enhanced carrier protein comprises a propargyl-containing nnAA and the antigen comprises an azido group. In another variation of this embodiment, the enhanced carrier protein comprises an azido-containing nnAA and the antigen comprises a propargyl group. Suitable conditions for CuAAC conjugation of biomolecules are found, e.g. Presolski et al. Curr Protoc Chem Biol. 2011; 3(4): 153-162, all of which involve the addition of $Cu^{2+}$. In some embodiments, the reaction is accelerated by the addition of a Cu-coordinating ligand, such as THPA. In some embodiments the reaction is accelerated by the addition of a reducing agent to maintain the oxidation state of $Cu^{2+}$. Suitable reducing agents include sodium ascorbate, DTT, or TCEP.

SPAAC: In some embodiments, the antigen is conjugated to the enhanced carrier protein by strain-promoted azide-alkyne cycloaddition (SPAAC). In one variation of these embodiments, the enhanced carrier protein comprises an azido-containing nnAA and the antigen comprises a cyclooctyne group. In another variation of these embodiments, the enhanced carrier protein comprises a cyclooctyne-containing nnAA and the antigen comprises an azido group. As SPAAC requires no additional catalysts or cofactors, this reaction is able to be performed in distilled water, 0.9% saline, PBS, or a physiologically buffered solution. In some embodiments, the enhanced carrier protein and antigen are combined at a mass ratio of 1.20:1 (w/w).

In some embodiments, the antigen is linked to an azido-containing nnAA in the enhanced carrier protein via a structure of formula (X) or (Xa):

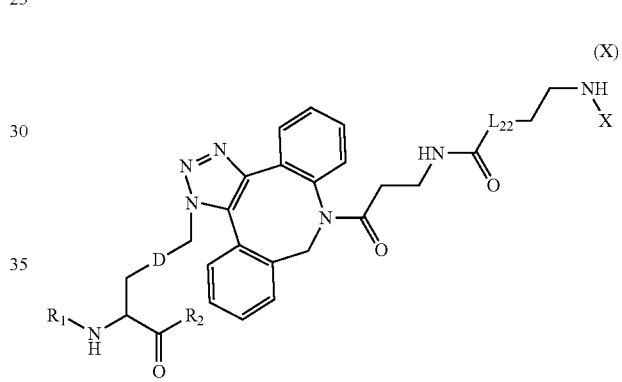

(X)

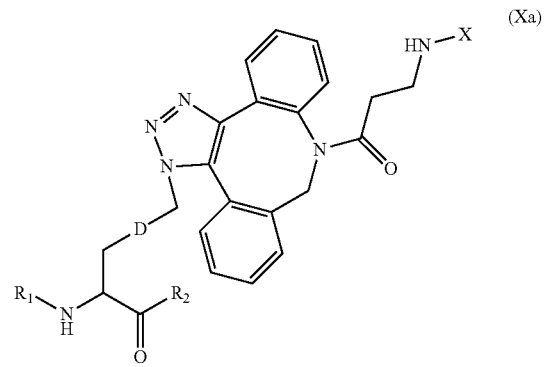

(Xa)

wherein:
$R_1$ is independently H, formyl, or at least one amino acid of the enhanced carrier protein;
$R_2$ is independently OH or at least one amino acid of the enhanced carrier protein;
D is —Ar—W³— or —W1-Y1-C(O)—Y2-W2-;

Ar is

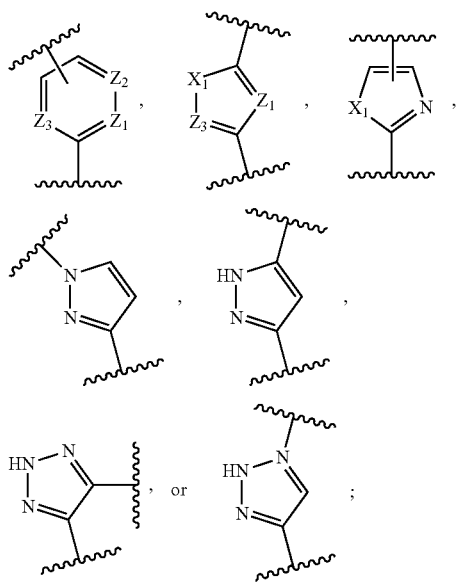

each of W1, W2, and W3 is independently a single bond or lower alkylene;

each X1 is independently —NH—, —O—, or —S—;

each Y1 is independently a single bond, —NH—, or —O—;

each Y2 is independently a single bond, —NH—, —O—, or an N-linked or C-linked pyrrolidinylene;

one of Z1, Z2, and Z3 is —N— and the others of Z1, Z2, and Z3 are independently —CH—;

$L_{22}$ is independently a bond, alkyl or poly(alkyloxy); and

X is at least one polyol of a polysaccharide.

In some embodiments, the antigen is linked to an azido-containing nnAA in the enhanced carrier protein via a structure of formula (XI) or (XIa):

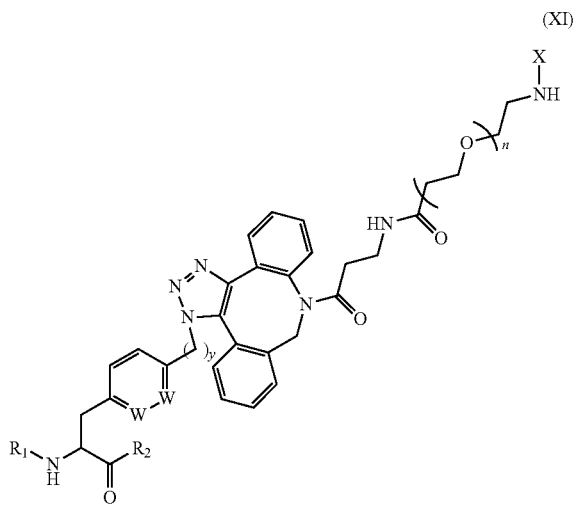

(XI)

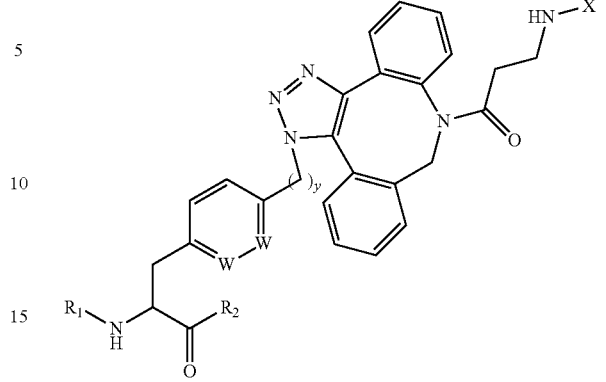

(XIa)

wherein:
$R_1$ is independently H, formyl, or at least one amino acid of the enhanced carrier protein;
$R_2$ is independently OH or at least one amino acid of the enhanced carrier protein;
W is C or N;
y is at least 1;
n is at least 1; and
X is independently at least one polyol of a capsular polysaccharide.

The value of 'n' is discussed above in relation to 'PEGn'. The value of 'y' is in the range 1-10, in line with formula (XII), and is preferably a lower alkylene e.g. a $C_1$-$C_4$ alkylene.

In some embodiments, the antigen is conjugated to the enhanced carrier protein by tetrazine-alkyne ligation. In one variation of these embodiments, the enhanced carrier protein comprises a 1,2,4,5-tetrazine-containing nnAA and the antigen comprises an alkene group. Similar to the SPAAC reaction, the tetrazine-alkyne ligation proceeds without the addition of cofactors this and this reaction is able to be performed in distilled water, 0.9% saline, PBS, or a physiologically buffered solution.

V.B. Conjugate Characterization and Exemplary Physical Parameters

Methods (size exclusion, diafiltration, dialysis): Following the conjugation reaction, the antigen-enhanced carrier protein conjugates of interest are optionally purified according to methods including, but not limited to, chromatography (e.g., ion exchange, affinity, hydrophobic interaction, and size exclusion), molecular size exclusion (dialysis, diafiltration, tangential flow filtration, depth filtration) electrophoretic procedures (e.g., preparative isoelectric focusing), differential solubility (e.g., ammonium sulfate precipitation), or SDS-PAGE (see, e.g., Protein Purification, J. C. Janson & Lars Ryden, editors, VCH Publishers, New York, 1989) to obtain substantially pure conjugates.

The conjugated proteins of interest are optionally quantitated according to methods including, but not limited to, microfluidic electrophoresis, gel electrophoresis, western blotting, immunoassays (e.g., ELISA), and other assays to assess the activity of the conjugated protein.

One important parameter for antigen-enhanced carrier protein conjugates is the molecular weight of the conjugate. Since conjugates optionally comprise variable numbers of antigen molecules conjugated to each protein molecule as well as variable higher-order crosslinking (protein-antigen-protein linkages, for example) the output molecular weight of a conjugate is not necessarily predictable from the input molecular weights of the enhanced carrier proteins and antigens. A wide body of literature (e.g. Howard et al. *Immunology*. 1971(21): 535-545 and Kabat & Bezer. *Arch Biochem Biophys*. 1958(78) 306-18) suggests that antigenic particle size has an important effect on immunogenicity. Wessels et al. (1998) *Infect Immun* 66:2186-92 report that conjugate size and cross-linking can influence the immunogenicity and protective efficacy of GBS type III conjugates.

In general term, conjugates can be formed by linking a carrier protein to an antigen which has either one or multiple handles per antigen. With multiple handles per antigen a crosslinked conjugate can be formed, involving protein-antigen-protein linkages. With a single handle per antigen (e.g. a terminal group in a polysaccharide) this sort of conjugate lattice does not form because a single antigen cannot bind to multiple carrier protein molecules. Cross-linked conjugates are useful (particularly for pneumococcus) where higher molecular weights are desired, and thus antigens with multiple handles may be useful.

In some embodiments, the antigen-enhanced carrier protein conjugate has a molecular weight of about 750 kDa, at least about 750 kDa, about 1,000 kDa, at least about 1,000 kDa, about 1,500 kDa, at least about 1,500 kDa, about 2,000 kDa, about 2,500 kDa, about 3,000 kDa, about 3,500 kDa, about 4,000 kDa, about 4,500 kDa, about 5,000 kDa, about 5,500 kDa, about 6,000 kDa, about 6,500 kDa, about 7,000 kDa, about 7,500 kDa, or about 8,000 kDa. In some embodiments, the antigen-enhanced carrier protein conjugate has a molecular weight of at least about 750 kDa, at least about 1,000 kDa, or at least about 1,500 kDa, In some embodiments, the antigen-enhanced carrier protein conjugate has a molecular weight of between about 750 kDa and about 2,800 kDa. In some embodiments, the antigen-enhanced carrier protein conjugate has a molecular weight of between about 800 kDa and about 2,800 kDa. In some embodiments, the antigen-enhanced carrier protein conjugate has a molecular weight of between about 850 kDa and about 2,800 kDa. In some embodiments, the antigen-enhanced carrier protein conjugate has a molecular weight of between about 900 kDa and about 2,800 kDa. In some embodiments, the antigen-enhanced carrier protein conjugate has a molecular weight of between about 950 kDa and about 2,800 kDa. In some embodiments, the antigen-enhanced carrier protein conjugate has a molecular weight of between about 1,000 kDa and about 2,800 kDa.

Another important parameter for the conjugate vaccines of the present disclosure is the ratio of the antigen (e.g., polysaccharide) to immunogenic polypeptide carrier (e.g., carrier proteins of the present disclosure). Using a polysaccharide-carrier protein conjugate as illustrative of the general principle, the polysaccharide-to-protein (PS:PC) ratio of the purified conjugate is generally expressed in terms of a weight-weight (w/w) ratio. Such ratios conventionally are expressed to include any free polysaccharide that is purified along with individual glycoconjugates. Higher PS:PC ratios of polysaccharide-carrier protein conjugates allow for more polysaccharide antigen to be delivered with a lower amount of enhanced carrier protein. For pneumococcal conjugate vaccines, the ratio is typically in the range 0.3-3.0, but this can vary with the serotype and aspects of the conjugation chemistry (*Annex 2: Recommendations for the production and control of pneumococcal conjugate vaccines*; WHO Technical Report Series, No. 927, 2005). The ratio of the commercial vaccine Prevnar-13 is 0.9 (see, Prevnar 13 Package Insert, M/2016 Revision, pg. 24; www.fda.gov/downloads/biologicsbloodvaccines/vaccines/approvedproducts/ucm201669.pdf). For compositions that include conjugates of multiple pneumococcal serotypes (e.g., more than 13 serotypes), the ratio for the complete composition is ideally above 1.0 (i.e., a weight excess of pneumococcal saccharide antigen) and can be 1.5 or more (e.g., within the range 1.5-3.0, or preferably 1.5-2.0).

In certain embodiments, the ratio (weight by weight) of polysaccharide to enhanced carrier protein in the polysaccharide-enhanced carrier protein conjugate is between 0.5 and 4.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0). In certain embodiments, the (w/w) PS:PC ratio in the carrier protein conjugate is between 0.7 and 2.8. In certain embodiments, the (w/w) PS:PC ratio in the carrier protein conjugate is between 1.0 and 2.8. In certain embodiments, the (w/w) PS:PC ratio in the carrier protein conjugate at least 0.8, at least 0.9, at least 1.0, at least 1.1, at least 1.2, at least 1.3. at least 1.4 or at least 1.5. In certain embodiments the ratio of polysaccharide to enhanced carrier protein in the polysaccharide-enhanced carrier protein conjugate is greater than 0.9 (w/w). In certain embodiments the ratio of polysaccharide to enhanced carrier protein in the polysaccharide-enhanced carrier protein conjugate is between about 0.9 and about 3.0 (w/w). Mixing of individual conjugates with such PS:PC ratios can yield a combination having a desired overall PS:PC ratio.

Presence of contaminants (free polysaccharide, C-poly): An important parameter for polysaccharide-enhanced carrier protein conjugates is the level of free polysaccharide that is not covalently conjugated to the enhanced carrier protein, but is nevertheless present in the conjugate composition. For example, in certain instances, the free polysaccharide is noncovalently associated with (i.e., noncovalently bound to, adsorbed to, or entrapped in or with) the polysaccharide-enhanced carrier protein conjugate. In some embodiments, polysaccharide-enhanced carrier protein conjugates described herein comprise less than about 50%, 45%, 40%, 35%, 30%, 25%, 20%, 15%, or 10% of free polysaccharide compared to the total amount of polysaccharide. In certain embodiments the polysaccharide-enhanced carrier proteins described herein comprise less than about 10% of free polysaccharide compared to the total amount of polysaccharide. In certain embodiments the polysaccharide-enhanced carrier proteins described herein comprise less than about 25% of free polysaccharide compared to the total amount of polysaccharide. In certain embodiments, the polysaccharide-enhanced carrier proteins described herein comprise less than about 30% of free polysaccharide compared to the total amount of polysaccharide. In certain embodiments the polysaccharide-enhanced carrier proteins described herein comprise less than about 15% of free polysaccharide compared to the total amount of polysaccharide. Free polysaccharide is optionally measured by any suitable method, including the method of Lei et al. (*Dev Biol (Basel)*. 2000; 103:259-64), which uses an HCl/deoxycholate-based precipitation method to distinguish the pools of polysaccharide. In certain compositions the amount of unconjugated bacterial polysaccharide is less than 5%, by weight, of the total amount of bacterial polysaccharide in the composition. In a composition with multiple pneumococcal conjugates it may be preferred that the amount of unconjugated bacterial polysaccharide for each serotype is less than 5%, by weight, of the total amount of that serotype's bacterial polysaccharide in the composition.

An important parameter for pneumococcal capsular polysaccharide-enhanced carrier protein conjugates is the level of C-polysaccharide contamination present in preparations of the conjugate. C-polysaccharide is an immunologically unproductive but highly immunogenic cell wall component of *S. pneumoniae* that "rides along" in many pneumococcal capsular polysaccharide preparation methods. As C-polysaccharide immune responses do not generally produce neutralizing antibodies, contamination with C-polysaccharide can interfere with proper assessments of antigen-enhanced carrier protein conjugate effectiveness when administered to animals.

The level of C-polysaccharide is optionally shown by total acid hydrolysis of a polysaccharide conjugate preparation, chromatography of the hydrolysate, and conductometric detection of choline. Alternatively, the non-hydrolyzed polysaccharide is analyzed by NMR for choline. The NMR technique uses the ratio of the choline signal to the rhamnose methyl signal (for capsular polysaccharides containing a rhamnose; a different signal for other capsular polysaccharides) for calculating the C-polysaccharide content. The chromatographic method uses the ratio of the choline signal to either the polysaccharide content determined by conductometric assay or to one of the capsular polysaccharide component peaks to calculate the C-polysaccharide content. In either method, standards of known concentrations of choline allow direct calculation of the level of choline present in a polysaccharide preparation once the choline concentration is known, using the theoretical repeat structure of C-polysaccharide [Hermans, et al., *Recl. Trav. Chim. Pays Bas*, 107, 600 (1988)], the concentration of C-polysaccharide in a polysaccharide preparation is known.

Polysaccharide concentrations of polysaccharide-enhanced carrier protein conjugate samples are optionally measured by a variety of techniques, for example, total polysaccharide concentration is optionally determined by total hydrolysis of the polysaccharide and measurement of the concentration of a specific monosaccharide. By comparing the C-polysaccharide concentration to total polysaccharide concentration, the degree of C-polysaccharide contamination (w/w) is determined. Levels of C-polysaccharide below 3% (w/w) of total polysaccharide are considered acceptable. In some embodiments, the C-polysaccharide levels are below 1%.

In some embodiments, the disclosure provides for a conjugate comprising a carrier protein and an antigen, wherein the antigen is linked to an nnAA in the carrier protein. In certain embodiments, the carrier protein retains a T-cell binding epitope of diphtheria toxoid (DT), tetanus toxoid (TT), *Haemophilus influenzae* protein D (PD), outer membrane protein complex of serogroup B *meningococcus* (OMPC), or CRM197. In certain embodiments, the nnAA is 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, or 2-amino-3-(4-(azidomethyl)phenyl)propanoic acid, and any combination thereof. In certain embodiments, the nnAA is not in a T-cell activating epitope of the carrier protein. In certain embodiments, the nnAA is substituted for one or more lysine residues in the carrier protein. In certain embodiments, the apparent molecular weight of the conjugate is between about 900 kDa and about 5 MDa. In certain embodiments, one or more lysine residues substituted are selected from the group consisting of K24, K33, K37, K39, K212, K214, K227, K244, K264, K385, K522 and K526, and any combination thereof of SEQ ID NO:11. In certain embodiments, one or more lysine residues substituted are selected from the group consisting of K25, K34, K38, K40, K213, K215, K228, K265, K386, K523 and K527, and any combination thereof of SEQ ID NO:1. In certain embodiments, the nnAA is not in a T-cell activating epitope of the carrier protein. In certain embodiments, the antigen is linked to the carrier protein according to formula XI or XIa:

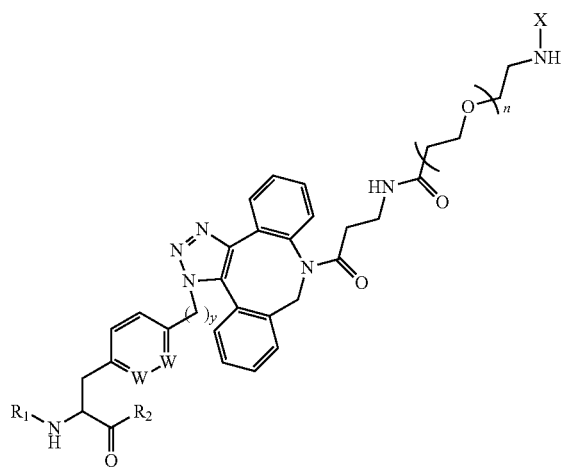

(formula XI)

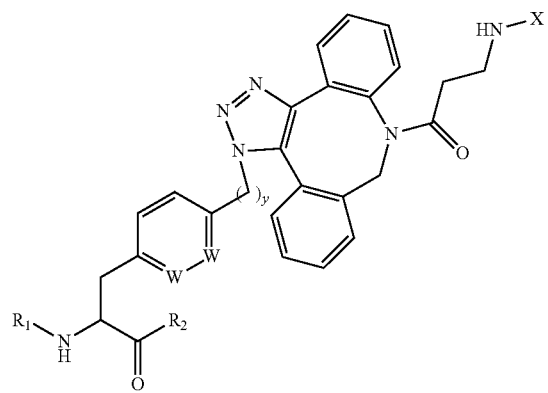

(formula XIa)

wherein
  $R_1$ is independently H, formyl, or at least one amino acid of the carrier protein;
  $R_2$ is independently OH or at least one amino acid of the carrier protein;
  W is C or N;
  y is at least 1;
  n is at least 1; and
  X is independently at least one polyol of a capsular polysaccharide.

In certain embodiments, the antigen is a polysaccharide, e.g., a capsular polysaccharide of *Streptococcus pneumoniae*, *Neisseria meningitides*, *Haemophilus influenzae*, *Streptococcus pyogenes*, or *Streptococcus agalactiae*. In certain embodiments, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, the antigen is a capsular polysaccharide derived from one of the six serotypes of *Porphyromonas gingivalis* (e.g., K1, K2, K3, K4, K5 and/or K6).

The conjugate comprises a polypeptide and an antigen, wherein the polypeptide is a carrier protein comprising at least one T-cell activating epitope and at least one nnAA, preferably at least two nnAA, wherein the antigen is conjugated to the at least one nnAA. In some embodiments, the at least one nnAA is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the conjugate comprises a polypeptide and an antigen, wherein the polypeptide is a carrier protein comprising at least one T-cell activating epitope and at least one an nnAA residue, wherein the antigen is conjugated to the nnAA and further wherein the nnAA residue corresponds to an amino acid having the structure of formula XII

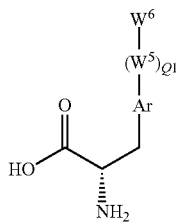

(XII)

wherein:
Ar comprises a 5-membered or 6-membered aromatic ring optionally containing at least one heteroatom;
$W^5$ is selected from $C_1$-$C_{10}$ alkylene, —NH—, —O— and —S—;
Q1 is zero or 1; and
$W^6$ is selected from azido, 1,2,4,5-tetrazinyl optionally C-substituted with a lower alkyl group, and ethynyl, such that the nnAA residue in the polypeptide has the structure of formula XIII

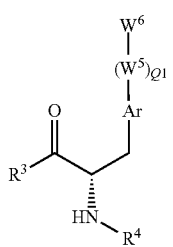

(XIII)

in which $R^3$ is OH or an amino acid residue of the carrier protein, and $R^4$ is H or an amino acid residue of the carrier protein.

V.C. Antigen Placement on the Carrier Protein

In some embodiments, the disclosure provides a method for identifying optimal placement of an antigen on a carrier protein to improve a host immune response, comprising: i) introducing into a carrier protein an nnAA substitution; ii) conjugating a polysaccharide to the nnAA to form a glycoconjugate; and iii) measuring the apparent molecular weight of the glycoconjugate. In certain embodiments, the nnAA substitution is not in a T-cell activating epitope of the carrier protein. In certain embodiments, the carrier protein retains a T-cell binding epitope of diphtheria toxoid (DT), tetanus toxoid (TT), *Haemophilus influenzae* protein D (PD), outer membrane protein complex of serogroup B *meningococcus* (OMPC), or CRM197. In certain embodiments, the antigen is a polysaccharide. In certain embodiments, the at least one or more polysaccharides is conjugated to the carrier protein according to formula XI or XIa:

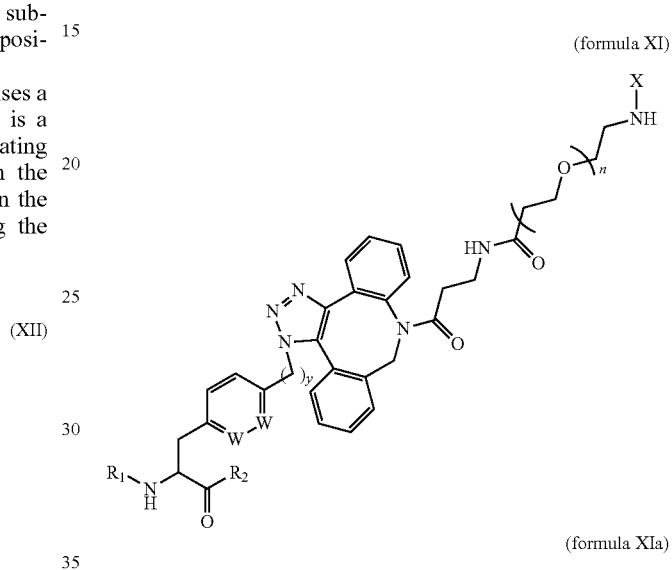

(formula XI)

(formula XIa)

where
$R_1$ is independently H, formyl, or at least one amino acid of the carrier protein;
$R_2$ is independently OH or at least one amino acid of the carrier protein; and
X is independently at least one polyol of a capsular polysaccharide.

In certain embodiments, the at least one or more non-natural amino acids substituted for is pAMF. In certain embodiments, the disclosure provides for a carrier protein with optimal placement of an antigen identified by the process of i)-iii). In certain embodiments, the substitution is introduced at least 2, at least 3, at least 4, at least 5, at least 6, at least 7, at least 8, or at least 9 times. In certain embodiments, the polysaccharide is a capsular polysaccharide of a bacterium. In certain embodiments, the bacterium is *Streptococcus pneumoniae, Neisseria meningitidis, Haemophilus influenzae, Streptococcus pyogenes*, or *Streptococcus agalactiae*. In certain embodiments, the bacterium is *Streptococcus pneumoniae*. In certain embodiments, polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, the antigen is a capsular polysaccharide derived from one of the six serotypes of *Porphyromonas gingivalis* (e.g., K1, K2, K3, K4, K5 and/or K6).

VI. Modified Polypeptides and Polysaccharides

In some embodiments, the disclosure provides for a modified polypeptide comprising at least one compound, or salt thereof, comprising Formula XI or XIa:

(formula XI)

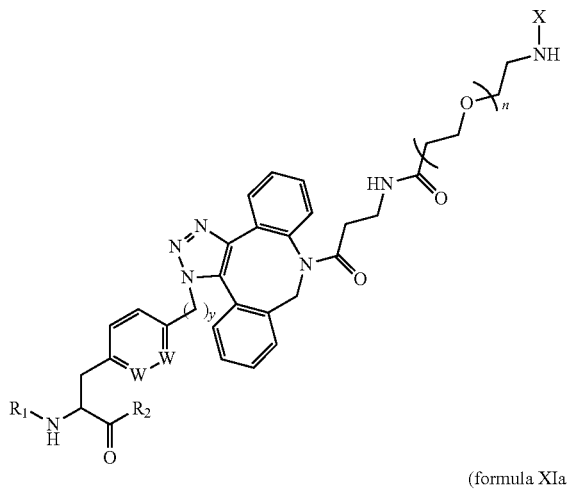

(formula XIa)

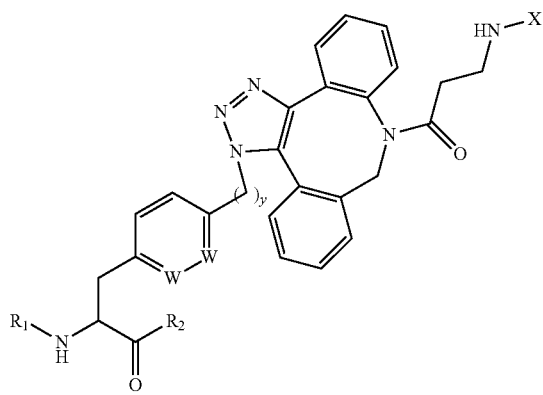

wherein
 $R_1$ is independently H, formyl, or at least one amino acid of a carrier protein;
 $R_2$ is independently OH or at least one amino acid of a carrier protein; and
 X is independently at least one polyol of a polysaccharide.
In certain embodiments, the carrier protein retains a T-cell binding epitope of diphtheria toxoid (DT), tetanus toxoid (TT), *Haemophilus* protein D (PD), outer membrane protein complex of serogroup B *meningococcus* (OMPC), or CRM197. In certain embodiments, the polysaccharide is a capsular polysaccharide of a bacterial species. In certain embodiments, the bacterial species is *Streptococcus pneumoniae*. In certain embodiments, the bacterial species is *Streptococcus pneumoniae, Neisseria meningitidis, Haemophilus influenzae, Streptococcus pyogenes*, or *Streptococcus agalactiae*. In certain embodiments, the polysaccharide is a capsular polysaccharide of a *Streptococcus pneumoniae* serotype selected from the group selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, R1 and R2 are not amino acids that occur in a T-cell epitope of the carrier protein. In certain embodiments, the antigen is a capsular polysaccharide derived from one of the six serotypes of *Porphyromonas gingivalis* (e.g., K1, K2, K3, K4, K5 and/or K6).

In some embodiments, the disclosure provides for a modified polysaccharide, comprising at least one compound, or salt thereof, comprising formula VII or VIIa

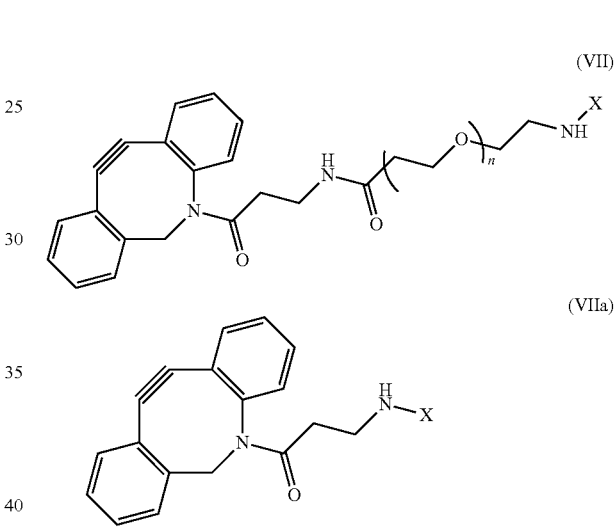

wherein
 X is independently at least one polyol of the capsular polysaccharide; and
 n is at least 1.

In certain embodiments, the modified polysaccharide of formula VII is further conjugated to a carrier protein comprising at least one nnAA. In certain embodiments, the modified polysaccharide is conjugated by a [2+3] cycloaddition. In certain embodiments, the polysaccharide is derived from a bacterial species. In certain embodiments, bacterial species is *Streptococcus pneumoniae*. In certain embodiments, the bacterial species is *Streptococcus pneumoniae, Neisseria meningitidis, Haemophilus influenzae, Streptococcus pyogenes*, or *Streptococcus agalactiae*. In certain embodiments, the polysaccharide is a bacterial capsular polysaccharide. In certain embodiments, the molar ratio of DBCO to repeating unit of the capsular polysaccharide is greater than 1. In certain embodiments, the capsular polysaccharide is of a *Streptococcus pneumoniae* serotype comprising 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, the antigen is a capsular polysaccharide derived from one of the six serotypes of *Porphyromonas gingivalis* (e.g., K1, K2, K3, K4, K5 and/or K6).

In some embodiments, the disclosure provides a modified polysaccharide according to $(A-X)_z-Y$
wherein
A is

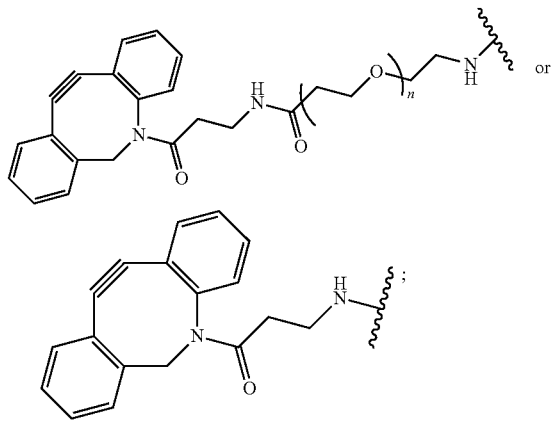

X is independently at least one polyol;
Y is independently at least one polyol of a polysaccharide;
n is at least 1; and
z is greater than 1.

In certain embodiments, the polysaccharide is derived from a bacterial species. In certain embodiments, the bacterial species is *Streptococcus pneumoniae*. In certain embodiments, the bacterial species is *Streptococcus pneumoniae, Neisseria meningitidis, Haemophilus influenzae, Streptococcus pyogenes*, or *Streptococcus agalactiae*. In certain embodiments, the polysaccharide is a bacterial capsular polysaccharide. In certain embodiments, the capsular polysaccharide is that of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, the antigen is a capsular polysaccharide derived from one of the six serotypes of *Porphyromonas gingivalis* (e.g., K1, K2, K3, K4, K5 and/or K6). In certain embodiments, the polysaccharide is further conjugated to a carrier protein. In certain embodiments, the polysaccharide is conjugated to a carrier protein via a linkage of formula II. In certain embodiments, the carrier protein retains a T-cell binding epitope of CRM197. In certain embodiments, the polysaccharide is conjugated by a [2+3] cycloaddition. In certain embodiments, the carrier protein comprises one or more non-natural amino acids. In certain embodiments, the carrier protein retains a T-cell binding epitope of diphtheria toxoid (DT), tetanus toxoid (TT), *Haemophilus influenzae* protein D (PD), outer membrane protein complex of serogroup B *meningococcus* (OMPC), or CRM197. In certain embodiments, the carrier protein is further conjugated to an antigen. In certain embodiments, the carrier protein is conjugated to an antigen via a linkage of formula II. In certain embodiments, a ratio (w/w) of the polysaccharide to the carrier protein (PS:PC) is between about 1.5 and about 4.

VII. Compositions of Polypeptide-Antigen Conjugates

Described herein are immunogenic compositions comprising at least one enhanced carrier protein-antigen conjugate together with at least one excipient, wherein the antigen is conjugated to the polypeptide via a nnAA residue in the enhanced carrier protein. In some embodiments, the disclosure provides for a vaccine composition comprising a glycoconjugate described herein. In some embodiments, the conjugate vaccine composition comprising at least one enhanced carrier protein-antigen conjugate as described herein elicits reduced carrier suppression in a subject compared to a conjugate vaccine composition comprising the native carrier protein. In some embodiments, the conjugate vaccine composition comprising at least one enhanced carrier protein-antigen conjugate as described herein improves the overall immune response and/or increases the T-cell dependent response in a subject compared to a conjugate vaccine composition comprising the native carrier protein.

In some embodiments the immunogenic composition comprises a single carrier-protein-antigen conjugate (e.g. a single serotype of pneumococcus). In some embodiments the immunogenic composition comprises multiple carrier-protein antigen conjugates (e.g. multiple serotypes of pneumococcus). In further embodiments, the multiple carrier-protein antigen conjugates optionally comprise: (a) multiple antigens conjugated to a common enhanced carrier protein; or (b) multiple antigens conjugated to different enhanced carrier proteins. In further embodiments, the multiple enhanced carrier protein antigen conjugates comprise antigens derived from different serotypes of the same organism (e.g. *S. pneumoniae*). Where a composition includes multiple different antigens (e.g. capsular polysaccharide from multiple serotypes of pneumococcus, or from multiple serogroups of *meningococcus*) it may be advantageous that the same type of carrier protein is used for each antigen e.g. each antigen is individually conjugated to the same nnAA-containing CRM197 variant, and the individual antigen-protein conjugates are then combined to give a multi-antigen composition.

VII.A. Multivalent Compositions

Exemplary compositions of the invention involve the use of two or more different conjugates e.g. within a single pharmaceutical composition. These embodiments are also referred to as multivalent. When any two conjugates are described as 'different', or provide different valencies in a 'multivalent' composition, this refers to a difference between the combination of carrier polypeptide and antigen in those two conjugates. For example, when a single type of modified CRM197 (e.g. SEQ ID NO:14) is conjugated to a capsular saccharide from a single serotype of pneumococcus, the reaction product will contain many different types of molecule (different molecular weights, different patterns of linkages within each molecule, etc.), but are considered as a single conjugate herein. Those of skill in the art are familiar with this heterogeneity at the molecular level and similarly define individual conjugates of a vaccine by the antigen-carrier combination of the particular conjugate, with other properties (such as molecular weight) being an average within the conjugate composition. Two 'different' conjugates have a different carrier polypeptide (i.e. having a different amino acid sequence) and/or a different antigen (i.e. having a different antigenic structure).

For instance, capsular saccharide antigens may be purified from two different serotypes of pneumococcus. These two different capsular saccharides can be separately conjugated to a carrier polypeptide (which may be the same or different) to provide two different conjugates. Thus, in relation to bacterial capsular saccharide conjugates, the difference between two 'different' conjugates will typically be that one contains capsular saccharide from a first serotype or serogroup of a bacterial species whereas the other contains capsular saccharide from a second serotype or serogroup of that bacterial species e.g. capsular saccharides from different serotypes of *S. pneumoniae*, or capsular saccharides from different serogroups of *N. meningitidis*. Two conjugates would also be 'different' if they included antigenically distinct capsular saccharides from multiple bacterial species e.g. a Hib saccharide conjugate and a meningococcal saccharide conjugate.

Exemplary multivalent compositions of the invention include n different immunogenic saccharide conjugates, wherein the saccharide antigen in each of then immunogenic conjugates is distinct from the saccharide antigen of the other n−1 immunogenic conjugates. For instance, if the composition includes antigens from a single bacterial species, there can be capsular saccharides from n different serotypes or n different serogroups of that species.

This nomenclature in relation to 'different' conjugates is used in the field of conjugate vaccine. For instance, Glesby et al. (2015) *J Infect Dis* 212:18-27 mentions that the Prevnar™ PCV13 vaccine contains '13 different conjugates' because it includes saccharide antigens from 13 different pneumococcal serotypes, separately conjugated to CRM197. Similarly, EP-A-2932979 refers to "an immunogenic composition comprising 13 different polysaccharide-protein conjugates."

Thus the PCV7 Prevnar™ vaccine has 7 different conjugates, the PCV13 Prevnar™ vaccine has 13 different conjugates, the Menveo™ vaccine has 4 different conjugates, the Menactra™ vaccine has 4 different conjugates, the Nimenrix™ vaccine has 4 different conjugates, the Menitorix™ vaccine has 2 different conjugates, the Menhibrix™ vaccine has 3 different conjugates, the Synflorix™ vaccine has 10 different conjugates, etc.

Multivalent compositions of pneumococcal conjugates preferably include more than 13 different conjugates e.g. 14, 15, 20, 21, 24, 25, or more. Suitable choices of serotypes for these >13-valent compositions are discussed above.

With respect to high valency vaccines (e.g., with greater than 13 different conjugates) it may sometimes be advantageous to use more than one carrier polypeptide to reduce the possibility of carrier suppression (e.g. see WO98/51339 and WO2011/110241). For example, in a multivalent vaccine comprising n different conjugates, a first carrier polypeptide is conjugated to n-y different antigens (e.g., the capsular saccharides from different bacterial serotypes or serogroups) and a second polypeptide carrier is conjugated to the remaining y antigens. In a similar manner, three, four or more carriers could be used with the n antigens divided among them. When more than one carrier is used, at least the first carrier is a nnAA-containing carrier polypeptide according to the present invention. In certain embodiments, at least the first and second carriers are nnAA-containing carrier polypeptide s according to the present invent VII.B. Adjuvants Pharmaceutical compositions of the invention can include an aluminum salt adjuvant. The adjuvant can enhance the immunogenicity of conjugates within the pharmaceutical composition. Conjugates within the composition may be adsorbed to the aluminum salt adjuvant.

Useful aluminum salt adjuvants include, but are not limited to, aluminum hydroxide adjuvants and aluminum phosphate adjuvants. These adjuvants are described e.g. in chapters 8 & 9 of *Vaccine Design* . . . (1995) eds. Powell & Newman. ISBN: 030644867X. Plenum. In particular embodiments, the adjuvant is aluminum potassium phosphate, aluminum hydroxyphosphate sulfate, aluminum hydroxide, or aluminum phosphate, or any combination thereof. In other variations, the adjuvant is an oil-in-water emulsion. In particular embodiments, the adjuvant is AS03, MF59, or AF03, or any combination thereof. In yet other variations the adjuvant is a TLR4-agonist. In a particular embodiment the adjuvant is RC529. Useful adjuvants for use with the invention are aluminum salts, such as an aluminum phosphate adjuvant (e.g. an aluminum hydroxyphosphate adjuvant).

The adjuvants commonly known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as $Al(OH)_3$, by infrared (IR) spectroscopy, in particular by the presence of an adsorption band at 1070 $cm^{-1}$ and a strong shoulder at 3090-3100 $cm^{-1}$ (chapter 9 of Powell & Newman). The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants e.g. with needle-like particles with diameters about 2 nm. The pI of aluminum hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminum hydroxide adjuvants.

The adjuvants commonly known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of Powell & Newman).

The $PO_4/Al^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with $PO_4$/Al molar ratio between 0.84 and 0.92, included at 0.6 mg $Al^{3+}$/ml. The aluminum phosphate will generally be particulate (e.g. plate-like morphology as seen in transmission electron micrographs, with primary particles in the range of 50 nm). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

The concentration of aluminum ions in a composition for administration to a patient is preferably less than 2.5 mg/ml e.g. ≤2.5 mg/ml, ≤2 mg/ml, ≤1 mg/ml, etc. A useful maximum concentration is ≤1.7 mg/mL. The range of $Al^{+++}$ in a composition of the invention can be from 0.3-1 mg/ml or from 0.3-0.5 mg/ml. A maximum of 0.85 mg/dose may be preferred.

In solution both aluminum phosphate and aluminum hydroxide adjuvants tend to form stable porous aggregates 1-10 μm in diameter. A composition can include a mixture of both an aluminum hydroxide adjuvant and an aluminum phosphate adjuvant.

Where a composition includes multiple conjugates and each of these is adsorbed to an aluminum salt adjuvant, each conjugate can be adsorbed to an aluminum salt individually and then mixed, or they can each be added in sequence to an aluminum salt, thereby forming the mixed conjugate composition. A mixture of both approaches can also be used.

VII.C. Excipients for Pharmaceutical Compositions

Pharmaceutical compositions of the invention will generally include one or more pharmaceutically acceptable excipient(s). A comprehensive discussion of such excipients can be found in *Handbook of Pharmaceutical Excipients* (ed. Rowe et al.), 6th edition 2009.

Pharmaceutical compositions are preferably in aqueous form, particularly at the point of administration, but they can also be presented in dried forms (e.g. as lyophilisates, etc.) which can be converted into aqueous forms for administration.

Pharmaceutical compositions can include a buffer or pH adjusting agent. The buffer can be selected from the group consisting of a phosphate buffer, an acetate buffer, a histidine buffer, a citrate buffer, a succinate buffer, a Tris buffer, a HEPES buffer, etc. Buffer salts will typically be included in the 5-20 mM range.

Pharmaceutical compositions can include a physiological salt, such as a sodium salt e.g. to control tonicity. Sodium chloride (NaCl) is typical, which may be present at from 1-20 mg/ml e.g. 10±2 mg/ml or 9 mg/ml. In addition to sodium chloride, other excipients to bring the osmolality of the composition into an acceptable range can also be employed, including dextrose and glycerin. Other salts that may be present include potassium chloride, potassium dihydrogen phosphate, disodium phosphate dehydrate, magnesium chloride, calcium chloride, etc. Other useful salts may have sodium, potassium or ammonium cations and chloride, citrate, ascorbate, borate, phosphate, bicarbonate, sulfate, thiosulfate or bisulfite anions.

Pharmaceutical compositions can include an organic acid, such as acetic acid or succinic acid. This may be part of a buffer system comprising a buffer or pH adjusting agent. In particular embodiments, the buffer or pH adjusting agent is selected from the group consisting of sodium borate, sodium phosphate, sodium citrate, ammonium sulfate, or succinate, and any combination thereof. Other examples of suitable buffers include acids such as acetic, boric, citric, lactic, phosphoric and hydrochloric acids; bases such as sodium hydroxide, sodium acetate, sodium lactate and tris-hydroxymethylaminomethane; and buffers such as citrate/dextrose, sodium bicarbonate and ammonium chloride. Histidine buffers are also useful in immunogenic compositions.

Pharmaceutical compositions can include a sugar alcohol such as mannitol or sorbitol. Pharmaceutical compositions can include a sugar such as sucrose or glucose.

Pharmaceutical compositions can include a surfactant. Suitable surfactants include, but are not limited to, polysorbate 20, polysorbate 80, and sodium dodecyl sulfate (SDS). In some embodiments the surface active agent is present at a concentration from 0.0003% and 0.3% (w/w) e.g. from 0.01-0.03%. Polysorbate 80 is a useful surfactant. In some embodiments the surface active agent is present at a concentration from 0.03% and 0.3% (w/w) e.g. from 0.01-0.03%. Polysorbate 80, from 0.03-0.3% polysorbate 80 or polysorbate 20, about 0.05-0.2% polysorbate 80 or polysorbate 20, about 0.05-0.15% polysorbate 80 or polysorbate 20, about 0.05%, 0.1%, 0.15%, 0.2%, 0.25%. An exemplary formulation comprises 0.1% polysorbate 20 or 0.1% polysorbate 80.

Pharmaceutical compositions can include a preservative such as thiomersal or 2-phenoxyethanol. It is preferred that a composition should be substantially free from (e.g. <10 μg/ml) mercurial material e.g. thiomersal-free. Compositions containing no mercury are more preferred. The inclusion of a preservative can be particularly useful when a composition includes an aluminum salt adjuvant because their insolubility means that the composition is generally a suspension having a cloudy appearance which can mask contaminating bacterial growth. A preservative is also particularly useful if a composition is to be used more than once e.g. in a multidose vial. Often, however, a pharmaceutical composition can be preservative-free.

In some embodiments, the excipients selected are suitable for parenteral administration of the composition. Examples of buffers suitable for parenteral administration include salts having sodium, potassium or ammonium cations and chloride, citrate, ascorbate, borate, phosphate, bicarbonate, sulfate, thiosulfate or bisulfite anions; suitable salts include potassium chloride, sodium thiosulfate, sodium bisulfite and ammonium sulfate.

In further embodiments, the at least one excipient optionally comprises a surface active agent (surfactant). In particular embodiments, the surface active agent is polyoxyethylene sorbitan monolaurate (polysorbate 20 or 'Tween 20'), polyoxyethylene sorbitan monooleate (polysorbate 80 or 'Tween 80'), Brij 35, Triton X-10, Pluronic F127, or sodium dodecyl sulfate (SDS). In some embodiments the surface active agent is present at a concentration between 0.0003% and 0.3% (w/w).

In some embodiments, the at least one excipient optionally comprises an adjuvant, an agent which increases the stimulation of the immune system by enhancing antigen presentation (depot formulation, delivery systems) and/or by providing costimulation signals (immunomodulators).

An exemplary composition comprises (i) one or more conjugates as defined herein e.g. capsular polysaccharide from multiple pneumococcal serotypes conjugated to nnAA-containing carrier proteins and (ii) an aluminum phosphate adjuvant.

VII.D. Conjugate Levels

A pharmaceutical composition of the invention can include multiple immunogenic conjugates. Currently licensed meningococcal conjugate vaccines include capsular saccharides from 4 different serogroups, and licensed pneumococcal conjugate vaccines include capsular saccharides from 7, 10, or 13 different serotypes. Thus a composition of the invention can include, for instance, from 3 to 50 different conjugates (e.g. 14, 15, 20, 21, 24, 25, or more). For example, each of these conjugates can include a capsular saccharide from a different serotype or serogroup of the same bacterial species (e.g. multiple meningococcal serogroups or multiple pneumococcal serotypes).

Where a pharmaceutical composition includes n different immunogenic conjugates, the total amount of carrier polypeptide in those n conjugates can be less than or equal to 3n μg per dose. In other words, the average amount of carrier polypeptide per conjugate is less than 31.1 g. The total amount can, for instance, be from n-2.5n μg per dose.

Where a pharmaceutical composition includes n different immunogenic conjugates, the total amount of saccharide antigen in those n conjugates can be less than or equal to 4.4n μg per dose. In other words, the average amount of saccharide per conjugate is less than 4.414. The total amount can, for instance, be from 0.4n-4.4n μg per dose e.g. from 1.1n-2.2n.

Where a pharmaceutical composition includes n different immunogenic conjugates, the total concentration of carrier polypeptide for those n conjugates can be less than or equal to 6n μg/mL. In other words, the average concentration of carrier polypeptide per conjugate is less than 61.1 g/mL. The total concentration can, for instance, be from n-4n μg/mL.

Where a pharmaceutical composition includes n different immunogenic conjugates, the total concentration of saccharide antigen for those n conjugates can be less than or equal to 8.8n μg/mL. In other words, the average concentration of saccharide per conjugate is less than 8.8 μg/mL. The total concentration can, for instance, be from 0.8n-8.8n μg/mL e.g. from 2.2n-4.4n μg/mL.

In some embodiments, the total amount of conjugated carrier polypeptide in a unit dose of a multivalent pharmaceutical composition of the invention can be from 4-12814 e.g. from 8-6414, or from 16-4814. The concentration of conjugated carrier polypeptide in a multivalent pharmaceutical composition of the invention can be from 8-25614/mL e.g. from 16-128 μg/mL, or from 32-96 μg/mL.

In some embodiments, the total amount of conjugated saccharide antigen in a unit dose of a multivalent pharmaceutical composition of the invention can be from 10-12014 e.g. from 20-9014, or from 30-6014. The concentration of conjugated saccharide antigen in a multivalent pharmaceutical composition of the invention can be from 20-24014/mL e.g. from 40-18014/mL, or from 60-120 μg/mL.

VII.E. Unconjugated Components

As noted above, a pharmaceutical composition can include multiple immunogenic conjugates e.g. from 3 to 50 different conjugates (e.g. 14, 15, 20, 21, 24, 25, or more). For example, each of these conjugates can include a capsular saccharide from a different serotype or serogroup of the same bacterial species.

In some embodiments, the composition is free from the conjugates' carrier polypeptide(s) in unconjugated form. In other embodiments, there is a low level of unconjugated carrier polypeptide(s), provided that the mass of the unconjugated carrier polypeptide(s) in the composition is <10% (e.g. <5% or <2%) of the mass of the carrier polypeptide(s) in the n immunogenic conjugates of the composition as a whole.

In some embodiments, the composition is free from the conjugates' saccharides in unconjugated form. In other embodiments, there is a low level of unconjugated saccharide, provided that the mass of the unconjugated saccharide in the composition is <10% (e.g. <5% or <2%) of the total mass of saccharides in then immunogenic conjugates of the composition.

VII.F. Containers, Delivery Devices, Etc.

Pharmaceutical compositions including immunogenic conjugates can be packaged within sterile containers, delivery devices, etc. Sterility can be maintained by hermetically sealing a container to make it airtight. Suitable containers include, but are not limited to, vials, syringes, nebulizers, sprayers, inhalers, dermal patches, etc. Vials and syringes are preferred.

Immunogenic compositions are often contained within vials. The vial is preferably made of a plastic material or, preferably, of glass. A vial is sealed after being filled, and the seal can be broken at the point of use. The vial is preferably sterilized before a composition is added to it, and is then sealed. To avoid problems with latex-sensitive patients, vials can be sealed with a latex-free stopper, and the absence of latex in all packaging material is preferred. The vial ideally includes a single unit dose of a composition, but it may sometimes include more than one dose (a 'multidose' vial) e.g. 10 doses. Preferred vials are made of colorless glass.

A vial can have a cap (e.g. a Luer lock) adapted such that a syringe can be inserted into the cap to facilitate transfer of material between vial and syringe (in both directions). After removal of the syringe from the vial, a needle can then be attached and the composition can be administered to a subject. The cap is preferably located inside a seal or cover, such that the seal or cover has to be removed before the cap can be accessed. A vial may have a cap that permits aseptic removal of its contents, particularly for multidose vials.

Compositions can be contained within delivery devices, ready for administration to a subject. The composition can be transferred into the delivery device at the point of use (e.g. from a vial), or it can be put into the delivery device at the manufacturing stage (e.g. in the form of a pre-filled syringe).

A syringe used with the invention may be made of glass or of a plastic (e.g. made of a cyclo-olefin polymer or a cyclo-olefin co-polymer). A syringe (particularly a glass syringe) may be a siliconized syringe. Non-siliconized syringes can also be used e.g. using the i-Coating™ system from Terumo, which is available in their PLAJEX™ syringes, or using Daikyo CZ™ syringes having an ethylene-tetrafluoroethylene (ETFE) copolymer, or using a TriboGlide™ syringe having a perfluoropolyether (PFPE). Carbon films may be used instead of siliconization (e.g. see JP2001190665). Silicone-free syringes are also disclosed in JP2011212183. A non-siliconized syringe including a plunger stopper as disclosed in EP-A-0375778 may be used i.e. where the stopper has a thermoplastic elastomer layer which is covered at least in part by a thermoplastic resin layer of low dynamic friction coefficient.

Where a composition is contained within a syringe, the syringe may have a needle attached to it, for injection of the syringe's contents into a subject or into a container. The syringe may be supplied with a needle already attached. If a needle is not attached, a separate needle may be supplied with the syringe for assembly and use, or a needle can be separately sourced. Such a needle should be sterile at the time of use, and may be sheathed. Safety needles can be used. 1-inch 23-gauge, 1-inch 25-gauge and ⅝-inch 25-gauge needles are typical. Needles ¼-1¼ inch, 22-25 gauge, can be used. If the syringe and needle are packaged separately then the needle is preferably fitted with a butyl rubber shield.

Syringes may be provided with peel-off labels on which a lot number and expiration date of the contents may be printed, to facilitate record keeping. A plunger in a syringe can have a stopper to prevent the plunger from being accidentally removed during aspiration. The syringes may have a latex rubber cap and/or plunger, but latex-free rubbers can be used e.g., latex-free chlorobutyl rubber or latex-free isoprene bromobutyl rubber. The syringe will generally have a tip cap to seal the tip prior to attachment of a needle, and the tip cap is preferably made of a butyl rubber e.g. latex-free isoprene bromobutyl rubber. Useful syringes are, for instance, those marketed under the trade name "Tip-Lok"™.

Containers may be marked to show a half-dose volume e.g. to facilitate delivery to children. For instance, a syringe containing a 0.5 ml dose may have a mark showing a 0.25 ml volume. The syringe itself may have a volume larger than the dose e.g. 1 ml syringe can be used to contain a 0.5 ml dose of a pharmaceutical composition. Disposable or pre-filled syringes usually contain a single dose of vaccine.

Where a glass container (e.g. a syringe or a vial) is used, then it is preferably made from a borosilicate glass rather than from a soda lime glass.

A container may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc. Multiple containers may be packaged together e.g. in the same box.

Pharmaceutical compositions can be presented in unit dose form, with a single dose per container (e.g. per syringe or per vial). Rather than manufacture each unit dose individually, a bulk composition is prepared and unit doses are extracted and individually packaged within their containers. Thus, for instance, a plurality of unit doses are extracted from the bulk and each unit dose is placed into a separate container e.g. into a syringe or a vial.

VII.G. Other Aspects of the Compositions:

In other embodiments, the overall (weight by weight) ratio of all serotype polysaccharides to carrier protein (PS:PC) in a composition of the invention is between 0.5 and 4.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0). In certain embodiments, the (w/w) PS:PC ratio in the carrier protein conjugate (or in the overall multivalent composition) is between 0.7 and 2.8. In certain embodiments, the (w/w) PS:PC ratio in the carrier protein conjugate (or in the overall multivalent composition) is between 1.0 and 2.8. In certain embodiments, the (w/w) PS:PC ratio in the carrier protein conjugate (or in the overall multivalent composition) is at least 0.8, at least 0.9, at least 1.0, at least 1.1, at least 1.2, at least 1.3. at least 1.4 or at least 1.5 (w/w). In certain embodiments the ratio of polysaccharide to enhanced carrier protein in the polysaccharide-enhanced carrier protein conjugate (or in the overall multivalent composition) is greater than 0.9 (w/w). In certain embodiments the ratio of polysaccharide to enhanced carrier protein in the polysaccharide-enhanced carrier protein conjugate (or in the overall multivalent composition) is between about 0.9 and about 3.0 (w/w). An exemplary composition includes protein-saccharide conjugates of capsular polysaccharides from multiple pneumococcal serotype with an overall mass excess of polysaccharide to protein e.g. a protein:polysaccharide ratio between 1:1.1 and 1:2 (w/w) e.g. between 1:1.5 and 1:1.9.

In some embodiments, the overall molecular weight range of all serotype polysaccharide-carrier protein conjugates in a multivalent serotype polysaccharide-carrier protein conjugate composition is within a particular range. In some embodiments, the antigen-enhanced carrier protein conjugates have a molecular weight of about 750 kDa, about 1,000 kDa, about 1,500 kDa, about 2,000 kDa, about 2,500 kDa, about 3,000 kDa, about 3,500 kDa, about 4,000 kDa, about 4,500 kDa, about 5,000 kDa, about 5,500 kDa, about 6,000 kDa, about 6,500 kDa, about 7,000 kDa, about 7,500 kDa, or about 8,000 kDa. In some embodiments, the antigen-enhanced carrier protein conjugates have a molecular weight of at least about 750 kDa, at least about 1,000 kDa, or at least about 1,500 kDa, In some embodiments, the antigen-enhanced carrier protein conjugates have a molecular weight of between about 750 kDa and about 2,800 kDa. In some embodiments, the antigen-enhanced carrier protein conjugates have a molecular weight of between about 800 kDa and about 2,800 kDa. In some embodiments, the antigen-enhanced carrier protein conjugates have a molecular weight of between about 850 kDa and about 2,800 kDa. In some embodiments, the antigen-enhanced carrier protein conjugates have a molecular weight of between about 900 kDa and about 2,800 kDa. In some embodiments, the antigen-enhanced carrier protein conjugates have a molecular weight of between about 950 kDa and about 2,800 kDa. In some embodiments, the antigen-enhanced carrier protein conjugates have a molecular weight of between about 1,000 kDa and about 2,800 kDa.

In further embodiments, the immunogenic composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 distinct enhanced carrier protein-antigen conjugates.

In any composition that includes multiple conjugates (e.g. a conjugate for each of multiple pneumococcal serotypes) it could be preferred in some instances that the carrier protein in each conjugate is identical. In an alternative embodiment of such compositions with multiple conjugates, it may be preferred to use more than one carrier. While it is possible that each antigen (e.g., capsular polysaccharides from different pneumococcal serotypes) could be conjugated to a different carrier, typically there would be only 2-4 (e.g., 2 or 3) different carriers represented among the individual conjugates in such compositions. By way of illustration and not of limitation, in a composition of 24 different conjugates, each conjugate comprising a capsular polysaccharides from a different pneumococcal serotype, some but not all of the 24 conjugates comprise a first carrier protein (e.g., based on CRM197) and the balance of the 24 conjugates comprise a second protein carrier (e.g., based on HiD). Thus, again by way of example and not of limitation, 12, 13, 15 or 20 of the 24 conjugates could comprise the first carrier protein, and the 12, 11, 9 or 4, respectively, remaining conjugates could comprise the second carrier protein.

VIII. Method for Increasing the PS:PC Ratio of an Immunogenic Composition

Also provided is a method for increasing the polysaccharide to protein carrier ratio (w/w) (PS:PC) of an immunogenic composition, comprising: (a) introducing into a carrier protein one or more nnAA substitutions; and (b) conjugating a polysaccharide to the carrier protein via the one or more non-natural amino acid substitutions. In certain embodiments, the one or more substitutions comprises at least 2, at least 3, at least 4, at least 5, at least 6, at least 7, at least 8, or at least 9 substitutions. In certain embodiments, the nnAA substitutions are not in a T-cell activating epitope of the carrier protein. In certain embodiments the nnAA is pAMF. In certain embodiments, the carrier protein retains a T-cell binding epitope of diphtheria toxoid (DT), tetanus toxoid (TT), Haemophilus protein D (PD), outer membrane protein complex of serogroup B meningococcus (OMPC), or CRM197. The non-natural amino acid substitutions can occur at lysine residues, such as lysine residues selected from the group consisting of. In certain embodiments, the lysine residues are selected from the group consisting of K24, K33, K37, K39, K212, K214, K227, K244, K264, K385, K522 and/or K526 in SEQ ID NO:11 or 12. In some embodiments, the lysine residues are selected from the group consisting of K25, K34, K38, K40, K213, K215, K228, K265, K386, K523 and K527, and any combination thereof of SEQ II) NO:1. In certain embodiments, the polysaccharide is conjugated to the carrier protein via a linkage of formula XI or XIa:

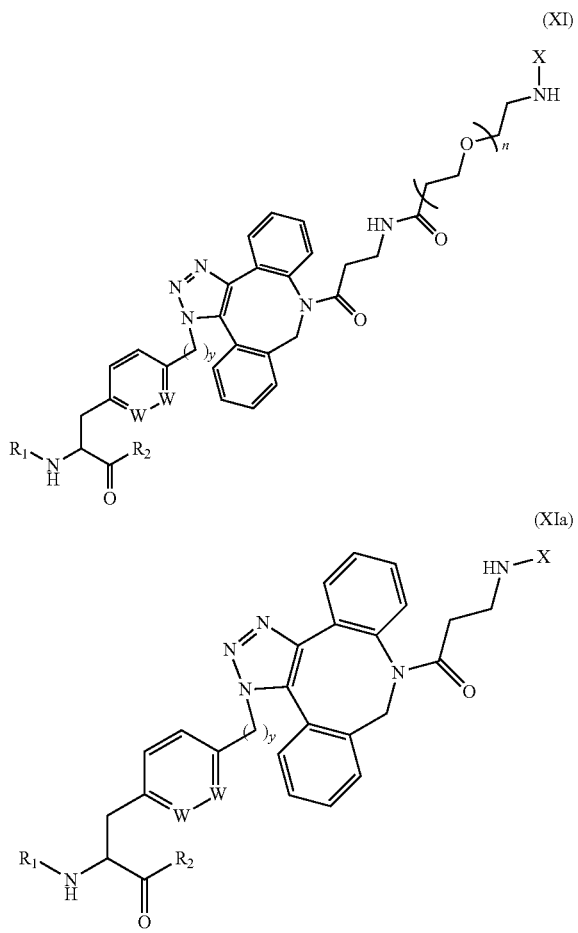

wherein
- $R_1$ is independently H, formyl, or at least one amino acid of the carrier protein;
- $R_2$ is independently OH or at least one amino acid of the carrier protein; and
- X is independently at least one polyol of a capsular polysaccharide.

In certain embodiments, the PS:PC ratio is between about 1.5 and about 4. In certain embodiments, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In certain embodiments, the antigen is a capsular polysaccharide derived from one of the six serotypes of *Porphyromonas gingivalis* (e.g., K1, K2, K3, K4, K5 and/or K6). In certain embodiments, the polysaccharide is a capsular polysaccharide of *Streptococcus pneumoniae, Neisseria meningitidis, Haemophilus influenzae, Streptococcus pyogenes*, or *Streptococcus agalactiae*. In certain embodiments, the disclosure provides a glycoprotein prepared by a process comprising steps (a)-(b).

IX. Raising Immune Responses

An immunogenic conjugate can be administered to a mammalian subject to elicit a protective immune response against the antigen in that conjugate. They will be administered in the form of a pharmaceutical composition. The composition can include multiple immunogenic conjugates as described elsewhere herein, so protective immune responses can be elicited against many antigens simultaneously.

Thus we provide a method of eliciting a protective antibody response to one or more antigen(s) in a mammalian subject by administering to the subject a conjugate of the antigen(s).

We also provide a conjugate as disclosed herein, for use in eliciting a protective antibody response.

We also provide the use of a conjugate as disclosed herein in the manufacture of a medicament for eliciting a protective antibody response.

We also provide (i) a method of eliciting a protective antibody response to multiple antigen(s) in a mammalian subject by administering to the subject a multivalent composition of the invention, (ii) a multivalent composition of the invention for use in eliciting a protective antibody response, and (iii) the use of multiple conjugates as disclosed herein in the manufacture of a multivalent pharmaceutical composition for eliciting a protective antibody response against multiple antigens.

The ability to elicit a protective immune response means that the conjugates can be used, for example, to provide active immunization for the prevention of invasive disease caused by *S. pneumoniae*, for the prevention of otitis media caused by *S. pneumoniae*, for the prevention of pneumonia caused by *S. pneumoniae*, for active immunization of subjects at risk of exposure to *N. meningitidis* to prevent invasive disease, etc.

Enumerated Embodiments

Some embodiments of this disclosure relate to Embodiment I, as follows:

Embodiment I-1

A sterile container containing a pharmaceutical composition which comprises an immunogenic conjugate comprising a carrier polypeptide and a saccharide antigen, wherein the saccharide antigen is covalently bonded to the carrier polypeptide via a non-natural amino acid residue therein.

Embodiment I-2

A hermetically sealed container containing a pharmaceutical composition which comprises an immunogenic conjugate comprising a carrier polypeptide and a saccharide antigen, wherein the saccharide antigen is covalently bonded to the carrier polypeptide via a non-natural amino acid residue therein. Suitable containers for hermetic sealing include e.g. a vial. The contents are preferably sterile at the point of hermetic sealing.

Embodiment I-3

The container of embodiment I-1 or I-2, which is a sterile glass container such as a vial.

Embodiment I-4

A delivery device containing a pharmaceutical composition which comprises an immunogenic conjugate comprising a carrier polypeptide and a saccharide antigen, wherein the saccharide antigen is covalently bonded to the carrier polypeptide via a non-natural amino acid residue therein.

Embodiment I-5

The container of embodiment I-1 or I-2, or the delivery device of embodiment I-4, which is a syringe.

Embodiment I-6

A pharmaceutical composition comprising two or more different immunogenic conjugates and an aluminum salt adjuvant, wherein: (i) each immunogenic conjugate comprises a carrier polypeptide and a saccharide antigen, wherein the saccharide antigen is covalently bonded to the carrier polypeptide via a non-natural amino acid residue therein; and (ii) the aluminum salt adjuvant is an aluminum hydroxide or aluminum phosphate adjuvant.

Embodiment I-7

A pharmaceutical composition comprising two or more different immunogenic conjugates, and an aluminum phosphate adjuvant, wherein: (i) each immunogenic conjugate comprises a carrier polypeptide and a saccharide antigen, wherein the saccharide antigen is covalently bonded to the carrier polypeptide via a non-natural amino acid residue therein; and (ii) the concentration of aluminum ions in the composition is ≤2.5 mg/mL.

Embodiment I-8

A pharmaceutical composition comprising two or more different immunogenic conjugates, wherein: (i) each immunogenic conjugate comprises a carrier polypeptide and a saccharide antigen, wherein the saccharide antigen is covalently bonded to the carrier polypeptide via a non-natural amino acid residue therein; and (ii) the volume of the pharmaceutical composition is from 0.25-1.25 mL.

Embodiment I-9

A pharmaceutical composition comprising two or more different immunogenic conjugates and a preservative, wherein each immunogenic conjugate comprises a carrier polypeptide and a saccharide antigen, wherein the saccharide antigen is covalently bonded to the carrier polypeptide via a non-natural amino acid residue therein.

Embodiment I-10

A preservative-free pharmaceutical composition comprising two or more different immunogenic conjugates, wherein each immunogenic conjugate comprises a carrier polypeptide and a saccharide antigen, wherein the saccharide antigen is covalently bonded to the carrier polypeptide via a non-natural amino acid residue therein.

Embodiment I-11

A pharmaceutical composition comprising two or more different immunogenic conjugates, wherein: (i) each immunogenic conjugate comprises a carrier polypeptide and a saccharide antigen, wherein the saccharide antigen is covalently bonded to the carrier polypeptide via a non-natural amino acid residue therein; (ii) the composition has an osmolality from 200-400 mOsm/kg.

Embodiment I-12

A pharmaceutical composition comprising two or more different immunogenic conjugates and at least one excipient wherein: (i) each immunogenic conjugate comprises a carrier polypeptide and a saccharide antigen, wherein the saccharide antigen is covalently bonded to the carrier polypeptide via a non-natural amino acid residue therein; and (ii) the at least one excipient is selected from the group consisting of sodium chloride, succinic acid, and polysorbate 80.

Embodiment I-13

A pharmaceutical composition comprising n different immunogenic conjugates wherein:
(i) each of the n immunogenic conjugates comprises a carrier polypeptide and a saccharide antigen, wherein the saccharide antigen is covalently bonded to the carrier polypeptide via a non-natural amino acid residue therein;
(ii) n is an integer from 3 to 50; and
(iii) the total amount of carrier polypeptide in the n immunogenic conjugates is less than or equal to 3n μg per dose;
(iv) the total concentration of carrier polypeptide in the n immunogenic conjugates is less than or equal to 6n μg/ml;
(v) the total amount of saccharide antigen in the n immunogenic conjugates is less than or equal to 3n μg per dose;
(vi) the total concentration of saccharide antigen in the n immunogenic conjugates is less than or equal to 6n μg/mL;
(vii) the average amount of carrier polypeptide per conjugate is from 1-4 μg per dose;
(viii) the average concentration of carrier polypeptide per conjugate is from 2-8 μg/mL;
(ix) the average amount of saccharide antigen per conjugate is from 1-4 μg per dose;
(x) the average concentration of saccharide antigen per conjugate is from 2-8 μg/mL;
(xi) the composition is free from the carrier polypeptide(s) in unconjugated form;
(xii) the composition contains the carrier polypeptide(s) in unconjugated form, wherein the mass of the carrier polypeptide(s) in unconjugated form in the composition is <10% of the mass of that carrier polypeptide in the n immunogenic conjugates;
(xiii) the composition is free from the saccharide antigens in unconjugated form; and/or (xiv) the composition contains at least one of the saccharide antigens in unconjugated form, wherein the total mass of the saccharide antigens in unconjugated form in the composition is <10% of the total mass of the saccharide antigens in then immunogenic conjugates.

Embodiment I-14

A process for preparing a plurality of unit doses of a pharmaceutical composition, wherein (i) the pharmaceutical composition comprises an immunogenic conjugate comprising a carrier polypeptide and a saccharide antigen, wherein the saccharide antigen is covalently bonded to the carrier polypeptide via a non-natural amino acid residue therein, and (ii) the process comprises steps of preparing a bulk composition comprising the immunogenic conjugate and packaging individual unit doses from the bulk composition into a plurality of individual containers.

Embodiment I-15

A process for preparing a pharmaceutical composition, wherein the pharmaceutical composition comprises two or more different immunogenic conjugates and an aluminum salt adjuvant, wherein (i) each of the immunogenic conjugates comprises a carrier polypeptide and a saccharide antigen, and (ii) the saccharide antigen is covalently bonded to the carrier polypeptide via a non-natural amino acid residue therein; and the process comprises either (A) steps of separately adsorbing each of the immunogenic conjugates to an aluminum salt adjuvant then mixing individual adsorbed conjugates together or (B) sequentially adsorbing each of the immunogenic conjugates to the aluminum salt adjuvant.

Embodiment I-16

A carrier polypeptide comprising an amino acid sequence which (i) has at least 80% sequence identity to SEQ ID NO: 11; (ii) is free from an Arg-Arg dipeptide sequence; and (iii) includes at least one nnAA residue.

Embodiment I-17

A carrier polypeptide comprising an amino acid sequence which (i) has at least 80% sequence identity to SEQ ID NO: 11 and (ii) includes a nnAA substitution at one or more of the following amino acid residues (numbered according to SEQ ID NO: 11): Asp-211; Asp-295; Asp-352; Asp-392; Asp-465; Asp-467; Asp 507; Asp 519; Asn 296; Asn 359; Asn 399; Asn 481; Asn 486; Asn 502; Asn 524; Glu 240; Glu 248; Glu 249; Glu 256; Glu 259; Glu 292; Glu 362; Gln 252; Gln 287; Lys 212; Lys 218; Lys 221; Lys 229; Lys 236; Lys 264; Lys 299; Lys 385; Lys 456; Lys 474; Lys 498; Lys 516; Lys 522; Lys 534; Arg 377; Arg 407; Arg 455; Arg 460; Arg 462; Arg 472; Arg 493; Ser 198; Ser 200; Ser 231; Ser 233; Ser 239; Ser 261; Ser 374; Ser 381; Ser 297; Ser 397; Ser 451; Ser 475; Ser 494; Ser 495; Ser 496; Ser 501; Ser 505; Thr 253; Thr 265; Thr 267; Thr 269; Thr 293; Thr 386; Thr 400; Thr 408; Thr-469; and/or Thr 517.

Embodiment I-18

The carrier polypeptide of embodiment I-16 or I-17, wherein Arg-193 of SEQ ID NO: 11 is substituted with a different amino acid, such as Asn.

Embodiment I-19

An immunogenic conjugate comprising the carrier polypeptide of embodiment I-16 or I-17 or I-18, conjugated via a nnAA residue therein to an antigen.

Embodiment I-20

An immunogenic conjugate comprising a carrier polypeptide and a saccharide antigen, wherein (i) the carrier polypeptide comprises amino acid sequence SEQ ID NO: 14; and (ii) the saccharide antigen is covalently bonded to the carrier polypeptide via at least one nnAA residue within SEQ ID NO: 14.

Embodiment I-21

A pharmaceutical composition comprising two or more different immunogenic conjugates according to embodiment I-20.

Embodiment I-22

The container, device, composition, process, polypeptide, or conjugate of any preceding embodiment, wherein the carrier polypeptide comprises 4 to 9 nnAA residues.

Embodiment I-23

The container, device, composition, process, polypeptide, or conjugate of any preceding embodiment, wherein at least one nnAA is substituted for a lysine in the carrier polypeptide's native sequence.

Embodiment I-24

The container, device, composition, process, polypeptide, or conjugate of any preceding embodiment, wherein the carrier polypeptide has at least 90% sequence identity to SEQ ID NO:11.

Embodiment I-25

The container, device, composition, process, polypeptide, or conjugate of embodiment I-24, wherein at least one nnAA is substituted for K24, K33, K37, K39, K212, K214, K227, K244, K264, K385, K522 and/or K526 in SEQ ID NO:11 or 12.

Embodiment I-26

The container, device, composition, process, polypeptide, or conjugate of any preceding embodiment, wherein the carrier polypeptide comprises amino acid sequence SEQ ID NO: 14.

Embodiment I-27

The container, device, composition, process, polypeptide, or conjugate of any preceding embodiment, wherein the nnAA is 2-amino-3-(4-(azidomethyl)phenyl)propanoic acid.

Embodiment I-28

The container, device, composition, process, polypeptide, or conjugate of any preceding embodiment, wherein the antigen has an alkyne group which is conjugated to the nnAA via an azido group.

Embodiment I-29

The container, device, composition, process, polypeptide, or conjugate of any preceding embodiment, wherein the antigen is a bacterial capsular saccharide; for example, a capsular saccharide from a bacterium selected from the group consisting of Streptococcus pneumoniae, Neisseria meningitidis, Haemophilus influenzae, Streptococcus pyogenes, Streptococcus agalactiae, and Porphyromonas gingivalis.

Embodiment I-30

The container, device, composition, process, polypeptide, or conjugate of any preceding embodiment, wherein the antigen is a capsular saccharide of a S. pneumoniae serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment I-31

The container, device, composition, process, polypeptide, or conjugate of any preceding embodiment, wherein ratio of saccharide to carrier polypeptide (w/w) in the conjugate(s) is greater than 1.

Embodiment I-32

The container, device, composition, process, polypeptide, or conjugate of any preceding embodiment, wherein the carrier polypeptide includes 3 or more nnAA residues and the conjugate has a molecular weight of at least 500 kDa.

Embodiment I-33

The container, device, composition, process, polypeptide, or conjugate of any preceding embodiment, wherein the conjugate has a molecular weight between 900 kDa and 5 MDa.

Embodiment I-34

The container, device, composition or process, of any one of embodiments I-1 to I-15 or embodiments I-21 to I-33, wherein pharmaceutical composition comprises:
  conjugates of capsular saccharides from 2 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 14 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 15 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 20 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 21 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 24 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 25 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
  conjugates of capsular saccharides from 4 or more different meningococcal serogroups selected from the group consisting of serogroups A, C, W135, X, and Y; or
  conjugates of capsular saccharides from 2 or more different P. gingivals serotypes selected from the group consisting of serotypes K1, K2, K3, K4, K5, and K6.

Embodiment I-35

A method of eliciting an immunoprotective antibody response to an antigen in a subject, comprising administering to the subject a pharmaceutical composition of any one of embodiments I-6 to I-13 or embodiments I-21 to I-34, or an immunogeinc conjugate according to any of embodiments I-19 to I-33, in an excipient suitable for parenteral administration.

Some embodiments of this disclosure relate to Embodiment II, as follows:

Embodiment II-1

A method for preparing a conjugate of a saccharide antigen and a carrier protein, comprising:
  (a) functionalizing the saccharide antigen with a reactive moiety capable of participating in a click chemistry reaction with a bio-orthogonal reactive moiety on a second reactant, by (i) providing the saccharide as a solution in an aqueous buffer having a pH in the range of 7 to 11; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the reactive moiety coupled to a primary amino group, under conditions effective to transfer the reactive moiety to the cyanate-substituted saccharide; and
  (b) combining the activated saccharide antigen with a carrier protein comprising a polypeptide having at least one T-cell activating epitope and at least one non-natural amino acid (nnAA) bearing the bio-orthogonal reactive moiety, such that a click chemistry reaction between the reactive moiety and the bio-orthogonal reactive moiety results in a conjugate of the saccharide antigen and the carrier protein.

Embodiment II-2

The method of embodiment II-1, wherein step (iii) is carried out about 3 to about 13 minutes after step (ii).

Embodiment II-3

The method of embodiment II-2, wherein step (iii) is carried out about 5 minutes after step (ii).

Embodiment II-4

The method of any one of embodiments II-1 through II-3, wherein (a) comprises a one-pot reaction without addition of a pH-adjusting agent during or subsequent to step (ii).

Embodiment II-5

The method of any one of embodiments II-1 through II-4, wherein the cyanylating reagent comprises cyano-4-dimethylamino pyridinium tetrafluoroborate (CDAP).

Embodiment II-6

The method of embodiment II-5, wherein the reactive moiety comprises an alkyne functionality.

Embodiment II-7

The method of embodiment II-6, wherein the alkyne functionality comprises a chemically constrained alkyne.

Embodiment II-8

The method of embodiment II-7, wherein the reactive moiety comprises a diarylcyclooctyne group.

Embodiment II-9

The method of embodiment II-8, wherein the diarylcyclooctyne group is a dibenzylcyclooctyne group.

Embodiment II-10

The method of embodiment II-9, wherein the activating reagent comprises a dibenzylcyclooctyne (DBCO) derivative having the structure (I)

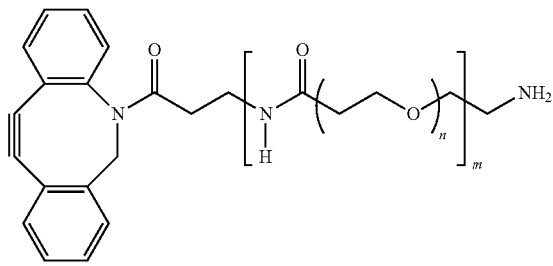

(I)

wherein m is zero or 1 and n is an integer in the range of 2 to 12.

Embodiment II-11

The method of embodiment II-10, wherein m is 1 and n is an integer in the range of 2 to 8.

Embodiment II-12

The method of embodiment II-11, wherein n is 4.

Embodiment II-13

The method of embodiment II-10, wherein m is zero.

Embodiment II-14

The method of embodiment II-10, wherein step (iii) is carried out using 0.25 equivalents to 3 equivalents of the DBCO derivative, relative to the saccharide.

Embodiment II-15

The method of embodiment II-14, wherein step (iii) is carried out using 0.25 equivalents to 1.5 equivalents of the DBCO derivative.

Embodiment II-16

The method of embodiment II-15, wherein step (iii) is carried out using 1.0 equivalents of the DBCO derivative.

Embodiment II-17

The method of embodiment II-15 or II-16, wherein the CDAP is added to the saccharide solution in an amount effective to achieve a target yield for step (iii) in the range of 5% to 10%, wherein the target yield is the percentage of the DBCO derivative that reacts with the cyanylated saccharide.

Embodiment II-18

The method of embodiment II-17, wherein step (i) is carried out using 0.5 equivalents to 5.0 equivalents CDAP, relative to the saccharide.

Embodiment II-19

The method of embodiment II-18, wherein the antigen is a bacterial capsular saccharide.

Embodiment II-20

The method of embodiment II-19, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-21

The method of embodiment II-20, wherein the capsular saccharide is from a bacterium selected from *Streptococcus pneumoniae*.

Embodiment II-22

The method of embodiment II-21, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-23

The method of embodiment II-1, further including, prior to (a), subjecting the saccharide to mechanical size reduction.

Embodiment II-24

The method of embodiment II-1, further including (c) recovering the conjugate.

Embodiment II-25

The method of embodiment II-1, wherein the polypeptide comprises at least two nnAA residues.

Embodiment II-26

The method of embodiment II-25, wherein the polypeptide comprises 4 to 9 nnAA residues.

Embodiment II-27

The method of embodiment II-1, wherein the at least one T-cell activating epitope is from a native carrier protein selected from the group consisting of *Corynebacterium diphtheriae* toxin, *Clostridium tetani* tetanospasmin, *Haemophilus influenzae* protein D, and CRM197.

Embodiment II-28

The method of embodiment II-1, wherein the at least one nnAA is substituted for a lysine in the native carrier protein.

Embodiment II-29

The method of embodiment II-1, wherein the polypeptide has at least 80% sequence identity to SEQ ID NO:11.

Embodiment II-30

The method of embodiment II-29, wherein the at least one nnAA is substituted for a lysine in SEQ ID NO:11.

Embodiment II-31

The method of embodiment II-30, wherein the at least one nnAA is substituted for herein at least one nnAA is substituted for K24, K33, K37, K39, K212, K214, K227, K244, K264, K385, K522 and K526 of SEQ ID NO:11.

Embodiment II-32

The method of embodiment II-31, wherein the at least one nnAA is a 2,3-disubstituted propanoic acid bearing an azido-containing substituent.

Embodiment II-33

The method of embodiment II-32, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-34

A method for preparing a conjugate of a saccharide antigen and a carrier protein, comprising:
(a) functionalizing the saccharide antigen with a reactive moiety capable of participating in a click chemistry reaction with a bio-orthogonal reactive moiety on a second reactant, by (i) providing the saccharide as a solution in an aqueous medium; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the reactive moiety coupled to a primary amino group, under conditions effective to transfer the reactive moiety to the cyanate-substituted saccharide; and
(b) combining the activated saccharide antigen with a carrier protein comprising a modified CRM197 carrier polypeptide comprising an amino acid sequence that (i) has at least 80% sequence identity to SEQ ID NO: 11; (ii) is free from an Arg-Arg dipeptide sequence; and (iii) includes at least one non-natural amino acid (nnAA) residue bearing the bio-orthogonal reactive moiety, such that a click chemistry reaction between the reactive moiety and the bio-orthogonal reactive moiety results in a conjugate of the saccharide antigen and the carrier protein.

Embodiment II-35

The method of embodiment II-34, further including (c) recovering the conjugate.

Embodiment II-36

The method of embodiment II-34 or II-35, further including, prior to (a), subjecting the saccharide antigen to mechanical size reduction.

Embodiment II-37

The method of any one of embodiments II-34 to II-36, wherein the polypeptide comprises at least two nnAA residues.

Embodiment II-38

The method of embodiment II-37, wherein the polypeptide comprises 4 to 9 nnAA residues.

Embodiment II-39

The method of embodiment II-38, wherein the at least one nnAA is a 2,3-disubstituted propanoic acid bearing an azido-containing substituent.

Embodiment II-40

The method of embodiment II-39, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-41

The method of embodiment II-34, wherein the antigen is a bacterial capsular saccharide.

Embodiment II-42

The method of embodiment II-41, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali.*

Embodiment II-43

The method of embodiment II-41, wherein the capsular saccharide is from a bacterium selected from *Streptococcus pneumoniae.*

Embodiment II-44

The method of embodiment II-43, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-45

A conjugate vaccine prepared according to the method of any one of embodiments II-34 through II-44.

Embodiment II-46

A method for preparing a conjugate of a saccharide antigen and a carrier protein, comprising:
(a) functionalizing the saccharide antigen with a reactive moiety capable of participating in a click chemistry reaction with a bio-orthogonal reactive moiety on a second reactant, by (i) providing the saccharide as a solution in an aqueous medium; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the reactive moiety coupled to a primary amino group, under conditions effective to transfer the reactive moiety to the cyanate-substituted saccharide; and
(b) combining the activated saccharide antigen with a carrier protein comprising a modified CRM197 carrier polypeptide comprising an amino acid sequence that (i) has at least 80% sequence identity to SEQ ID NO: 11 and (ii) includes a nnAA substitution at one or more of the following amino acid residues (numbered according to SEQ ID NO: 11): Asp-211; Asp-295; Asp-352; Asp-392; Asp-465; Asp-467; Asp-507; Asp-519; Asn-296; Asn-359; Asn-399; Asn-481; Asn-486; Asn-502; Asn-524; Glu-240; Glu-248; Glu-249; Glu-256; Glu-259; Glu-292; Glu-362; Gln-252; Gln-287; Lys-212; Lys-218; Lys-221; Lys-229; Lys-236; Lys-264; Lys-299; Lys-385; Lys-456; Lys-474; Lys-498; Lys-516; Lys-522; Lys-534; Arg-377; Arg-407; Arg-455; Arg-460; Arg-462; Arg-472; Arg-493; Ser-198; Ser-200; Ser-231; Ser-233; Ser-239; Ser-261; Ser-374; Ser-381; Ser-297; Ser-397; Ser-451; Ser-475; Ser-494; Ser-495; Ser-496; Ser-501; Ser-505; Thr-253; Thr-265; Thr-267; Thr-269; Thr-293; Thr-386; Thr-400; Thr-408; Thr-469; and/or Thr-517, such that a click chemistry reaction between the reactive moiety and the bio-orthogonal reactive moiety results in a conjugate of the saccharide antigen and the carrier protein.

Embodiment II-47

The method of embodiment II-46, further including (c) recovering the conjugate.

Embodiment II-48

The method of embodiment II-46 or II-47, further including, prior to (a), subjecting the saccharide antigen to mechanical size reduction.

Embodiment II-49

The method of any one of embodiments II-46 to II-48, wherein the polypeptide comprises at least two nnAA residues.

Embodiment II-50

The method of embodiment II-49, wherein the polypeptide comprises 4 to 9 nnAA residues.

Embodiment II-51

The method of embodiment II-50, wherein the at least one nnAA is a 2,3-disubstituted propanoic acid bearing an azido-containing substituent.

Embodiment II-52

The method of embodiment II-51, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-53

The method of embodiment II-46, wherein the antigen is a bacterial capsular saccharide.

Embodiment II-54

The method of embodiment II-53, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali.*

Embodiment II-55

The method of embodiment II-54, wherein the capsular saccharide is from a bacterium selected from *Streptococcus pneumoniae*.

Embodiment II-56

The method of embodiment II-55, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-57

A conjugate vaccine prepared according to the method of any one of embodiments II-46 through II-56.

Embodiment II-58

A method for preparing a conjugate of a saccharide antigen and a carrier protein, comprising:
 (a) functionalizing the saccharide antigen with a reactive moiety capable of participating in a click chemistry reaction with a bio-orthogonal reactive moiety on a second reactant, by (i) providing the saccharide as a solution in an aqueous medium; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the reactive moiety coupled to a primary amino group, under conditions effective to transfer the reactive moiety to the cyanate-substituted saccharide; and
 (b) combining the activated saccharide antigen with a carrier protein comprising a modified CRM197 carrier polypeptide comprising: an amino acid sequence which (i) has at least 90% sequence identity to SEQ ID NO: 11; (ii) is free from an Arg-Arg dipeptide sequence; and (iii) includes a nnAA substitution at one or more of the following amino acid residues (numbered according to SEQ ID NO: 11): Asp-211; Asp-295; Asp-352; Asp-392; Asp-465; Asp-467; Asp 507; Asp 519; Asn 296; Asn 359; Asn 399; Asn 481; Asn 486; Asn 502; Asn 524; Glu 240; Glu 248; Glu 249; Glu 256; Glu 259; Glu 292; Glu 362; Gln 252; Gln 287; Lys 212; Lys 218; Lys 221; Lys 229; Lys 236; Lys 264; Lys 299; Lys 385; Lys 456; Lys 474; Lys 498; Lys 516; Lys 522; Lys 534; Arg 377; Arg 407; Arg 455; Arg 460; Arg 462; Arg 472; Arg 493; Ser 198; Ser 200; Ser 231; Ser 233; Ser 239; Ser 261; Ser 374; Ser 381; Ser 297; Ser 397; Ser 451; Ser 475; Ser 494; Ser 495; Ser 496; Ser 501; Ser 505; Thr 253; Thr 265; Thr 267; Thr 269; Thr 293; Thr 386; Thr 400; Thr 408; Thr-469; and/or Thr 517, such that a click chemistry reaction between the reactive moiety and the bio-orthogonal reactive moiety results in a conjugate of the saccharide antigen and the carrier protein.

Embodiment II-59

The method of embodiment II-58, further including (c) recovering the conjugate.

Embodiment II-60

The method of embodiment II-58 or II-59, further including, prior to (a), subjecting the saccharide antigen to mechanical size reduction.

Embodiment II-61

The method of any one of embodiments II-58 to II-60, wherein the polypeptide comprises at least two nnAA residues.

Embodiment II-62

The method of embodiment II-61, wherein the polypeptide comprises 4 to 9 nnAA residues.

Embodiment II-63

The method of embodiment II-62, wherein the at least one nnAA is a 2,3-disubstituted propanoic acid bearing an azido-containing substituent.

Embodiment II-64

The method of embodiment II-63, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-65

The method of embodiment II-58, wherein the antigen is a bacterial capsular saccharide.

Embodiment II-66

The method of embodiment II-65, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-67

The method of embodiment II-66, wherein the capsular saccharide is from a bacterium selected from *Streptococcus pneumoniae*.

Embodiment II-68

The method of embodiment II-67, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-69

A conjugate vaccine prepared according to the method of any one of embodiments II-58 through II-68.

Embodiment II-70

A method for functionalizing a saccharide with a reactive moiety capable of participating in a click chemistry reaction with a second reactant comprising a bio-orthogonal reactive moiety, the method comprising:

(a) providing the saccharide as a solution in an aqueous buffer having a pH in the range of 7 toll;

(b) cyanylating hydroxyl groups on the saccharide by adding a cyanylating reagent to the buffered saccharide solution to provide a cyanate-substituted saccharide; and thereafter (c) contacting the cyanate-substituted saccharide with an activating reagent comprising the reactive moiety coupled to a primary amino group, under conditions effective to transfer the reactive moiety to the cyanate-substituted saccharide.

Embodiment II-71

The method of embodiment II-70, wherein step (c) is carried out about 3 to about 13 minutes after step (b).

Embodiment II-72

The method of embodiment II-71, wherein step (c) is carried out about 5 minutes after step (b).

Embodiment II-73

The method of any one of embodiments II-70 through II-72, comprising a one-pot reaction without addition of a pH-adjusting agent during or subsequent to step (b).

Embodiment II-74

The method of any one of embodiments II-70 through II-73, wherein the cyanylating reagent comprises cyano-4-dimethylamino pyridinium tetrafluoroborate (CDAP).

Embodiment II-75

The method of embodiment II-74, wherein the reactive moiety comprises an alkyne functionality.

Embodiment II-76

The method of embodiment II-75, wherein the alkyne functionality comprises a chemically constrained alkyne.

Embodiment II-77

The method of embodiment II-76, wherein the reactive moiety comprises a diarylcyclooctyne group.

Embodiment II-78

The method of embodiment II-77, wherein the diarylcyclooctyne group is a dibenzylcyclooctyne group.

Embodiment II-79

The method of embodiment II-78, wherein the activating reagent comprises a dibenzylcyclooctyne (DBCO) derivative having the structure (I)

(I)

wherein m is zero or 1 and n is an integer in the range of 2 to 12.

Embodiment II-80

The method of embodiment II-79, wherein m is 1 and n is an integer in the range of 2 to 8.

Embodiment II-81

The method of embodiment II-80, wherein n is 4.

Embodiment II-82

The method of embodiment II-79, wherein m is zero.

Embodiment II-83

The method of embodiment II-79, wherein step (c) is carried out using 0.25 equivalents to 3 equivalents of the DBCO derivative, relative to the saccharide.

Embodiment II-84

The method of embodiment II-83, wherein step (c) is carried out using 0.25 equivalents to 1.5 equivalents of the DBCO derivative.

Embodiment II-85

The method of embodiment II-84, wherein step (c) is carried out using 1.0 equivalents of the DBCO derivative.

Embodiment II-86

The method of embodiment II-84 or II-85, wherein the CDAP is added to the saccharide solution in an amount effective to achieve a target yield for step (c) in the range of 5% to 10%, wherein the target yield is the percentage of the DBCO derivative that reacts with the cyanylated saccharide.

Embodiment II-87

The method of embodiment II-86, wherein step (a) is carried out using 0.5 equivalents to 5.0 equivalents CDAP, relative to the saccharide.

Embodiment II-88

The method of embodiment II-70, wherein the saccharide comprises an antigen.

Embodiment II-89

The method of embodiment II-88, wherein the antigen is a bacterial capsular saccharide.

Embodiment II-90

The method of embodiment II-89, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-91

The method of embodiment II-90, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-92

The method of embodiment II-70, further including, prior to (a), subjecting the saccharide to mechanical size reduction.

Embodiment II-93

A method for functionalizing a saccharide with a reactive moiety capable of participating in a click chemistry reaction with a second reactant comprising a bio-orthogonal reactive moiety, the method comprising:
  (a) providing the saccharide as a solution in an aqueous medium;
  (b) oxidizing the saccharide by adding a periodate reagent to the solution, thereby providing an aldehyde-bearing saccharide;
  (c) purifying the aldehyde-bearing saccharide;
  (d) dissolving the aldehyde-bearing saccharide in an aqueous buffer;
  (e) in a reductive amination reaction, contacting the aldehyde-bearing saccharide with an activating reagent comprising the reactive moiety coupled to a primary amino group, followed by admixture with 8 to 12 equivalents of sodium cyanoborohydride for a time period effective to transfer the reactive moiety to the cyanate-substituted saccharide, thereby providing an activated saccharide antigen; and
  (f) combining the activated saccharide antigen with a carrier protein comprising a polypeptide having at least one T-cell activating epitope and at least one non-natural amino acid (nnAA) bearing the bio-orthogonal reactive moiety, such that a click chemistry reaction between the reactive moiety and the bio-orthogonal reactive moiety results in a conjugate of the saccharide antigen and the carrier protein.

Embodiment II-94

The method of embodiment II-93, wherein after step (c) and prior to step (d), the aldehyde-bearing saccharide is dissolved in an aqueous buffer having a pH in the range of 5.5 to 6.9.

Embodiment II-95

The method of embodiment II-94, wherein the aqueous buffer has a pH of 5.7.

Embodiment II-96

The method of any one of embodiments II-93, II-94, and II-95, wherein the activating reagent comprises a dibenzylcyclooctyne (DBCO) derivative having the structure (I)

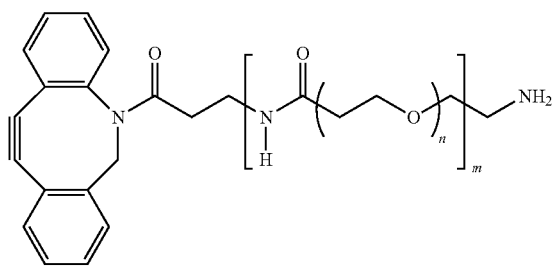

(I)

wherein m is zero or 1 and n is an integer in the range of 2 to 12.

Embodiment II-97

The method of embodiment II-96, wherein m is 1 and n is an integer in the range of 2 to 8.

Embodiment II-98

The method of embodiment II-97, wherein n is 4.

Embodiment II-99

The method of embodiment II-96, wherein m is zero.

Embodiment II-100

The method of any one of embodiments II-96 through II-99, wherein step (e) is carried out using 1 equivalent to 3 equivalents of the DBCO derivative, relative to the saccharide.

Embodiment II-101

The method of embodiment II-100, wherein step (e) is carried out using 2 equivalents to 3 equivalents of the DBCO derivative, relative to the saccharide.

Embodiment II-102

The method of embodiment II-101, wherein step (e) is carried out for 24 hours.

Embodiment II-103

The method of embodiment II-93, wherein the antigen is a bacterial capsular saccharide.

Embodiment II-104

The method of embodiment II-103, wherein the capsular saccharide is from a bacterium selected from *Streptococcus*

117

*pneumoniae, Neisseria meningitidis, Haemophilus influenzae, Streptococcus pyogenes, Streptococcus agalactiae*, and *Porphyromonas gingivali*.

Embodiment II-105

The method of embodiment II-104, wherein the capsular saccharide is from a bacterium selected from *Streptococcus pneumoniae*.

Embodiment II-106

The method of embodiment II-105, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-107

The method of embodiment II-93, further including, prior to (a), subjecting the saccharide to mechanical size reduction.

Embodiment II-108

The method of embodiment II-93, further including (c) recovering the conjugate.

Embodiment II-109

The method of embodiment II-93, wherein the polypeptide comprises at least two nnAA residues.

Embodiment II-110

The method of embodiment II-109, wherein the polypeptide comprises 4 to 9 nnAA residues.

Embodiment II-111

The method of embodiment II-93, wherein the at least one T-cell activating epitope is from a native carrier protein selected from the group consisting of *Corynebacterium diphtheriae* toxin, *Clostridium tetani* tetanospasmin, *Haemophilus influenzae* protein D, and CRM197.

Embodiment II-112

The method of embodiment II-93, wherein the at least one nnAA is substituted for a lysine in the native carrier protein.

Embodiment II-113

The method of embodiment II-93, wherein the polypeptide has at least 80% sequence identity to SEQ ID NO:11.

Embodiment II-114

The method of embodiment II-113, wherein the at least one nnAA is substituted for a lysine in SEQ ID NO:11.

Embodiment II-115

The method of embodiment II-114, wherein the at least one nnAA is substituted for herein at least one nnAA is

118 substituted for K24, K33, K37, K39, K212, K214, K227, K244, K264, K385, K522 and K526 of SEQ ID NO:11.

Embodiment II-116

The method of embodiment II-115, wherein the at least one nnAA is a 2,3-disubstituted propanoic acid bearing an azido-containing substituent.

Embodiment II-117

The method of embodiment II-116, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl) propanoic acid, 2-amino-5-azidopentanoic acid, and 2-amino-3-(4-(azidomethyl)phenyl)propanoic acid, and any combination thereof.

Embodiment II-118

A method for functionalizing a saccharide with a reactive moiety capable of participating in a click chemistry reaction with a second reactant comprising a bio-orthogonal reactive moiety, the method comprising:
(a) providing the saccharide as a solution in an aqueous medium;
(b) oxidizing the saccharide by adding a periodate reagent to the solution, thereby providing an aldehyde-bearing saccharide;
(c) purifying the aldehyde-bearing saccharide;
(d) dissolving the aldehyde-bearing saccharide in an aqueous buffer having a pH in the range of 5.5 to 5.9;
(e) in a reductive amination reaction, contacting the aldehyde-bearing saccharide with an activating reagent comprising the reactive moiety coupled to a primary amino group, followed by admixture with sodium cyanoborohydride for a time period effective to transfer the reactive moiety to the cyanate-substituted saccharide, thereby providing an activated saccharide antigen; and
(f) combining the activated saccharide antigen with a carrier protein comprising a polypeptide having at least one T-cell activating epitope and at least one non-natural amino acid (nnAA) bearing the bio-orthogonal reactive moiety, such that a click chemistry reaction between the reactive moiety and the bio-orthogonal reactive moiety results in a conjugate of the saccharide antigen and the carrier protein.

Embodiment II-119

The method of embodiment II-118, wherein the aqueous buffer has a pH of 5.7.

Embodiment II-120

The method of embodiment II-118, wherein after step (c) and prior to step (d), the aldehyde-bearing saccharide is dissolved in an aqueous buffer having a pH in the range of 5.5 to 6.9.

Embodiment II-121

The method of any one of embodiments II-118, II-119, and II-120, wherein the activating reagent comprises a dibenzylcyclooctyne (DBCO) derivative having the structure (I)

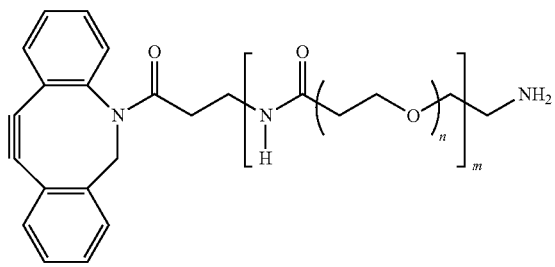

(I)

wherein m is zero or 1 and n is an integer in the range of 2 to 12.

Embodiment II-122

The method of embodiment II-121, wherein m is 1 and n is an integer in the range of 2 to 8.

Embodiment II-123

The method of embodiment II-122, wherein n is 4.

Embodiment II-124

The method of embodiment II-121, wherein m is zero.

Embodiment II-125

The method of any one of embodiments II-121 through II-124, wherein step (e) is carried out using 1 equivalent to 3 equivalents of the DBCO derivative, relative to the saccharide.

Embodiment II-126

The method of embodiment II-125, wherein step (e) is carried out using 2 equivalents to 3 equivalents of the DBCO derivative, relative to the saccharide.

Embodiment II-127

The method of embodiment II-126, wherein step (e) is carried out for 24 hours.

Embodiment II-128

The method of embodiment II-118, wherein the antigen is a bacterial capsular saccharide.

Embodiment II-129

The method of embodiment II-128, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-130

The method of embodiment II-129, wherein the capsular saccharide is from a bacterium selected from *Streptococcus pneumoniae*.

Embodiment II-131

The method of embodiment II-130, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-132

The method of embodiment II-118, further including, prior to (a), subjecting the saccharide to mechanical size reduction.

Embodiment II-133

The method of embodiment II-118, further including (c) recovering the conjugate.

Embodiment II-134

The method of embodiment II-118, wherein the polypeptide comprises at least two nnAA residues.

Embodiment II-135

The method of embodiment II-134, wherein the polypeptide comprises 4 to 9 nnAA residues.

Embodiment II-136

The method of embodiment II-118, wherein the at least one T-cell activating epitope is from a native carrier protein selected from the group consisting of *Corynebacterium diphtheriae* toxin, *Clostridium tetani* tetanospasmin, *Haemophilus influenzae* protein D, and CRM197.

Embodiment II-137

The method of embodiment II-118, wherein the at least one nnAA is substituted for a lysine in the native carrier protein.

Embodiment II-138

The method of embodiment II-118, wherein the polypeptide has at least 80% sequence identity to SEQ ID NO:11.

Embodiment II-139

The method of embodiment II-138, wherein the at least one nnAA is substituted for a lysine in SEQ ID NO:11.

Embodiment II-140

The method of embodiment II-139, wherein the at least one nnAA is substituted for herein at least one nnAA is substituted for K24, K33, K37, K39, K212, K214, K227, K244, K264, K385, K522 and K526 of SEQ ID NO:11.

Embodiment II-141

The method of embodiment II-140, wherein the at least one nnAA is a 2,3-disubstituted propanoic acid bearing an azido-containing substituent.

Embodiment II-142

The method of embodiment II-141, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-143

A method for functionalizing a saccharide with a reactive moiety capable of participating in a click chemistry reaction with a second reactant comprising a bio-orthogonal reactive moiety, the method comprising:
(a) providing the saccharide as a solution in an aqueous medium;
(b) oxidizing the saccharide by adding a periodate reagent to the solution, thereby providing an aldehyde-bearing saccharide;
(c) purifying the aldehyde-bearing saccharide;
(d) dissolving the aldehyde-bearing saccharide in an aqueous buffer;
(e) in a reductive amination reaction, contacting the aldehyde-bearing saccharide with an activating reagent comprising the reactive moiety coupled to a primary amino group, followed by admixture with sodium cyanoborohydride for a time period effective to transfer the reactive moiety to the cyanate-substituted saccharide, thereby providing an activated saccharide antigen; and
(f) combining the activated saccharide antigen with a carrier protein comprising a modified CRM197 carrier polypeptide comprising an amino acid sequence that (i) has at least 80% sequence identity to SEQ ID NO: 11; (ii) is free from an Arg-Arg dipeptide sequence; and (iii) includes at least one non-natural amino acid (nnAA) residue bearing the bio-orthogonal reactive moiety, such that a click chemistry reaction between the reactive moiety and the bio-orthogonal reactive moiety results in a conjugate of the saccharide antigen and the carrier protein.

Embodiment II-144

The method of embodiment II-143, wherein the aqueous buffer has a pH in the range of 5.5 to 5.9.

Embodiment II-145

The method of embodiment II-143 or II-144, wherein the activating reagent comprises a dibenzylcyclooctyne (DBCO) derivative having the structure (I)

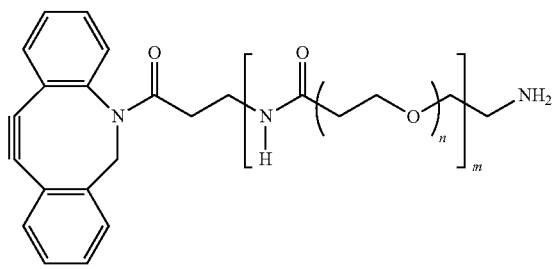

(I)

wherein m is zero or 1 and n is an integer in the range of 2 to 12.

Embodiment II-146

The method of embodiment II-145, wherein m is 1 and n is an integer in the range of 2 to 8.

Embodiment II-147

The method of embodiment II-146, wherein n is 4.

Embodiment II-148

The method of embodiment II-145, wherein m is zero.

Embodiment II-149

The method of any one of embodiments II-145 through II-148, wherein step (e) is carried out using 1 equivalents to 3 equivalents of the DBCO derivative, relative to the saccharide.

Embodiment II-150

The method of embodiment II-149, wherein step (e) is carried out using 2 equivalents to 3 equivalents of the DBCO derivative, relative to the saccharide.

Embodiment II-151

The method of embodiment II-150, wherein step (e) is carried out for 24 hours.

Embodiment II-152

The method of embodiment II-143, further including (g) recovering the conjugate.

Embodiment II-153

The method of embodiment II-143, further including, prior to (a), subjecting the saccharide antigen to mechanical size reduction.

Embodiment II-154

The method of any one of embodiment II-143, wherein the polypeptide comprises at least two nnAA residues.

Embodiment II-155

The method of embodiment II-154, wherein the polypeptide comprises 4 to 9 nnAA residues.

Embodiment II-156

The method of embodiment II-154, wherein the at least one nnAA is a 2,3-disubstituted propanoic acid bearing an azido-containing substituent.

Embodiment II-157

The method of embodiment II-156, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)

propanoic acid, 2-amino-3-(6-(azidomethyl)pyridin-3-yl) propanoic acid, 2-amino-5-azidopentanoic acid, and 2-amino-3-(4-(azidomethyl)phenyl)propanoic acid, and any combination thereof.

Embodiment II-158

The method of embodiment II-143, wherein the antigen is a bacterial capsular saccharide.

Embodiment II-159

The method of embodiment II-158, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-160

The method of embodiment II-159, wherein the capsular saccharide is from a bacterium selected from *Streptococcus pneumoniae*.

Embodiment II-161

The method of embodiment II-160, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-162

A conjugate vaccine prepared according to the method of any one of embodiments II-143 through II-161.

Embodiment II-163

A method for functionalizing a saccharide with a reactive moiety capable of participating in a click chemistry reaction with a second reactant comprising a bio-orthogonal reactive moiety, the method comprising:
(a) providing the saccharide as a solution in an aqueous medium;
(b) oxidizing the saccharide by adding a periodate reagent to the solution, thereby providing an aldehyde-bearing saccharide;
(c) purifying the aldehyde-bearing saccharide;
(d) dissolving the aldehyde-bearing saccharide in an aqueous buffer;
(e) in a reductive amination reaction, contacting the aldehyde-bearing saccharide with an activating reagent comprising the reactive moiety coupled to a primary amino group, followed by admixture with sodium cyanoborohydride for a time period effective to transfer the reactive moiety to the cyanate-substituted saccharide, thereby providing an activated saccharide antigen; and
(f) combining the activated saccharide antigen with a carrier protein comprising a modified CRM197 carrier polypeptide comprising an amino acid sequence that (i) has at least 80% sequence identity to SEQ ID NO: 11 and (ii) includes a nnAA substitution at one or more of the following amino acid residues (numbered according to SEQ ID NO: 11): Asp-211; Asp-295; Asp-352; Asp-392; Asp-465; Asp-467; Asp-507; Asp-519; Asn-296; Asn-359; Asn-399; Asn-481; Asn-486; Asn-502; Asn-524; Glu-240; Glu-248; Glu-249; Glu-256; Glu-259; Glu-292; Glu-362; Gln-252; Gln-287; Lys-212; Lys-218; Lys-221; Lys-229; Lys-236; Lys-264; Lys-299; Lys-385; Lys-456; Lys-474; Lys-498; Lys-516; Lys-522; Lys-534; Arg-377; Arg-407; Arg-455; Arg-460; Arg-462; Arg-472; Arg-493; Ser-198; Ser-200; Ser-231; Ser-233; Ser-239; Ser-261; Ser-374; Ser-381; Ser-297; Ser-397; Ser-451; Ser-475; Ser-494; Ser-495; Ser-496; Ser-501; Ser-505; Thr-253; Thr-265; Thr-267; Thr-269; Thr-293; Thr-386; Thr-400; Thr-408; Thr-469; and/or Thr-517, such that a click chemistry reaction between the reactive moiety and the bio-orthogonal reactive moiety results in a conjugate of the saccharide antigen and the carrier protein.

Embodiment II-164

The method of embodiment II-163, wherein the aqueous buffer has a pH in the range of 5.5 to 5.9.

Embodiment II-165

The method of embodiment II-163 or II-164, wherein the activating reagent comprises a dibenzylcyclooctyne (DBCO) derivative having the structure (I)

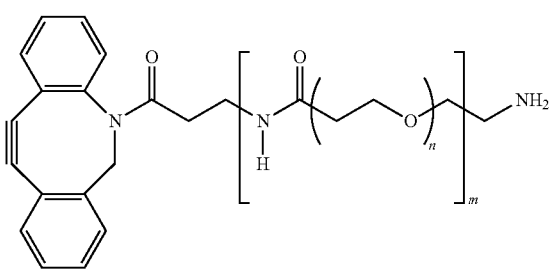

wherein m is zero or 1 and n is an integer in the range of 2 to 12.

Embodiment II-166

The method of embodiment II-165, wherein m is 1 and n is an integer in the range of 2 to 8.

Embodiment II-167

The method of embodiment II-166, wherein n is 4.

Embodiment II-168

The method of embodiment II-165, wherein m is zero.

Embodiment II-169

The method of any one of embodiments II-165 through II-168, wherein step (e) is carried out using 1 equivalents to 3 equivalents of the DBCO derivative, relative to the saccharide.

Embodiment II-170

The method of embodiment II-169, wherein step (e) is carried out using 2 equivalents to 3 equivalents of the DBCO derivative, relative to the saccharide.

Embodiment II-171

The method of embodiment II-170, wherein step (e) is carried out for 24 hours.

Embodiment II-172

The method of embodiment II-163, further including (g) recovering the conjugate.

Embodiment II-173

The method of embodiment II-163, further including, prior to (a), subjecting the saccharide antigen to mechanical size reduction.

Embodiment II-174

The method of any one of embodiment II-163, wherein the polypeptide comprises at least two nnAA residues.

Embodiment II-175

The method of embodiment II-174, wherein the polypeptide comprises 4 to 9 nnAA residues.

Embodiment II-176

The method of embodiment II-175, wherein the at least one nnAA is a 2,3-disubstituted propanoic acid bearing an azido-containing substituent.

Embodiment II-177

The method of embodiment II-176, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl) propanoic acid, 2-amino-5-azidopentanoic acid, and 2-amino-3-(4-(azidomethyl)phenyl)propanoic acid, and any combination thereof.

Embodiment II-178

The method of embodiment II-163, wherein the antigen is a bacterial capsular saccharide.

Embodiment II-179

The method of embodiment II-178, wherein the capsular saccharide is from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment II-180

The method of embodiment II-179, wherein the capsular saccharide is from a bacterium selected from *Streptococcus pneumoniae*.

Embodiment II-181

The method of embodiment II-180, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-182

A conjugate vaccine prepared according to the method of any one of embodiments II-163 through II-181.

Embodiment II-183

A method for functionalizing a saccharide with a reactive moiety capable of participating in a click chemistry reaction with a second reactant comprising a bio-orthogonal reactive moiety, the method comprising:
(a) providing the saccharide as a solution in an aqueous medium;
(b) oxidizing the saccharide by adding a periodate reagent to the solution, thereby providing an aldehyde-bearing saccharide;
(c) purifying the aldehyde-bearing saccharide;
(d) dissolving the aldehyde-bearing saccharide in an aqueous buffer;
(e) in a reductive amination reaction, contacting the aldehyde-bearing saccharide with an activating reagent comprising the reactive moiety coupled to a primary amino group, followed by admixture with sodium cyanoborohydride for a time period effective to transfer the reactive moiety to the cyanate-substituted saccharide, thereby providing an activated saccharide antigen; and
(f) combining the activated saccharide antigen with a carrier protein comprising a modified CRM197 carrier polypeptide comprising: an amino acid sequence which (i) has at least 90% sequence identity to SEQ ID NO: 11; (ii) is free from an Arg-Arg dipeptide sequence; and (iii) includes a nnAA substitution at one or more of the following amino acid residues (numbered according to SEQ ID NO: 11): Asp-211; Asp-295; Asp-352; Asp-392; Asp-465; Asp-467; Asp 507; Asp 519; Asn 296; Asn 359; Asn 399; Asn 481; Asn 486; Asn 502; Asn 524; Glu 240; Glu 248; Glu 249; Glu 256; Glu 259; Glu 292; Glu 362; Gln 252; Gln 287; Lys 212; Lys 218; Lys 221; Lys 229; Lys 236; Lys 264; Lys 299; Lys 385; Lys 456; Lys 474; Lys 498; Lys 516; Lys 522; Lys 534; Arg 377; Arg 407; Arg 455; Arg 460; Arg 462; Arg 472; Arg 493; Ser 198; Ser 200; Ser 231; Ser 233; Ser 239; Ser 261; Ser 374; Ser 381; Ser 297; Ser 397; Ser 451; Ser 475; Ser 494; Ser 495; Ser 496; Ser 501; Ser 505; Thr 253; Thr 265; Thr 267; Thr 269; Thr 293; Thr 386; Thr 400; Thr 408; Thr-469; and/or Thr 517, such that a click chemistry reaction between the reactive moiety and the bio-orthogonal reactive moiety results in a conjugate of the saccharide antigen and the carrier protein.

Embodiment II-184

The method of embodiment II-183, wherein the aqueous buffer has a pH in the range of 5.5 to 5.9.

Embodiment II-185

The method of embodiment II-183 or II-184, wherein the activating reagent comprises a dibenzylcyclooctyne (DBCO) derivative having the structure (I)

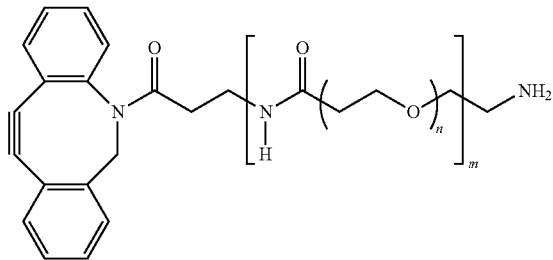

(I)

wherein m is zero or 1 and n is an integer in the range of 2 to 12.

Embodiment II-186

The method of embodiment II-185, wherein m is 1 and n is an integer in the range of 2 to 8.

Embodiment II-187

The method of embodiment II-186, wherein n is 4.

Embodiment II-188

The method of embodiment II-185, wherein m is zero.

Embodiment II-189

The method of any one of embodiments II-185 through II-188, wherein step (e) is carried out using 1 equivalents to 3 equivalents of the DBCO derivative, relative to the saccharide.

Embodiment II-190

The method of embodiment II-189, wherein step (e) is carried out using 2 equivalents to 3 equivalents of the DBCO derivative, relative to the saccharide.

Embodiment II-191

The method of embodiment II-190, wherein step (e) is carried out for 24 hours.

Embodiment II-192

The method of embodiment II-183, further including (g) recovering the conjugate.

Embodiment II-193

The method of embodiment II-183, further including, prior to (a), subjecting the saccharide antigen to mechanical size reduction.

Embodiment II-194

The method of any one of embodiment II-183, wherein the polypeptide comprises at least two nnAA residues.

Embodiment II-195

The method of embodiment II-194, wherein the polypeptide comprises 4 to 9 nnAA residues.

Embodiment II-196

The method of embodiment II-195, wherein the at least one nnAA is a 2,3-disubstituted propanoic acid bearing an azido-containing substituent.

Embodiment II-197

The method of embodiment II-196, wherein the at least one nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, and any combination thereof.

Embodiment II-198

The method of embodiment II-183, wherein the antigen is a bacterial capsular saccharide.

Embodiment II-199

The method of embodiment II-198, wherein the capsular saccharide is from a bacterium selected from *Streptococcus pneumoniae, Neisseria meningitidis, Haemophilus influenzae, Streptococcus pyogenes, Streptococcus agalactiae,* and *Porphyromonas gingivali.*

Embodiment II-200

The method of embodiment II-199, wherein the capsular saccharide is from a bacterium selected from *Streptococcus pneumoniae.*

Embodiment II-201

The method of embodiment II-200, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-202

A conjugate vaccine prepared according to the method of any one of embodiments II-183 through II-201.

Embodiment II-203

A method for functionalizing a saccharide with a reactive moiety capable of participating in a click chemistry reaction with a second reactant comprising a bio-orthogonal reactive moiety, the method comprising:
(a) providing the saccharide as a solution in an aqueous medium;
(b) oxidizing the saccharide by adding a periodate reagent to the solution, thereby providing an aldehyde-bearing saccharide;
(c) purifying the aldehyde-bearing saccharide;
(d) dissolving the aldehyde-bearing saccharide in an aqueous buffer having a pH in the range of 5.5 to 5.9;
(e) in a reductive amination reaction, contacting the aldehyde-bearing saccharide with at least two equivalents of an activating reagent comprising the reactive moiety coupled to a primary amino group, followed by admixture with 8 to 12 equivalents of sodium cyanoborohydride for a time period effective to transfer the reactive moiety to the cyanate-substituted saccharide, thereby providing an activated saccharide antigen.

Embodiment II-204

The method of embodiment II-203, wherein the aqueous buffer has a pH of 5.7.

Embodiment II-205

The method of embodiment II-203 or II-204, wherein the activating reagent comprises a dibenzylcyclooctyne (DBCO) derivative having the structure (I)

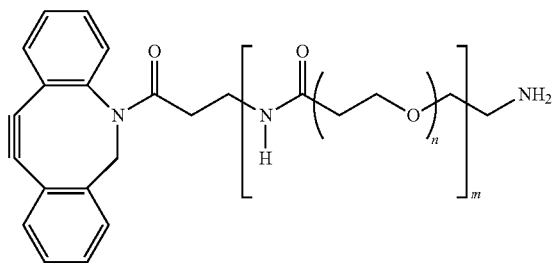

(I)

wherein m is zero or 1 and n is an integer in the range of 2 to 12.

Embodiment II-206

The method of embodiment II-205, wherein m is 1 and n is an integer in the range of 2 to 8.

Embodiment II-207

The method of embodiment II-206, wherein n is 4.

Embodiment II-208

The method of embodiment II-205, wherein m is zero.

Embodiment II-209

The method of any one of embodiments II-205 through II-208, wherein step (e) is carried out using 3 equivalents of the DBCO derivative, relative to the saccharide.

Embodiment II-210

The method of embodiment II-209, wherein step (e) is carried out for 24 hours.

Embodiment II-211

The method of embodiment II-203, wherein the antigen is a bacterial capsular saccharide.

Embodiment II-212

The method of embodiment II-211, wherein the capsular saccharide is from a bacterium selected from *Streptococcus pneumoniae, Neisseria meningitidis, Haemophilus influenzae, Streptococcus pyogenes, Streptococcus agalactiae,* and *Porphyromonas gingivali.*

Embodiment II-213

The method of embodiment II-212, wherein the capsular saccharide is from a bacterium selected from *Streptococcus pneumoniae.*

Embodiment II-214

The method of embodiment II-213, wherein the antigen is a capsular saccharide of an *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment II-215

The method of embodiment II-203, further including, prior to (a), subjecting the saccharide to mechanical size reduction.

Embodiment II-216

A method for functionalizing a saccharide antigen with a reactive moiety capable of participating in a click chemistry reaction with a second reactant comprising a bio-orthogonal reactive moiety, the method substantially applicable to saccharide antigens across a plurality of serotypes and comprising:
(a) providing the saccharide antigen as a solution in an aqueous buffer having a pH in the range of 7 to 11;
(b) cyanylating hydroxyl groups on the saccharide antigen with an effective cyanylating amount of CDAP to provide a cyanate-substituted saccharide;
(c) after 3 to 13 minutes, contacting the cyanate-substituted saccharide with 0.25 equivalents to 2.0 equivalents of a dibenzylcyclooctyne (DBCO) derivative having the structure (I)

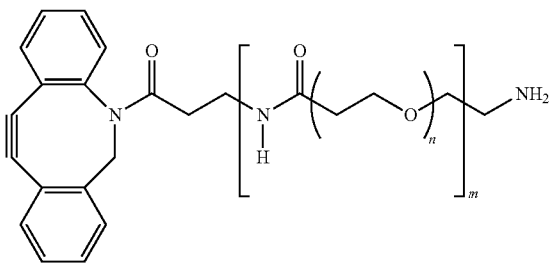

(I)

wherein m is zero or 1 and n is an integer in the range of 2 to 12, thereby transferring the DBCO moiety to the cyanate-substituted saccharide,
wherein the effective cyanylating amount of CDAP is selected to correspond to a particular serotype.

Embodiment II-217

The method of embodiment II-216, wherein the aqueous buffer has a pH in the range of 8.75 to 9.5.

Embodiment II-218

The method of embodiment II-216 or II-217, wherein step (c) is carried out 5 minutes after step (b).

Embodiment II-219

The method of any one of embodiments II-216 through II-218, wherein in step (c), the cyanate-substituted saccharide is contacted with 1 equivalent of the DBCO derivative.

Embodiment II-220

A method for functionalizing a saccharide antigen with a reactive moiety capable of participating in a click chemistry reaction with a second reactant comprising a bio-orthogonal reactive moiety, the method being substantially applicable to saccharide antigens across a plurality of serotypes and comprising:
(a) providing the saccharide antigen as a solution in an aqueous buffer having a pH in the range of 5,5 to 5.9;
(b) oxidizing the saccharide antigen with an effective oxidizing amount of a periodate reagent, thereby providing an aldehyde-bearing saccharide;
(c) purifying the aldehyde-bearing saccharide;
(d) in a reductive amination reaction, contacting the aldehyde-bearing saccharide with an activating reagent comprising the reactive moiety coupled to a primary amino group, followed by admixture with 8 to 12 equivalents of sodium cyanoborohydride for a time period in the range of 18 to 30 hours, thereby providing an activated saccharide antigen.

Embodiment II-221

The method of embodiment II-220, wherein the time period is 24 hours.

Some embodiments of this disclosure relate to Embodiment III, as follows:

Embodiment III-1

A conjugate comprising a polypeptide and antigen, wherein the polypeptide is a carrier protein comprising at least one T-cell activating epitope and at least two non-natural amino acid ('nnAA') residues, wherein (i) the carrier protein comprises at least one T-cell activating epitope from a protein selected from the group consisting of *Corynebacterium diphtheriae* toxin, *Clostridium tetani* tetanospasmin, *Haemophilus influenzae* protein D, and CRM197, and (ii) the antigen is conjugated to the nnAA residues.

Embodiment III-2

The conjugate of embodiment III-1, wherein the carrier protein comprises 4 to 9 nnAA residues.

Embodiment III-3

The conjugate of any preceding embodiment, wherein at least one nnAA is substituted for a lysine in the native carrier protein.

Embodiment III-4

The conjugate of any preceding embodiment, wherein the carrier protein has at least 80% sequence identity to SEQ ID NO:1.

Embodiment III-5

The conjugate of embodiment III-4, wherein at least one nnAA is substituted for K25, K34, K38, K40, K213, K215, K228, K245, K265, K386, K523, or K527 of SEQ ID NO:1.

Embodiment III-6

The conjugate of any preceding embodiment, wherein the carrier protein comprises amino acid sequence SEQ ID NO:9.

Embodiment III-7

The conjugate of any preceding embodiment, wherein the at least one nnAA is a 2,3-disubstituted propanoic acid bearing: an amino substituent at the 2-position; and an azido-containing substituent, a 1,2,4,5-tetrazinyl substituent, or an ethynyl-containing substituent at the 3-position.

Embodiment III-8

The conjugate of any preceding embodiment, wherein the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

Embodiment III-9

The conjugate of any preceding embodiment, wherein the antigen is conjugated to the nnAA via a triazole linking moiety.

Embodiment III-10

A conjugate comprising a polypeptide and an antigen, wherein the polypeptide is a carrier protein comprising at least one T-cell activating epitope and at least one non-natural amino acid (nnAA), wherein the antigen is conjugated to the nnAA, and further wherein the at least one nnAA residue corresponds to an amino acid having the structure of formula XII

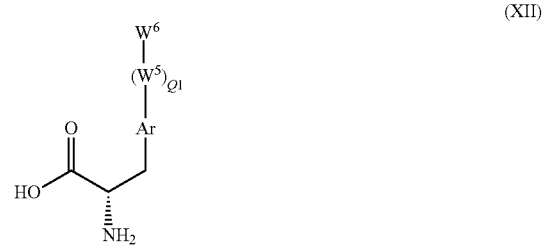

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAA residue in the polypeptide has the structure of formula XIII

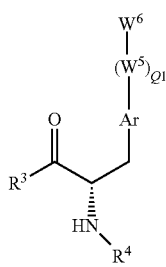

(XIII)

in which $R^3$ is OH or an amino acid residue of the carrier protein, and $R^4$ is H or an amino acid residue of the carrier protein.

Embodiment III-11

The conjugate of embodiment III-10, wherein: $W^6$ is azido; Ar is phenylene, or Ar contains a nitrogen heteroatom and optionally at least one additional heteroatom selected from N, O, and S; Q1 is 1; and/or $W^5$ is lower alkylene.

Embodiment III-12

The conjugate of any preceding embodiment, wherein the antigen is linked to the carrier protein according to formula XI or XIa:

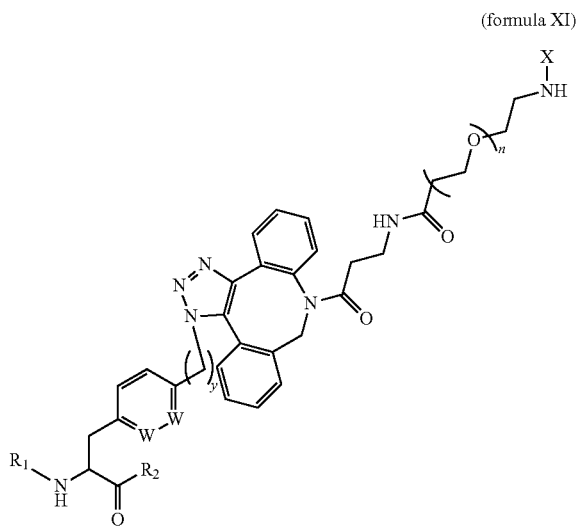

(formula XI)

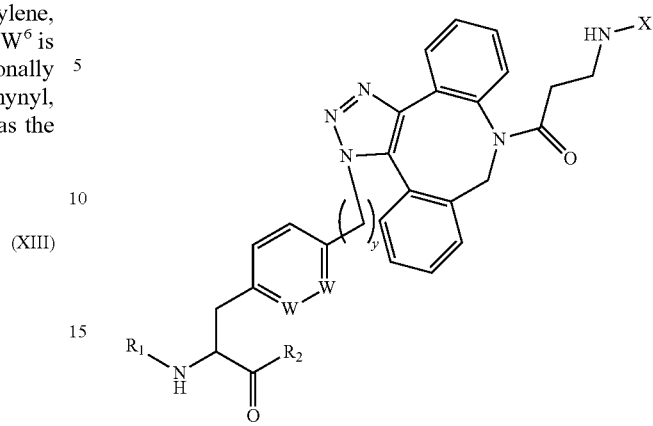

(formula XIa)

wherein $R_1$ is H, formyl, or at least one amino acid of the carrier protein;

$R_2$ is OH or at least one amino acid of the carrier protein;

W is C or N;

y is at least 1;

n is at least 1; and

X is at least one polyol of a capsular polysaccharide.

Embodiment III-13

The conjugate of any preceding embodiment, wherein the antigen is a bacterial capsular polysaccharide; for example, a capsular polysaccharide from a bacterium selected from the group consisting of *Streptococcus pneumoniae, Neisseria meningitidis, Haemophilus influenzae, Streptococcus pyogenes, Streptococcus agalactiae*, and *Porphyromonas gingivalis*.

Embodiment III-14

The conjugate of embodiment III-12, wherein the antigen is a capsular polysaccharide of a *S. pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F.

Embodiment III-15

The conjugate of any preceding embodiment, wherein the ratio of polysaccharide to carrier protein (w/w) is greater than 1.

Embodiment III-16

The conjugate of any preceding embodiment, wherein the polypeptide includes 3 or more nnAA residues and the conjugate has a molecular weight of at least 500 kDa.

Embodiment III-17

The conjugate of embodiment III-15, wherein the polypeptide (a) is a CRM197 or comprises an amino acid sequence having at least 80% sequence identity to SEQ ID NO:1, and (b) comprises 3-9 nnAA residues.

Embodiment III-18

The conjugate of any preceding embodiment, wherein the conjugate is crosslinked through protein-antigen-protein linkages.

Embodiment III-19

The conjugate of any preceding embodiment, wherein the conjugate has a molecular weight of at least 900 kDa.

Embodiment III-20

The conjugate of embodiment III-19, with molecular weight between 900 kDa and 5 MDa.

Embodiment III-21

A method for producing a conjugate, comprising:
a. Providing an activated antigen comprising a plurality of functional groups comprising a first chemical handle capable of conjugating to a second chemical handle of a non-natural amino acid ('nnAA');
b. Combining the activated antigen with a polypeptide comprising at least one of the nnAA under conditions wherein the first and second chemical handles react to form an antigen-polypeptide conjugate, wherein the polypeptide comprises at least one T-cell activating epitope; and
c. Recovering a composition comprising the conjugate.

Embodiment III-22

The method of embodiment III-21, wherein the first chemical handle comprises an alkyne group and/or the second chemical handle comprises an azido group.

Embodiment III-23

The method of embodiment III-21 or III-22, wherein the antigen was reacted with a second reagent comprising a functional group selected from the group consisting of propargyl, DIFO, DBCO, DBCO-NH$_2$, and DBCO(PEG)n-NH$_2$.

Embodiment III-24

The method of embodiment III-21 or III-22, wherein (i) the antigen

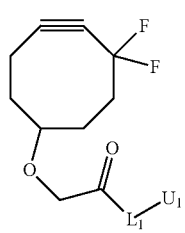

(V)

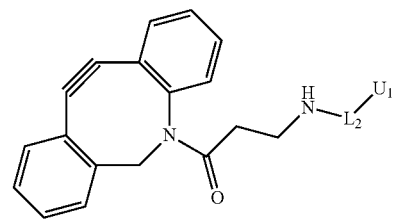

(VI)

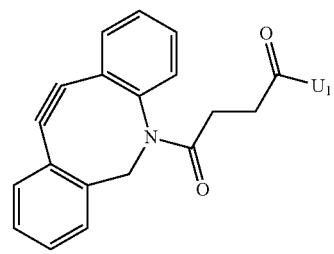

(VIa)

wherein: L$_1$ is a bond, —NH—, —O—, —S—, —NH(L$_{12}$)—, —O(L$_{12}$)—, or —S(L$_{12}$)—;

L$_2$ is a bond, —C(═O)—, —S(═O)$_2$—, —C(═O)L$_{12}$-, —S(═O)$_2$L$_{12}$;

L$_{12}$ is L$_{22}$ or L$_{22}$NH—

L$_{22}$ is C$_{1-10}$ alkyl or —(CH$_2$CH$_2$O)$_{1-10}$—; and

U$_1$ is at least one moiety of the antigen, or (ii) wherein the antigen comprises a structure of formula VII or formula VIIa:

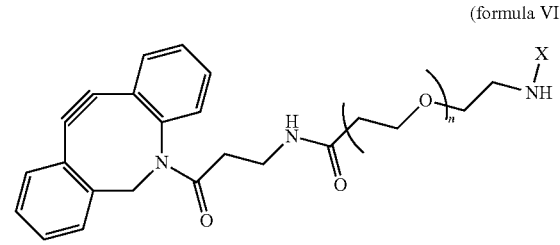

(formula VII)

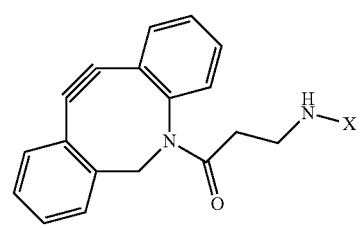

(formula VIIa)

wherein: X is at least one polyol of a polysaccharide; and
n is at least 1,
or (iii) wherein the antigen comprises a structure of formula VIII) or formula VIIc:

(formula VIIb)

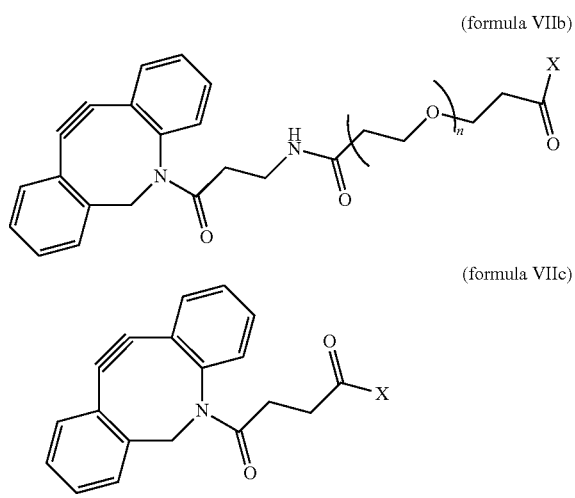

(formula VIIc)

wherein: X is an amine of at least one aminosugar of a polysaccharide; and n is at least 1, or (iv) wherein the antigen comprises z moieties of structure A-X, wherein:

A is

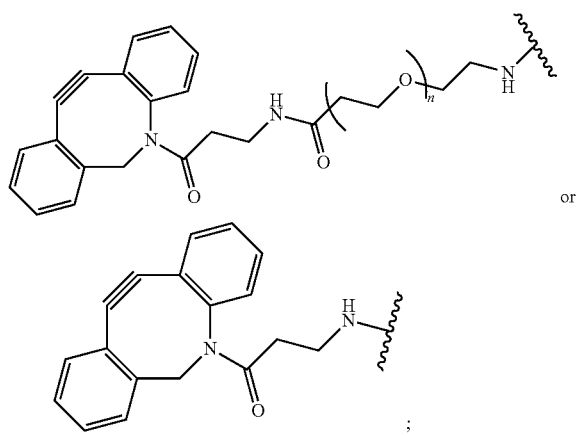

X is at least one polyol of a polysaccharide;

n is at least 1; and z is greater than 1, or (v) wherein the antigen comprises a structure of formula VIII:

(VIII)

wherein: $L_{22}$ is a bond, alkyl, or poly(alkyloxy); and $U_1$ is at least one moiety of an antigen, or (vi) wherein the antigen comprises a structure of formula IX:

(IX)

wherein: $U_1$ is at least one moiety of an antigen.

or (vii) wherein the antigen comprises a structure of formula IXa:

(IXa)

wherein: $L_{22}$ is $C_{1-10}$ alkyl or —$(CH_2CH_2O)_{1-10}$—; and $U_1$ is at least one moiety of an antigen.

Embodiment III-25

The method of any one of embodiments III-21 to III-24 for producing the conjugate of any one of embodiments III-1 to III-20.

Embodiment III-26

An improved method of making a protein-conjugate vaccine wherein an antigen is conjugated to a carrier protein that provides a T-cell dependent immune response, the improvement comprising employing as the carrier protein a polypeptide comprising at least one non-natural amino acid, the non-natural amino acid comprising a bio-orthogonal reactive moiety through which the antigen is conjugated to the polypeptide.

Embodiment III-27

A carrier protein comprising at least one T-cell activating epitope and at least two non-natural amino acid ('nnAA') residues, wherein (i) the carrier protein comprises at least one T-cell activating epitope from a protein selected from the group consisting of *Corynebacterium diphtheriae* toxin, *Clostridium tetani* tetanospasmin, *Haemophilus influenzae* protein D, and CRM197.

Embodiment III-28

A carrier protein comprising an amino acid sequence having at least 80% sequence identity to SEQ ID NO: 1, and comprising at least one nnAA substituted for a naturally occurring amino acid within SEQ ID NO: 1, wherein the at least one nnAA is substituted for K25, K34, K38, K40, K213, K215, K228, K245, K265, K386, K523, or K527 of SEQ ID NO:1, and wherein the nnAA comprises a linking moiety.

Embodiment III-29

A carrier protein for preparing an immunogenic polysaccharide-protein conjugate, wherein the protein (i) comprises at least one T-cell activating epitope (ii) includes at least one nnAA and (iii) has a solubility of at least 50 mg/L at 20° C. in pH 7.4 Tris buffer.

Embodiment III-30

A process for producing the carrier protein of any of embodiments III-26 to III-28 comprising:

(a) providing a nucleic acid encoding the carrier protein, wherein the nucleic acid comprises a plurality of suppression codons;
(b) creating a reaction mixture by combining the nucleic acid with a cell-free cellular extract comprising the non-natural amino acids, a tRNA complementary to the suppression codons, and an aminoacyl-tRNA synthetase; and
(c) incubating the reaction mixture of (b) under conditions sufficient to selectively incorporate the non-natural amino acid at the site corresponding to each suppression codon in the carrier protein.

Embodiment III-31

The method of embodiment III-30, wherein the non-natural amino acid is 4-azidomethyl-phenylalanine (pAMF) and the tRNA in (b) is capable of being charged with pAMF.

Embodiment III-32

A method for synthesis of a polypeptide comprising at least 2 nnAAs in a cell-free expression mixture maintained at a temperature between about 10° C. and about 30° C., wherein the polypeptide produced comprises both a soluble and an insoluble fraction, and wherein the ratio of the soluble fraction to the insoluble fraction is at least 30% (w/w).

Embodiment III-33

The method of embodiment III-32, wherein the temperature is (i) above about 20° C. or (ii) below about 20° C., for instance wherein the temperature is between about 14° C. and about 18° C.

Embodiment III-34

A composition comprising multiple conjugates according to embodiments III-1 to III-19, wherein each of the multiple conjugates comprises a different antigen.

Embodiment III-35

The composition of embodiment III-34, comprising:
conjugates of capsular polysaccharides from 2 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 14 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 15 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 20 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 21 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 24 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 25 or more different pneumococcal serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
conjugates of capsular polysaccharides from 4 or more different meningococcal serogroups selected from the group consisting of serogroups A, C, W135, X, and Y; or
conjugates of capsular polysaccharides from 2 or more different *P. gingivals* serotypes selected from the group consisting of serotypes K1, K2, K3, K4, K5, and K6.

Embodiment III-36

A method of eliciting an immunoprotective antibody response to an antigen in a subject, comprising administering to the subject a conjugate according to any of embodiments III-1 to III-20 or a composition according to embodiment III-34 or III-35, in an excipient suitable for parenteral administration.

Some embodiments of this disclosure relate to Embodiment IV, as follows:

Embodiment IV-1

A carrier protein for use in a protein-conjugate vaccine comprising:
a) at least 2 non-natural amino acid residues (nnAArs) at nn sites wherein each said nnAAr (i) comprises a reactive group that provides site-specific conjugation of an antigen to the carrier protein, and (ii) was introduced site-specifically during synthesis of the carrier protein;
b) wherein nn is an integer selected from the group consisting of ≥2, ≥3, ≥4, 3, 4, 5, 6, 3-9, 4-8, and 4-6; and
c) at least 1 T-cell activating epitope that has not been inactivated by the presence of an nnAA residue.

Embodiment IV-2

A carrier protein according to embodiment IV-1, wherein the at least 1 T-cell activating epitopes are from a native protein carrier selected from the group consisting of *Corynebacterium diphtheriae* toxin, *Clostridium tetani* tetanospasmin, *Haemophilus influenzae* protein D, and CRM197.

Embodiment IV-3

A carrier protein according to any of embodiments IV-1 or IV-2 wherein the reactive group comprises a bio-orthogonal reactive moiety.

Embodiment IV-4

A carrier protein according to embodiment IV-3 wherein the bio-orthogonal reactive moiety is selected from the group consisting of azides, phosphines, alkynes, alkenes, and 1,2,4,5-tetrazines.

Embodiment IV-5

A carrier protein according to embodiment IV-3 wherein the at least 2 nnAArs:
(a) correspond to a non-natural amino acid (nnAA) having the structure of formula XII

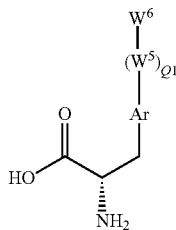

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

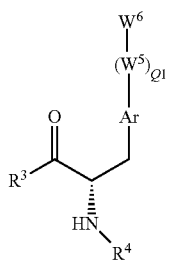

(XIII)

in which $R^3$ is OH or an amino acid residue of the carrier protein, and $R^4$ is H or an amino acid residue of the carrier protein;
(b) correspond to an nnAA according to (a) wherein $W^6$ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and $W^5$ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position;
(f) correspond to an nnAA according to (e) wherein the 2,3-disubstituted propanoic acid has an azido-containing substituent at the 3-position; or
(g) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-6

A carrier protein according to embodiment IV-1 wherein the at least 2 nnAArs are pAMF residues.

Embodiment IV-7

A carrier protein according to any of embodiments IV-1 through IV-6 comprising a plurality of T-cell activating epitopes from CRM197.

Embodiment IV-8

A carrier protein according to any of embodiments IV-1 through IV-7 comprising at least 80% sequence identity to SEQ ID NO:1 or SEQ ID NO:11.

Embodiment IV-9

A carrier protein according to embodiment IV-8 comprising at least one residue sequence selected from the group consisting of residue sequences 271-290, 321-340, 331-350, 351-370, 411-430, and 431-450 of SEQ ID NO:1 that does not contain the at least 2 nnAArs.

Embodiment IV-10

A carrier protein according to embodiment IV-8 wherein at least one nnAAr is substituted for a canonical amino acid residue corresponding to a position in SEQ ID NO:1 wherein the position is selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

Embodiment IV-11

A carrier protein according to embodiment IV-8 wherein at least one nnAAr is substituted for a canonical amino acid residue corresponding to a position in SEQ ID NO:1 wherein the position is selected from:
a) a first group consisting of K25, K34, K38, K40, K213, K215, K228, K245, K265, K386, K523, and K527;
b) a second group consisting of K25, K34, K38 and K40;
c) a third group consisting of K213 and K215;
d) a fourth group consisting of K11, K25, K34, K38, K40, K83, K104, K105, K126, K158, K173, K213, K215, K222, K228, K237, K243, K245, K265, K386, K475, K499, K523, K527, F13, F54, F124, F128, F141, F168, F251, F390, F531, and F532; and
e) a fifth group consisting of K25, K215, K228, K265, K386, and K523

Embodiment IV-12

A carrier protein according to any of embodiments IV-1 to IV-11 wherein 2-4 nnAArs are substituted for a canonical amino acid residue corresponding to a position in SEQ ID NO:1 wherein the position is selected from the group consisting of K228, K245, K265, K386, K523, and K527.

Embodiment IV-13

A carrier protein according to any of embodiments IV-1 to IV-12 that does not contain the dipeptide Arg-Arg.

Embodiment IV-14

A carrier protein according to embodiment IV-8 wherein the reactive group comprises a bio-orthogonal reactive moiety.

Embodiment IV-15

A carrier protein according to embodiment IV-8 wherein the at least 2 nnAArs are selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

Embodiment IV-16

A carrier protein according to embodiment IV-8 wherein the at least 2 nnAArs are pAMF residues.

Embodiment IV-17

A carrier protein according to any of embodiments IV-1 to IV-16 wherein the synthesis of the carrier protein was cell-free.

Embodiment IV-18

A carrier protein according to any of embodiments IV-1 to IV-17 comprising a second nnAAr comprising a reactive group different from the reactive group of the nnAArs at nn sites.

Embodiment IV-19

A protein-antigen conjugate comprising a carrier protein and an antigen wherein the antigen has been site-specifically conjugated to a reactive group of nnAArs in an unconjugated carrier protein through a chemical handle introduced into the antigen, and further wherein the unconjugated carrier protein is a carrier protein according to any of embodiments IV-1 to IV-18.

Embodiment IV-20

A protein-antigen conjugate according to embodiment IV-19 wherein the at least 1 T-cell activating epitopes are from a native protein carrier selected from the group consisting of Corynebacterium diphtheriae toxin, Clostridium tetani tetanospasmin, Haemophilus influenzae protein D, and CRM197.

Embodiment IV-21

A protein-antigen conjugate according to embodiment IV-19 wherein the reactive group comprises a bio-orthogonal reactive moiety.

Embodiment IV-22

A protein-antigen conjugate according to embodiment IV-19 wherein the at least 2 nnAArs:
(a) correspond to a non-natural amino acid (nnAA) having the structure of formula XII

(XII)

wherein Ar comprises a 5-membered or 6-membered aromatic ring optionally containing at least one heteroatom; $W^5$ is selected from $C_1$-$C_{10}$ to alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

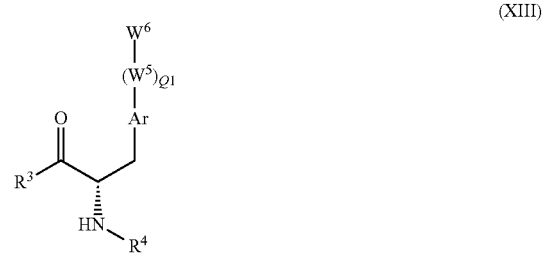

(XIII)

in which $R^3$ is OH or an amino acid residue of the carrier protein, and $R^4$ is H or an amino acid residue of the carrier protein;
(b) correspond to an nnAA according to (a) wherein $W^6$ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and $W^5$ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position;
(f) correspond to an nnAA according to (e) wherein the 2,3-disubstituted propanoic acid has an azido-containing substituent at the 3-position; or
(g) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-23

A protein-antigen conjugate according to embodiment IV-19 wherein the chemical handle is introduced into the antigen by a linker molecule.

Embodiment IV-24

A protein-antigen conjugate according to embodiment IV-23 wherein the site-specific conjugation is the product of strain-promoted azide-alkyne cycloaddition between the chemical handle of the unconjugated antigen and the reactive group of the unconjugated carrier protein wherein the chemical handle comprises a cyclooctyne group and the reactive group comprises an azide group.

Embodiment IV-25

A protein-antigen conjugate according to embodiment IV-23 wherein the antigen is linked to the carrier protein via a structure of formula XI or XIa:

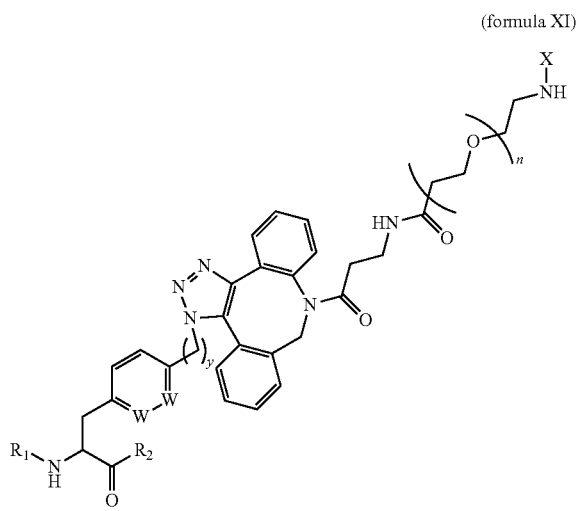

(formula XI)

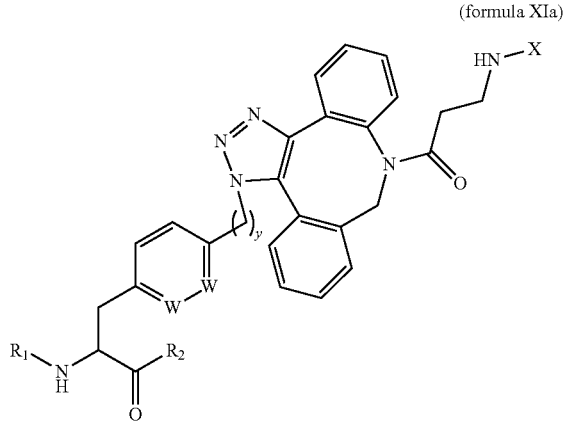

(formula XIa)

wherein $R_1$ is independently H, formyl, or at least one amino acid of the enhanced carrier protein;

$R_2$ is independently OH or at least one amino acid of the enhanced carrier protein;

W is C or N;

y is at least 1;

n is at least 1; and

X is independently at least one polyol of a polysaccharide antigen.

Embodiment IV-26

A protein-antigen conjugate according to embodiment IV-19 wherein the antigen is a bacterial or viral antigen.

Embodiment IV-27

A protein-antigen conjugate according to embodiment IV-19 wherein the antigen is a bacterial polysaccharide selected from the group consisting of capsular polysaccharides from *Streptococcus pneumoniae*, capsular polysaccharides from *Streptococcus pyogenes*, group-A-strep cell wall polysaccharides from *Streptococcus pyogenes*, capsular polysaccharides of *Streptococcus agalactiae*, capsular polysaccharides of *Haemophilus influenzae*, capsular polysaccharides of *Neisseria meningitidis*, and capsular polysaccharides from *Porphyromonas gingivalis*.

Embodiment IV-28

A protein-antigen conjugate according to embodiment IV-19 wherein the antigen is a capsular polysaccharide of a *Streptococcus pneumoniae* serotype selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48.

Embodiment IV-29

A protein-antigen conjugate according to embodiment IV-28 wherein the protein-antigen conjugate has a molecular weight of at least 900 kDa.

Embodiment IV-30

A protein-antigen conjugate according to embodiment IV-19 wherein the ratio (weight by weight) of polysaccharide to carrier protein (PS:PC) is (i) at least 1.0, or (ii) between 1.5 and 4.0.

Embodiment IV-31

A protein-antigen conjugate according to embodiment IV-19 wherein the synthesis of the carrier protein was cell-free.

Embodiment IV-32

A protein-antigen conjugate according to embodiment IV-19 wherein the carrier protein comprises at least 80% sequence identity to SEQ ID NO:1 or SEQ ID NO:11.

Embodiment IV-33

A protein-antigen conjugate according to embodiment IV-22 or IV-25 wherein the carrier protein comprises at least 80% sequence identity to SEQ ID NO:1 or SEQ ID NO:11.

Embodiment IV-34

A protein-antigen conjugate according to embodiment IV-32 wherein the carrier protein comprises at least one sequence of residue sequences selected from the group consisting of residue sequences 271-290, 321-340, 331-350, 351-370, 411-430, and 431-450 of SEQ ID NO:1, wherein the at least one selected sequence of residues does not contain the nnAArs.

Embodiment IV-35

A protein-antigen conjugate according to embodiment IV-32 wherein at least 1 nnAArs is substituted for a canonical amino acid residue corresponding to a position in SEQ ID NO:1 wherein the position is selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

Embodiment IV-36

A protein-antigen conjugate according to embodiment IV-32 wherein at least one nnAArs is substituted for a canonical amino acid residue corresponding to a position in SEQ ID NO:1 wherein the position is selected from:
  a) a group consisting of K25, K34, K38, K40, K213, K215, K228, K245, K265, K386, K523, and K527;
  b) a group consisting of K25, K34, K38 and K40;
  c) a group consisting of K213 and K215;
  c) a group consisting of K11, K25, K34, K38, K40, K83, K104, K105, K126, K158, K173, K213, K215, K222, K228, K237, K243, K245, K265, K386, K475, K499, K523, K527, F13, F54, F124, F128, F141, F168, F251, F390, F531, and F532; and
  e) a group consisting of K25, K215, K228, K265, K386, and K523

Embodiment IV-37

A protein-antigen conjugate according to embodiment IV-32 wherein 2-4 nnAAs are substituted for a canonical amino acid residue corresponding to a position in SEQ ID NO:1 wherein the position is selected from the group consisting of K228, K245, K265, K386, K523, and K527.

Embodiment IV-38

An immunogenic composition comprising at least 2 protein-antigen conjugates and at least one excipient suitable for parenteral administration wherein the at least 2 protein-antigen conjugates comprise multiple antigens and further wherein:

a) the antigen of each of the at least 2 protein-antigen conjugates is distinct from the antigens of the other at least 2 protein-antigen conjugates; and
b) the at least 2 protein-antigen conjugates comprise a protein-antigen conjugate according to embodiment IV-19.

Embodiment IV-39

An immunogenic composition according to embodiment IV-38 wherein the antigens are bacterial or viral antigens.

Embodiment IV-40

An immunogenic composition according to embodiment IV-38 wherein the distinct antigens comprise bacterial polysaccharides selected from the group consisting of capsular polysaccharides from *Streptococcus pneumoniae*, capsular polysaccharides from *Streptococcus pyogenes*, group-A-strep cell wall polysaccharides from *Streptococcus pyogenes*, capsular polysaccharides of *Streptococcus agalactiae*, capsular polysaccharides of *Haemophilus influenzae*, capsular polysaccharides of *Neisseria meningitidis*, and capsular polysaccharides from *Porphyromonas gingivalis*.

Embodiment IV-41

An immunogenic composition according to embodiment IV-39 comprising at least 4, 11, 14, 15, 16, 20, 21, or 24 of the at least 2 protein-antigen conjugates.

Embodiment IV-42

An immunogenic composition according to embodiment IV-40 wherein the ratio (w/w) of the bacterial polysaccharides antigens to carrier protein is at least 1.0, at least 1.1, at least 1.2, at least 1.3. at least 1.4, at least 1.5 or between 1.5 and 4.0.

Embodiment IV-43

An immunogenic composition according to embodiment IV-38 wherein the distinct antigens are capsular polysaccharides from *Streptococcus pneumoniae* and the ratio of *Streptococcus pneumoniae* capsular polysaccharides to carrier protein is from about 1.0 to about 4.0.

Embodiment IV-44

An immunogenic composition according to embodiment IV-43 wherein the capsular polysaccharides from *Streptococcus pneumoniae* are independently selected from capsular polysaccharides of *Streptococcus pneumoniae* serotypes selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A and 48.

Embodiment IV-45

An immunogenic composition according to embodiment IV-43 wherein the capsular polysaccharides from *Streptococcus pneumoniae are independently selected from capsular polysaccharides of Streptococcus pneumoniae serotypes selected from:
- a) a first group consisting of serotypes 1, 2, 3, 4, 5, 6A, 6B, 7F, 8, 9V, 9N, 10A, 11A, 13, 14, 16, 17F, 18C, 19A, 19F, 20, 22F, 23F, 24F, 31, and 33F;
- b) a second group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- c) a third group consisting of serotypes 1, 2, 3, 4, 5, 6A, 6B, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48;
- d) a fourth group consisting of serotypes 3, 4, 18C, and 11A;
- e) a fifth group consisting of serotypes 3, 7F and 10A;
- f) a sixth group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F; or
- g) a seventh group consisting of serotypes 6C, 7C, 13, 15A, 15C, 16, 16F, 23A, 23B, 24F, 31, 34, 35B, 33F, 35F, 37 and 38.

Embodiment IV-46

An immunogenic composition according to embodiment IV-38 wherein the distinct antigens comprise capsular polysaccharides from:
- a) 2 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- b) 14 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- c) 15 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- d) 20 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- e) 21 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- f) 24 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- g) 25 or more different Streptococcus pneumoniae serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
- h) 4 or more different Neisseria meningitidis serogroups selected from the group consisting of serogroups A, C, W135, X, and Y; or
- i) 2 or more different Porphyromonas gingivalis serotypes selected from the group consisting of serotypes K1, K2, K3, K4, K5, and K6.

Embodiment IV-47

An immunogenic composition according to embodiment IV-38 wherein the bacterial polysaccharides are capsular polysaccharides from Streptococcus pneumoniae independently selected from capsular polysaccharides of Streptococcus pneumoniae serotypes selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A and 48.

Embodiment IV-48

An immunogenic composition according to any of embodiment IV-38, IV-41 or IV-42 wherein the carrier protein comprises a plurality of T-cell activating epitopes from a native protein carrier selected from the group consisting of Corynebacterium diphtheriae toxin, Clostridium tetani tetanospasmin, Haemophilus influenzae protein D, and CRM197.

Embodiment IV-49

An immunogenic composition according to any of embodiments IV-38, IV-41 and IV-42 wherein the reactive group comprises a bio-orthogonal reactive moiety and the synthesis of the carrier protein of the at least one protein-antigen conjugate was cell-free synthesis.

Embodiment IV-50

An immunogenic composition according to embodiment IV-49 wherein the bio-orthogonal reactive moiety is selected from the group consisting of azides, phosphines, alkynes, alkenes, and 1,2,4,5-tetrazines.

Embodiment IV-51

An immunogenic composition according to embodiment IV-49 wherein the at least 2 nnAArs:
- (a) correspond to a non-natural amino acid (nnAA) having the structure of formula XII

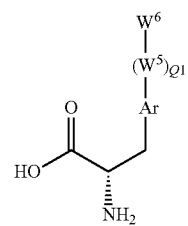

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

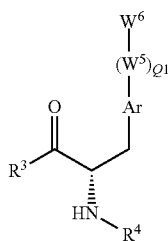

(XIII)

in which $R^3$ is OH or an amino acid residue of the carrier protein, and $R^4$ is H or an amino acid residue of the carrier protein;
(b) correspond to an nnAA according to (a) wherein $W^6$ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and $W^5$ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position; or
(f) correspond to an nnAA according to (e) wherein the 2,3-disubstituted propanoic acid has an azido-containing substituent at the 3-position; or (g) are selected from 2-amino-3-(4-azidophenyl) propanoic acid (pAF), 2-amino-3-(4 (azidomethyl)phenyl) propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl) pyridin-3-yl) propanoic acid, 2-amino-5-azidopentanoic acid, and 2-amino-3-(4-(azidomethyl)phenyl) propanoic acid, or any combination thereof.

Embodiment IV-52

An immunogenic composition according to embodiment IV-38 wherein the protein-antigen conjugates comprise the same carrier protein.

Embodiment IV-53

An immunogenic composition according to embodiment IV-38 wherein the carrier protein of the at least 2 protein-antigen conjugates comprises at least 80% sequence identity to SEQ ID NO:1 or SEQ ID NO:11.

Embodiment IV-54

An immunogenic composition according to embodiment IV-53 wherein the carrier protein of the at least 2 protein-antigen conjugates comprises at least one sequence of residues selected from the group consisting of residue sequences 271-290, 321-340, 331-350, 351-370, 411-430, and 431-450 of SEQ ID NO:1, and wherein the at least one selected sequence of residues does contain an nnAA.

Embodiment IV-55

An immunogenic composition according to embodiment IV-53 wherein at least one nnAArs is substituted for a canonical amino acid residue corresponding to a position in SEQ ID NO:1 wherein the position is selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N, 297, N, 360, N, 400, N, 482, N, 487, N, 503, N, 525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, 5506, T254, T266, T268, T270, T294, T387, T401, T409, T470, and T518

Embodiment IV-56

A multivalent immunogenic composition comprising carrier protein-antigen conjugates wherein:
(a) the carrier protein-antigen conjugates comprise at least 14 distinct carrier protein-antigen conjugates wherein the antigens are capsular polysaccharides of *Streptococcus pneumoniae*;
(b) the at least 14 distinct carrier protein-antigen conjugates each comprise a capsular polysaccharide from a different serotype of *Streptococcus pneumoniae* wherein:
 (i) 13 of the distinct carrier protein-antigen conjugates comprise a capsular polysaccharide from *Streptococcus pneumoniae* serotypes 1, 3, 4, 5, 6A, 6B, 7F, 9V, 14, 18C, 19A, 19F and 23F; and
 (ii) at least one distinct carrier protein-antigen conjugate wherein the antigen is a capsular polysaccharide from *Streptococcus pneumoniae* serotype selected from the group consisting of serotypes 2, 6C, 8, 9N, 10A, 12F, 15A, 15B, 15C, 16F, 17F, 20 (e.g., 20A, 20B), 22F, 23A, 23B, 24F, 24B, 31, 33F, 34, 35B, 35F and 38;
(c) the carrier protein in each of the at least 14 distinct carrier protein-antigen conjugates comprises:
 (i) at least 3 (e.g., at least 4, or 4-6) non-natural amino acid residues (nnAArs); at nn sites, wherein nn i is an integer selected from the group consisting of ≥3, ≥4 and 4-6;
 (ii) at least one T-cell activating epitopes not comprising the at least 3 nnAAs;
(d) the *Streptococcus pneumoniae* capsular polysaccharides of the at least 14 distinct carrier protein-antigen conjugates are conjugated to the nnAAs; and
(e) the overall (weight by weight) ratio of polysaccharides to carrier protein (PS:PC) in the multivalent immunogenic composition is at least 1.1.

Embodiment IV-57

A multivalent immunogenic composition according to embodiment IV-56 wherein the at least 14 distinct carrier protein-antigen conjugates comprise at least 24 distinct carrier protein-antigen conjugates each comprise a capsular polysaccharide from a different serotype of *Streptococcus* pneumoniae selected from the group consisting of serotypes 1, 3, 4, 5, 6A, 6B, 7F, 9V, 14, 18C, 19A, 19F, 23F, 2, 6C, 8, 9N, 10A, 12F, 15A, 15B, 15C, 16F, 17F, 20 (e.g., 20A, 20B), 22F, 23A, 23B, 24F, 24B, 31, 33F, 34, 35B, 35F and 38.

Embodiment IV-58

A multivalent immunogenic composition according to embodiment IV-57 wherein the at least 24 distinct carrier protein-antigen conjugates each comprise a capsular polysaccharide from a different serotype of Streptococcus pneumoniae selected from the group consisting of serotypes 1, 2, 3, 4, 5, 6A, 6B, 7F, 8, 9V, 9N, 10A, 11A, 12F, 14, 15B, 17F, 18C, 19A, 19F, 20, 22F, 23F and 33F.

Embodiment IV-59

A multivalent immunogenic composition according to any of embodiment IV-56, IV-57 or IV-58 wherein the Streptococcus pneumoniae capsular polysaccharides are conjugated to the nnAArs by strain-promoted azide-alkyne cycloaddition between a cyclooctyne group and an azido group.

Embodiment IV-60

A multivalent immunogenic composition according to any of embodiment IV-56, IV-57 or IV-58 wherein the nnAArs in the at least 14 distinct carrier protein-antigen conjugates are selected from 2-amino-3-(4-azidophenyl) propanoic acid (pAF), 2-amino-3-(4 (azidomethyl)phenyl) propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl)phenyl) propanoic acid.

Embodiment IV-61

A multivalent immunogenic composition according to embodiment IV-59 wherein the nnAArs in the at least 14 distinct carrier protein-antigen conjugates are pAMF residues.

Embodiment IV-62

A multivalent immunogenic composition according to embodiment IV-56 wherein the at least 1 T-cell activating epitopes are from a native protein carrier selected from the group consisting of Corynebacterium diphtheriae toxin, Clostridium tetani tetanospasmin, Haemophilus influenzae protein D, and CRM197.

Embodiment IV-63

A multivalent immunogenic composition according to embodiment IV-59 wherein the carrier protein in the at least 14 distinct carrier protein-antigen conjugates has at least 80% sequence identity to SEQ ID NO:1 or SEQ ID NO:11.

Embodiment IV-64

A method of making a conjugate vaccine comprising multiple distinct carrier protein-antigen conjugates, wherein each distinct carrier protein-antigen conjugate comprises a distinct antigen that is different from the antigens in the other distinct carrier protein-antigen conjugates, the improvement comprising using an enhanced carrier protein as the carrier protein in at least one of the distinct carrier-protein conjugates wherein the enhanced carrier protein is a carrier protein that:

a) was made by cell-free protein synthesis;
b) comprises at least 2 non-natural amino acid residues (nnAArs) at nn sites wherein each said nnAAr (i) comprises a reactive group that provides site-specific conjugation of an antigen to the carrier protein, and (ii) was introduced site-specifically during synthesis of the carrier protein;
c) wherein nn is an integer selected from the group consisting of ≥2, ≥3, ≥4, 3, 4, 5, 6, 3-9, 4-8, and 4-6; and
d) at least 1 T-cell activating epitope that has not been inactivated by the presence of an nnAA residue.

Embodiment IV-65

A method according to embodiment IV-64 wherein the at least 1 T-cell activating epitopes are from a native protein carrier selected from the group consisting of Corynebacterium diphtheriae toxin, Clostridium tetani tetanospasmin, Haemophilus influenzae protein D, and CRM197.

Embodiment IV-66

A method according to embodiment IV-64 wherein the reactive group comprises a bio-orthogonal reactive moiety and the bio-orthogonal reactive moiety is selected from the group consisting of azides, phosphines, alkynes, alkenes, and 1,2,4,5-tetrazines.

Embodiment IV-67

A method according to embodiment IV-64 wherein the at least 2 nnAArs:

(a) correspond to a non-natural amino acid (nnAA) having the structure of formula XII

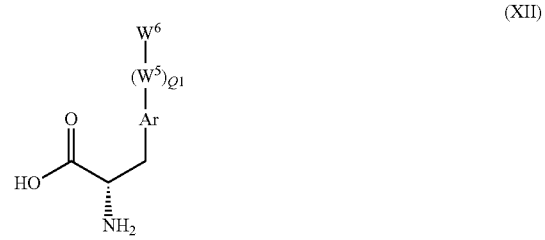

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

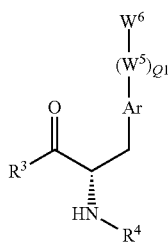

(XIII)

in which R³ is OH or an amino acid residue of the carrier protein, and R⁴ is H or an amino acid residue of the carrier protein;
(b) correspond to an nnAA according to (a) wherein W⁶ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and W⁵ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position;
(f) correspond to an nnAA according to (e) wherein the 2,3-disubstituted propanoic acid has an azido-containing substituent at the 3-position; or
(g) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-68

A method according to embodiment IV-64 wherein the nnAArs are pAMF residues and the antigen conjugated to the enhanced carrier protein is conjugated by strain-promoted azide-alkyne cycloaddition between the azide group of pAMF and a cyclooctyne group on a linker attached to the antigen.

Embodiment IV-69

A method according to embodiment IV-64 wherein the distinct antigens comprise capsular polysaccharides from:
a) 2 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
b) 14 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
c) 15 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
d) 20 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
e) 21 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
f) 24 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
g) 25 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
h) 4 or more different *Neisseria meningitidis* serogroups selected from the group consisting of serogroups A, C, W135, X, and Y; or
i) 2 or more different *Porphyromonas gingivalis* serotypes selected from the group consisting of serotypes K1, K2, K3, K4, K5, and K6.

Embodiment IV-70

A method according to embodiment IV-64 wherein the enhanced carrier protein comprises at least 80% sequence identity to SEQ ID NO:1 or SEQ ID NO:11.

Embodiment IV-71

A method according to embodiment IV-69 wherein the enhanced carrier protein comprises at least 80% sequence identity to SEQ ID NO:1 or SEQ ID NO:11.

Embodiment IV-72

A method according to embodiment IV-70 wherein the enhanced carrier protein comprises at least one nnAA is substituted for K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, 5506, T254, T266, T268, T270, T294, T387, T401, T409, T470, or T518 of SEQ ID NO:1

Embodiment IV-73

A method for producing a carrier protein according to embodiment IV-1 by cell-free protein synthesis comprising:
a) providing a nucleic acid encoding the carrier protein, wherein the nucleic acid comprises a plurality of suppression codons encoding the site of the nnAArs;
b) creating a reaction mixture by combining the nucleic acid with a cell-free bacterial extract comprising canonical amino acids, the nnAArs, a tRNA complementary to the suppression codons and specific for the nnAAs, and an aminoacyl-tRNA synthetase; and c) incubating the reaction mixture of b) under conditions sufficient to selectively incorporate the non-natural amino acid in the carrier protein at the site corresponding to each suppression codon.

Embodiment IV-74

A method according to embodiment IV-73 wherein the reactive group comprises a bio-orthogonal reactive moiety selected from the group consisting of azides, phosphines, alkynes, alkenes, and 1,2,4,5-tetrazines.

Embodiment IV-75

A method according to embodiment IV-73 wherein the nnAArs:
(a) have the structure of formula XII

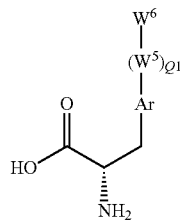

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl;
(b) are according to (a) wherein $W^6$ is azido and Ar is phenylene;
(c) are according to (b) wherein Ar contains a nitrogen heteroatom and optionally at least one additional heteroatom selected from N, O, and S;
(d) are according to (b) wherein Q1 is 1 and $W^5$ is lower alkylene; or
(e) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-76

A method according to embodiment IV-73 wherein the nnAArs are pAMF and step c) is at a temperature between about 10° C. and about 20° C.

Embodiment IV-77

A method according to embodiment IV-73 wherein the carrier protein produced in step c) comprises both a soluble and an insoluble fraction, and wherein the amount of soluble carrier protein to the total protein is at least 60% (w/w).

Embodiment IV-78

A method of making a protein-antigen conjugate according to embodiment IV-19 wherein the reactive group is reacted with the chemical handle under conditions that result in the covalent conjugation of the antigen to the carrier protein.

Embodiment IV-79

A method according to embodiment IV-78 wherein the reactive group of the nnAArs comprises a bio-orthogonal reactive moiety.

Embodiment IV-80

A method according to embodiment IV-79 wherein the bio-orthogonal reactive moiety is selected from the group consisting of azides, phosphines, alkynes, alkenes, and 1,2,4,5-tetrazines.

Embodiment IV-81

A method according to embodiment IV-78 wherein the nnAAs:
(a) have the structure of formula XII

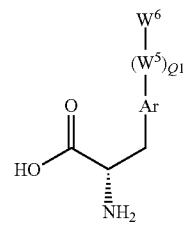

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl;
(b) are according to (a) wherein $W^6$ is azido and Ar is phenylene;
(c) are according to (b) wherein Ar contains a nitrogen heteroatom and optionally at least one additional heteroatom selected from N, O, and S;
(d) are according to (b) wherein Q1 is 1 and $W^5$ is lower alkylene; or
(e) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-82

A method according to embodiment IV-78 wherein the chemical handle is attached to the antigen by a linker molecule.

Embodiment IV-83

A method according to embodiment IV-82 wherein the antigen is linked to the carrier protein via a structure of formula XI or XIa:

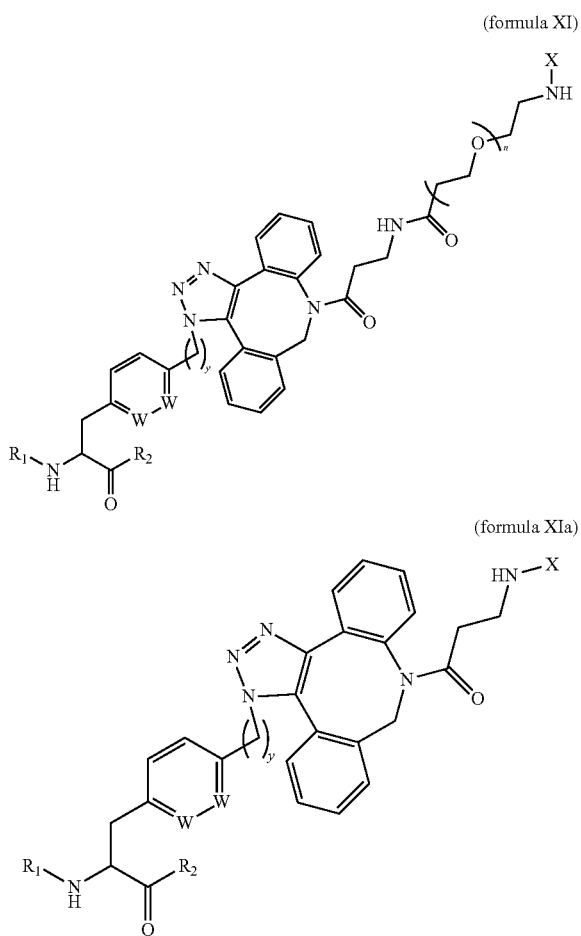

(formula XI)

(formula XIa)

wherein $R_1$ is independently H, formyl, or at least one amino acid of the enhanced carrier protein;

$R_2$ is independently OH or at least one amino acid of the enhanced carrier protein;

W is C or N;

y is at least 1;

n is at least 1; and

X is independently at least one polyol of a polysaccharide antigen.

Embodiment IV-84

A method according to embodiment IV-82 wherein the antigen is a bacterial polysaccharide selected from the group consisting of capsular polysaccharides from *Streptococcus pneumoniae*, capsular polysaccharides from *Streptococcus pyogenes*, group-A-strep cell wall polysaccharides from *Streptococcus pyogenes*, capsular polysaccharides of *Streptococcus agalactiae*, capsular polysaccharides of *Haemophilus influenzae*, capsular polysaccharides of *Neisseria meningitidis*, and capsular polysaccharides from *Porphyromonas gingivalis*.

Embodiment IV-85

A method according to embodiment IV-78 wherein the antigen is a capsular polysaccharide of a *Streptococcus pneumoniae* serotype selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48.

Embodiment IV-86

A method according to embodiment IV-84 wherein the ratio (w/w) of the bacterial polysaccharides antigens to carrier protein is at least 1.0, at least 1.1, at least 1.2, at least 1.3. at least 1.4, at least 1.5 or between 1.5 and 4.0.

Embodiment IV-87

A method of making an immunogenic composition comprising combining at least 2 enhanced protein-antigen conjugates with at least one excipient suitable for parenteral administration, wherein the at least 2 enhanced protein-antigen conjugates are protein-antigen conjugates according to embodiment IV-19, and further wherein the antigen of each of the enhanced protein-antigen conjugates is distinct from the antigens of the other enhanced protein-antigen conjugates.

Embodiment IV-88

A method according to embodiment IV-87 wherein at least 1 T-cell activating epitopes are from a native protein carrier selected from the group consisting of *Corynebacterium diphtheriae* toxin, *Clostridium tetani* tetanospasmin, *Haemophilus influenzae* protein D, and CRM197.

Embodiment IV-89

A method according to embodiment IV-87 wherein the carrier protein of the enhanced protein-antigen conjugates comprises at least 80% sequence identity to SEQ ID NO:1 or SEQ ID NO:11.

Embodiment IV-90

A method according to embodiment IV-89 wherein at least one nnAAr is substituted for a canonical amino acid residue corresponding to a position in SEQ ID NO:1 wherein the position is selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

Embodiment IV-91

A method according to embodiment IV-89 wherein the reactive group comprises a bio-orthogonal reactive moiety.

Embodiment IV-92

A method according to embodiment IV-89 wherein the at least 2 nnAArs:
(a) correspond to a non-natural amino acid (nnAA) having the structure of formula XII

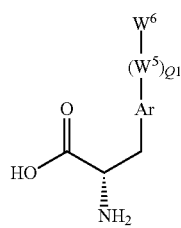

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

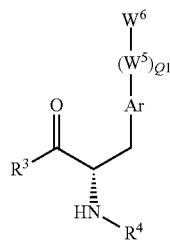

(XIII)

in which $R^3$ is OH or an amino acid residue of the carrier protein, and $R^4$ is H or an amino acid residue of the carrier protein;
(b) correspond to an nnAA according to (a) wherein $W^6$ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and $W^5$ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position;
(f) correspond to an nnAA according to (e) wherein the 2,3-disubstituted propanoic acid has an azido-containing substituent at the 3-position; or
(g) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-93

A method according to embodiment IV-91 wherein the antigens comprise bacterial polysaccharides selected from the group consisting of capsular polysaccharides from *Streptococcus pneumoniae*, capsular polysaccharides from *Streptococcus pyogenes*, group-A-strep cell wall polysaccharides from *Streptococcus pyogenes*, capsular polysaccharides of *Streptococcus agalactiae*, capsular polysaccharides of *Haemophilus influenzae*, capsular polysaccharides of *Neisseria meningitidis*, and capsular polysaccharides from *Porphyromonas gingivalis*.

Embodiment IV-94

A method according to embodiment IV-93 wherein the antigens comprise capsular polysaccharides from:
a) 2 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
b) 14 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
c) 15 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
d) 20 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
e) 21 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
f) 24 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
g) 25 or more different *Streptococcus pneumoniae* serotypes selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F;
h) 4 or more different *Neisseria meningitidis* serogroups selected from the group consisting of serogroups A, C, W135, X, and Y; or
i) 2 or more different *Porphyromonas gingivalis* serotypes selected from the group consisting of serotypes K1, K2, K3, K4, K5, and K6.

Embodiment IV-95

A method of eliciting an immunoprotective response to an antigen in a subject, comprising administering to the subject a conjugate according to any of embodiment IV-19, IV-20, IV-21, IV-22, IV-24, IV-25 or IV-27 in an excipient suitable for parenteral administration.

Embodiment IV-96

A method of eliciting an immunoprotective response to an antigen in a subject, comprising administering to the subject an immunogenic composition according to any of embodiments IV-38, IV-40, IV-41, IV-42, IV-46, IV-47, IV-56 and IV-57.

Embodiment IV-97

A method according to embodiment IV-95 wherein the carrier protein comprises a plurality of T-cell activating epitopes from a native protein carrier selected from the group consisting of *Corynebacterium diphtheriae* toxin, *Clostridium tetani* tetanospasmin, *Haemophilus influenzae* protein D, and CRM197.

Embodiment IV-98

A method according to embodiment IV-95 wherein the carrier protein of the at least two protein-antigen conjugate comprises at least 80% sequence identity to SEQ ID NO:1 or SEQ ID NO:11.

Embodiment IV-99

A method according to embodiment IV-97 wherein at least one nnAA is substituted for a canonical amino acid residue corresponding to a position in SEQ ID NO:1 wherein the position is selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518

Embodiment IV-100

A method according to embodiment IV-97 wherein the reactive group comprises a bio-orthogonal reactive moiety selected from the group consisting of azides, phosphines, alkynes, alkenes, and 1,2,4,5-tetrazines.

Embodiment IV-101

A method according to embodiment IV-97 wherein the at least 2 nnAArs:
(a) correspond to a non-natural amino acid (nnAA) having the structure of formula XII

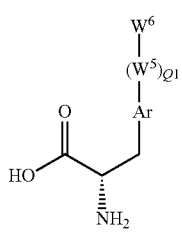

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII

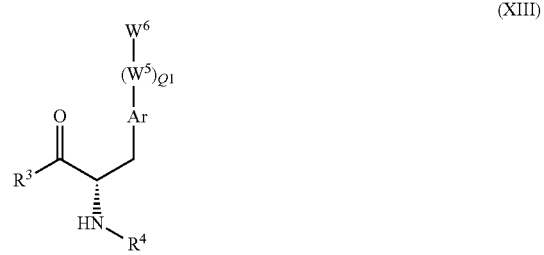

(XIII)

in which $R^3$ is OH or an amino acid residue of the carrier protein, and $R^4$ is H or an amino acid residue of the carrier protein;
(b) correspond to an nnAA according to (a) wherein $W^6$ is azido and Ar is phenylene;
(c) correspond to an nnAA according to (b) wherein Ar contains a nitrogen heteroatom and optionally at least one additional heteroatom selected from N, O, and S;
(d) correspond to an nnAA according to (b) wherein Q1 is 1 and $W^5$ is lower alkylene;
(e) are a 2,3-disubstituted propanoic acid bearing an amino substituent at the 2-position and an azido-containing substituent, a 1,2,4,5-tetrazinyl substituent, or an ethynyl-containing substituent at the 3-position;
(f) correspond to an nnAA according to (e) wherein the 2,3-disubstituted propanoic acid has an azido-containing substituent at the 3-position; or
(g) are selected from 2-amino-3-(4-azidophenyl) propanoic acid (pAF), 2-amino-3-(4 (azidomethyl)phenyl) propanoic acid (pAMF), 2-amino-3-(5-(azidomethyl) pyridin-2-yl)propanoic acid, 2-amino-3-(4-(azidomethyl)pyridin-2-yl)propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

Embodiment IV-102

A method of making a protein-antigen conjugate according to embodiment IV-19 selected from a cyanylation or a periodate method wherein the antigen is a saccharide and the cyanylation method comprises the steps of:
(a) functionalizing the saccharide with a chemical handle capable of participating in a click chemistry reaction with a bio-orthogonal reactive moiety coupled to a nnAA residue in the carrier protein by (i) providing the saccharide as a solution in an aqueous buffer having a pH in the range of 7 to 11; (ii) cyanylating hydroxyl groups on the saccharide by adding a cyanylating reagent to the saccharide solution to provide a cyanate-substituted saccharide, and thereafter (iii) contacting the cyanate-substituted saccharide with an activating reagent comprising the chemical handle coupled to a primary amino group under conditions that couple the chemical handle to the cyanate-substituted saccharide thereby providing an activated saccharide antigen; the periodate method comprises the steps of:
(b) oxidizing a solution of the saccharide in an aqueous medium by adding a periodate reagent to the solution, thereby providing an aldehyde-bearing saccharide;
(c) purifying the aldehyde-bearing saccharide;
(d) dissolving the aldehyde-bearing saccharide in an aqueous buffer having a pH in the range of 5.5 to 5.9; and
(e) in a reductive amination reaction, contacting the dissolved aldehyde-bearing saccharide of step (d) with an activating reagent comprising the chemical handle coupled to a primary amino group, followed by admixture with sodium cyanoborohydride for a time period effective to couple the chemical handle to the cyanate-substituted saccharide, thereby providing an activated saccharide antigen; and combining the activated saccharide antigen of step (a) or step (e) with the carrier protein comprising at least one nnAA bearing the bio-orthogonal reactive moiety, such that a click chemistry reaction between the chemical handle and the bio-orthogonal reactive moiety results in a conjugate of the saccharide and the carrier protein.

Embodiment IV-103

A method of embodiment IV-102 wherein when the cyanylation method is selected and step (a)(iii) is carried out about 3 to about 13 minutes after step (a)(ii); and when the periodate method is chosen the aldehyde-bearing saccharide is dissolved in an aqueous buffer having a pH in the range of 5.5 to 6.9 after step (c) and prior to step (d).

Embodiment IV-104

A method according to embodiment IV-103 wherein when the cyanylation method is selected step (a) comprises a one-pot reaction without addition of a pH-adjusting agent during or subsequent to step (a)(ii); and when the periodate method is selected the admixture with sodium cyanoborohydride for a time period of step (e) comprises 8 to 12 equivalents of sodium cyanoborohydride for a time period in the range of 18 to 30 hours.

Embodiment IV-105

A method according to embodiment IV-104 wherein the cyanylating reagent comprises cyano-4-dimethylamino pyridinium tetrafluoroborate (CDAP).

Embodiment IV-106

A method according to embodiment IV-103 wherein the chemical handle comprises an alkyne functionality.

Embodiment IV-107

A method according to embodiment IV-106 wherein the alkyne functionality comprises a chemically constrained alkyne.

Embodiment IV-108

A method according to embodiment IV-107 wherein the chemical handle comprises a diarylcyclooctyne group.

Embodiment IV-109

A method according to embodiment IV-108 wherein the activating agent comprises a dibenzylcyclooctyne (DBCO) derivative having the structure (I)

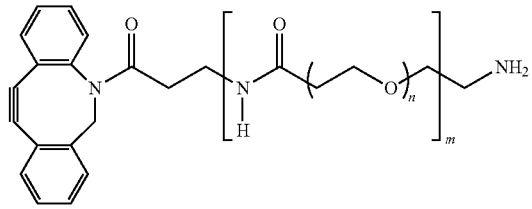

(I)

wherein m is zero or 1 and n is an integer in the range of 2 to 12.

Embodiment IV-110

A method according to embodiment IV-109 wherein m is 1 and n is an integer in the range of 2 to 8.

Embodiment IV-111

A method according to embodiment IV-109 wherein step (a)(iii) is carried out using 0.25 equivalents to 3 equivalents of the DBCO derivative, relative to the saccharide; or step (e) is carried out using 1 equivalents to 3 equivalents of the DBCO derivative, relative to the saccharide, over 24 hours.

Embodiment IV-112

A method according to embodiment IV-111 wherein the first method is selected and the CDAP is added to the saccharide solution of step (a) in an amount effective to achieve a target yield for step (a)(iii) in the range of 5% to 10%, wherein the target yield is the percentage of the DBCO derivative that reacts with the cyanylated saccharide.

Embodiment IV-113

A method according to embodiment IV-112 wherein step (a)(i) is carried out using 0.5 equivalents to 5.0 equivalents CDAP, relative to the saccharide.

Embodiment IV-114

A method according to embodiment IV-102 wherein the saccharide is a capsular polysaccharide from a bacterium selected from *Streptococcus pneumoniae, Neisseria meningitidis, Haemophilus influenzae, Streptococcus pyogenes, Streptococcus agalactiae*, and *Porphyromonas gingivali*.

Embodiment IV-115

A method according to embodiment IV-114 wherein the saccharide is a capsular polysaccharide of a *Streptococcus pneumoniae* serotype selected from the group consisting of serotypes 1, 2, 3, 4, 5, 6A, 6B, 6C, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16, 16F, 16A, 17F, 17A, 18F, 18A, 18B, 18C, 19F, 19A, 19B, 19C, 20 (e.g., 20A, 20B), 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48.

Embodiment IV-116

A method according to embodiment IV-114 further comprising prior to (a) subjecting the saccharide to mechanical size reduction.

Embodiment IV-117

A method according to any of embodiment IV-102, IV-110, IV-114 or IV-115 wherein the carrier protein comprises a plurality of T-cell activating epitopes from a native carrier protein selected from the group consisting of *Corynebacterium diphtheriae* toxin, *Clostridium tetani* tetanospasmin, *Haemophilus influenzae* protein D, and CRM197.

Embodiment IV-118

A method according to embodiment IV-117 wherein the carrier protein (i) comprises at least 80% sequence identity to SEQ ID NO:1, (ii) does not contain an Arg-Arg dipeptide sequence, and at least one of the nnAAs is a 2,3-disubstituted propanoic acid bearing an azido-containing substituent.

Embodiment IV-119

A method according to embodiment IV-118 wherein the carrier protein comprises at least one nnAA substituted for K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, 5506, T254, T266, T268, T270, T294, T387, T401, T409, T470, or T518 of SEQ ID NO:1.

Embodiment IV-120

A method according to any of embodiment IV-102, IV-110, IV-114 or IV-115 wherein the at least 2 nnAArs:
(a) correspond to a non-natural amino acid (nnAA) having the structure of formula XII

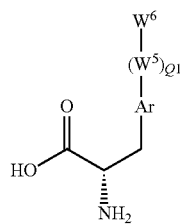

(XII)

wherein Ar comprises a 5-membered or 6-membered aromatic ring optionally containing at least one heteroatom; $W^5$ is selected from $C_1$-$C_{10}$ alkylene, —NH—, —O— and —S—; Q1 is zero or 1; and $W^6$ is selected from azido, 1,2,4,5-tetrazinyl optionally C-substituted with a lower alkyl group, and ethynyl, such that the nnAArs in the carrier protein have the structure of formula XIII.

EXAMPLES

Example 1: Synthesis of Single-Site eCRM Moieties K11TAG, K25TAG, K34TAG, K38TAG, K40TAG, K52TAG, K60TAG, K77TAG, K83TAG, K91TAG, K96TAG, and K103TAG (Numbered According to SEQ ID NO:1)

eCRM was expressed in a cell-free protein synthesis (CFPS) extract provided by Sutro Biopharma, Inc. (South San Francisco, Calif.). Features and preparation of such an extract are described in other publications; in this case the extract was generally prepared as described in Zawada et al., 2011, *Biotechnol. Bioeng.*, 108(7), 1570-1578 with the following modifications from US2016/0257946: (1) cell-free extract was prepared from an OmpT sensitive RF-1 attenuated strain engineered to overexpress *E. coli* DsbC; (2) cell-free extract was prepared from a similar RF-1 attenuated *E. coli* strain engineered to produce an orthogonal CUA-encoding tRNA for insertion of a non-natural amino acid at an amber stop codon; (3) the cell-free extracts from (1) and (2) were blended (at a ratio of 85:15) and treated with 50 μM iodoacetamide for 30 min at RT (20° C.); and (4) the blended extracts were added to a premix containing all other components of a cell-free protein synthesis system except for DNA encoding eCRM. The final concentration in the cell-free protein synthesis reaction was 30% (by volume) cell extract, 2 mM para-methylazido-L-phenylalanine (pAMF) (RSP Amino Acids, Shirley, Mass.), 5 μM pAMF-specific tRNA synthetase ('RS'), 2 mM GSSG (oxidized glutathione), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNAP, and 2.5 μM eCRM plasmid encoding the nnAA variants. The cell-free synthesis reactions were initiated by the addition of the plasmid DNA encoding eCRM.

The reactions were incubated 14 h on a shaker at 650 rpm in 48-well Flower plates (m2p-labs #MTP-48-B). After the incubation period, the reaction was held at 4° C. until it was processed for purification or analysis. Following the cell-free protein synthesis reaction, the mixture containing pAMF-eCRM was transferred to a 96-well plate (DyNa Block™, 2 mL; Labnet, Edison, N.J.) and centrifuged at 5000×g for 15 minutes at 40° C.

First, an optimization experiment was performed to assess the best temperature and additives for the CFPS production of eCRM. CFPS reactions were performed at 30, 25, and 20, degrees Celsius, with additional supplementation of CUA-encoding tRNA (0, 1, 2, 4, 8, 12% v/v) and nnAA/synthetase mix (50, 100, 150, 200 μg/ml) at each of the three temperatures. Samples of CFPS mixture pre- and post-centrifugation were collected and analyzed by SDS-PAGE electrophoresis, and bands were quantitated by densitometry to assess the amount of soluble protein (post-centrifugation sample) of total protein (pre-centrifugation sample) produced in each condition.

FIG. 1 shows yield of nnAA-eCRM produced in each condition as assessed by quantitative densitometry. While CFPS reactions at 30 degrees produced a relatively small fraction of soluble protein (max ~0.33 of total among all conditions), the yield of soluble protein was enhanced (>~0.40 soluble/total among all conditions) at 25 degrees and further enhanced (>~0.60 soluble/total among all conditions) at 20 degrees. At both of the "low" temperature conditions, soluble protein yield is further enhanced by increasing the tRNA concentration (1-12× show increasing yield), whereas increasing the nnAA/synthetase concentration had a detrimental to no effect on soluble yield.

Based on the experiment of FIG. 1, temperatures less than 20 degrees and tRNA concentration of at least 20 μM were chosen for the synthesis of K11TAG, K25TAG, K34TAG, K38TAG, K40TAG, K52TAG, K60TAG, K77TAG, K83TAG, K91TAG, K96TAG, and K103TAG variants (numbered according to SEQ ID NO:1)

CFPS reactions were performed as above. For convenience of purification in these preliminary experiments a histidine tag (GSGHHHHHH; SEQ II) NO:10) was fused to the C-terminus of the carrier protein sequence via the expression vector, and purification of eCRM variants from the post-centrifugation supernatant was carried out by using IMAC Phytips (Phynexus, San Jose, Calif.) containing 40 μL resin. The resin bed was pre-equilibrated in IMAC equilibration buffer (1×PBS and 10 mM imidazole) and the clarified supernatant was pipetted up and down 10 times through equilibrated IMAC Phytips at a flow rate of 4.2 μL/min. The bound protein was washed with IMAC equilibration buffer, and then eluted with 125 μL IMAC elution buffer (1×PBS and 0.5M imidazole). The histidine tag is not essential and is omitted for larger-scale purification.

nnAA incorporation and reactivity was assessed by SDS-PAGE and fluorescent analysis after reaction with DBCO-fluorescein (FIG. 2). 2-12 μM eCRM was incubated with 50 μM DBCO-fluorescein for 16 hours, subjected to nonreducing SDS-PAGE, and visualized with coomassie blue (visible light) and a Sypro-ruby filter set (fluorescent, fluorescein).

Figure 2:
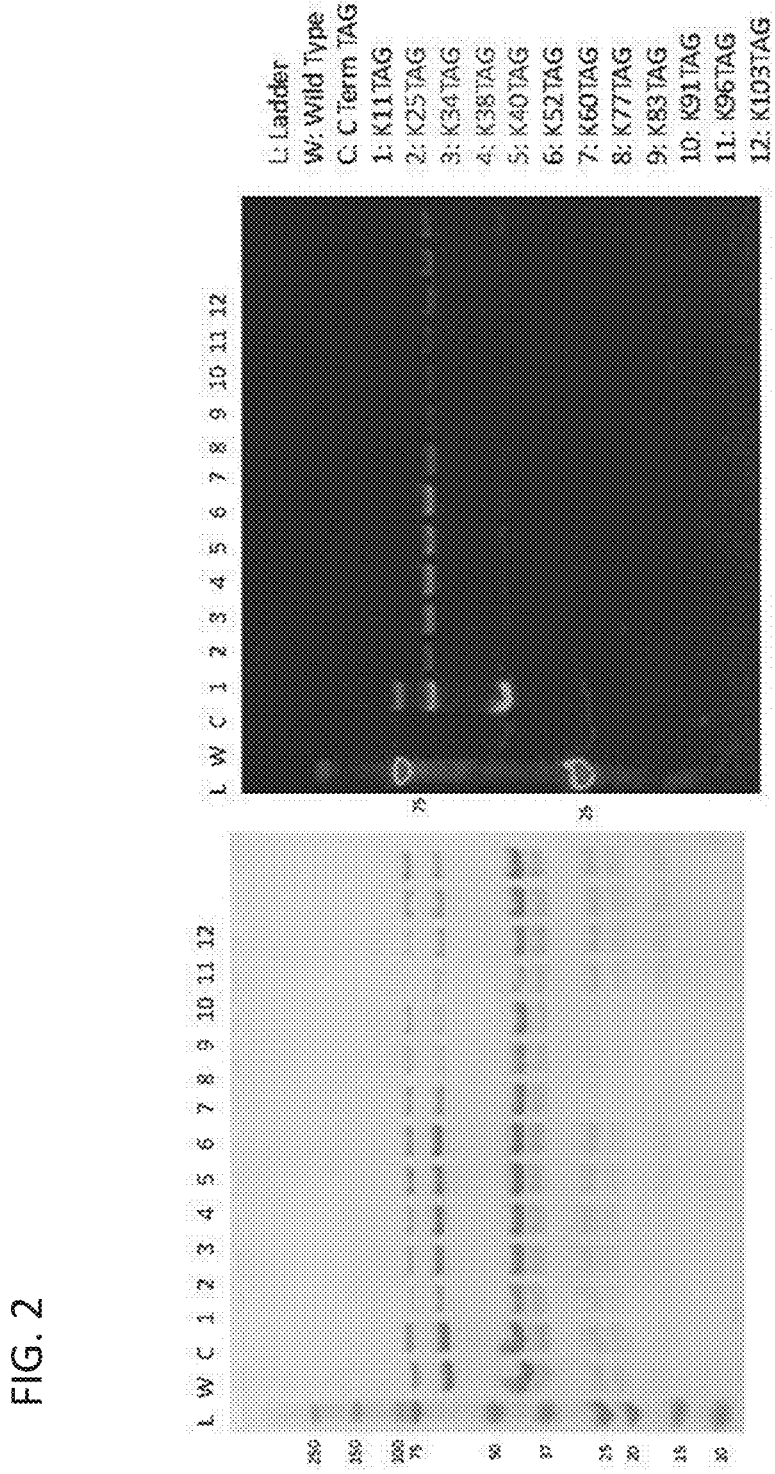
FIG. 2 shows coomassie (2A) and fluorescent (2B) gel images demonstrating the relative yield of synthesized protein (2A) and the ability of pAMF incorporated into eCRM to react with DBCO-fluorescein (2B) for single-site eCRM produced in cell-free protein synthesis (CFPS) reactions.

FIG. 2 shows the corresponding coomassie (left) and fluorescent (right) gel images showing the ability of pAMF incorporated into eCRM to react with DBCO. K25, K34, K38, and K40 amber substitutions show high expression and conjugation efficiency, while others do not.

Protein content was measured using the bicinchoninic acid (BCA) assay or the Lowry protein assay, as indicated. Purity determinations made using the anthrone test are identified as dry weight purity.

Example 2: Design of Multiple nnAA eCRM

Multiple nnAA eCRM variants were selected as described in the detailed description above. Variants were synthesized via CFPS and tested along the lines of Example 1.

TABLE 3

Multiple nnAA eCRM variants (numbering according to SEQ ID NO. 1)

| Variant # | K25 | K34 | K38 | K40 | K213 | K215 | K228 | K245 | K265 | K386 | K523 | K527 |
|---|---|---|---|---|---|---|---|---|---|---|---|---|
| 1 | ✓ | | | | ✓ | | ✓ | | ✓ | ✓ | ✓ | |
| 2 | ✓ | | | | ✓ | | ✓ | | ✓ | ✓ | | ✓ |
| 3 | ✓ | | | | ✓ | | | ✓ | ✓ | ✓ | ✓ | |
| 4 | ✓ | | | | ✓ | | | ✓ | ✓ | ✓ | | ✓ |
| 5 | ✓ | | | | | ✓ | ✓ | | ✓ | ✓ | ✓ | |
| 6 | ✓ | | | | | ✓ | ✓ | | ✓ | ✓ | | ✓ |
| 7 | ✓ | | | | | ✓ | | ✓ | ✓ | ✓ | ✓ | |
| 8 | ✓ | | | | | ✓ | | ✓ | ✓ | ✓ | | ✓ |
| 9 | | ✓ | | | ✓ | | ✓ | | ✓ | ✓ | ✓ | |
| 10 | | ✓ | | | ✓ | | ✓ | | ✓ | ✓ | | ✓ |
| 11 | | ✓ | | | ✓ | | | ✓ | ✓ | ✓ | ✓ | |
| 12 | | ✓ | | | ✓ | | | ✓ | ✓ | ✓ | | ✓ |
| 13 | | ✓ | | | | ✓ | ✓ | | ✓ | ✓ | ✓ | |
| 14 | | ✓ | | | | ✓ | ✓ | | ✓ | ✓ | | ✓ |
| 15 | | ✓ | | | | ✓ | | ✓ | ✓ | ✓ | ✓ | |
| 16 | | ✓ | | | | ✓ | | ✓ | ✓ | ✓ | | ✓ |
| 17 | | | ✓ | | ✓ | | ✓ | | ✓ | ✓ | ✓ | |
| 18 | | | ✓ | | ✓ | | ✓ | | ✓ | ✓ | | ✓ |
| 19 | | | ✓ | | ✓ | | | ✓ | ✓ | ✓ | ✓ | |
| 20 | | | ✓ | | ✓ | | | ✓ | ✓ | ✓ | | ✓ |
| 21 | | | ✓ | | | ✓ | ✓ | | ✓ | ✓ | ✓ | |
| 22 | | | ✓ | | | ✓ | ✓ | | ✓ | ✓ | | ✓ |
| 23 | | | ✓ | | | ✓ | | ✓ | ✓ | ✓ | ✓ | |
| 24 | | | ✓ | | | ✓ | | ✓ | ✓ | ✓ | | ✓ |
| 25 | | | | ✓ | ✓ | | ✓ | | ✓ | ✓ | ✓ | |
| 26 | | | | ✓ | ✓ | | ✓ | | ✓ | ✓ | | ✓ |
| 27 | | | | ✓ | ✓ | | | ✓ | ✓ | ✓ | ✓ | |
| 28 | | | | ✓ | ✓ | | | ✓ | ✓ | ✓ | | ✓ |
| 29 | | | | ✓ | | ✓ | ✓ | | ✓ | ✓ | ✓ | |
| 30 | | | | ✓ | | ✓ | ✓ | | ✓ | ✓ | | ✓ |
| 31 | | | | ✓ | | ✓ | | ✓ | ✓ | ✓ | ✓ | |
| 32 | | | | ✓ | | ✓ | | ✓ | ✓ | ✓ | | ✓ |

Further variants including different numbers of Lys-pAMF substitutions were prepared. In general it was found that higher numbers of substitutions gave carriers which led to higher MW conjugates (e.g. for serotype 14, rising from 998 kDa with 2 substitutions to 1238 kDa with 3 substitutions, to 1789 kDa with 4 substitutions, and to 2547 kDa with 5 substitutions) but the carriers had lower solubility. Carriers with six pAMF residues generally provided both good solubility (>>50 mg/mL) and immunogenicity. The high solubility was surprising because replacement of charged Lys residues in the native sequence with hydrophobic pAMF residues increased the hydrophobicity of CRM197, which is a protein whose hydrophobicity has already been reported to affect its solubility (Orr et al. 1999 *Infect Immun* 67:4290-4). Thus these results show that it is possible to maintain the same attachment sites which have been used in known CRM197 conjugates (namely Lys residues) without causing insolubility when the charged residues are lost.

Useful Lys residues for substitution by a nnAA in SEQ ID NO:1 are thus K25, K34, K38, K40, K213, K215, K228, K245, K265, K386, K523, and K527, as shown in Table 2 above.

It is desirable that conjugated polysaccharides are not localized too tightly in one area of the CRM197 surface. Thus, within closely-spaced residues, it is preferred to pick (i) only one of K25, K34, K38, and K40 and (ii) either K213 or K215 (numbered according to SEQ ID NO:1).

One sequence which has been particularly useful in creating pneumococcal conjugates is variant 12 in Table 3, in which K34, K213, K245, K265, K386 and K527 of SEQ ID NO:1 are replaced by a nnAA. This protein has amino acid sequence SEQ ID NO:9 where each X is pAMF (a preferred nnAA). This protein is used for preparing the conjugates described below.

Lysine residues may be useful because they are the amino acids which have been used in known CRM197 conjugates, so nnAAs at these positions permit conjugation to occur at the same sites as are already known to be compatible with CRM197. As mentioned above, however, loss of charged lysine can lead to structural changes, increased hydrophobicity, and lower solubility. Modification of phenylalanine residues to phenylalanine-based nnAAs (such as para-azido-Phe, para-azido-methyl-Phe, para-fluoro-Phe, para-acetyl-Phe, or para-benzoyl-Phe) may reduce the risk of these changes. Thus residues F13, F54, F124, F128, F141, F168, F251, F390, F531, or F532 of SEQ ID NO:1 are also selected for substitution, singly and in combination. Substitution of up to five Phe residues by pAMF was tested and provided soluble conjugates, but with a tendency for lower MW conjugates than achieved with the same number of multiple Lys substitutions.

Rather than substituting amino acids within CRM197 it is also possible to insert nnAA within the CRM197 sequence. For example, a TAG codon encoding pAMF is inserted directly downstream of lysine residues K34, K213, K245, K265, K386 and K527 (according to SEQ ID NO:1), either individually (to create six point insertions) or in combination (inserting 2, 3, 4, 5 or 6 nnAA). Carriers with inserted nnAA, such as these, are useful for making the conjugates and multivalent compositions as described above.

Example 3: Identification of T-Cell Epitopes in Pfs25

The T-cell activating epitopes of malaria ookinete specific surface protein Pfs25 are determined experimentally along the lines of the methods described in, e.g., Diethelm-Okita et al., *J Infect Dis*. 1997 February; 175(2):382-91. Briefly, peptide fragments of 20 amino acids and overlapping by 5 amino acids are synthesized corresponding to the complete expressed sequence of Pfs25. CD8+-depleted and CD4+-enriched human peripheral blood lymphocytes (PBL) are obtained from multiple subjects. The PBLs are plated in triplicate and cultured with the individual synthetic peptides spanning the Pfs25 sequence serving as experimental stimuli. The proliferation of PBLs in response to each peptide fragment is measured by pulsing the cultures with [3H]-thymidine and compared across cultures originating from different individuals. Pfs25 fragments that stimulate proliferation are identified to comprise a T-cell epitope. Fragments that stimulate proliferation of PBLs from a plurality or all subjects are classified as comprising a universal or immunodominant T-cell epitope in Pfs25.

Example 4: General Protocol for Polysaccharide Activation with Sodium Meta-Periodate (Through Example 43)

Serotype polysaccharides (~30 µmol) were dissolved in aqueous solution (10 mM HCl). The solution was then heated at 45° C. for 30 min and then cooled, at which time NaOH solution was added to adjust pH to 6.70. The reaction mixture was dialyzed using AMICON ultra centrifuge (30 kDa MWCO) against HPLC grade water. The supernatant was transferred to a 50 mL of falcon tube, acetate buffer (pH 5.35) was added to 25 mM, and 0.5 eq $NaIO_4$ was added. The mixture was stirred at 25° C. for 17 hours, after which the time, the oxidized sample was optionally treated with an excess of sodium borohydride (10 eq) and purified using AMICON ultra centrifuge (30 kDa MWCO) against several changes of HPLC grade water to give oxidized polysaccharide solution.

Example 5: General Procedure for Periodate-Oxidized Polysaccharide Derivatization with DBCO (Through Example 43)

Oxidized polysaccharide (~30 µmol) was combined with DBCO-PEG$_4$-NH$_2$ (~30 µmol; obtained from Click Chemistry Tools, Scottsdale AZ) or DBCO-NH$_2$ (~30 µmol) in 72 mM sodium phosphate pH 6.79 containing 16% DMSO at 25° C. The reaction mixture was then stirred at 25° C. for 30 min, after which time sodium cyanoborohydride solution (16 mg/ml solution in water; 59.54 µmol, 20 equivalents) was added and kept stirring for overnight-2 days at 25° C. The reaction mixture was then washed 3× with ethyl acetate, transferred to an AMICON ultra centrifuge (30 kDa MWCO), and then dialyzed using 6 exchanges of 20% ethanol in water followed by 3 exchanges with water to give a solution of type the polysaccharide-DBCO derivative. The polysaccharide-DBCO derivative was then compounded with 10:1 (w/w) sucrose and lyophilized to give a white powder for use in the next conjugation reaction.

Example 6: General Protocol for Polysaccharide Activation with CDAP (Through Example 43)

Capsular polysaccharide (30 mg) (PS 3) was dissolved in aqueous solution (13.5 mL $H_2O$ with 1.5 mL 2M acetic acid). The mixture was heated at 85° C. for 1 hour and an excess of magnesium chloride was added from a 1M solution after cooling to ambient temperature. The resultant polysaccharide was purified using Amicon centrifugal 30 kDa MWCO dialysis using 6 exchanges of water.

Prepared polysaccharide was then dissolved in pH 7.0 water and cyanylation reagent CDAP (1-Cyano-4-dimethylaminopyridinium tetrafluoroborate, in acetonitrile) was added. The solution was then adjusted to pH 9.5 or trimethylamine (2.5 eq) was added. DBCO-PEG$_4$-NH$_2$ or DBCO-NH$_2$ was then added to the solution. Solution was adjusted to 5% DMSO and stirred overnight at 25° C. The solution was washed 3× with 20 mL ethyl acetate, and purified using Amicon 30 kDa MWCO dialysis units using 7 exchanges with 3% DMSO, 20% ethanol, 0.9% sodium chloride and 3 exchanges with water. The polysaccharide-DBCO derivative was then compounded 10:1 (w/w) with sucrose and lyophilized.

Example 7: General Procedure for Conjugation of Polysaccharide DECO with eCRM (Through Example 40)

Polysaccharide-DBCO sample lyophilized and compounded with 10:1 w/w sucrose (prepared by the procedure of examples 4 or 5) was dissolved in 0.9% NaCl and mixed with eCRM in solution to provide a PS:eCRM input mass ratio of 1:1 (w/w). The reaction mixture was gently mixed by hand before gently mixing on an orbital shaker at room temperature (20° C.) for 18 hours. The click reaction was quenched by the addition of an excess of sodium azide solution. The conjugated PS-eCRM mixture was transferred to a prewashed dialysis tube (SpectrumLab Float-A-Lyzer G2, Cat. No. G235060, 300K MWCO) and then dialyzed against 5 exchanges of 0.9% sodium chloride solution over 24 hours. The dialyzed solution was filtered through a Millex-GP (0.22 µm, 33 mm polyethersulfone) to give a PS-eCRM conjugate solution.

Example 8: Preparation of Pneumococcal PS Serotype 1 Conjugates to an eCRM from Table 3

1. Oxidation

Purity of type 1 PS: 80% (uronic)

Mol. wt: 625 g mol$^{-1}$ (per repeating unit)

Reaction Procedure:

The native polysaccharide PS1 (19.7 mg, corrected to 80%, 15.8 mg, 25.2 µmol) was dissolved in 9.85 mL of aqueous solution (7.0 mL water and 2.85 mL acetate buffer, 200 mM, pH 5.5). To this solution was added 300 µL of sodium periodate solution (104 µg, 3.78 µmol, 0.15 eq). The mixture was stirred at 25° C. for 18 hours after which time a large molar excess of sodium borohydride (10 mol. eq) was added. The oxidized PS was purified using Amicon centrifugal 30 k Da MWCO dialysis using at least 6 exchanges with water to give purified oxidized polysaccharide type 1 (PS1-OX) solution. Protein content was determined using a bicinchoninic acid (BCA) assay.

| Mol eq of NaIO$_4$ | PS 1 (mg) | Vol. after purification (mL) | Uronic assay (µM) | % Oxidation (BCA) | % Oxidation (aldehyde assay) | PS1-OX yield (%) | Note |
|---|---|---|---|---|---|---|---|
| 0.15 | 19.7 | 2.86 | 11040 | 1.4 | n/d | 100 | N/A |

2. DBCO Derivatization

Reaction Procedure:

PS1-OX (15.8 mg, 25.2 µmol) was dissolved in phosphate buffer (3.6 mL, 50 mM pH 7.0) to which was added DBCO-PEG$_4$-NHS ester (1.0 eq., 649.1 g mol$^{-1}$ in DMSO, 0.35 mL). The reaction mixture was stirred at 37° C. for two days in a thermostatted water bath followed by extraction with ethyl acetate (3×20 mL). The DBCO derivative was purified by centrifugal dialysis units (Amicon 30 kDa MWCO) using 6 exchanges with 20% ethanol in water followed by 3 exchanges with water (12 mL each) to give the PS1-DBCO derivative. To this solution (2.20 mL, 9.59 mg) was added a solution of sucrose (96 mg in 1 mL water). The combined solution were divided into three equal portions and each lyophilized to give three samples of white powder. Each sample contained 3.18 mg of PS1-DBCO and 32 mg of sucrose for use in the next conjugation reaction.

| oxidized PS 1 (mg) | Vol. after purification (mL) | Uronic assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 15.8 | 2.20 | 6976 | 0.280 × 4 | 116.16 | 1.67 | 65 | 602 |

3. Conjugation of PS1-DBCO Derivative with eCRM

PS1-DBCO: 3.18 mg (with 32 mg sucrose) lyophilized powder

% DBCO: 1.67%

CRM concentration: 6.5 mg/mL solution

PS:CRM (input ratio): 1:1

Reaction Procedure:

PS1-DBCO was dissolved in azido-functionalized eCRM solution (0.51 mL) to provide a PS1:CRM input mass ratio of 1:1 (w/w). Further dilution with 0.9% sodium chloride solution (0.22 µm filtered) was necessary to 1.0 mg mL-1 to mitigate gel formation. The solution was very gently mixed by hand before gently mixing on an orbital shaker at room temperature (20° C.) for 18 hours. The click reaction was quenched by the addition of sodium azide solution (10 mg/mL, 50 µL). The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was filtered through a Millex-GP syringe filter (0.22 µm, 33 mm polyethersulfone) to give a PS1-CRM conjugate solution.

| PS1-DBCO (mg) | CRM (mg) | Vol. after purification (mL) | Anthrone (mg/mL) | PS recovery (%) | BCA (CRM) (mg/mL) | CRM recovery (%) | PS1:CRM CJD* Ratio | Free PS (%) | SEC-MALS MDa |
|---|---|---|---|---|---|---|---|---|---|
| 3.18 | 3.315 | 7.17 | 0.177 | 40 | 0.099 | 21 | 1.79:1 | 9.39 | 2.13 |

*CJD = dialysed conjugate

Example 9: Preparation of Pneumococcal PS Serotype 2 Conjugates to an eCRM from Table 3

1. Oxidation

Purity of type 2 PS: 80%

Mol. wt: 960.84 g mol$^{-1}$

Reaction Procedure:

The native polysaccharide PS2 (25.5 mg, 26.5 µmol) was dissolved in 12.75 mL of aqueous solution (9.24 mL water and 3.51 mL acetate buffer, 200 mM, pH 5.5). To this solution was added 216 µL of sodium periodate solution (5.26 mg/ml, 0.20 eq). The mixture was stirred at 25° C. for 18 hours with monitoring by UV absorption at 222 nm for NaIO$_4$. The oxidized PS was purified using Amicon centrifugal 100 kDa MWCO dialysis using at least 6 exchanges with water to give purified, oxidized PS2 (PS2-OX) solution.

| Mol eq of NaIO$_4$ | PS 2 (mg) | Vol. after purification (mL) | Anthrone assay (µM) | % Oxidation (BCA) | % Oxidation (aldehyde assay) | PS2-OX yield (%) | Note |
|---|---|---|---|---|---|---|---|
| 0.20 | 25.5 | 2.28 | 9041 | 22.8 | 5.4 | 78 | N/A |

2. DBCO Derivatization

Reaction Procedure:

PS2-OX (18.1 mg, 18.8 µmol) in 2.14 mL water was diluted with phosphate buffer (1.95 mL, 200 mM pH 6.0) to which was added DBCO-PEG$_4$-NH$_2$ (9.85 mg, 1 eq., in DMSO, 0.197 mL). After 25 minutes NaCNBH$_3$ (2.36 mg, 2 eq. 59 µL from a solution in H$_2$O) was added. The reaction mixture was stirred at 25° C. for two days in a thermostatted water bath followed by addition of phosphate buffer (0.5 mL of 200 mM pH=6). To this was added NaBH$_4$ (60 µL of a 10 mg/mL aqueous solution, 1 eq.) After stirring for 30 min the mixture was extraction with ethyl acetate (4×5 mL). The residual ethyl acetate was removed by bubbling with nitrogen gas and the mixture transferred to 100 kDa MWCO Amicon centrifuge filters. The DBCO derivative was purified by centrifugal dialysis using 1 exchange of water followed by 6 exchanges with 20% ethanol in water followed by 3 exchanges with water (12 mL each) to give the PS2-DBCO derivative. To this solution (2.14 mL, 14.3 mg) was added a solution of sucrose (100 mg in 1 mL water). The combined solution were divided into three almost equal portions and each lyophilized to give three samples of white powder (4.96 mg, 4.96 mg and 4.4 mg).

| PX2-OX (mg) | Vol. after purification (mL) | Anthrone assay (µM) | DBCO derivatization 309 nm Abs | DBCO derivatization (µM) | DBCO incorporation (%) | PS2-DBCO yield (%) | SEC-MALS kDa |
|---|---|---|---|---|---|---|---|
| 18.1 | 2.14 | 1956 | 0.848 × 4 | 315.5 | 4.03 | 89 | 375 |

3. Conjugation of PS 2-DBCO derivative with eCRM

PS 2-DBCO: 4.4 mg (with 32 mg sucrose) lyophilized powder

% DBCO: 4.03%

CRM concentration: 3.18 mg/mL solution

PS:CRM (input ratio): 1.5:1

Reaction Procedure:

PS2-DBCO was dissolved in 0.9% NaCl (3.01 mL) and DMSO (0.44 mL) was added. Then azido-functionalized eCRM solution (0.95 mL) was added to provide a PS2:CRM input mass ratio of 1.5:1 (w/w). The solution was very gently mixed by hand before gently mixing on an orbital shaker at room temperature (20° C.) for 18 hours. The click reaction was quenched by the addition of sodium azide solution (10 mg/mL, 100 µL). The CRM conjugate was transferred to two pre-washed dialysis tubes (SpectrumLab Float-A-Lyzer G2, 300K MWCO) and then dialyzed with 0.9% sodium chloride solution for 24 hours (5 exchanges, 1000 ml each). The dialyzed solution was filtered through a Millex-GP syringe filter (0.22 µm, 33 mm polyethersulfone) to give a PS2-CRM conjugate solution.

| PS2-DBCO (mg) | CRM (mg) | Vol. after purification (mL) | Anthrone (mg/mL) | PS2 recovery (%) | BCA (CRM) (mg/mL) | CRM recovery (%) | PS2:CRM CJD ratio | Free PS2 (%) | SEC-MALS MDa |
|---|---|---|---|---|---|---|---|---|---|
| 4.4 | 2.93 | 4.77 | 0.683 | 91 | 0.387 | 75 | 1.76:1 | LLOQ | 1.37 |

Example 10: Preparation of Pneumococcal PS Serotype 3 Conjugates to an eCRM from Table 3

1. Hydrolysis

Purity of type 3 PS: 86% (anthrone)

Mol. wt: 360.3 g mol$^{-1}$

Reaction Procedure:

The native polysaccharide PS3 (30.0 mg) was dissolved in 15.0 mL of aqueous solution (13.5 mL water and 1.5 mL acetic acid, 2M). The mixture was heated at 85° C. for 1 hour after which time magnesium chloride solution was added (1.5 mL, 1M) after cooling for ambient temperature. The hydrolyzed PS was purified using Amicon centrifugal 30 k Da MWCO dialysis using at least 6 exchanges with water to give purified PS3 solution which was then lyophilized in two equal aliquots.

| Native PS3 (mg) | Water (mL) | AcOH, 2M (mL) | Anthrone assay (µM) | Purified PS3 yield (%) | MALS (kDa) |
|---|---|---|---|---|---|
| 30.0 | 13.5 | 1.50 | 10477.22 | 85 | 294 |

2. DBCO Derivatization

Reaction Procedure:

Hydrolyzed PS3 (12.75 mg, 35.4 µmol) was dissolved in water (6.4 mL) adjusted to pH 7.0 with sodium hydroxide solution (0.2M, 100 µL). The cyanylation reagent, CDAP, was then added dropwise (0.426M in acetonitrile, 0.2 eq., 16.7 µL). After 90 s, the solution was quickly adjusted to pH 9.5 with sodium hydroxide solution (0.2M, 300 µL). DBCO-PEG$_4$-NH$_2$ (0.032M in DMSO, 0.1 eq., 523 g mol$^{-1}$, 0.110 mL) was added immediately, dropwise. Additional DMSO was added to give 5% (v/v) DMSO (0.320 mL). The reaction mixture was stirred at 25° C. overnight in a thermostatted water bath followed by filtration through a 0.22 µm PES syringe filter. The filtrate was extracted with ethyl acetate (3×20 mL). The DBCO derivative was purified by centrifugal dialysis units (Amicon 30 kDa MWCO) using a total of 7 exchanges with 3% DMSO, 20% ethanol in water, 0.9% sodium chloride followed by 3 exchanges with water (12 mL each) to give type the polysaccharide (PS)$_3$-DBCO derivative. The aqueous solution was then filtered through a 0.45 µm PVDF syringe filter. To this solution (3.84 mL, 8.52 mg) was added a 10-fold mass excess of sucrose (85 mg in 0.85 mL water). The combined solution was divided into three portions which were lyophilized to give three samples of white powder. Two samples contained 5.0 mg of PS3-DBCO and 50 mg of sucrose for use in the next conjugation reaction, with 8.5 mg in the remaining sample, for a total of three.

| hydrolyzed PS 3 (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 12.8 | 4.04 | 2063.47 | 1.095 × 3 | 102.64 | 5.0 | 70 | 409 |

3. Conjugation of PS3-DBCO Derivative with eCRM
 PS3-DBCO: 5.0 mg (with 50 mg sucrose) lyophilized powder
 % DBCO: 5.0%
 CRM concentration: 4.0 mg/mL solution
 PS:CRM (input ratio): 1:1
Reaction Procedure:
 PS3-DBCO was dissolved in 0.9% sodium chloride solution (6.39 mL, 0.22 µm filtered), phosphate buffer (pH 7.0, 0.5M, 0.333 mL) and DMSO (0.833 mL). Azido-functionalized eCRM solution (0.770 mL) was added dropwise to provide a PS3:CRM input mass ratio of 1:1 (w/w). The solution was very gently mixed by hand before gently mixing on an orbital shaker at room temperature (20° C.) for 18 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a PS3-CRM conjugate solution.

Example 11: Preparation of Pneumococcal PS Serotype 3 Conjugates to an eCRM from Table 3

1. Oxidation
 Purity of type 3 PS: 86% (anthrone)
 Mol. wt: 360.3 g mol$^{-1}$
Reaction Procedure:
 The native polysaccharide PS3 (14.4 mg, corrected to 86%, 12.4 mg, 34.4 µmoles) was dissolved in 7.2 mL of aqueous solution (5.9 mL water and 1.3 mL acetate buffer, 200 mM, pH 5.5). To this solution was added 300 µL of sodium periodate solution (1.10 mg, 5.16 µmol, 0.15 eq.). The mixture was stirred at 25° C. for 18 hours. The oxidized PS was purified using Amicon centrifugal 30 k Da MWCO dialysis using at least 6 exchanges with water to give purified PS3-OX solution.

| Mol eq of NaIO$_4$ | PS3 (mg) | Vol. after purification (mL) | Anthrone assay (µM) | % Oxidation (BCA) | % Oxidation (aldehyde assay) | PS yield (%) |
|---|---|---|---|---|---|---|
| 0.15 | 14.4 | 1.84 | 15940.33 | 3.9 | 0.8 | 73 |

2. DBCO Derivatization
Reaction Procedure:
 PS3-OX (9.05 mg, 25.1 µmol) was dissolved in phosphate buffer (2.11 mL, 50 mM, pH 6.7) to which was added DBCO-PEG$_4$-NH$_2$ (1.0 eq., 523 g mol$^{-1}$ in DMSO, 0.40 mL). The reaction mixture was stirred at 25° C. for 25 mins. prior to the addition of a solution of sodium cyanoborohydride (2 eq., 44.5 mg/mL, 35 µL) and stirred for two days. At this time the reaction mixture was extracted with ethyl acetate (3×20 mL). The DBCO derivative was purified by centrifugal dialysis units (Amicon 30 kDa MWCO) using 6 exchanges with 20% ethanol in water followed by 3 exchanges with water (12 mL each) to give the PS3-DBCO derivative. To this solution (3.20 mL, 8.60 mg) was added a 10-fold mass excess of sucrose (86 mg in 0.86 mL water). The combined solution was divided into four portions and each lyophilized to give three samples of white powder. Three samples contained 2.0 mg of PS3-DBCO and 20 mg of sucrose for use in the next conjugation reaction, with 2.6 mg in the remaining sample, for a total of four.

| PS3-DBCO (mg) | CRM (mg) | Vol. after purification (mL) | Anthrone (mg/mL) | PS recovery (%) | BCA (CRM) (mg/mL) | CRM recovery (%) | PS3:CRM CJF* Ratio | Free PS (%) | SEC-MALS MDa |
|---|---|---|---|---|---|---|---|---|---|
| 5.0 | 5.0 | 3.63 | 0.402 | 70 | 0.423 | 74 | 0.95:1 | 2.55 | 3.2 |

*CJF = dialysed and filtered conjugate

| PS3-OX (mg) | Vol. after purification (mL) | Anthrone assay (μM) | DBCO derivatization 309 nm Abs | DBCO derivatization (μM) | DBCO incorporation (%) | PS3-DBCO yield (%) | SEC-MALS kDa |
|---|---|---|---|---|---|---|---|
| 15.8 | 2.76 | 2681.28 | 0.683 × 3 | 64.47 | 2.3 | 95 | 304 |

3. Conjugation of PS3-DBCO Derivative with eCRM

PS3-DBCO: 2.0 mg (with 20 mg sucrose) lyophilized powder

% DBCO: 2.3%

CRM concentration: 4.0 mg/mL solution

PS:CRM (input ratio): 1:1

Reaction Procedure:

PS3-DBCO was dissolved in 0.9% sodium chloride solution (0.400 mL, 0.22 μm filtered) and DMSO (0.100 mL). Azido-functionalized eCRM solution (0.330 mL) was added dropwise to provide a PS3:CRM input mass ratio of 1:1 (w/w). The solution was very gently mixed by hand before gently mixing on an orbital shaker at room temperature (20° C.) for 48 hours. The click reaction was quenched by the addition of sodium azide solution (10 mg/mL, 50 μL). The CRM conjugate was transferred to two pre-washed dialysis tubes (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 μm, 33 mm polyethersulfone) to give a PS3-CRM conjugate solution.

| PS3-DBCO (mg) | CRM (mg) | Vol. after purification (mL) | Anthrone (mg/mL) | PS recovery (%) | BCA (CRM) (mg/mL) | CRM recovery (%) | PS3:CRM CJF ratio | Free PS (%) | SEC-MALS MDa |
|---|---|---|---|---|---|---|---|---|---|
| 2.0 | 2.0 | 3.63 | 0.226 | 41 | 0.307 | 59 | 0.74:1 | 21.0 | 3.42 |

Example 12: Preparation of Pneumococcal PS Serotype 4 Conjugates to an eCRM from Table 3

1. Oxidation

Purity of type 4 PS: 80% (Anthrone)

Mol. wt: 825.78

Reaction Procedure:

Type 4 PS (27.5 mg, 33.30 μmol) powder was dissolved in 13.75 mL of aqueous solution (12.38 mL of water and 1.37 mL of 0.1 M HCl). The solution was then heated at 45° C. for 30 min and then cooled, at which time, NaOH solution (0.1 M, 1.37 mL) was added to adjust pH to 6.70. The reaction mixture was dialyzed using AMICON ultra centrifuge (30 kDa MWCO 6-12 mL) by 3 exchanges with HPLC grade water (12 mL each). The supernatant was transferred to a 50 mL of falcon tube with 9.84 mL of water. To this solution was added 3.43 mL of 200 mM acetate buffer (pH 5.35) and 632 μL of NaIO$_4$ solution (3.56 mg, 16.65 μmol, 0.5 eq). The mixture was stirred at 25° C. for 17 hours, after which the time, the oxidized sample was purified using AMICON ultra centrifuge (30 kDa MWCO 6-12 mL) 6 exchanges (12 mL) of HPLC grade water to give oxidized PS4 (PS4-OX) solution.

| Mol eq of NaIO$_4$ | mg of PS4 | Vol. after purification ml | Anthrone | % oxidation uM (BCA) | % oxidation (aldehyde assay) | PS4-OX yield (%) |
|---|---|---|---|---|---|---|
| 0.5 | 27.5 | 2.71 | 12078 | 10.8 | 2.58 | 101 |

2. DBCO Derivatization

Reaction Procedure:

To a solution of oxidized (assume 10% oxidation level) Type 4 PS (24.58 mg, 29.77 μmol, 2.4 mL water) was added buffer solution (1.8 mL of 200 mM phosphate buffer, pH=6.79), DMSO (0.6 mL) and a solution of DBCO-PEG$_4$-NH$_2$ (15 mg in 200 μL of DMSO; 28.65 μmol, 9.6 equivalent) all at 25° C. The reaction mixture was then stirred at 25° C. for 30 min, after which time 224 μL of a sodium cyanoborohydride solution (5.0 mg in 300 μL of water; 59.54 μmol, 20 equivalent) was added and kept stirring for 2 days at 25° C. The reaction mixture was diluted with phosphate buffer (500 μL of 200 mM solution, pH=6) before adding 225 μL solution of sodium borohydride (0.01 mg/μL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give a solution of the PS4-DBCO derivative. To this solution (4.75 mL, 15.25 mg) was added a solution of sucrose (153 mg in 1 mL water). The combined solution were divided into three portions and each lyophilized to give three samples of white powder. Two samples contained 5.35 mg of 4 DBCO and 54 mg of sucrose and one sample contained 4.55 mg of PS4-DBCO and 45 mg of sucrose for use in the next conjugation reaction.

| PS4-OX (mg) | Vol. after purification ml | Anthrone uM | DBCO derivatization 309 nm Abs | DBCO derivatization uM | % DBCO (%) | PS4-DBCO yield (%) | SEC-MALS kDa |
|---|---|---|---|---|---|---|---|
| 24.58 | 5.25 | 3897 | 0.472 × 3 | 137.16 | 3.52 | 69 | 343 |

3. Conjugation of PS4-DBCO Derivative with eCRM
 PS4-DBCO: 5.35 mg (with 54 mg of sucrose) white powder
 % DBCO: 3.52%
 CRM concentration: 4 mg/mL solution
 PS:CRM (input ratio): 1.20:1
Reaction Procedure:
 Type PS4-DBCO sample (5.35 mg white powder with 54 mg of sucrose) was dissolved in 0.67 mL of 0.9% of NaCl solution and then azido-functionalized eCRM solution (0.74 mL) was added. After 10 min, another portion of azido-functionalized eCRM (0.37 mL) was added providing a PS4:CRM mass ratio of 1.20:1 (w/w). The reaction mixture was gently mixed by hand before gently mixing on an orbital shaker at room temperature (20° C.) for 2 days. The conjugated PS4-CRM mixture was transferred to a prewashed dialysis tube (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give a PS4-CRM conjugate solution.

PS-5 Conjugation:
 To 3.377 mL of water was added 0.108 mL potassium phosphate (0.5 M, pH 7.5), 0.343 mL NaCl (5M), and 0.857 mL of DMSO. The mixture was stirred to homogeneity, then 0.870 mL of serotype 5 activated polysaccharide (PS5-DBCO, 2.3 mg/mL) was added. After mixing to homogeneity eCRM (0.160 mL, 5.2 mg/mL) was added and the reaction was stirred at 80 rpm for 15 h. The unreacted DBCO was quenched by addition of sodium azide (0.057 mL, 10 mg/mL in water) followed by stirring for 2 h. The resulting quenched conjugate was purified via dialysis, then analyzed to determine total saccharide concentration, total protein concentration, molecular weight, and free saccharide content.

Example 14: Preparation of Pneumococcal PS Serotype 5 Conjugates to an eCRM from Table 3

1. Oxidation
 Purity of type 5 PS: 89% (Uronic Acid)
 Mol. wt: 919.32
Reaction Procedure:
 Polysaccharide PS5 (22.8 mg, 24.36 µmol) powder was dissolved in 8.26 mL of water and 3.14 mL of 200 mM

| PS4-DBCO (mg) | CRM (mg) | Vol. after purification (mL) | Anthrone (mg/mL) | PS recovery (%) | BCA (CRM) (mg/mL) | CRM recovery (%) | PS4:CRM CJD ratio | Free PS (%) | SEC-MALS MDa |
|---|---|---|---|---|---|---|---|---|---|
| 5.35 | 4.46 | 5.31 | 0.595 | 65 | 0.360 | 45 | 1.65:1 | 23.63 | 4.55 |

Example 13: Pneumococcal PS Serotype 5 Sizing, Activation, and Conjugation

PS5 Sizing and Activation:
 Serotype 5 polysaccharide (PS5) at 3 mg/mL was reduced in size via high pressure homogenization using 20,000 psi for 20 passes. The sized polysaccharide was analyzed via anthrone assay to determine the concentration.
 To the sized PS5 (42.2 mL, 2.275 mg/mL) was added 2.286 mL water and 2.4 mL acetate buffer (1.0 M, pH 5.4). The solution was stirred at 250 rpm and 1.116 mL sodium periodate solution (5 mg/mL in water) was added. After 3 h of reaction time at room temperature, the solution was purified by tangential flow filtration against 10 diavolumes of water. The concentration of the oxidized polysaccharide PS5-OX was measured by anthrone assay.
 To PS5-OX (17 mL, 4.322 mg/mL) was added 2.190 mL water and 2.449 mL sodium phosphate buffer (1.0 M, pH 5.1). The solution was stirred and then DBCO-PEG$_4$-amine was added (2.449 mL, 34.1 mg/mL in DMSO). After the solution was stirred to homogeneity, sodium cyanoborohydride was added (0.402 mL, 100 mg/mL in water). After 19 h of stirring at room temperature, the solution was purified by tangential flow filtration. The concentration of the activated polysaccharide PS5-DBCO was measured by anthrone assay and the concentration of DBCO-PEG$_4$-amine measured by absorbance at 309 nm.

acetate buffer (pH 5.26) and 163 µL of NaIO$_4$ solution (1.3 mg, 6.1 µmol, 0.25 eq). The mixture was stirred at 25° C. for 18 hours, after which the time, the oxidized sample was purified using AMICON ultra centrifuge (100 kDa MWCO 6-12 mL) 6 exchanges (12 mL) of HPLC grade water to give oxidized PS5 (PS5-OX) solution.

| Mol eq of NaIO$_4$ | PS5 (mg) | Vol. after purification (mL) | Uronic Acid (µM) | % Oxidation (BCA) | % Oxidation (aldehyde assay) | PS5-OX yield (%) |
|---|---|---|---|---|---|---|
| 0.25 | 22.8 | 2.44 | 6735.97 | 84.87 | 5.71 | 68 |

2. DBCO Derivatization
Reaction Procedure:
 To a solution of oxidized (assume 10% oxidation level) Type 5 PS (6.25 mg, 6.68 µmol, 0.992 mL water) was added buffer solution (0.063 mL of 200 mM phosphate buffer, pH=6.74), DMSO (25 µL) and a solution of DBCO-PEG$_4$-NH$_2$ (3.5 mg in 100 µL of DMSO; 6.68 µmol, 10 equivalent) all at 25° C. The reaction mixture was then stirred at 37° C. for 30 min, after which time 84 µL of a sodium cyanoborohydride solution (0.84 mg in 84 µL of water; 13.36 µmol, 20 equivalents) was added and kept stirring for 24 hr at 37° C. The reaction mixture was extracted with ethyl acetate (6×10 mL). The extract was transferred to an AMICON ultra centrifuge filter (30 kDa MWCO 6-12 mL) and then dialyzed using 8 exchanges with 20% ethanol in water (12 mL each) followed by 3 exchanges with water (12 mL each) to give the PS5-DBCO derivative. To this solution (5.35 mL, 6.0 mg) was added a solution of sucrose (60 mg in 0.6 mL water). The combined solution was divided into two equal portions and each lyophilized to give two samples of white powder. Each sample contained 3.0 mg of PS5-DBCO and 30 mg of sucrose for use in the next conjugation reaction.

| PS5-OX (mg) | Vol. after purification (mL) | Uronic Acid (μM) | DBCO derivatization 309 nm Abs | DBCO derivatization (μM) | DBCO incorporation (%) | PS5-DBCO yield (%) | SEC-MALS kDa |
|---|---|---|---|---|---|---|---|
| 6.25 | 5.38 | 1219.4 | 0.688 × 3 | 63.044 | 5.17 | 98 | 300 |

3. Conjugation of PS5-DBCO Derivative with eCRM
   PS5-DBCO: 3.0 mg (with 30 mg of sucrose) white powder
   % DBCO: 5.17%
   CRM concentration: 3.25 mg/mL solution
   PS5:CRM (input ratio): 1:1
Reaction Procedure:
   The PS5-DBCO derivative (3.0 mg white powder with 30 mg of sucrose) was dissolved in 0.9% sodium chloride solution (4.48 mL) and DMSO (0.6 mL). Azido-functionalized eCRM solution (0.92 mL) was added providing a PS5:CRM mass ratio of 1:1 (w/w). The reaction mixture was gently mixed before gently mixing on an orbital shaker at room temperature (20° C.) for 5 hours. Sodium azide solution (20 μL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 μm, 33 mm polyethersulfone) to give PS5-CRM conjugate solution.

| PS5-DBCO (mg) | CRM (mg) | Vol. after purification (mL) | Uronic Acid (mg/mL) | PS recovery (%) | BCA (CRM) (mg/mL) | CRM recovery (%) | PS5:CRM CJD ratio | Free PS (%) | SEC-MALS MDa |
|---|---|---|---|---|---|---|---|---|---|
| 3.0 | 3.0 | 5.466 | 0.231 | 46 | 0.239 | 48 | 0.97 | LLOQ | 2.74 |

Example 15: Preparation of Pneumococcal PS Serotype 6A Conjugates to an eCRM from Table 3

1. Oxidation
   Type 6A PS Mol. wt: 706
   NaIO$_4$ solution in water (10 mg/mL)
Reaction Procedure:
   PS6A (15 mg, 21.2 μmol) powder was dissolved in 7.5 mL of aqueous solution (10 mM sodium acetate solution, PH 4.5). To this solution was added 36.3 μL of NaIO$_4$ solution (0.363 mg, 1.69 μmol, 0.08 eq). The mixture was stirred at 4° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS6A (PS6A-OX) solution. After dialysis, add DMSO to make PS-6A in 10% DMSO with 50 mm PB buffer, PH 6.8.

| Mol eq of NaIO$_4$ | PS6A (mg) | Vol. after purification (mL) | Anthrone (μM) | % Oxidation (BCA) | PS6A-OX yield (%) |
|---|---|---|---|---|---|
| 0.08 | 15 | 4 | 4780 | 9.0 | 90 |

2. DBCO Derivatization
   Final concentration of PS: 3.37 mg/ml,
   Final concentration of buffer: 10% DMSO in 50 mM PB (pH 6.8)
Reaction Procedure:
   To a solution of PS6A-OX (13.5 mg, 19.1 μmol, 4 mL in 10% DMSO, 50 Mm PB, pH 6.8), a solution of DBCO-PEG$_4$-NH$_2$ (10.01 mg in 100.1 μL of DMSO; 19.1 μmol, 10 equivalent) was added at 25° C. The reaction mixture was then stirred at 25° C. for 60 min, after which time sodium cyanoborohydride solution (1.2 mg in 120 μL of water; 19.1 μmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give the PS6A-DBCO derivative.

| PS6A-OX (mg) | Vol. after purification (mL) | Anthrone (μM) | DBCO derivatization (μM) | DBCO incorporation (%) | PS6A-DBCO yield (%) | SEC-MALS kDa |
|---|---|---|---|---|---|---|
| 13.5 | 8 | 1685 | 148 | 8.78 | 70 | 193 |

3. Conjugation of PS6A-DBCO Derivative with eCRM
   PSA-DBCO: 7.1 mg (with 71 mg of sucrose) white powder
   DBCO: 9%
   CRM concentration: 2.617 mg/mL solution
   PS:CRM (input ratio): 2:1
   Final concentration of PS: 5.2 mg/ml
Reaction Procedure:
   Azido-functionalized eCRM solution (1.4 mL) was added to the PS6A-DBCO derivative (7.1 mg white powder with 71 mg of sucrose) providing a PS 6A:CRM mass ratio of 2:1

(w/w). The reaction mixture was gently mixed by hand before gently mixing on an orbital shaker at room temperature (23° C.) for 17 hours. The mixture was then put into an incubator (37° C.) for 3 hours. After reaction, the mix was diluted 2 fold by 0.9% sodium chloride solution and reduced by sodium borohydride (1.9 mg in 191 µL of water; 50.2 µmol, 50 equivalent) for 3 hours. The conjugated PS-CRM mixture was transferred to a prewashed dialysis tube (SpectrumLab Float-A-Lyzer G2, Cat. No. G235072, 300K MWCO) and then dialyzed with PBS, PH 7 for 24 hours (3 exchanges, 1000 ml each). The dialyzed solution was filtered through a Millex-GP (0.22 µm, 33 mm polyethersulfone) to give a PS6A-CRM conjugate solution.

| PS6A-DBCO (mg) | CRM (mg) | Vol. after purification (mL) | Anthrone (mg/mL) | PS recovery (%) | BCA (CRM) (mg/mL) | CRM recovery (%) | PS6A: CRM CJD ratio | Free PS (%) | SEC-MALS MDa |
|---|---|---|---|---|---|---|---|---|---|
| 7.1 | 3.6 | 10 | 0.424 | 60 | 0.170 | 47 | 2.5:1 | 16.1 | 1.15 |

Example 16: Preparation of Pneumococcal PS Serotype 6B Conjugates to an eCRM from Table 3

1. Oxidation
Purity of type 6B PS: 80% (Anthrone)
Mol. wt: 706.18
NaIO4 solution in water (5.45 mg/mL)
Reaction Procedure:
Polysaccharide type PS6B (27.28 mg corrected to 80%, 21.82 mg, 30.9 µmol) powder was dissolved in 14 mL of aqueous solution (9.5 mL of water and 4.5 mL of 0.2 M acetate buffer; pH=5.5). To this solution was added 145 µL of NaIO$_4$ solution (0.79 mg, 3.71 µmol, 0.12 eq). The mixture was stirred at 25° C. for 18 hours, after which the time, the oxidized sample was purified using AMICON ultra centrifugal device (30 kDa MWCO 6-12 mL) 6 exchanges (12 mL) of HPLC grade water to give oxidized PS6B (PS6B-OX) solution.

| Mol eq of NaIO$_4$ | PS6B (mg) | Vol. after purification (mL) | Anthrone (µM) | % Oxidation (BCA) | % Oxidation (aldehyde assay) | PS yield (%) |
|---|---|---|---|---|---|---|
| 0.12 | 27.28 | 3.54 | 7783 | 8.1 | 7.33 | 89 |

2. DBCO Derivatization
Final concentration of PS: 3.5 mg/ml
Final concentration of buffer: 53 µM (pH 6.0)
Reaction Procedure:
To a solution of PS6B-OX (assume 10% oxidation level) (18.4 mg, 27.6 µmol, 3.35 mL water) was added buffer solution (1.4 mL of 200 mM phosphate buffer, pH=6.01), DMSO (700 µL) and a solution of DBCO-PEG$_4$-NH$_2$ (14.43 mg in 295 µL of DMSO; 27.6 µmol, 10 equivalent) all at 25° C. The reaction mixture was then stirred at 25° C. for 30 min, after which time 75 µL of a sodium cyanoborohydride solution (9.39 mg in 200 µL of water; 55.6 µmol, 20 equivalent) was added and kept stirring for 2 days at 25° C. The reaction mixture was diluted with phosphate buffer (500 µL of 200 mM solution, pH=6) before adding 104 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give a solution of the PS6B-DBCO derivative. To this solution (2.96 mL, 20.1 mg) was added a solution of sucrose (200 mg in 1 mL water). The combined solution were divided into three equal portions and each lyophilized to give three samples of white powder. Each sample contained 6.7 mg of PS6B-DBCO and 67 mg of sucrose for use in the next conjugation reaction.

| PS6B-OX (mg) | Vol. after purification (mL) | Anthrone (µM) | DBCO derivatization 309 nm Abs | DBCO derivatization (µM) | DBCO incorporation (%) | PS6B-DBCO yield (%) | SEC-MALS KDa |
|---|---|---|---|---|---|---|---|
| 18.4 | 3.11 | 9620 | 0.796 × 4 | 311.17 | 3.2 | 115 | 403 |

3. Conjugation of PS 6B-DBCO Derivative with eCRM
PS6B-DBCO: 6.7 mg (with 67 mg of sucrose) white powder
% DBCO: 3.2%
CRM concentration: 2.617 mg/mL solution
PS:CRM (input ratio): 2:1
Final concentration of PS: 5.23 mg/ml
Reaction Procedure:
Azido-functionalized eCRM solution (1.28 mL) was added to the PS6B-DBCO derivative (6.70 mg white powder with 67 mg of sucrose) providing a PS6B:CRM mass ratio of 2:1 (w/w). The reaction mixture was gently mixed by hand before gently mixing on an orbital shaker at room temperature (20° C.) for 17 hours. The mixture was then put into an oven (37° C.) for 2 hours. The conjugated PS6B-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-GP (0.22 µm, 33 mm polyethersulfone) to give a PS6B-CRM conjugate solution.

| PS6B-DBCO (mg) | CRM (mg) | Vol. after purification (mL) | Anthrone (mg/mL) | PS recovery (%) | BCA (CRM) (mg/mL) | CRM recovery (%) | PS6B:CRM CJD ratio | Free PS (%) | SEC-MALS MDa |
|---|---|---|---|---|---|---|---|---|---|
| 6.70 | 3.35 | 6.18 | 0.68 | 67 | 0.347 | 67 | 1.96:1 | 8.72 | 1.30 |

Example 17: Alternative Method for Periodate Activation of Pneumococcal PS Serotype 6B To 6B sized polysaccharide (47.3 mL, 2.73 mg/mL) was added 9.019 mL water and 7.106 mL acetate buffer (1.0 M, pH 5.4). The solution was stirred at 250 rpm and 1.173 mL sodium periodate solution (5 mg/mL in water) was added. After 3 h of reaction time at room temperature, the solution was purified by tangential flow filtration against 10 diavolumes of water. The concentration of the oxidized polysaccharide PS6B-OX was measured by anthrone assay.

To the 6B oxidized polysaccharide (31.3 mL, 3.75 mg/mL) was added 3.908 mL sodium phosphate buffer (1.0 M, pH 5.1). The solution was stirred and then DBCO-PEG$_4$-amine was added (3.908 mL, 44.5 mg/mL in DMSO). After solution was stirred to homogeneity, sodium cyanoborohydride was added (0.556 mL, 150 mg/mL in water). After 16.5 h of stirring at room temperature, the solution was purified by tangential flow filtration. The concentration of the activated polysaccharide (PS6B-DBCO) was measured by anthrone assay and the concentration of DBCO-PEG$_4$-amine measured by absorbance at 309 nm.

Example 18: Preparation of Pneumococcal PS Serotype 7F Conjugates to an eCRM from Table 3

1. CDAP Activation and DBCO Crosslink
    Purity PS 7F: n.d. % (Anthrone)—assumed 100%
    Mol. wt: 1227 g mol$^{-1}$ (repeat unit)
Reaction Procedure:
    The native polysaccharide PS7F (6.2 mg, 5.1 μmol) was dissolved in water (3.1 mL) to which was added CDAP (2.0 eq., 100 mg/mL in acetonitrile, 24 μL). The reaction mixture was stirred at room temperature (RT) for 30 s. At this time, triethylamine (TEA, 2.5 eq., 0.2M, 63 μL) was added and the reaction mixture was stirred for 120 s. DBCO-PEG$_4$-NH$_2$ (1.0 eq., 28.7 μmol/mL in DMSO, 180 μL) was added along with borate buffer (0.1M, pH8.5, 1.0 mL) and stirred at RT overnight. The DBCO-derivatized PS7F (PS7F-DBCO) was purified by ethanol precipitation and by centrifugal dialysis (Amicon 100 kDa MWCO) using 3 exchanges with water. After analysis by UV absorbance spectroscopy, anthrone assay and SEC, this solution (3.61 mL, 3.05 mg) was diluted with a sucrose solution (10-fold mass content, 100 mg/mL) and lyophilized to a white powder.

| PS7F (mg) | Vol. after purification (mL) | Anthrone assay (μM) | DBCO derivatization 309 nm Abs | DBCO derivatization (μM) | DBCO incorporation (%) | PS7F-DBCO yield (%) | SEC-MALS kDa |
|---|---|---|---|---|---|---|---|
| 6.2 | 3.61 | 686.3 | 0.619 | 55.52 | 8.1 | 49 | n.d. |

2. Conjugation of PS7F-DBCO Derivative with eCRM
    PS7F-DBCO: 2.62 mg (with 26.2 mg sucrose) lyophilized powder
    % DBCO: 8.1%
    CRM: 5.0 mg/mL in PBS buffer
    PS:CRM (input mass ratio): 1.73:1
Reaction Procedure:
    Lyophilized PS7F-DBCO was dissolved in brine (0.9% (w/v), 0.938 mL), phosphate buffer (0.5 M, pH 7.0, 58 μL) and DMSO (144 μL) to which was added eCRM solution (0.300 mL) to provide a PS7F:CRM input mass ratio of 1.73:1.00 (w/w). The solution was very gently mixed by hand before gently mixing on an orbital shaker at room temperature (20° C.) for 17 hours. The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was sterile-filtered through a Millex-GP syringe filter (0.22 μm, 33 mm polyethersulfone) to give a PS7F-CRM conjugate solution.

| PS7F-DBCO (mg) | CRM (mg) | Vol. after purification (mL) | Anthrone (mg/mL) | PS recovery (%) | BCA (CRM) (mg/mL) | PS7F:CRM CJF ratio | Free PS (%) | SEC-MALS MDa |
|---|---|---|---|---|---|---|---|---|
| 2.62 | 1.5 | 7.17 | 0.450 | 65 | 0.224 | 2.0:1.0 | LLOQ (<21.4 ug/mL) | 1.95 |

Example 19: Preparation of Pneumococcal PS Serotype 8 Conjugates to an eCRM from Table 3

1. Oxidation

Purity of type 8 PS 84%
Mol. Wt: 684.54 g mol$^{-1}$
Reaction Procedure:

The native polysaccharide PS8 (42 mg, 61.3 µmol) was dissolved in 21 mL of aqueous solution (14.7 mL water and 6.3 mL acetate buffer, 200 mM, pH 5.5). To this solution was added a sodium periodate solution (calculated for 2.63 mg, 0.20 eq.). The mixture was stirred at 25° C. for 18 hours with monitoring by UV absorption at 222 nm for NaIO$_4$. The oxidized PS (PS8-OX) was purified using Amicon centrifugal 30 kDa MWCO dialysis using at least 6 exchanges with water to give purified, oxidized PS8 (PS8-OX) solution.

Reaction Procedure:

The PS8-DBCO conjugate was dissolved in 0.9% NaCl (2.28 mL), phosphate buffer (0.126 mL, 0.5 M pH 7.0) and DMSO (0.314 mL) was added. Then azido-functionalized eCRM solution (0.42 mL) was added to provide a PS8:CRM input mass ratio of 1.5:1 (w/w). The solution was very gently mixed by hand before gently mixing on an orbital shaker at room temperature (20° C.) for 1 hour and then put in oven at 37° C. overnight. The click reaction was quenched by the addition of sodium azide solution (10 mg/mL, 100 µL). The CRM conjugate was transferred to pre-washed dialysis tube (SpectrumLab Float-A-Lyzer G2, 300K MWCO) and then dialyzed with 0.9% sodium chloride solution for 48 hours (8 exchanges, 1000 ml each). The dialyzed solution was filtered through a Millex-GP syringe filter (0.22 µm, 33 mm polyethersulfone) to give a PS8-CRM conjugate solution.

| PS8-DBCO (mg) | CRM (mg) | Vol. after purification (mL) | Anthrone (mg/mL) | PS recovery (%) | BCA (CRM) (mg/mL) | CRM recovery (%) | PS8:CRM CJD ratio | Free PS (%) | SEC-MALS MDa |
|---|---|---|---|---|---|---|---|---|---|
| 3.77 | 2.51 | 7.13 | 0.372 | 70 | 0.237 | 67 | 1.57:1 | 11.53 | 1.2 |

| Mol eq of NaIO$_4$ | PS8 (mg) | Vol. after purification (mL) | Anthrone assay (µM) | % Oxidation (BCA) | % Oxidation (aldehyde assay) | PS yield (%) |
|---|---|---|---|---|---|---|
| 0.20 | 42 | 3.26 | 15724 | 8.96 | 2.28 | 84 |

2. DBCO Derivatization

Reaction Procedure:

PS8-OX (33.8 mg, 49.4 µmol) in 3.14 mL water was diluted with phosphate buffer (789 µL, 0.5 M pH 6.0), 1 mL of H$_2$O and DMSO (313 µL) to which was added DBCO-PEG$_4$-NH$_2$ (25 mg, 1 eq., in DMSO, 250 µL). After 10 minutes NaCNBH$_3$ (6.2 mg, 2 eq. by adding 132 µL from 9.43 mg in 200 µL H$_2$O) was added. The reaction mixture was stirred at 25° C. for two days in a thermostatted water bath followed by addition of phosphate buffer (0.5 mL of 200 mM pH=6). To this was added NaBH$_4$ (1 eq.). After stirring for 30 min the mixture was extraction with ethyl acetate (3×5 mL). The residual ethyl acetate was removed by bubbling with nitrogen gas and the mixture transferred to 100 kDa MWCO Amicon centrifuge filters. The DBCO derivative was purified by centrifugal dialysis using 6 exchanges with 20% EtOH and 3 exchanges with water (12 mL each) to give the PS8-DBCO derivative. To this solution (5.63 mL, 25 mg) was added a solution of sucrose and lyophilized.

Example 20: Preparation of Pneumococcal PS Serotype 9N Conjugates to an eCRM from Table 3

1. Oxidation

Purity of type 9N PS: 75%
Mol. Wt: 928.29 g mol$^{-1}$
Reaction Procedure:

The native polysaccharide PS9N (19.0 mg, 20.4 µmol) was dissolved in 9.49 mL of aqueous solution (7.12 mL water and 2.37 mL acetate buffer, 200 mM, pH 5.5). To this solution was added a sodium periodate solution (1.31 mg, 0.30 eq., 56 µL from a 23.65 mg in 1.0 mL aqueous solution). The mixture was stirred at 25° C. for 18 hours with monitoring by UV absorption at 222 nm for NaIO$_4$. The oxidized PS (PS9N-OX) was purified using Amicon centrifugal 30 kDa MWCO dialysis using 4 exchanges with water to give purified PS9N-OX solution.

| Mol eq of NaIO$_4$ | PS9N (mg) | Vol. after purification (mL) | Anthrone assay (µM) | % Oxidation (BCA) | % Oxidation (aldehyde assay) | PS9N-OX yield (%) |
|---|---|---|---|---|---|---|
| 0.30 | 19.0 | 1.643 | 9229 | 7.0 | N.D. | 71 |

2. DBCO Derivatization
Reaction Procedure:

PS9N-OX (12.6 mg, 13.6 µmol) in 1.643 mL water was diluted with phosphate buffer (0.945 mL, 200 mM pH 6.0

| PS8-OX (mg) | Vol. after purification (mL) | Anthrone assay (µM) | DBCO derivatization 309 nm Abs | DBCO derivatization (µM) | DBCO incorporation (%) | PS8-DBCO yield (%) | SEC-MALS kDa |
|---|---|---|---|---|---|---|---|
| 33.8 | 5.63 | 6492 | 0.813 × 3 | 232 | 3.57 | 74 | 392 |

3. Conjugation of PS8-DBCO Derivative with eCRM
PS8-DBCO: 3.77 mg (with 38 mg sucrose) lyophilized powder
% DBCO: 3.57%
CRM concentration: 5.966 mg/mL solution
PS:CRM (input ratio): 1.5:1 containing 94.5 mg sucrose) and DMSO (0.33 mL) to which was added DBCO-PEG$_4$-NH$_2$ (7.2 mg, 1 eq., in DMSO, 0.142 mL). After 10 minutes NaCNBH$_3$ (1.71 mg, 2 eq. by adding 47 µL from 7.36 mg in 200 µL H$_2$O) was added. The reaction mixture was stirred at 25° C. for two days in a thermostatted water bath followed by addition of phosphate buffer (0.4 mL of 200 mM pH=6). To this was added NaBH$_4$ (0.51 mg, 1 eq.) After stirring for 30 min the mixture was extraction with ethyl acetate (5×5 mL). The residual ethyl acetate was removed by bubbling with nitrogen gas and the mixture transferred to 30 kDa MWCO Amicon centrifuge filters. The DBCO derivative was purified by centrifugal dialysis using 3 exchanges with water (12 mL each) followed by 6 exchanges with 20% aqueous ethanol (12 mL each) and finally 3 exchanges with water (12 mL each) to give the PS9N-DBCO derivative. To this solution (2.388 mL, 9.05 mg) was added a solution of sucrose and lyophilized.

| PS9N-OX (mg) | Vol. after purification (mL) | Anthrone assay (μM) | DBCO derivatization 309 nm Abs | DBCO derivatization (μM) | DBCO incorporation (%) | PS9N-DBCO yield (%) | SEC-MALS kDa |
|---|---|---|---|---|---|---|---|
| 12.6 | 2.388 | 1485 | 0.782 | 72.8 | 4.9 | 78 | 474 |

3. Conjugation of PS9N-DBCO Derivative with eCRM
   PS9N-DBCO: 4.5 mg (with 45 mg sucrose) lyophilized powder
   % DBCO: 4.9%
   CRM concentration: 3.0 mg/mL solution
   PS:CRM (input ratio): 1.5:1
Reaction Procedure:
   The PS9N-DBCO conjugate was dissolved in 0.9% NaCl (1.30 mL) along with pH=7 phosphate buffer (96 μL of 0.5 M) and DMSO (0.24 mL) was added. Then azido-functionalized eCRM solution (0.60 mL) was added to provide a PS:CRM input mass ratio of 1.5:1 (w/w). The solution was very gently mixed by hand before gently mixing on an orbital shaker at room temperature (20° C.) for 18 hours. The click reaction was quenched by the addition of sodium azide solution (10 mg/mL, 100 μL). The CRM conjugate was transferred to two pre-washed dialysis tubes (SpectrumLab Float-A-Lyzer G2, 300K MWCO) and then dialyzed with 0.9% sodium chloride solution with 3 mL of pH=7 buffer added to it, for 24 hours (7 exchanges, 1000 ml each). The dialyzed solution was filtered through a Millex-GP syringe filter (0.22 μm, 33 mm polyethersulfone) to give a PS9N-CRM conjugate solution.

| PS9N-DBCO (mg) | CRM (mg) | Vol. after purification (mL) | Anthrone (mg/mL) | PS recovery (%) | BCA (CRM) (mg/mL) | CRM recovery (%) | PS9N:CRM CJD ratio | Free PS (%) | SEC-MALS MDa |
|---|---|---|---|---|---|---|---|---|---|
| 4.5 | 3.0 | 5.28 | 0.77 | 90 | 0.407 | 72 | 1.89:1 | 10.9 | 1.17 |

Example 21: Preparation of Pneumococcal PS Serotype 9V Conjugates to an eCRM from Table 3

1. Oxidation
   Purity of type 9V PS: 85% (Anthrone)
   Mol. wt: 704 kDa (Repeat Unit=971.8 g/mol)
Reaction Procedure:
   Polysaccharide type 9V (35.90 mg, 37.80 μmol) powder was dissolved in 17.95 mL of aqueous solution (12.565 mL of water and 5.385 mL of 0.2 M Acetate buffer, pH 5.5) in a 50-mL polystyrene sample tube with stirring bar. Once the PS was solubilized, 852 μL of NaIO$_4$ solution (2.83 mg, 13.23 μmol, 0.35 mol eq.) was added. The reaction tube was wrapped in foil and placed in a water bath at 24° C. The mixture was stirred at 24° C. After 18 hrs, the reaction mixture was dialyzed using three AMICON® Ultra-15 centrifugal filter devices (30 kDa MWCO; 15 mL) by 4 exchanges with HPLC-grade water (15 mL each) to render oxidized PS9V (PS9V-OX) solution.

| Mol eq of NaIO$_4$ | PS9V (mg) | Vol. after purification (mL) | Anthrone (μM) | % Oxidation (BCA) | % Oxidation (aldehyde assay) | PS9V-OX yield (%) |
|---|---|---|---|---|---|---|
| 0.35 | 35.90 | 4.55 | 5213.14 | 9.06 | 7.30 | 64 |

2. DBCO Derivatization
Reaction Procedure:
   To a solution of PS9V-OX (21.64 mg, 22.78 μmol, 4.27 mL), buffer solution (0.541 mL of 0.5 M phosphate buffer pH 6.0), DMSO (66 μL) and a solution of DBCO-PEG$_4$-NH$_2$ (11.9 mg in 475 μL DMSO; 22.78 μmol, 1 mol eq.) were added. The reaction mixture was stirred at 25° C. for 30 min, after which time 140 μL of a sodium cyanoborohydride solution (2.86 mg in 140 μL of water; 45.56 μmol, 2 mol eq.) was added. The reaction mixture was wrapped in aluminum foil and kept stirring in a water bath set to 25° C. for 2 days. The reaction was halted on the second day by the addition of 163 μL of a sodium borohydride solution (1.72 mg in 163 μL of water; 45.56 μmol, 2 mol eq.). After stirring for 30 minutes (when observable bubbling had ceased), the reaction mixture was extracted with ethyl acetate (2×10 mL) followed by dichloromethane (2×10 mL). The extract was bubbled with N$_2$ for 20 minutes to remove residual dichloromethane and was then transferred to 2 AMICON® Ultra-15 centrifugal filter devices (50 kDa MWCO; 15 mL). Dialysis was performed by conducting three exchanges with a 3% DMSO solution (15 mL each), three exchanges with a 20% ethanol solution (15 mL each), and two exchanges with HPLC-grade water (15 mL each) to give the PS9V-DBCO derivative. To this solution (4.40 mL, 12.144 mg) was added a solution of sucrose (121.44 mg 1.214 mL water). This combined solution was divided into three fractions (2×5 mg and 1×2.14 mg) and each lyophilized to give a fine, white powder. All fractions were stored at 4° C. until needed for the conjugation reaction.

| PS9V-OX (mg) | Vol. after purification (mL) | Anthrone (μM) | DBCO derivatization 309 nm Abs | DBCO derivatization (μM) | DBCO incorporation (%) | PS9V-DBCO yield (%) | SEC-MALS kDa |
|---|---|---|---|---|---|---|---|
| 21.6 | 4.40 | 949.00 | 0.341 | 28.00 | 3.0 | 56 | 267 |

3. Conjugation of PS9V-DBCO Derivative with eCRM
   PS9V-DBCO: 5 mg (with 50 mg of sucrose) white powder
   % DBCO: 3.0%
   CRM concentration: 6.009 mg/mL solution
   PS:CRM (input ratio): 1.5:1

Reaction Procedure:

PS9V-DBCO derivative (5.0 mg white powder with 50 mg of sucrose) was dissolved in 0.9% sodium chloride solution (0.881 mL), phosphate buffer pH 7 (0.067 mL, 0.5 M) and DMSO (0.167 mL). Azido-functionalized eCRM solution (0.555 mL solution) was added providing a PS9V:CRM mass ratio of 1.5:1 (w/w). The reaction mixture was gently mixed on an orbital shaker at room temperature (20° C.) for 18 hours then for a further 2 hours at 37° C. After the total reaction time, a volume of sodium azide was added to the conjugation mixture (0.33 mg; 5.15 µmol). The reaction mixture was then diluted with 0.9% sodium chloride solution (2.83 mL) and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 µm, 33 mm polyethersulfone) to give a PS-9V-CRM conjugate solution.

min, after which time 41 µL of a sodium cyanoborohydride solution (15.5 mg in 200 µL of water; 32.34 µmol, 20 equivalent) was added and kept stirring for 2 days at 25° C. The reaction mixture was diluted with phosphate buffer (500 µL of 200 mM solution, pH=6) before adding 62 µL solution of sodium borohydride (0.01 mg/µL, 10 equiv) in water. After stirring for 30 min, the reaction mixture was extracted with ethyl acetate (3×20 mL). The extract was transferred to an AMICON ultra centrifuge filter (30 kDa MWCO 6-12 mL) and then dialyzed using 6 exchanges with 20% ethanol in water (12 mL each) followed by 3 exchanges with water (12 mL each) to give the PS9V-DBCO derivative. To this solution (4.0 mL, 10.08 mg) was added a solution of sucrose (100 mg in 1 mL water). The combined solution were divided into two equal portions and each lyophilized to give three samples of white powder. Each sample contained 5.04 mg of PS9V-DBCO and 50 mg of sucrose for use in the next conjugation reaction.

| PS9V-DBCO (mg) | CRM (mg) | Vol. after purification (mL) | Anthrone (mg/mL) | PS recovery (%) | BCA (CRM) (mg/mL) | CRM recovery (%) | PS9V:CRM CJD ratio | Free PS (%) | SEC-MALS MDa |
|---|---|---|---|---|---|---|---|---|---|
| 5.0 | 3.33 | 1.67 | 0.86 | 87 | 0.450 | 68 | 1.9 | 14.2 | 0.94 |

Example 22: Preparation of Pneumococcal PS Serotype 9V Conjugates to an eCRM from Table 3

1. Oxidation

Purity of type 9V PS: 81% (Anthrone)

Mol. wt: 949.83

NaIO$_4$ solution in water (5.41 mg/mL)

Reaction Procedure:

Polysaccharide type 9V (21.15 mg corrected to 81%, 17.13 mg, 18.04 µmol) powder was dissolved in 10.57 mL of aqueous solution (7.4 mL of water and 3.17 mL of 0.2 M acetate buffer; pH=5.5). To this solution was added 214 µL of NaIO$_4$ solution (1.16 mg, 5.41 µmol, 0.3 eq). The mixture was stirred at 25° C. for 20 hours. The oxidized sample was purified via an AMICON ultra centrifuge filter (30 kDa MWCO 6-12 mL) using 6 exchanges (12 mL) of HPLC grade water to give oxidized PS9V (PS9V-OX) solution.

| Mol eq of NaIO$_4$ | PS9V (mg) | Vol. after purification (mL) | Anthrone (µM) | % Oxidation (BCA) | % Oxidation (aldehyde assay) | PS9V-OX yield (%) |
|---|---|---|---|---|---|---|
| 0.30 | 21.15 | 2.49 | 7352 | 7.4 | 9.6 | 82 |

2. DBCO Derivatization

Reaction Procedure:

To a solution of PS9V-OX (assume 10% oxidation level; 15.36 mg, 16.17 µmol, 2.20 mL water) was added buffer solution (1.4 mL of 200 mM phosphate buffer, pH=6.01), DMSO (500 µL) and a solution of DBCO-PEG$_4$-NH$_2$ (8.46 mg in 131 µL of DMSO; 16.17 µmol, 10 equivalent) all at 25° C. The reaction mixture was then stirred at 25° C. for 30

| PS9V-OX (mg) | Vol. after purification (mL) | Anthrone (µM) | DBCO derivatization 309 nm Abs | DBCO derivatization (µM) | DBCO incorporation (%) | PS9V-DBCO yield (%) | SEC-MALS kDa |
|---|---|---|---|---|---|---|---|
| 15.36 | 5.42 | 2642 | 0.216 × 4 | 90.32 | 3.42 | 89 | 324 |

3. Conjugation of PS9V-DBCO Derivative with eCRM

PS9V-DBCO: 5.04 mg (with 50 mg of sucrose) white powder

% DBCO: 3.42%

CRM concentration: 3.923 mg/mL solution

PS:CRM (input ratio): 1.11:1

Reaction Procedure:

Azido-functionalized eCRM solution (CRM in 0.1.156 mL solution) was added to the PS9V-DBCO derivative (5.04 mg white powder with 50 mg of sucrose) providing a PS9V:CRM mass ratio of 1.11:1 (w/w). The reaction mixture was gently mixed by hand before gently mixing on an orbital shaker at room temperature (20° C.) for 18 hours. The conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give the PS9V-CRM conjugate solution.

| PS9V-DBCO (mg) | CRM (mg) | Vol. after purification (mL) | Anthrone (mg/mL) | PS recovery (%) | BCA (CRM) (mg/mL) | CRM recovery (%) | PS9V: CRM CJD ratio | Free PS (%) | SEC-MALS MDa |
|---|---|---|---|---|---|---|---|---|---|
| 5.04 | 4.53 | 5.73 | 0.61 | 69 | 0.298 | 39 | 2.05:1 | 14.64 | 1.26 |

Example 23: Preparation of Pneumococcal PS Serotype 10A Conjugates to an eCRM from Table 3

1. CDAP Activation and DBCO Crosslink

Purity PS 10A: 77% (Anthrone)

Mol. wt: 1227 g mol$^{-1}$ (repeat unit)

Reaction Procedure:

The native polysaccharide type 10A (PS10A) (18.7 mg, 15.2 μmol) was dissolved in water (7.9 mL) to which was added CDAP (0.8 eq., 100 mg/mL in acetonitrile, 30 μL). The reaction mixture was stirred at room temperature (RT) for 30 s. At this time, sodium hydroxide solution (0.2 M, 200 μL) was added to achieve pH 9.5 and the reaction mixture was stirred for 150 s. DMSO (1.2 mL) was then added, followed by DBCO-PEG$_4$-NH$_2$ (0.5 eq., 32.0 μmol/mL in DMSO, 238 μL) and stirred at RT overnight. The DBCO-derivatized PS 10A (PS 10A-DBCO) was purified by solvent extraction and by centrifugal dialysis (Amicon 30 kDa MWCO) using 3 exchanges of 3% (v/v) DMSO, 2 exchanges with 0.9% (v/v) brine and 3 exchanges with water. After analysis by UV absorbance spectroscopy, anthrone assay and SEC, this solution (3.18 mL, 13.5 mg) was diluted with a sucrose solution (10-fold mass content, 100 mg/mL) and lyophilized to a white powder.

| PS10A (mg) | Vol. after purification (mL) | Anthrone assay (μM) | DBCO derivatization 309 nm Abs | DBCO derivatization (μM) | DBCO incorporation (%) | PS10A-DBCO yield (%) | SEC-MALS kDa |
|---|---|---|---|---|---|---|---|
| 18.7 | 3.18 | 1150.41 | 1.081 | 101.26 | 8.8 | 72 | 579 |

2. Conjugation of PS10A-DBCO Derivative with eCRM

PS10A-DBCO: 5.00 mg (with 50.0 mg sucrose) lyophilized powder

% DBCO: 8.8%

CRM: 5.0 mg/mL in PBS buffer

PS:CRM (input mass ratio): 1.75:1

Reaction Procedure:

Lyophilized PS10A-DBCO was dissolved brine (0.9% (w/v), 3.759 ml), phosphate buffer (0.5 M, pH 7.0, 200 μL) and DMSO (500 μL) to which was added eCRM solution (0.541 mL) to provide a PS10A:CRM input mass ratio of 1.75:1.00 (w/w). The solution was very gently mixed by hand before gently mixing on an orbital shaker at room temperature (20° C.) for 17 hours. The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was sterile-filtered through a Millex-GP syringe filter (0.22 μm, 33 mm polyethersulfone) to give a PS10A-CRM conjugate solution.

| PS10A-DBCO (mg) | CRM (mg) | Vol. after purification (mL) | Anthrone (mg/mL) | PS recovery (%) | BCA (CRM) (mg/mL) | PS10A: CRM CJF ratio | Free PS (%) | SEC-MALS MDa |
|---|---|---|---|---|---|---|---|---|
| 5.00 | 2.86 | 6.86 | 0.678 | 93 | 0.311 | 2.18:1.0 | 5.64 | 1.048 |

Example 24: Preparation of Pneumococcal PS Serotype 11A Conjugates to an eCRM from Table 3

1. Hydrolysis

Purity of type 11A PS: 69% (anthrone)

Mol. wt: 908.7 g mol$^{-1}$

Reaction Procedure:

The native polysaccharide PS11A (35.0 mg) was dissolved in 17.5 mL of aqueous solution (15.75 mL water and 1.75 mL acetic acid, 2M). The mixture was heated at 80° C. for 1 hour after which time sodium hydroxide solution was added to pH 5.5 (3.2 mL, 1M) after cooling to ambient temperature. The hydrolyzed PS was purified using Amicon centrifugal 30 k Da MWCO dialysis using at least 6 exchanges with water to give purified PS3 solution which was then lyophilized as one aliquot.

| PS11A (mg) | Water (mL) | AcOH, 2M (mL) | Anthrone assay (μM) | PS yield (%) | MALS (kDa) |
|---|---|---|---|---|---|
| 35.0 | 15.75 | 1.75 | 6294.58 | 85 | 461 |

2. Oxidation

Reaction Procedure:

To the hydrolyzed polysaccharide solution (5.027 mL, 28.75 mg, 31.6 μmoles) was further added water (5.75 mL) and acetate buffer (0.2M, pH 5.5, 3.6 mL). To this solution was added 135 μL of sodium periodate solution dropwise (1.35 mg, 6.32 μmol, 0.20 eq.). The mixture was stirred at 25° C. for 18 hours. The oxidized PS was purified using Amicon centrifugal 100 k Da MWCO dialysis using at least 6 exchanges with water to give purified PS11A-OX solution.

| Mol eq of NaIO$_4$ | PS11A (mg) | Vol. after purification (mL) | Anthrone assay (μM) | % Oxidation (BCA) | % Oxidation (aldehyde assay) | PS11A-OX yield (%) |
|---|---|---|---|---|---|---|
| 0.20 | 28.75 | 2.42 | 9525.39 | 10.2 | 4.82 | 73 |

3. DBCO Derivatization

Reaction Procedure:

PS11A-OX (22.0 mg, 24.2 μmol, 2.235 mL) was added to phosphate buffer (1.37 mL, 200 mM, pH 6.0) to which was added DBCO-PEG$_4$-NH$_2$ (1.0 eq., 523 g mol$^{-1}$ in DMSO, 100 mg/mL, 127 μL) and an additional quantity of DMSO (560 μL). The reaction mixture was stirred at 25° C. for 25 mins. prior to the addition of a solution of sodium cyanoborohydride (2 eq., 44.5 mg/mL, 68 μL) and stirred for two days. The reaction mixture was extracted with ethyl acetate (3×20 mL) and filtered through a 0.45 μm syringe filter. The DBCO derivative was purified by centrifugal dialysis units (Amicon 100 kDa MWCO) using 7 exchanges with 20% ethanol in water followed by 3 exchanges with water (12 mL each) to give the PS11A-DBCO derivative. To this solution (2.535 mL, 15.00 mg) was added a solution of sucrose (150 mg in 1.5 mL water). The combined solution was divided into three equal portions and each lyophilized to give three samples of white powder. Each sample contained 5.00 mg of PS11A-DBCO and 50 mg of sucrose for use in the next conjugation reaction.

| hydrolyzed PS11A (mg) | Vol. after purification (mL) | Anthrone assay (μM) | DBCO derivatization 309 nm Abs | DBCO derivatization (μM) | DBCO incorporation (%) | PS11A-DBCO yield (%) | SEC-MALS kDa |
|---|---|---|---|---|---|---|---|
| 22.0 | 3.44 | 1628.30 | 1.000 × 4 | 93.93 | 5.77 | 93 | 543 |

4. Conjugation of PS11A-DBCO Derivative with eCRM

PS11A-DBCO: 5.0 mg (with 50 mg sucrose) lyophilized powder
% DBCO: 5.77%
CRM concentration: 5.42 mg/mL solution
PS:CRM (input ratio): 1.5:1

Reaction Procedure:

PS11A-DBCO was dissolved in 0.9% sodium chloride solution (7.656 mL, 0.22 μm filtered), phosphate buffer (pH 7.0, 0.5M, 0.385 mL) and DMSO (0.962 mL). Azido-functionalized eCRM solution (5.42 mg/mL, 0.617 mL) was added dropwise to provide a PS11A:CRM input mass ratio of 1.5:1 (w/w). The solution was very gently mixed by hand before gently mixing on an orbital shaker at room temperature (20° C.) for 17 hours. The click reaction was quenched by the addition of sodium azide solution (10 mg/mL, 50 μL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 μm, 33 mm polyethersulfone) to give a PS11A-CRM conjugate solution.

| PS11A-DBCO (mg) | CRM (mg) | Vol. after purification (mL) | Anthrone (mg/mL) | PS recovery (%) | BCA (CRM) (mg/mL) | CRM recovery (%) | PS:CRM CJF ratio | Free PS (%) | SEC-MALS MDa |
|---|---|---|---|---|---|---|---|---|---|
| 5.0 | 3.33 | 9.14 | 0.454 | 83 | 0.271 | 74 | 1.68:1 | 0.92 | 0.987 |

Example 25: Preparation of Pneumococcal PS Serotype 12F Conjugates to an eCRM from Table 3

1. Oxidation

Purity of type 12F PS: 82% (anthrone)
Mol. wt: 1094 g mol$^{-1}$

Reaction Procedure:

Polysaccharide type 12F (21.8 mg, 20 μmol) powder was dissolved in 10.9 mL of aqueous solution (8.175 mL of water and 2.725 mL of 0.2 M acetate buffer, pH 5.5) in a 50-mL polystyrene sample tube with stirring bar. Once the PS was solubilized, 160 μL of NaIO$_4$ solution (0.64 mg, 3 μmol, 0.15 mol. eq.) was added. The reaction tube was wrapped in foil and placed in a water bath at 25° C. The mixture was stirred at 25° C. After 18 hrs, the reaction mixture was dialyzed using two AMICON® Ultra-15 centrifugal filter devices (30 kDa MWCO; 15 mL) by 6 exchanges with HPLC-grade water (15 mL each) to render oxidized PS-12F (PS12F-OX) solution.

| Mol eq of NaIO$_4$ | PS12F (mg) | Vol. after purification (mL) | Anthrone assay (μM) | % Oxidation (BCA) | % Oxidation (aldehyde assay) | PS12F-OX yield (%) |
|---|---|---|---|---|---|---|
| 0.15 | 21.8 | 3.06 | 4462.11 | 37 | 5.62 | 69 |

2. DBCO Derivatization

Reaction Procedure:

PS12F-OX (13.1 mg, 12 μmol, 2.68 mL) was added to phosphate buffer (1.00 mL, 200 mM, pH 6.0) to which was added DBCO-PEG$_4$-NH$_2$ (1.0 eq., 523 g mol$^{-1}$ in DMSO, 33 mg/mL, 199 μL) and an additional quantity of DMSO (500 μL). The reaction mixture was stirred at 25° C. for 25 mins. prior to the addition of a solution of sodium cyanoborohydride (2 eq., 52.5 mg/mL, 29 μL) and stirred for two days. The reaction mixture was extracted with ethyl acetate (3×20 mL) and bubbled free of solvent. The DBCO derivative was purified by centrifugal dialysis units twice (Amicon 30 kDa MWCO) using 6 exchanges with 20% ethanol in water followed by 3 exchanges with water each time (12 mL each) to give the PS12F-DBCO derivative. To this solution (2.2 mL, 10.45 mg) was added a solution of sucrose (104.5 mg in 1.05 mL water). The combined solution was divided into two equal portions and each lyophilized to give three samples of white powder. Each sample contained 5.0 mg of PS12F-DBCO and 50 mg of sucrose for use in the conjugation reaction.

| PS12F-OX (mg) | Vol. after purification (mL) | Anthrone assay (μM) | DBCO derivatization 309 nm Abs | DBCO derivatization (μM) | DBCO incorporation (%) | PS12F-DBCO yield (%) | SEC-MALS kDa |
|---|---|---|---|---|---|---|---|
| 13.1 | 2.20 | 1447.92 | 0.302 × 3 | 28.2 | 2.0 | 80 | 544 |

3. Conjugation of PS12F-DBCO Derivative with eCRM

PS12F-DBCO: 5.0 mg (with 50 mg sucrose) lyophilized powder
% DBCO: 2.0%
CRM concentration: 5.29 mg/mL solution
PS:CRM (input ratio): 1.5:1

Reaction Procedure:

PS12F-DBCO was dissolved in 0.9% sodium chloride solution (6.542 mL, 0.22 μm filtered), phosphate buffer (pH 7.0, 0.5M, 0.334 mL) and DMSO (0.834 mL). Azido-functionalized eCRM solution (5.29 mg/mL, 0.630 mL) was added dropwise to provide a PS12F:CRM input ratio of 1.5:1 (w/w). The solution was very gently mixed by hand before gently mixing on an orbital shaker at room temperature (20° C.) for 17 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a sterile PS12F-CRM conjugate solution.

| PS12F-DBCO (mg) | CRM (mg) | Vol. after purification (mL) | Anthrone (mg/mL) | PS recovery (%) | BCA (CRM) (mg/mL) | CRM recovery (%) | PS12F:CRM CJF ratio | Free PS (%) | SEC-MALS MDa |
|---|---|---|---|---|---|---|---|---|---|
| 5.0 | 3.33 | 8.06 | 0.547 | 88 | 0.200 | 48 | 2.73:1 | 13.3 | 0.931 |

Example 26: Preparation of Pneumococcal PS Serotype 14 Conjugates to an eCRM from Table 3

1. Oxidation

Purity of type 14 PS: 91% (Anthrone)
Mol. wt: 689.25
$NaIO_4$ solution in water (7.8 mg/mL)
Reaction Procedure:

Polysaccharide type 14 (PS14; 28.3 mg corrected to 80%, 25.75 mg, 37.36 µmol) powder was dissolved in 14 mL of aqueous solution (10 mL of water and 4 mL of 0.2 M acetate buffer; pH=5.5). To this solution was added 110 µL of $NaIO_4$ solution (0.86 mg, 4.05 µmol, 0.13 eq). The mixture was stirred at 25° C. for 3 hours, after which the time, the oxidized sample was purified using AMICON ultra centrifuge (30 kDa MWCO 6-12 mL) 6 exchanges (12 mL) of HPLC grade water to give oxidized PS14 (PS14-OX) solution.

| Mol eq of $NaIO_4$ | PS14 (mg) | Vol. after purification (mL) | Anthrone (µM) | % Oxidation (BCA) | % Oxidation (aldehyde assay) | PS14-OX yield (%) |
|---|---|---|---|---|---|---|
| 0.13 | 28.3 | 3.042 | 10189 | 6.59 | 3.67 | 83 |

2. DBCO Derivatization

Reaction Procedure:

To a solution of PS14-OX (assume 10% oxidation level; 20.5 mg, 29.74 µmol, 2.92 mL water) was added buffer solution (1.3 mL of 200 mM phosphate buffer, pH=6.8), DMSO (550 µL) and a solution of $DBCO-PEG_4-NH_2$ (11.68 mg in 150 µL of DMSO; 22.3 µmol, 0.75 equivalent) all at 25° C. The reaction mixture was then stirred at 25° C. for 30 min, after which time 70 µL of a sodium cyanoborohydride solution (6.39 mg in 120 µL of water; 59.48 µmol, 20 equivalents) was added and kept stirring for 2 days at 25° C. The reaction mixture was diluted with phosphate buffer (500 µL of 200 mM solution, pH=6) before adding 100 µL solution of sodium borohydride (1.13 mg 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 7 exchanges with 20% ethanol in water (12 mL each) followed by 3 exchanges with water (12 mL each) to give the PS14-DBCO derivative. To this solution (3.78 mL, 17.7 mg) was added a solution of sucrose (177 mg in 1.17 mL water). The combined solution were divided into three equal portions and each lyophilized to give three samples of white powder. Each sample contained 5.9 mg of PS14-DBCO and 59 mg of sucrose for use in the next conjugation reaction.

| PS14-OX (mg) | Vol. after purification (mL) | Anthrone (µM) | DBCO derivatization 309 nm Abs | DBCO derivatization (µM) | DBCO incorporation (%) | PS14-DBCO yield (%) | SEC-MALS kDa |
|---|---|---|---|---|---|---|---|
| 20.5 | 3.91 | 1694.06 | 0.622 × 4 | 238 | 3.51 | 91 | 463 |

3. Conjugation of PS 14-DBCO Derivative with eCRM

PS 6B-DBCO: 5.9 mg (with 59 mg of sucrose) white powder

% DBCO: 3.5%

CRM concentration: 5.06 mg/mL solution

PS:CRM (input ratio): 1.5:1

Reaction Procedure:

Azido-functionalized eCRM solution (0.779 mL) was added to 14 DBCO derivative (5.9 mg white powder with 59 mg of sucrose) providing a PS14:CRM mass ratio of 1.5:1 (w/w). The reaction mixture was gently mixed by hand before gently mixing on an orbital shaker at room temperature (20° C.) for 18 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 48 hours (8 exchanges, 800 ml each). The dialyzed solution was filtered through a Millex-GP (0.22 µm, 33 mm polyethersulfone) to give a 14 PS-CRM conjugate solution.

| PS14-DBCO (mg) | CRM (mg) | Vol. after purification (mL) | Anthrone (mg/mL) | PS recovery (%) | BCA (CRM) (mg/mL) | CRM recovery (%) | PS14:CRM CJD ratio | Free PS (%) | SEC-MALS MDa |
|---|---|---|---|---|---|---|---|---|---|
| 5.9 | 3.94 | 4.27 | 0.648 | 93 | 0.283 | 61 | 2.29:1 | 5.29 | 0.925 |

Example 27: Preparation of Pneumococcal PS Serotype 14 Conjugates to an eCRM from Table 3

1. Oxidation

Purity of type 14 PS: 91% (Anthrone)
Mol. wt: 689.25
NaIO4 solution in water (10.19 mg/mL)
Reaction Procedure:
Polysaccharide type 14 (PS14; 23.5 mg corrected to 80%, 21.38 mg, 31.02 µmol) powder was dissolved in 11.75 mL of aqueous solution (8.2 mL of water and 3.55 mL of 0.2 M acetate buffer; pH=5.5). To this solution was added 97 µL of NaIO$_4$ solution (0.95 mg, 4.03 µmol, 0.13 eq). The mixture was stirred at 25° C. for 18 hours, after which the time, the oxidized sample was purified using AMICON ultra centrifuge (30 kDa MWCO 6-12 mL) 6 exchanges (12 mL) of HPLC grade water to give oxidized PS14 (PS14-OX) solution.

| Mol eq of NaIO$_4$ | PS14 (mg) | Vol. after purification (mL) | Anthrone (µM) | % Oxidation (BCA) | % Oxidation (aldehyde assay) | PS14-OX yield (%) | Note |
|---|---|---|---|---|---|---|---|
| 0.13 | 23.5 | 3.76 | 5994 | 6.60 | 2.28 | 73 | N/A |

2. DBCO Derivatization

Reaction Procedure:
To a solution of PS14-OX (assume 10% oxidation level; 14.3 mg, 20.75 µmol, 3.46 mL water) was added buffer solution (1.3 mL of 200 mM phosphate buffer, pH=6.8), DMSO (637 µL) and a solution of DBCO-PEG$_4$-NH$_2$ (10.86 mg in 263 µL of DMSO; 20.75 µmol, 10 equivalent) all at 25° C. The reaction mixture was then stirred at 25° C. for 30 min, after which time 51 µL of a sodium cyanoborohydride solution (10.2 mg in 200 µL of water; 41.50 µmol, 20 equivalent) was added and kept stirring for 2 days at 25° C. The reaction mixture was diluted with phosphate buffer (500 µL of 200 mM solution, pH=6) before adding 78 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water (12 mL each) followed by 3 exchanges with water (12 mL each) to give the PS14-DBCO derivative. To this solution (4.12 mL, 12.24 mg) was added a solution of sucrose (12 mg in 1 mL water). The combined solution were divided into three equal portions and each lyophilized to give three samples of white powder. Each sample contained 6.12 mg of PS14-DBCO and 6 mg of sucrose for use in the next conjugation reaction.

| PS14-OX (mg) | Vol. after purification (mL) | Anthrone (µM) | DBCO derivatization 309 nm Abs | DBCO derivatization (µM) | DBCO incorporation (%) | PS14-DBCO yield (%) |
|---|---|---|---|---|---|---|
| 14.3 | 4.43 | 4307 | 0.621 × 3 | 190.14 | 4.42 | 92 |

3. Conjugation of PS14-DBCO Derivative with eCRM

PS 14B-DBCO: 6.12 mg (with 62 mg of sucrose) white powder
% DBCO: 4.42%
CRM concentration: 2.617 mg/mL solution
PS:CRM (input ratio): 1.8:1

Reaction Procedure:

Azido-functionalized eCRM solution (1.3 mL) was added to PS14-DBCO derivative (6.12 mg white powder with 62 mg of sucrose) providing a PS14:CRM mass ratio of 1.8:1 (w/w). The reaction mixture was gently mixed by hand before gently mixing on an orbital shaker at room temperature (20° C.) for 17 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution (1.5 mL) was filtered through a Millex-GP (0.22 µm, 33 mm polyethersulfone) to give a PS14-CRM conjugate solution.

| PS14-DBCO (mg) | CRM (mg) | Vol. after purification (mL) | Anthrone (mg/mL) | PS recovery (%) | BCA (CRM) (mg/mL) | CRM recovery (%) | PS14:CRM ratio | Free PS (%) | SEC-MALS MDa | Lot# |
|---|---|---|---|---|---|---|---|---|---|---|
| 6.12 | 3.4 | 4.85 | 1.24 | 98 | 0.472 | 67 | 2.63:1 | 3.48 | 2.5 | CJD |
| 6.12 | 3.4 | 2.31 | 0.24 |  | 0.094 |  | 2.55:1 | N/A | 1.56 | CJF |

Example 28: Preparation of Pneumococcal PS Serotype 15B Conjugates to an eCRM from Table 3

1. Oxidation

Purity of type 15B PS: 71% (Anthrone)

Mol. wt: 1185 kDa (Repeat Unit=1069.80 g/mol)

Reaction Procedure:

Polysaccharide type 15B (PS15B; 14.6 mg, 13.65 µmol) powder was dissolved in 7.30 mL of aqueous solution (5.1 mL of water and 2.2 mL of 0.2 M Acetate buffer, pH 5.5) in a 50-mL polystyrene sample tube with stirring bar. Once the PS was solubilized, 160 µL of $NaIO_4$ solution (0.59 mg, 2.75 µmol, 0.20 mol eq.) was added. The reaction tube was wrapped in foil and placed in a water bath to stir at 24° C. After 3.5 hours, the reaction mixture was dialyzed using one AMICON® Ultra-15 centrifugal filter device (30 kDa MWCO; 15 mL) by 6 exchanges with HPLC-grade water (15 mL each) to render oxidized PS15B (PS15-OX) solution.

| Mol eq of $NaIO_4$ | PS15B (mg) | Vol. after purification (mL) | Anthrone (µM) | % Oxidation (BCA) | % Oxidation (Aldehyde assay) | PS15-OX yield (%) |
|---|---|---|---|---|---|---|
| 0.20 | 14.6 | 1.521 | 5560.34 | 27.01 | 9.52 | 62 |

2. DBCO Derivatization

Reaction Procedure:

To a solution of PS15B-OX (7.56 mg, 7.07 µmol, 1.271 mL), buffer solution (0.640 mL of 0.5 M phosphate buffer pH 6.0), DMSO (0.063 mL), and a solution of DBCO-PEG$_4$-NH$_2$ (17 mg in 221 µL DMSO; 7.07 µmol, 1 mol eq.) were added. The reaction mixture was stirred at 25° C. for 30 min, after which time 350 µL of a sodium cyanoborohydride solution (0.90 mg in 350 µL of water, 2 mol eq.) was added. The reaction mixture was wrapped in aluminum foil and kept stirring in a water bath set to 25° C. for 2 days. The reaction was halted on the second day by the addition of 163 µL of a sodium borohydride solution (0.27 mg; 7.07 µmol, 2 mol eq.). After stirring for 30 minutes, the reaction mixture was extracted with dichloromethane (3×15 mL). The extract was bubbled with $N_2$ for 20 minutes to remove residual dichloromethane and was then transferred to one AMICON® Ultra-15 centrifugal filter device (30 kDa MWCO; 15 mL). Dialysis was performed by conducting three exchanges with a 3% DMSO solution (15 mL each), three exchanges with a 20% ethanol solution (15 mL), and three exchanges with HPLC-grade water (15 mL each) to give the PS15B-DBCO derivative. To this solution (1.982 mL, 6.86 mg) was added a solution of sucrose (68.6 mg in 0.686 mL water). This combined solution was divided into two fractions and each lyophilized to give a fine, white powder. All fractions were stored at 4° C. after lyophilized to dryness until needed for the conjugation reaction.

| PS15B-OX (mg) | Vol. after purification (mL) | Anthrone (µM) | DBCO derivatization 309 nm Abs | DBCO derivatization (µM) | DBCO incorporation (%) | PS15B-DBCO yield (%) | SEC-MALS kDa |
|---|---|---|---|---|---|---|---|
| 7.56 | 1.982 | 1122.13 | 0.732 | 66.71 | 5.9 | 91 | n/a |

3. Conjugation of PS15B-DBCO Derivative with eCRM

PS15B-DBCO: 3.85 mg (with 38.5 mg of sucrose) white powder

% DBCO: 5.9%

CRM concentration: 6.009 mg/mL solution

PS:CRM (input ratio): 1.5:1

Reaction Procedure:

PS15B-DBCO derivative (3.85 mg white powder with 38.5 mg of sucrose) was dissolved in 0.9% sodium chloride solution (4.302 mL), phosphate buffer pH 7 (0.220 mL, 0.5 M) and DMSO (0.550 mL). Azido-functionalized eCRM solution (0.467 mL solution) was added providing a PS15B:CRM mass ratio of 1.5:1 (w/w). The reaction mixture was gently mixed on an orbital shaker at room temperature (20° C.) for 18 hours then for a further 2 hours at 37° C. The conjugation reaction was terminated with the addition of sodium azide (0.23 mg; 3.60 µmol). The reaction mixture was then diluted with 0.9% sodium chloride solution to a final volume of 7 mL and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 µm, 33 mm polyethersulfone) to give the PS15B-CRM conjugate solution.

| PS15B-DBCO (mg) | CRM (mg) | Vol. after purification (mL) | Anthrone (mg/mL) | PS recovery (%) | BCA (CRM) (mg/mL) | CRM recovery (%) | PS15:CRM CJD ratio | Free PS (%) | SEC-MALS MDa |
|---|---|---|---|---|---|---|---|---|---|
| 3.85 | 2.57 | 7.52 | 0.515 | 100 | 0.289 | 85 | 1.8:1 | 7.68 | 2.40 |

Example 29: Preparation of Pneumococcal PS Serotype 17F Conjugates to an eCRM from Table 3

1. Oxidation

Purity of type 17F PS: 84% (Anthrone)
Mol. wt: 1274 kDa (Repeat Unit=1203.00 g/mol)
Reaction Procedure:

Polysaccharide type 17F (PS17F; 28.50 mg, 23.69 μmol) powder was dissolved in 14.25 mL of aqueous solution (9.925 mL of water and 4.275 mL of 0.2 M Acetate buffer, pH 5.5) in a 50-mL polystyrene sample tube with stirring bar. Once the PS was solubilized, 53.8 μL of NaIO₄ solution (0.65 mg, 3.03 μmol, 0.128 mol eq.) was added. The reaction tube was wrapped in foil and placed in a water bath to stir at 24° C. After 1 hour, the reaction mixture was dialyzed using two AMICON® Ultra-15 centrifugal filter device (30 kDa MWCO; 15 mL) by 5 exchanges with HPLC-grade water (15 mL each) to render oxidized PS17F (PS17F-OX) solution.

| Mol eq of NaIO₄ | PS17F (mg) | Vol. after purification (mL) | Anthrone (μM) | % Oxidation (BCA) | % Oxidation (Aldehyde assay) | PS15-OX yield (%) |
|---|---|---|---|---|---|---|
| 0.128 | 28.50 | 2.63 | 7378.81 | 12.60 | 6.81 | 82 |

2. DBCO Derivatization
Reaction Procedure:

To a solution of PS17F-OX (22.0 mg, 18.29 μmol, 2.48 mL), buffer solution (1.31 mL of 0.5 M phosphate buffer pH 6.0), and a solution of DBCO-PEG₄-NH₂ (9.58 mg in 95.8 μL DMSO; 18.29 μmol, 1 mol eq.) were added. The reaction mixture was stirred at 25° C. for 30 min, after which time sodium cyanoborohydride solution (2.30 mg in 200 μL of water; 36.60 μmol, 2 mol eq.) was added. The reaction mixture was wrapped in aluminum foil and kept stirring in a water bath set to 25° C. for 2 days. The reaction was halted on the second day by the addition of sodium borohydride solution (0.48 mg; 18.29 μmol, 1 mol eq.). After stirring for 30 minutes, the reaction mixture was extracted with dichloromethane (3×15 mL). The extract was bubbled with N₂ for 20 minutes to remove residual dichloromethane and was then transferred to one AMICON® Ultra-15 centrifugal filter device (30 kDa MWCO; 15 mL). Dialysis was performed by conducting five exchanges with a 20% ethanol solution (15 mL) and three exchanges with HPLC-grade water (15 mL each) to give the PS17F-DBCO derivative. To this solution (3.27 mL, 11.58 mg) was added a solution of sucrose (115.8 mg in 1.158 mL water). This combined solution was divided into three fractions (2×5 mg; 1×1.58 mg) and each lyophilized to give a fine, white powder. All fractions were stored at 4° C. after lyophilized to dryness until needed for the conjugation reaction.

| PS17F-OX (mg) | Vol. after purification (mL) | Anthrone (μM) | DBCO derivatization 309 nm Abs | DBCO derivatization (μM) | DBCO incorporation (%) | PS17F-DBCO yield (%) | SEC-MALS kDa |
|---|---|---|---|---|---|---|---|
| 22 | 4.40 | 978.16 | 0.350 | 30.45 | 3.1 | 53 | 209 |

3. Conjugation of PS17F-DBCO Derivative with eCRM
PS17F-DBCO: 5 mg (with 50 mg of sucrose) white powder
% DBCO: 3.1%
CRM concentration: 5.996 mg/mL solution
PS:CRM (input ratio): 1.5:1
Reaction Procedure:

PS17F-DBCO derivative (5 mg white powder with 50 mg of sucrose) was dissolved in 0.9% sodium chloride solution (3.742 mL), phosphate buffer pH 7 (0.200 mL, 0.5 M) and DMSO (0.500 mL). Azido-functionalized eCRM solution (0.558 mL solution) was added providing a PS17F:CRM mass ratio of 1.5:1 (w/w). The reaction mixture was gently mixed on an orbital shaker at room temperature (20° C.) for 19 hours. The conjugation reaction was terminated with the addition of sodium azide (0.27 mg; 4.16 μmol; 1 mol eq.). The reaction mixture was then diluted with 0.9% sodium chloride solution to a final volume of 8 mL and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 μm, 33 mm polyethersulfone) to give the PS17F-CRM conjugate solution.

| PS17F-DBCO (mg) | CRM (mg) | Vol. after purification (mL) | Anthrone (mg/mL) | PS recovery (%) | BCA (CRM) (mg/mL) | CRM recovery (%) | PS17F:CRM CJD ratio | Free PS (%) | SEC-MALS MDa |
|---|---|---|---|---|---|---|---|---|---|
| 5 | 3.33 | 6.71 | 461.30 | 99 | 0.349 | 70 | 1.59:1 | 9.41 | 1.072 |

Example 30: Preparation of Pneumococcal PS Serotype 18C Conjugates to an eCRM from Table 3

1. Oxidation

Purity of type 18C PS: 72% (Anthrone)
Mol. wt: 970.76
NaIO$_4$ solution in water (5.41 mg/mL)
Reaction Procedure:

Polysaccharide type 18C (PS18C; 61 mg, 62.84 μmol) powder was dissolved in 30.5 mL of aqueous solution (27.45 mL of water and 3.05 mL of 2 M Acetic acid). The solution was then heated at 95° C. for 40 min and then cooled, at which time; NaOH solution (1 N, 5.2 mL) was added to adjust pH to 6.0. The reaction mixture was dialyzed using AMICON ultra centrifuge (100 kDa MWCO 6-12 mL) by 3 exchanges with HPLC grade water (12 mL each). The supernatant was transferred to a 50 mL of falcon tube with 12.4 mL of water. To this solution was added 5.15 mL water and 5.8 mL of 200 mM acetate buffer (pH 5.35) and 153 μL of NaIO$_4$ solution (1.53 mg, 7.175 μmol, 0.15 eq). The mixture was stirred at 25° C. for 3 hours, after which the time, the oxidized sample was purified using AMICON ultra centrifuge (100 kDa MWCO 6-12 mL) 6 exchanges (12 mL) of HPLC grade water to give oxidized PS18C (PS18C-OX) solution.

| Mol eq of NaIO$_4$ | PS18C (mg) | Vol. after purification (mL) | Anthrone (μM) | % Oxidation (BCA) | % Oxidation (aldehyde assay) | PS18C-OX yield (%) |
|---|---|---|---|---|---|---|
| 0.15 | 61 | 5.29 | 6480.2 | 4.84 | 7.1 | 55 |

2. DBCO Derivatization

Reaction Procedure:

To a solution of PS18C-OX (assume 10% oxidation level; 10.0 mg, 10.3 μmol, 1.55 mL water) was added buffer solution (0.211 mL of 200 mM phosphate buffer, pH=6.74), DMSO (141 μL) and a solution of DBCO-PEG$_4$-NH$_2$ (5.4 mg in 54 μL of DMSO; 16.17 μmol, 10 equivalent) all at 25° C. The reaction mixture was then stirred at 25° C. for 30 min, after which time 130 μL of a sodium cyanoborohydride solution (1.3 mg in 130 μL of water; 20.6 μmol, 20 equivalents) was added and kept stirring for 2 days at 37° C. The reaction mixture was diluted with phosphate buffer (500 μL of 200 mM solution, pH=6) before adding 80 μL solution of sodium borohydride (0.01 mg/μL, 10 equiv) in water. After stirring for 30 min, the reaction mixture was extracted with dichloromethane (2×10 mL) followed by ethyl acetate (10 mL). The extract was transferred to an AMICON ultra centrifuge filter (100 kDa MWCO 6-12 mL) and then dialyzed using 4 exchanges with 20% ethanol in water (12 mL each) followed by 3 exchanges with water (12 mL each) to give the PS18C-DBCO derivative. To this solution (1.31 mL, 7.0 mg) was added a solution of sucrose (70 mg in 0.7 mL water). The combined solution was divided into two equal portions and each lyophilized to give two samples of white powder. Each sample contained 3.5 mg of PS18C-DBCO and 35 mg of sucrose for use in the next conjugation reaction.

| PS18C-OX (mg) | Vol. after purification (mL) | Anthrone (μM) | DBCO derivatization 309 nm Abs | DBCO derivatization (μM) | DBCO incorporation (%) | PS18C-DBCO yield (%) | SEC-MALS kDa |
|---|---|---|---|---|---|---|---|
| 10.0 | 1.52 | 5469.4 | 1.031 × 3 | 291 | 5.32 | 81 | 203 |

3. Conjugation of PS18C-DBCO Derivative with eCRM

PS18C-DBCO: 3.5 mg (with 35 mg of sucrose) white powder
% DBCO: 5.32%
CRM concentration: 2.76 mg/mL solution
PS:CRM (input ratio): 1.5:1

Reaction Procedure:

The PS18C-DBCO derivative (3.5 mg white powder with 35 mg of sucrose) was dissolved in 0.9% sodium chloride solution (0.661 mL), phosphate buffer pH 7 (0.07 mL, 0.5 M) and DMSO (0.175 mL). Azido-functionalized eCRM solution (0.844 mL solution) was added providing a PS18C:CRM mass ratio of 1.5:1 (w/w). The reaction mixture was gently mixed before gently mixing on an orbital shaker at room temperature (20° C.) for 2 hours. Then the reaction mixture was diluted with 0.9% sodium chloride solution (0.661 mL), phosphate buffer pH 7 (0.07 mL, 0.5 M) and DMSO (0.175 mL) to make the PS-18 final concentration to 1 mg/mL and allowed to react for 18 hours. Sodium azide solution (23 μL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 48 hours (8 exchanges, 800 ml each). The dialyzed solution was filtered through a Millex-GP (0.22 μm, 33 mm polyethersulfone) to give PS18C-CRM conjugate solution.

| PS18C-DBCO (mg) | CRM (mg) | Vol. after purification (mL) | Anthrone (mg/mL) | PS recovery (%) | BCA (CRM) (mg/mL) | CRM recovery (%) | PS18C:CRM CJD ratio | Free PS (%) | SEC-MALS MDa |
|---|---|---|---|---|---|---|---|---|---|
| 3.5 | 2.33 | 4.11 | 0.287 | 34 | 0.168 | 29.6 | 1.7 | 13.7 | 1.97 |

Example 31: Preparation of Pneumococcal PS Serotype 18C Conjugates to an eCRM from Table 3

1. Oxidation

Type 18C PS Repeating unit Mol. wt: 1012
NaIO$_4$ solution in water (10 mg/mL)

Reaction procedure:

Polysaccharide PS18C (20 mg, 19.76 μmol) powder was dissolved in 3 mL of aqueous solution (10 mM sodium acetate solution, PH 4.5). To this solution was added 63.4 μL of $NaIO_4$ solution (0.634 mg, 2.96 μmol, 0.15 eq). The mixture was stirred at 23° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS-18C (PS18C-OX) solution. After dialysis, DMSO was added to make PS18C in 10% DMSO with 50 mm PB buffer, pH 6.8.

| Mol eq of $NaIO_4$ | PS18C (mg) | Vol. after purification (mL) | Anthrone (μM) | % Oxidation (BCA) | PS18C-OX yield (%) |
|---|---|---|---|---|---|
| 0.15 | 20 | 4 | 3705 | 7.05 | 75 |

2. DBCO Derivatization

Final concentration of PS: 3.75 mg/ml,

Final concentration of buffer: 10% DMSO in 50 mM PB (pH 6.8)

Reaction Procedure:

To a solution of PS18C-OX (15 mg, 14.8 μmol, 4.4 mL in 10% DMSO 50 mM PB, PH 6.8), a solution of DBCO-$PEG_4$-$NH_2$ (7.76 mg in 77.6 μL of DMSO; 14.8 μmol, 10 equivalent) was added at 25° C. The reaction mixture was then stirred at 25° C. for 60 min, after which time sodium cyanoborohydride solution (0.93 mg in 93 μL of water; 14.8 μmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give the PS18C-DBCO derivative.

| PS18C-OX (mg) | Vol. after purification (mL) | Anthrone (μM) | DBCO derivatization (μM) | DBCO incorporation (%) | PS18C-DBCO yield (%) | SEC-MALS kDa |
|---|---|---|---|---|---|---|
| 15 | 5 | 2460.4 | 75.12 | 3.05 | 83 | 350 |

3. Conjugation of PS18C-DBCO Derivative with eCRM

PS18C-DBCO: 6 mg (with 60 mg of sucrose) white powder

DBCO: 3% eCRM concentration: 6.5 mg/mL

PS:CRM (input ratio): 1.5:1

Final concentration of PS: 2 mg/ml

Reaction Procedure:

Azido-functionalized eCRM solution (0.615 mL) was added to the PS18C-DBCO derivative (6 mg white powder pre-dissolve in 3 mL Water, 5.9 μmol) providing a PS18C:CRM mass ratio of 1.5:1 (w/w). The reaction mixture was gently mixed by hand before gently mixing on an orbital shaker at room temperature (23° C.) for 17 hours. The mixture was then put into an incubator (37° C.) for 3 hours. After reaction, the mix was dilute 2 fold by 0.9% sodium chloride solution and reduced by sodium borohydride (1.12 mg in 112 μL of water; 29.64 μmol, 50 equivalent) for 3 hours. The conjugated PS-CRM mixture was transferred to a prewashed dialysis tube (Spectrum Lab Float-A-Lyzer G2, Cat. No. G235072, 300K MWCO) and then dialyzed with PBS, PH 7 for 24 hours (3 exchanges, 1000 ml each). The dialyzed solution was filtered through a Millex-GP (0.45 μm and 0.22 μm, 33 mm polyethersulfone) to give a PS18C-CRM conjugate solution.

| PS18C-DBCO (mg) | CRM (mg) | Vol. after purification (mL) | Anthrone (mg/mL) | PS recovery (%) | BCA (CRM) (mg/mL) | PS18C:CRM CJD ratio | Free PS (%) | SEC-MALS MDa (0.22 μm filtered) |
|---|---|---|---|---|---|---|---|---|
| 6 | 4 | 10 | 0.42 | 70 | 0.15 | 2.65:1 | 14.80 | 8.25 |

Example 32: Preparation of Pneumococcal PS Serotype 19A Conjugates to an eCRM from Table 3

1. Oxidation

Purity of type 19A PS: 90% (Anthrone)
Mol. wt: 614.44
NaIO$_4$ solution in water (5.69 mg/mL)

Reaction Procedure:

Polysaccharide type 19A (PS19A; 22.10 mg corrected to 90%, 19.89 mg, 32.37 µmol) powder was dissolved in 11.05 mL of aqueous solution (7.73 mL of water and 3.32 mL of 0.2 M acetate buffer; pH=5.5). To this solution was added 304 µL of NaIO$_4$ solution (1.73 mg, 8.09 µmol, 0.25 eq). The mixture was stirred at 25° C. for 18 hours, after which the time, the oxidized sample was purified using AMICON ultra centrifuge (30 kDa MWCO 6-12 mL) 6 exchanges (10 mL) of HPLC grade water to give oxidized PS19A (PS19A-OX) solution.

| Mol eq of NaIO$_4$ | PS19A (mg) | Vol. after purification (mL) | Anthrone (µM) | % Oxidation (BCA) | % Oxidation (aldehyde assay) | PS19A-OX yield (%) |
|---|---|---|---|---|---|---|
| 0.25 | 22.10 | 2.72 | 11148 | 11.5 | 6.1 | 99.39 |

2. DBCO Derivatization

Reaction Procedure:

To a solution of PS19A-OX (assume 10% oxidation level; 17.14 mg, 27.9 µmol, 2.50 mL water) was added buffer solution (1.0 mL of 200 mM phosphate buffer, pH=6.01), DMSO (0.4 mL) and a solution of DBCO-PEG$_4$-NH$_2$ (14.61 mg in 190 µL of DMSO; 27.9 µmol, 10 equivalent) all at 25° C. The reaction mixture was then stirred at 25° C. for 30 min, after which time 70.2 µL of a sodium cyanoborohydride solution (15.6 mg in 313 µL of water; 55.8 µmol, 20 equivalent) was added and kept stirring for 2 days at 25° C. The reaction mixture was diluted with phosphate buffer (500 µL of 200 mM solution, pH=6) before adding 105 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give the PS19A-DBCO derivative. To this solution (3.12 mL, 11.4 mg) was added a solution of sucrose (114 mg in 1 mL water). The combined solution were divided into two equal portions and each lyophilized to give two samples of white powder. Each sample contained 5.70 mg of PS19A-DBCO and 57 mg of sucrose for use in the next conjugation reaction.

| PS19A-OX (mg) | Vol. after purification (mL) | Anthrone (µM) | DBCO derivatization 309 nm Abs | DBCO derivatization (µM) | DBCO incorporation (%) | PS19A-DBCO yield (%) | SEC-MALS kDa |
|---|---|---|---|---|---|---|---|
| 17.14 | 4.87 | 5976 | 0.482 × 4 | 197.76 | 3.31 | 105 | 139 |

3. Conjugation of PS19A-DBCO Derivative with eCRM

PS19A-DBCO: 5.7 mg (with 57 mg of sucrose) white powder

% DBCO: 3.31%
CRM concentration: 6.5 mg/mL solution
PS:CRM (input ratio): 1.8:1

Reaction Procedure:

Azido-functionalized eCRM solution (0.49 mL) was added to the PS19A-DBCO derivative (5.7 mg white powder with 57 mg of sucrose) providing a PS19A:CRM mass ratio of 1.8:1 (w/w). The reaction mixture was gently mixed by hand before gently mixing on an orbital shaker at room temperature (20° C.) for 18 hours. The conjugated PS-CRM mixture was transferred to a prewashed dialysis tube (SpectrumLab Float-A-Lyzer G2, Cat. No. G235060, 300K MWCO) and then dialyzed with 0.9% sodium chloride solution for 24 hours (3 exchanges, 800 ml each). The dialyzed solution was filtered through a Millex-GP (0.22 µm, 33 mm polyethersulfone) to give a PS19A-CRM conjugate solution.

| PS19A-DBCO (mg) | CRM (mg) | Vol. after purification (mL) | Anthrone (mg/mL) | PS recovery (%) | BCA (CRM) (mg/mL) | CRM recovery (%) | PS19A:CRM CJD ratio | Free PS (%) | SEC-MALS MDa |
|---|---|---|---|---|---|---|---|---|---|
| 5.7 | 3.185 | 5.42 | 0.62 | 70 | 0.40 | 61 | 1.55:1 | 25.23 | 1 |

Example 33: Preparation of Pneumococcal PS Serotype 19A Conjugates to an eCRM from Table 3

1. Oxidation

Purity of type 19A PS: 90% (Anthrone)
Mol. wt: 614.44
$NaIO_4$ solution in water (5.45 mg/mL)

Reaction Procedure:

Polysaccharide type 19A (PS19A; 20.83 mg corrected to 90%, 18.75 mg, 30.5 µmol) powder was dissolved in 9.5 mL of aqueous solution (6.5 mL of water and 3 mL of 0.2 M acetate buffer; pH=5.5). To this solution was added 305 µL of $NaIO_4$ solution (1.63 mg, 7.62 µmol, 0.25 eq). The mixture was stirred at 25° C. for 18 hours, after which the time, the oxidized sample was purified using AMICON ultra centrifuge (30 kDa MWCO 6-12 mL) 6 exchanges (10 mL) of HPLC grade water to give oxidized PS19A (PS19A-OX) solution.

| Mol eq of $NaIO_4$ | PS19A (mg) | Vol. after purification (mL) | Anthrone (µM) | % Oxidation (BCA) | % Oxidation (aldehyde assay) | PS19A-OX yield (%) | Note |
|---|---|---|---|---|---|---|---|
| 0.25 | 20.83 | 2.95 | 9858 | 7.2 | 4.2 | 95.32 | N/A |

2. DBCO Derivatization

Reaction Procedure:

To a solution of PS19A-OX (assume 10% oxidation level; 17.57 mg, 28.59 µmol, 2.90 mL water) was added buffer solution (0.87 mL of 200 mM phosphate buffer, pH=6.01), DMSO (0.7 mL) and a solution of DBCO-PEG$_4$-NH$_2$ (14.97 mg in 306 µL of DMSO; 28.59 µmol, 10 equivalent) all at 25° C. The reaction mixture was stirred at 25° C. for 30 min, after which time 79 µL of a sodium cyanoborohydride solution (9.39 mg in 200 µL of water; 57.2 µmol, 20 equivalent) was added and kept stirring for 2 days at 25° C. The reaction mixture was diluted with phosphate buffer (500 µL of 200 mM solution, pH=6) before adding 110 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give the PS19A-DBCO derivative. To this solution (3.56 mL, 11.9 mg) was added a solution of sucrose (120 mg in 1 mL water). The combined solution were divided into two equal portions and each lyophilized to give two samples of white powder. Each sample contained 5.95 mg of PS19A-DBCO and 60 mg of sucrose for use in the next conjugation reaction.

| PS19A-OX (mg) | Vol. after purification (mL) | Anthrone (µM) | DBCO derivatization 309 nm Abs | DBCO derivatization (µM) | DBCO incorporation (%) | PS19A-DBCO yield (%) | SEC-MALS kDa |
|---|---|---|---|---|---|---|---|
| 17.57 | 3.76 | 5424 | 0.831 × 3 | 254.1 | 4.68 | 71 | 111 |

3. Conjugation of PS19A-DBCO Derivative with eCRM

PS19A-DBCO: 5.95 mg (with 60 mg of sucrose) white powder
% DBCO: 4.68%
CRM concentration: 6.5 mg/mL solution
PS:CRM (input ratio): 1.8:1

Reaction Procedure:

Azido-functionalized eCRM solution (0.51 mL) was added to PS19A-DBCO derivative (5.95 mg white powder with 60 mg of sucrose) providing a PS19A:CRM mass ratio of 1.8:1 (w/w). The reaction mixture was gently mixed by hand before gently mixing on an orbital shaker at room temperature (20° C.) for 18 hours. The mixture was then put into an oven (37° C.) for 2 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-GP (0.22 µm, 33 mm polyethersulfone) to give a PS19A-CRM conjugate solution.

| PS19A-DBCO (mg) | CRM (mg) | Vol. after purification (mL) | Anthrone (mg/mL) | PS recovery (%) | BCA (CRM) (mg/mL) | CRM recovery (%) | PS19A:CRM CJD ratio | Free PS (%) | SEC-MALS MDa |
|---|---|---|---|---|---|---|---|---|---|
| 5.95 | 3.305 | 6.821 | 0.53 | 61 | 0.314 | 65 | 1.68:1 | 9.48 | 0.752 |

Example 34: Preparation of Pneumococcal PS Serotype 19F Conjugates to an eCRM from Table 3

1. Oxidation

Purity of type 19F PS: 90.7% (Anthrone)
Mol. wt: 614.44
$NaIO_4$ solution in water (5.21 mg/mL)
Reaction Procedure:

Polysaccharide type 19F (PS19F; 22.0 mg, 35.8 μmol) powder was dissolved in 13.75 mL of aqueous solution (11 mL of water and 2.75 mL of 0.2 M acetate buffer; pH=5.5). To this solution was added 117 μL of $NaIO_4$ solution (0.61 mg, 2.86 μmol, 0.08 eq). The mixture was stirred at 4° C. in a fridge for 17 hours, after which the time, the oxidized sample was purified using AMICON ultra centrifuge (30 kDa MWCO 6-12 mL) 6 exchanges (12 mL) of 10 mM phosphate buffer pH 6.7 to give oxidized PS19F (PS19F-OX) solution.

| Mol eq of $NaIO_4$ | PS19F (mg) | Vol. after purification (mL) | Anthrone (μM) | % Oxidation (BCA) | % Oxidation (aldehyde assay) | PS19F-OX yield (%) |
|---|---|---|---|---|---|---|
| 0.08 | 22.0 | 2.89 | 8786.24 | 5.56 | N/A | 99.39 |

2. DBCO Derivatization

Reaction Procedure:

To a solution of PS19F-OX (assume 10% oxidation level; 13.7 mg, 22.3 μmol, 2.50 mL water) was added buffer solution (1.0 mL of 200 mM phosphate buffer, pH=6.0), DMSO (0.483 mL) and a solution of DBCO-$PEG_4$-$NH_2$ (11.68 mg in 117 μL of DMSO; 22.3 μmol, 10 equivalent) all at 25° C. The reaction mixture was then stirred at 25° C. for 30 min, after which time 70.2 μL of a sodium cyanoborohydride solution (2.8 mg in 280 μL of water; 44.6 μmol, 20 equivalents) was added and kept stirring overnight at 25° C. The reaction mixture was diluted with phosphate buffer (500 μL of 200 mM solution, pH=6) before adding 84 μL solution of sodium borohydride (0.01 mg/μL, 10 equiv) in water. After stirring for 30 min, the reaction mixture was extracted with ethyl acetate (5×12 mL ethyl acetate) and then transferred to an AMICON ultra centrifuge (30 kDa MWCO 6-12 mL) and then dialyzed using 5 exchanges with 20% ethanol in water followed by 3 exchanges with 5 mM phosphate buffer pH 7.0 (12 mL each) to give the PS19F-DBCO derivative. To this solution (1.11 mL, 7.0 mg) was added a solution of sucrose (70 mg in 1 mL water). The combined solution was divided into two portions of 4 mg and 3 mg each and lyophilized to give two samples of white powder. These lyophilized samples of PS19F-DBCO were used in the next conjugation reaction.

| PS19F-OX (mg) | Vol. after purification (mL) | Anthrone (μM) | DBCO derivatization 309 nm Abs | DBCO derivatization (μM) | DBCO incorporation (%) | PS19F-DBCO yield (%) | SEC-MALS kDa |
|---|---|---|---|---|---|---|---|
| 13.7 | 1.92 | 1714 | 0.920 × 4 | 1714 | 5.14 | 88 | 93 |

3. Conjugation of PS19F-DBCO Derivative with eCRM

PS19F-DBCO: 4.0 mg (with 40 mg of sucrose) white powder
% DBCO: 5.14%
CRM concentration: 5.0 mg/mL solution
PS:CRM (input ratio): 1.6:1

Reaction Procedure:

Azido-functionalized eCRM solution (0.5 mL) was added to PS19F DBCO derivative (4.0 mg white powder with 40 mg of sucrose) providing a PS19F:CRM mass ratio of 1.6:1 (w/w). The reaction mixture was gently mixed by hand before gently mixing on an orbital shaker at room temperature (20° C.) for 18 hours followed by 37° C. for 1 hour. 42 µL of sodium azide (0.42 mg, 1 equivalent) was added. After 30 min the conjugated PS-CRM mixture was transferred to a prewashed dialysis tube (SpectrumLab Float-A-Lyzer G2, Cat. No. G235060, 300K MWCO) and then dialyzed with 0.9% sodium chloride solution for 2 days (8 exchanges, 800 ml each). The dialyzed solution was filtered through a Millex-GP (0.22 µm, 33 mm polyethersulfone) to give a PS19F-CRM conjugate solution.

| PS19F-DBCO (mg) | CRM (mg) | Vol. after purification (mL) | Anthrone (mg/mL) | PS recovery (%) | BCA (CRM) (mg/mL) | CRM recovery (%) | PS:CRM ratio | Free PS (%) | SEC-MALS MDa |
|---|---|---|---|---|---|---|---|---|---|
| 4.0 | 2.5 | 3.75 | 0.84 | 79 | 0.52 | 77 | 1.63:1 | 16.55 | 1.89 |

Example 35: Preparation of Pneumococcal PS Serotype 19F Conjugates to an eCRM from Table 3

1. Oxidation

Type 19F PS Mol. wt: 613

NaIO$_4$ solution in water (10 mg/mL)

Reaction Procedure:

Polysaccharide type 19F (PS19F; 10 mg, 16.31 µmol) powder was dissolved in 2 mL of aqueous solution (10 mM sodium acetate solution, PH 4.5). To this solution was added 34.9 µL of NaIO$_4$ solution (0.349 mg, 1.63 µmol, 0.1 eq). The mixture was stirred at 4° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS19F (PS19F-OX) solution. After dialysis, DMSO was added to make PS19F in 10% DMSO with 50 mm PB buffer, PH 6.8.

| Mol eq of NaIO$_4$ | PS19F (mg) | Vol. after purification (mL) | Anthrone (M) | % Oxidation (BCA) | PS yield (%) | Note |
|---|---|---|---|---|---|---|
| 0.1 | 10 | 2 | 6769 | 9.0 | 83 | N/A |

2. DBCO Derivatization

Final concentration of PS: 3.32 mg/ml,

Final concentration of buffer: 10% DMSO in 50 mM PB (pH 6.8)

Reaction Procedure:

To a solution of PS19F-OX (8.3 mg, 13.53 µmol, 2.5 mL in 10% DMSO 50 Mm PB, PH 6.8), a solution of DBCO-PEG$_4$-NH$_2$ (7.08 mg in 70.84 µL of DMSO; 13.53 µmol, 10 equivalent) was added at 25° C. The reaction mixture was then stirred at 25° C. for 60 min, after which time sodium cyanoborohydride solution (0.85 mg in 85 µL of water; 13.53 µmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give the PS19F-DBCO derivative.

| oxidized PS19F (mg) | Vol. after purification (mL) | Anthrone (µM) | DBCO derivatization (µM) | DBCO incorporation (%) | PS19F-DBCO yield (%) | SEC-MALS KDa |
|---|---|---|---|---|---|---|
| 8.3 | 4 | 3385 | 235.4 | 7.15 | 78 | 186 |

3. Conjugation of PS19F-DBCO Derivative with eCRM
 PS19F-DBCO: 6 mg (with 60 mg of sucrose) white powder
 DBCO: 7%
 CRM concentration: 2.617 mg/mL solution
 PS:CRM (input ratio): 2:1
 Final concentration of PS: 5.2 mg/ml Reaction Procedure:

Azido-functionalized eCRM solution (1.15 mL) was added to 19F DBCO derivative (6 mg white powder with 60 mg of sucrose, 9.7 μmol) providing a PS19F:CRM mass ratio of 2:1 (w/w). The reaction mixture was gently mixed by hand before gently mixing on an orbital shaker at room temperature (23° C.) for 17 hours. The mixture was then put into an incubator (37° C.) for 3 hours. After reaction, the mix was dilute 2 fold by 0.9% sodium chloride solution and reduced by sodium borohydride (1.849 mg in 184.9 μL of water; 48.9 μmol, 50 equivalent) for 3 hours. The conjugated PS-CRM mixture was transferred to a prewashed dialysis tube (SpectrumLab Float-A-Lyzer G2, Cat. No. G235071, 100K MWCO) and then dialyzed with PBS, PH 7 for 24 hours (3 exchanges, 1000 ml each). The dialyzed solution was filtered through a Millex-GP (0.22 μm, 33 mm polyethersulfone) to give a 19F PS-CRM conjugate solution.

| Mol eq of $NaIO_4$ | PS 20A (mg) | Vol. after purification (mL) | Anthrone assay (μM) | % Oxidation (BCA) | % Oxidation (aldehyde assay) | PS yield (%) | Note |
|---|---|---|---|---|---|---|---|
| 0.20 | 30.1 | 2.6 | 6254.57 | 59.06 | 10.34 | 63 | — |

2. DBCO Derivatization

Reaction Procedure:

PS20-OX (11.7 mg, 10.1 μmol, 1.61 mL) was added to phosphate buffer (0.600 mL, 200 mM, pH 6.0) to which was added DBCO-PEG$_4$-NH$_2$ (1.0 eq., 523 g mol$^{-1}$ in DMSO, 33 mg/mL, 160 μL) and an additional quantity of DMSO (207 μL). The reaction mixture was stirred at 25° C. for 25 mins. prior to the addition of a solution of sodium cyanoborohydride (2 eq., 52.5 mg/mL, 24 μL) and stirred for one day. After capping with 1 eq. of sodium borohydride solution, the reaction mixture was extracted with ethyl acetate (3×20 mL)

| PS19F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS KDa |
|---|---|---|---|---|---|---|---|---|---|
| 6 | 3 | 12 | 0.241 | 48 | 0.166 | 66 | 1.5:1 | 15.12 | 736 (1.05 mDa-414 KDa) |

Example 36: Preparation of Pneumococcal PS Serotype 20A Conjugates to an eCRM from Table 3

1. Oxidation
 Purity of type 20A PS: 68% (anthrone)
 Mol. wt: 1157.9 g mol$^{-1}$ Reaction Procedure:

Type 20A PS (30.1 mg, 26 μmol; ATCC® 526-X™, obtained from the American Type Culture Collection) powder was dissolved in 15.00 mL of aqueous solution (11.25 mL of water and 3.75 mL of 0.2 M acetate buffer, pH 5.5) in a 50-mL polystyrene sample tube with stirring bar. Once the PS was solubilized, 160 μL of NaIO$_4$ solution (1.11 mg, 5.2 μmol, 0.20 mol. eq.) was added. The reaction tube was wrapped in foil and placed in a water bath at 25° C. The mixture was stirred at 25° C. After 18 hrs, the reaction mixture was dialyzed using three AMICON® Ultra-15 centrifugal filter devices (30 kDa MWCO; 15 mL) by 5 exchanges with HPLC-grade water (15 mL each) to render oxidized PS-20 solution.

and bubbled free of solvent. The DBCO derivative was purified by centrifugal dialysis units twice (Amicon 30 kDa MWCO) using 5 exchanges with 20% ethanol in water followed by 3 exchanges with water each time (12 mL each) to give the 20-DBCO derivative. To this solution (2.09 mL, 13.65 mg) was added a solution of sucrose (136.5 mg in 1.37 mL water). The combined solution was divided into two equal portions and each lyophilized to give three samples of white powder. Each sample contained 6.0 mg of 20A-DBCO and 60 mg of sucrose for use in the conjugation reaction.

| PS 20A-OX (mg) | Vol. after purification (mL) | Anthrone assay (μM) | DBCO derivatization 309 nm Abs | DBCO derivatization (PM) | DBCO incorporation (%) | PS-DBCO yield (%) | SEC-MALS KDa |
|---|---|---|---|---|---|---|---|
| 11.7 | 2.09 | 1112.43 | 0.336 × 4 | 29.04 | 2.6 | 123 | 610 |

3. Conjugation of PS 20A-DBCO Derivative with eCRM
 PS 20A-DBCO: 5.0 mg (with 50 mg sucrose) lyophilized powder
 % DBCO: 2.0%
 CRM concentration: 5.29 mg/mL solution
 PS:CRM (input ratio): 1.5:1

Reaction Procedure:

PS20A-DBCO was dissolved in 0.9% sodium chloride solution (2.684 mL, 0.22 μm filtered), phosphate buffer (pH 7.0, 0.5M, 0.160 mL) and DMSO (0.400 mL). Azido-CRM solution (5.29 mg/mL, 0.756 mL) was added dropwise to provide a PS20:CRM input ratio of 1.5:1 (w/w). The solution was very gently mixed by hand before gently mixing on an orbital shaker at room temperature (20° C.) for 36 hours.

The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a sterile PS20A-CRM conjugate solution.

| PS20A-DBCO (mg) | CRM (mg) | Vol. after purification (mL) | Anthrone (mg/mL) | PS recovery (%) | BCA (CRM) (mg/mL) | CRM recovery (%) | PS20A: CRM CJF ratio | Free PS (%) | SEC-MALS MDa |
|---|---|---|---|---|---|---|---|---|---|
| 6.0 | 4.0 | 7.00 | 0.640 | 75 | 0.366 | 64 | 1.75:1 | LLOQ | 1.224 |

Example 37: Preparation of Pneumococcal PS Serotype 22F Conjugates to an eCRM from Table 3

1. Oxidation

Purity of type 22F PS: 89% (Anthrone)
Mol. wt: 996.88
$NaIO_4$ solution in water (5 mg/mL)
Reaction Procedure:

Polysaccharide type 22F (PS22F; 30.2 mg, 30.3 µmol) powder was dissolved in 10.5 mL of water and 4.5 mL of 200 mM acetate buffer (pH 5.26) and 132 µL of $NaIO_4$ solution (0.65 mg, 3.03 µmol, 0.1 eq). The mixture was stirred at 25° C. for 18 hours, after which the time, the oxidized sample was purified using AMICON ultra centrifuge (100 kDa MWCO 6-12 mL) 6 exchanges (12 mL) of HPLC grade water to give oxidized PS22F (PS22F-OX) solution.

| Mol eq of $NaIO_4$ | PS22F (mg) | Vol. after purification (mL) | Anthrone (µM) | % Oxidation (BCA) | % Oxidation (aldehyde assay) | PS22F yield (%) |
|---|---|---|---|---|---|---|
| 0.10 | 30.2 | 3.351 | 7389.41 | 20.02 | 3.3 | 81.73 |

2. DBCO Derivatization
Reaction Procedure:

To a solution of PS22F-OX (assume 10% oxidation level; 7.0 mg, 7.02 µmol, 0.956 mL water) was added buffer solution (0.525 mL of 200 mM phosphate buffer, pH=6.0), DMSO (151 µL) and a solution of DBCO-PEG$_4$-NH$_2$ (3.67 mg in 112 µL of DMSO; 7.02 µmol, 10 equivalent) all at 25° C. The reaction mixture was then stirred at 25° C. for 30 min, after which time 17 µL of a sodium cyanoborohydride solution (0.88 mg in 17 µL of water; 14.06 µmol, 20 equivalents) was added and kept stirring for 2 days at 25° C. The reaction mixture was diluted with phosphate buffer (250 µL of 200 mM solution, pH=6) before adding 9 µL solution of sodium borohydride (31 mg/mL, 10 equiv) in water. After 30 min the reaction mixture was extracted with ethyl acetate (4×5 mL). The extract was transferred to an AMICON ultra centrifuge filter (100 kDa MWCO 6-12 mL) and then dialyzed using 6 exchanges with 20% ethanol in water (12 mL each) followed by 3 exchanges with water (12 mL each). SEC-HPLC shows free DBCO therefore the sample was redialyzed using 3 exchanges with 20% ethanol in water (12 mL each) followed by 3 exchanges with water (12 mL each) to give the PS22F-DBCO derivative. To this solution (2.35 mL, 5.2 mg) was added a solution of sucrose (52 mg in 0.520 mL water). The combined solution was divided into two portions and each lyophilized to give two samples of white powder. The sample contained 2.4 mg and 2.8 mg of PS22F-DBCO and 24 mg and 28 mg of sucrose respectively for use in the next conjugation reaction.

| oxidized PS22F (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 7.0 | 2.53 | 739.74 | 0.144 × 3 | 27.57 | 1.24 | 80 | 844 |

3. Conjugation of PS22F-DBCO Derivative with eCRM

PS22F-DBCO: 2.4 mg (with 24 mg of sucrose) white powder
% DBCO: 1.24%
CRM concentration: 4 mg/mL solution
PS:CRM (input ratio): 1.4:1

Reaction Procedure:

The PS22F-DBCO derivative (2.4 mg white powder with 24 mg of sucrose) was dissolved in 0.9% sodium chloride solution (0.075 mL). Azido-functionalized eCRM solution (0.142 mL solution) was added providing a PS22F:CRM mass ratio of 1.4:1 (w/w). The reaction mixture was gently mixed before gently mixing on an orbital shaker at room temperature (20° C.) for 48 hours. Sodium azide solution (16 µL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give PS22F-CRM conjugate solution.

| PS22F-DBCO (mg) | CRM (mg) | Vol. after purification (mL) | Anthrone (mg/mL) | PS recovery (%) | BCA (CRM) (mg/mL) | CRM recovery (%) | PS22F:CRM CJD ratio | Free PS (%) | SEC-MALS MDa |
|---|---|---|---|---|---|---|---|---|---|
| 2.4 | 1.71 | 3.834 | 0.29 | 55 | 0.37 | 49 | 1.53 | 20.6 | 2.42 |

Example 38: Preparation of Pneumococcal PS Serotype 23F Conjugates to an eCRM from Table 3

1. Oxidation

Purity of type 23F PS: 85% (Anthrone)
Mol. wt: 792.62
$NaIO_4$ solution in water (5.86 mg/mL)
Reaction Procedure:

Polysaccharide type 23F (PS23F; 20.21 mg corrected to 85%, 17.18 mg, 26.7 μmol) powder was dissolved in 10 mL of aqueous solution (7.5 mL of water and 2.5 mL of 0.2 M acetate buffer; pH=5.5). To this solution was added 119 μL of $NaIO_4$ solution (0.695 mg, 4.0 μmol, 0.15 eq). The mixture was stirred at 25° C. for 4 hours. The oxidized sample was then purified using an AMICON ultra centrifuge filter (30 kDa MWCO 6-12 mL) 6 exchanges (12 mL) of HPLC grade water to give oxidized PS23F (PS23F-OX) solution.

| Mol eq of $NaIO_4$ | PS23F (mg) | Vol. after purification (mL) | Anthrone (μM) | % Oxidation (BCA) | % Oxidation (aldehyde assay) | PS23F-OX yield (%) | Note |
|---|---|---|---|---|---|---|---|
| 0.15 | 20.21 | 2.41 | 7967 | 4.11 | 3.51 | 88 | N/A |

2. DBCO derivatization

Reaction Procedure:

To a solution of PS23F-OX (assume 10% oxidation level; 13.51 mg, 17.0 μmol, 2.14 mL water) was added buffer solution (0.85 mL of 200 mM phosphate buffer, pH=6.01), DMSO (310 μL) and a solution of $DBCO-PEG_4-NH_2$ (8.93 mg in 170 μL of DMSO; 17.0 μmol, 10 equivalent) all at 25° C. The reaction mixture was then stirred at 25° C. for 30 min, after which time 42 μL of a sodium cyanoborohydride solution (6.1 mg in 120 μL of water; 34.0 μmol, 20 equivalent) was added and kept stirring for 2 days at 25° C. The reaction mixture was extracted with ethyl acetate (3×20 mL ethyl acetate) and then transferred to an AMICON ultra centrifuge filter (30 kDa MWCO 6-12 mL) and then dialyzed using 6 exchanges with 20% ethanol (12 ml each) in water followed by 3 exchanges with water (12 mL each) to the PS23F-DBCO derivative. To this solution (7.58 mL, 13.8 mg) was added a solution of sucrose (138 mg in 1 mL water). The combined solution were divided into two equal portions and each lyophilized to give three samples of white powder. Each sample contained 6.9 mg of PS23F-DBCO and 69 mg of sucrose for use in the next conjugation reaction.

| PSPS23F-OX (mg) | Vol. after purification (mL) | Anthrone (μM) | DBCO derivatization 309 nm Abs | DBCO derivatization (μM) | DBCO incorporation (%) | PS23F-DBCO yield (%) | SEC-MALS kDa |
|---|---|---|---|---|---|---|---|
| 13.51 | 7.61 | 2292 | 0.601 × 2 | 116.98 | 5.1 | 102 | 361 |

3. Conjugation of PS23F-DBCO Derivative with eCRM
PS23F-DBCO: 6.90 mg white powder with 69 mg of sucrose
% DBCO: 5.1%
CRM concentration: 2.617 mg/mL solution
PS:CRM (input ratio): 2:1

Reaction Procedure:

Azido-functionalized eCRM solution (1.32 mL solution) was added to 23F DBCO derivative (6.90 mg white powder with 69 mg of sucrose) providing a PS23F:CRM mass ratio of 2:1 (w/w). The reaction mixture was gently mixed by hand before gently mixing on an orbital shaker at room temperature (20° C.) for 17 hours. The mixture was then put into an oven (37° C.) for 3 hours. The conjugated PS-CRM mixture was transferred to a prewashed dialysis filter (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-HV filter (0.45 μm, 33 mm polyethersulfone) to give 23F PS-CRM conjugate solution.

was added. The reaction tube was wrapped in foil and placed in a water bath at 4° C. The mixture was stirred at 4° C. After 18 hrs, the reaction mixture was dialyzed using three AMICON® Ultra-15 centrifugal filter devices (100 kDa MWCO; 15 mL) by 4 exchanges with HPLC-grade water (15 mL each) to render oxidized PS-33F solution.

| Mol eq of NaIO$_4$ | PS 33F (mg) | Vol. after purification (mL) | Anthrone (μM) | % Oxidation (BCA) | % Oxidation (aldehyde assay) | Ps yield (%) |
|---|---|---|---|---|---|---|
| 0.20 | 34.0 | 2.74 | 4637.58 | 47.90 | 7.62 | 36 |

| PS23F-DBCO (mg) | CRM (mg) | Vol. after purification (mL) | Anthrone (mg/mL) | PS recovery (%) | BCA (CRM) (mg/mL) | CRM recovery (%) | PS23F:CRM CJD ratio | Free PS (%) | SEC-MALS MDa |
|---|---|---|---|---|---|---|---|---|---|
| 6.90 | 3.45 | 5.65 | 0.87 | 71 | 0.422 | 69 | 2.06:1 | 23.62 | 1.4 |

Example 39: Alternative Method for Periodate Activation of Pneumococcal PS Serotype 23F To 23F sized polysaccharide (54.0 mL, 2.517 mg/mL) was added 5.016 mL water and 7.475 mL acetate buffer (1.0 M, pH 5.4). The solution was stirred at 250 rpm and 1.467 mL sodium periodate solution (5 mg/mL in water) was added. After 3 h of reaction time at room temperature, the solution was purified by tangential flow filtration against 10 diavolumes of water. The concentration of the oxidized polysaccharide was measured by anthrone assay.

To 23F oxidized polysaccharide (25.5 mL, 4.726 mg/mL) was added 4.626 mL water and 4.017 mL sodium phosphate buffer (1.0 M, pH 5.1). The solution was stirred and then DBCO-PEG$_4$-amine was added (4.017 mL, 39.6 mg/mL in DMSO). After solution was stirred to homogeneity, sodium cyanoborohydride was added (2.008 mL, 38.056 mg/mL in water). After 18 h of stirring at room temperature, the solution was purified by tangential flow filtration. The concentration of the activated polysaccharide was measured by anthrone assay and the concentration of DBCO-PEG$_4$-amine measured by absorbance at 309 nm.

Example 40: Preparation of Pneumococcal PS Serotype 33F Conjugates to an eCRM from Table 3

1. Oxidation

Purity of Type 33F PS: 75% (Anthrone)
Mol. wt: 973

Reaction Procedure:

Type 33F PS (34.0 mg, 35.0 μmol) powder was dissolved in 17.0 mL of aqueous solution (12.0 mL of water and 5.0 mL of 0.2 M acetate buffer, pH 5.5) in a 50-mL polystyrene sample tube with stirring bar. Once the PS was solubilized, 59 μL of NaIO$_4$ solution (1.49 mg, 7.0 μmol, 0.20 mol eq.)

2. DBCO Derivatization

Reaction Procedure:

To a solution of oxidized type 33F PS (11.2 mg, 11.51 μmol, 2.49 mL), buffer solution (0.114 mL of 0.5 M phosphate buffer pH 6.0), A solution of DBCO-PEG$_4$-NH$_2$ (6.039 mg in 200 μL DMSO; 6.33 μmol, 0.55 eq.) were added. The reaction mixture was stirred at 25° C. for 30 min, after which time 63 μL of a sodium cyanoborohydride solution (4.5 mg in 100 μL of water; 34.54 μmol, 2.0 eq.) was added. The reaction mixture was wrapped in aluminum foil and kept stirring in a water bath set to 25° C. for 2 days. The reaction was halted on the second day by the addition of 44 μL of a sodium borohydride solution (3.12 mg in 312 μL of water; 11.51 μmol, 1.0 eq.). After stirring for 30 minutes, the reaction mixture was extracted with dichloromethane (3×10 mL) followed by ethyl acetate (3×10 mL). The extract was bubbled with N$_2$ for 20 minutes to remove residual ethyl acetate and was then transferred to 2 AMICON® Ultra-15 centrifugal filter devices (100 kDa MWCO; 15 mL). Dialysis was performed by conducting three exchanges with a 3% DMSO solution (15 mL each), six exchanges with a 20% ethanol solution (15 mL each), and three exchanges with HPLC-grade water (15 mL each) to give the 33F DBCO derivative. To this solution (1.23 mL, 4.0 mg) was added a solution of sucrose (40 mg 0.4 mL water). This combined solution was lyophilized to give a fine, white powder. PS33F DB sample was stored at 4° C. until needed for the conjugation reaction.

| Oxidized PS 33F (mg) | Vol. after purification (mL) | Anthrone (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 11.2 | 2.44 | 1112.4 | 0.390 | 32.85 | 3.0 | 71 | 1290 |

3. Conjugation of PS 33F-DBCO Derivative with eCRM

PS 33F-DBCO: 4 mg (with 40 mg of sucrose) white powder

% DBCO: 3.0%

CRM concentration: 6.009 mg/mL solution

PS:CRM (input ratio): 1.5:1

Reaction Procedure:

33F DBCO derivative (4.0 mg white powder with 40 mg of sucrose) was dissolved in 0.9% sodium chloride solution (5.32 mL), phosphate buffer pH 7 (0.267 mL, 0.5 M) and DMSO (0.667 mL). Azido-functionalized eCRM solution (0.445 mL solution) was added providing a PS33F:CRM mass ratio of 1.5:1 (w/w). The reaction mixture was gently mixed on an orbital shaker at room temperature (20° C.) for 6.2 μmol, 1.0 eq) was added to the stirring solution. After 5 min stirring, 0.039 mL of NaCNBH$_3$ (20 mg/mL in water; 12.4 μmol, 2.0 eq) was added to the stirring solution. The reaction was stirred at 22° C. for 40 hours. To the solution was then added 0.024 mL sodium borohydride (10 mg/mL in water; 6.3 μmol, 1.0 eq). After 15 min of stirring, the PS was purified by buffer exchange into water via gel filtration columns (Thermo Zeba Columns, 40 kDa MWCO).

| Oxidized PS 7F (mg) | Vol. after purification (mL) | Anthrone assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 7.6 | 2.3 | 2282 | 0.14 × 2 | 111 | 4.8 | 85 | 175 |

19 hours. The click reaction was quenched by the addition of sodium azide solution (10 mg/mL, 50 μL). The reaction mixture was then diluted with 0.9% sodium chloride solution (7.0 mL) and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 μm, 33 mm polyethersulfone) to give 33F PS-CRM conjugate solution.

3. Conjugation of PS 7F-DBCO Derivative with eCRM
   PS 7F-DBCO: 2.8 mg (2.8 mg/mL in water)
   % DBCO: 4.8%
   CRM concentration: 4.7 mg/mL solution
   PS:CRM (input ratio): 1.6:1

Reaction Procedure:

To PS7F-DBCO (1 mL of 2.8 mg/mL in water) in a 5 mL centrifuge tube was added 0.128 mL potassium phosphate (0.5 M, pH 7.5). To this solution was then added 0.372 mL

| PS 33F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC MALS MDa |
|---|---|---|---|---|---|---|---|---|---|
| 4.0 | 2.67 | 7.82 | 0.545 | 106 | 0.212 | 62 | 2.57 | LLOQ | 1.87 |

Example 41: Preparation of Pneumococcal PS Serotype 7F Conjugates to an eCRM from Table 3

1. Oxidation

Purity of type 7F PS: 86% (anthrone, CRB-21-20)
Mol. wt: 1227 g mol$^{-1}$

Reaction Procedure:

The native polysaccharide 7F (19.5 mg, corrected to 86%, 16.8 mg, 13.7 μmol) was dissolved in 3.9 mL water. To this solution was added 4.58 mL water and 0.293 mL sodium acetate buffer (1.5 M, pH 5.4). Then 30 μL of sodium periodate solution (300 μg, 1.4 μmol, 0.1 eq) was added to the stirring solution. The reaction was stirred at 22° C. for 3 hours. The oxidized PS was then concentrated two-fold using a spin concentrator (Amicon 30 k Da MWCO). The concentrated PS was then buffer exchanged into water using gel filtration columns (GE Healthcare PD-10, spin method).

| Mol eq of NaIO$_4$ | PS 7F (mg) | Vol. after purification (mL) | Anthrone assay (μM) | % Oxidation (BCA) | % Oxidation (aldehyde assay) | PS yield (%) | Note |
|---|---|---|---|---|---|---|---|
| 0.1 | 16.8 | 4.0 | 3260 | 6.2 | n/d | 95 | N/A |

2. DBCO Derivatization

Reaction Procedure:

To PS7F-OX (1.9 mL of 4.0 mg/mL; 7.6 mg, 6.2 μmol) was added 0.15 mL sodium phosphate (1 M, pH 6.3). Then 0.23 mL DBCO-PEG$_4$-NH$_2$ (27.1 mM in DMSO, lot 1730;

azide-functionalized eCRM (4.7 mg/mL in 20 mM potassium phosphate, pH 7.1, 7.5% sucrose), thus giving an input mass ratio of 1.6:1 (w/w). The solution was placed on an orbital rocker and rocked (such that solution moved from end to end of tube) for 16 hours at 22° C. The conjugate was then dialyzed into 0.9% sodium chloride using a 300 kDa dialysis membrane (SpectrumLab Float-A-Lyzer G2, 1 mL) for 48 hours with dialysate changes (500 mL) after 1 hour and 4 hours. The dialyzed solution was filtered through a syringe filter (Pall Acrodisc Supor, 0.22 μm, 13 mm diameter) to give PS7F-CRM conjugate solution.

Example 42: Preparation of Pneumococcal PS Serotype 1 Conjugates to an eCRM from Table 3

1. Oxidation

Purity of type 1 PS: 80% (Uronic acid assay)
Mol. wt: 625 g mol$^{-1}$

Reaction Procedure:

The native polysaccharide PS1 (20.2 mg, 32.32 μmol) was dissolved in 9.5 mL of aqueous solution (7.0 mL water and 2.5 mL acetate buffer, 200 mM, pH 5.24). To this solution was added 492 μL of sodium periodate solution (3.45 mg, 16.16 μmol, 0.5 eq). The mixture was stirred at 25° C. for 18 hours. The oxidized PS was purified using Amicon centrifugal 30 kDa MWCO dialysis using 6 exchanges with water to give purified PS-1 solution.

| Mol eq of NaIO$_4$ | PS 1 (mg) | Vol. after purification (mL) | Uronic assay (μM) | % Oxidation (BCA) | % Oxidation (aldehyde assay) | PS yield (%) |
|---|---|---|---|---|---|---|
| 0.50 | 20.2 | 2.61 | 10777.6 | 2.3 | 2.16 | 87 |

2. DBCO Derivatization
Reaction Procedure:

To a solution of oxidized (assume 10% oxidation level) type-1 PS (16 mg, 25.6 μmol, 2.4 mL water) was added buffer solution (0.424 mL of 500 mM phosphate buffer, pH=6.74), DMSO (572 μL) and a solution of DBCO-PEG$_4$-NH$_2$ (13.4 mg in 134 μL of DMSO; 25.6 μmol, 10 eq). The reaction mixture was then stirred at 25° C. for 30 min, after which time 32 μL of a sodium cyanoborohydride solution (3.2 mg in 32 μL of water; 51.2 μmol, 20 eq) was added and kept stirring for 3 days at 25° C. Buffer solution (0.300 mL of 200 mM phosphate buffer, pH=6.0) was added followed by sodium borohydride (0.97 mg in 100 μL, 25.6 μmol, 10 eq) and stirred for 30 min at 25° C. The reaction mixture was extracted with dichloromethane (4×5 mL). The aqueous extract was transferred to two AMICON ultra centrifuge filters (30 kDa MWCO 6-12 mL) and then dialyzed using 5 exchanges with 20% ethanol in water (12 mL each) followed by 3 exchanges with 3% DMSO in water (12 mL each), 3 exchanges with 0.9% sodium chloride and 3 exchanges with water to give type 1 DBCO derivative. To this solution (1.37 mL, 10.0 mg) was added a solution of sucrose (100 mg in 1 mL water). The combined solution was divided into two equal portions and each lyophilized to give two samples of white powder. Each sample contained 5.0 mg of 1-DBCO and 50 mg of sucrose for use in the next conjugation reaction.

| Oxidized PS 1 (mg) | Vol. after purification (mL) | Uronic Acid assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 16 | 2.0 | 2909.0 | 0.784 × 4 | 290.19 | 2.5 | 91 | 315 |

3. Conjugation of PS1-DBCO derivative with eCRM
PS1-DBCO: 5.0 mg (with 50 mg sucrose) lyophilized powder
% DBCO: 2.5%
CRM concentration: 4.86 mg/mL solution
PS:CRM (input ratio): 1.7:1
Reaction Procedure:
The lyophilized type 1-DBCO powder (5 mg) was dissolved in a solution of filtered 0.9% sodium chloride (5.39 mL) and phosphate buffer (250 μL, 0.5 M, pH 7.0). Azido-functionalized eCRM solution (0.47 mL) was added to provide a PS-1:CRM input mass ratio of 1.7:1 (w/w). The solution was very gently mixed by hand before gently mixing on an orbital shaker at room temperature (20° C.) for 18 hours. The click reaction was quenched by the addition of sodium azide solution (10 mg/mL, 52 μL). The CRM conjugate was transferred to pre-washed dialysis tubes (SpectrumLab Float-A-Lyzer G2, 300K MWCO, 10 mL) and then dialyzed with 0.9% sodium chloride solution for 48 hours (8 exchanges, 800 ml each). The dialyzed solution was filtered through a Millex-GP syringe filter (0.22 μm, 33 mm polyethersulfone) to give a 1-CRM conjugate solution.

| PS 1-DBCO (mg) | CRM (mg) | Vol. after purification (mL) | Uronic Acid (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.0 | 2.94 | 6.47 | 0.56 | 72 | 0.283 | 62 | 1.98:1 | 8.25 | 1.02 |

Example 43: Preparation of Pneumococcal PS Serotype 10A Conjugates to an eCRM from Table 3

1. Oxidation
PS Serotype 10A lot #: 63662302 (ATCC)
Purity PS10A: 77% (Anthrone)
Mol. wt: 1013 kDa (Repeat Unit=1227 g/mol)
Reaction Procedure:

Type 10A PS (25.99 mg, 21.18 μmol) powder was dissolved in 12.995 mL of aqueous solution (9.746 mL of water and 3.249 mL of 0.2 M Acetate buffer, pH 5.5) in a 50-mL polystyrene sample tube with stirring bar. Once the PS was solubilized, 135 μL of NaIO$_4$ solution (0.27 mg, 1.26 μmol, 0.06 mol eq.) was added. The reaction tube was wrapped in foil and placed in a refrigerator to stir at 4° C. After 45 minutes, the reaction mixture was dialyzed using three AMICON® Ultra-15 centrifugal filter devices (30 kDa MWCO; 15 mL) by 6 exchanges with HPLC-grade water (15 mL each) to render oxidized PS10A solution.

| Mol eq of NaIO$_4$ | PS 10A (mg) | Vol. after purification (mL) | Anthrone (μM) | % Oxidation (BCA) | % Oxidation (Aldehyde assay) | PS yield (%) |
|---|---|---|---|---|---|---|
| 0.06 | 25.99 | 2.381 | 6757.20 | 16.58 | 3.13 | 76 |

2. DBCO Derivatization
Reaction Procedure:
To a solution of oxidized type 10A PS (18.15 mg, 14.79 μmol, 3.371 mL), buffer solution (0.259 mL of 0.5 M phosphate buffer pH 6.0), DMSO (0.145 mL) and a solution of DBCO-PEG$_4$-NH$_2$ (7.7 mg in 154 µL DMSO; 14.79 µmol, 1 mol eq.) were added. The reaction mixture was stirred at 4° C. for 30 min, after which time 101 µL of a sodium cyanoborohydride solution (1.9 mg in 101 µL of water, 2 mol eq.) was added. The reaction mixture was wrapped in aluminum foil and kept stirring in a refrigerator at 4° C. for 2 days. The reaction was halted on the second with 0.9% sodium chloride solution to a final volume of 7 mL and transferred to a prewashed dialysis device (SpectrumLab Float-A-Lyzer G2, Cat. No. G235060, 300K MWCO). The sample underwent dialysis in 0.9% sodium chloride solution for 48 hours (2 exchanges, 1 L each; 1 exchange, 4 L). The dialyzed solution was filtered through a Millex-GP (0.22 µm, 33 mm polyethersulfone) to give the 10A PS-CRM conjugate solution.

| PS 10A-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS (MDa) |
|---|---|---|---|---|---|---|---|---|---|
| 5.20 | 4.16 | 8.21 | 0.553 | 87 | 0.229 | 45 | 2.4:1 | 17.71 | 1.047 | day by the addition of 85 µL of a sodium borohydride solution (0.56 mg; 14.79 µmol, 1 mol eq.). After stirring for 30 minutes, the reaction mixture was extracted with dichloromethane (3×15 mL). The extract was bubbled with N$_2$ for 15 minutes to remove residual dichloromethane and was then transferred to one AMICON® Ultra-15 centrifugal filter device (30 kDa MWCO; 15 mL). Dialysis was performed by conducting three exchanges with a 3% DMSO solution (15 mL each), three exchanges with a 20% ethanol solution (15 mL), two exchanges with 0.9% sodium chloride solution, and two exchanges with HPLC-grade water (15 mL each) to give the 10A DBCO derivative. To this solution (3.371 mL, 15.06 mg) was added a solution of sucrose (150.6 mg in 1.506 mL water). This combined solution was divided into three equal fractions, and each lyophilized to give a fine, white powder. After lyophilization, all fractions were stored at 4° C. until needed for the conjugation reaction.

General Protocols for Antigen Activation, Examples 44 and Up:

The following protocol was used to activate saccharide antigens using periodate oxidation followed by reductive amination:

To a 50 mM pH 5.4 acetate buffered polysaccharide solution was added (0.1-0.5) molar equivalents (to polysaccharide repeating unit) of sodium periodate with vigorous stirring. The reaction was stirred for (2-24) hours at (4-25) ° C. The oxidized polysaccharide was then purified via dialysis, size exclusion chromatography, or UF/DF.

To a 110 mM pH (5.7-6.7) phosphate buffered oxidized polysaccharide solution was added (1-3) molar equivalents of dibenzocyclooctyne-PEG$_4$-amine linker (dissolved in DMSO). The final concentration of DMSO in the reaction was (5-20)% v/v. Then (2-12) molar equivalents of sodium cyanoborohydride was added and the reaction was stirred for (6-48) hours at (20-25) ° C. The dibenzocyclooctyne-de-

| Oxidized PS 10A (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 18.15 | 3.371 | 1290.30 | 0.333 | 27.21 | 2.1 | 88 | 540 |

3. Conjugation of PS10A-DBCO Derivative with eCRM

PS10A-DBCO: 5.20 mg (with 52.0 mg sucrose) lyophilized powder

% DBCO: 2.1%

CRM: 4.962 mg/mL in 20 mM Histidine pH 7.1 (7.5% Sucrose)

PS:CRM (input mass ratio): 1.25:1

Reaction Procedure:

The PS10A-DBCO derivative (5.2 mg white powder with 52.0 mg of sucrose) was dissolved in 0.9% sodium chloride solution (1.502 mL), phosphate buffer pH 7 (0.104 mL, 0.5 M), and DMSO (0.156 mL). Azido-functionalized eCRM solution (0.838 mL solution) was added providing a PS10A:CRM mass ratio of 1.25:1 (w/w). The reaction mixture, at a concentration of 2.0 mg/mL PS, was gently mixed on an orbital shaker at room temperature (22° C.) for 2 hours. The reaction mixture was then diluted to 1.0 mg/mL and left stirring at 22° C. for a further 20 hrs. The conjugation reaction was terminated with the addition of sodium azide (7.5 mg, 115 µmol). The reaction mixture was then diluted rivatized polysaccharide was then purified via dialysis, size exclusion chromatography, or UF/DF.

For activation of saccharide antigens via CDAP, the following protocol was used:

To a 100 mM pH (8-10) borate buffered polysaccharide solution was added (0.5-5) molar equivalents (to polysaccharide repeating unit) of 1-cyano-4-dimethylaminopyridinium tetrafluoroborate (CDAP; from 100 mg/mL solution in acetonitrile) with vigorous stirring. (3-13) min after addition of CDAP, (0.5-2.5) molar equivalents of dibenzocyclooctyne-PEG$_4$-amine linker (dissolved in DMSO) was added. The final concentration of DMSO in the reaction was (5-10)% v/v. After 1 h of further reaction, the reaction was quenched by addition of glycine. The dibenzocyclooctyne-derivatized polysaccharide was then purified via dialysis, size exclusion chromatography, or UF/DF. All steps were performed at (20-25) ° C.

General Protocol for the Conjugation Reaction:

To a solution of dibenzocyclooctyne-derivatized polysaccharide was added potassium phosphate pH 7.5 buffer, DMSO for a final concentration of (0-15)% v/v, and sodium chloride for a final concentration of (0-300) mM. The carrier protein used for conjugation was the polypeptide having SEQ ID NO: 14 where each X is pAMF, which was then added for a final ratio of polysaccharide to carrier of (0.5-2.5) w/w. The solution was gently mixed for (4-48) hours typically at (20-25) ° C. but as low as 4° C. and as high as 37° C. Unreacted dibenzocyclooctyne groups were quenched by addition of (0.25-2) molar equivalents of sodium azide and stirring for (0.5-2) hours. For serotypes prepared with periodate chemistry, unreacted aldehyde groups were quenched by addition of (0.5-2) molar equivalents of sodium borohydride and stirring for (1-4) hours. For serotypes prepared with CDAP chemistry, no sodium borohydride quench was performed. The polysaccharide-carrier conjugate was then purified via dialysis, size exclusion chromatography, or UF/DF.

Example 44: Preparation of Pneumococcal PS Serotype 6B Conjugate with an eCRM (from Table 3)

1. Oxidation
PS Serotype 6B lot #: 62922708 (Pfizer)
Purity PS 6B: 94% (Anthrone)
Mol. wt: 1360 kDa (Repeat Unit=706.18 g/mol)

Reaction Procedure:
Polysaccharide type 6B (PS6B; 53.2 mg, 75.33 µmol) powder was dissolved in 26.60 mL of aqueous solution (18.62 mL of water and 8.0 mL of 0.2 M Acetate buffer, pH 5.5) in a 50-mL polystyrene sample tube with stirring bar. Once the PS was solubilized, 253 µL of NaIO₄ solution (2.58 mg, 12.05 µmol, 0.12 mol eq.) was added. The reaction tube was wrapped in foil and placed in a water bath to stir at 24° C. After 18 hrs, the reaction mixture was dialyzed using five AMICON® Ultra-15 centrifugal filter devices (30 kDa MWCO; 15 mL) by 5 exchanges with HPLC-grade water (15 mL each) to render oxidized PS6B solution.

| Mol eq of NaIO₄ | PS6B (mg) | Vol. after purification (mL) | Anthrone (µM) | % Oxidation (BCA) | % Oxidation (Aldehyde assay) | PS yield (%) |
|---|---|---|---|---|---|---|
| 0.12 | 53.2 | 7.389 | 6892.60 | 16.58 | 3.13 | 76 |

* 72% PS yield based on mass of starting (no purity correction performed)
ᴬ SRS-4-31 (20 Dec. 2016);
ᴮ SSG-3-90 (24 Dec. 2016);
ᶜ SJN-1-29 (21 Dec. 2016)

2. DBCO Derivatization
Reaction Procedure:
To a solution of PS6B-OX (36.83 mg, 52.2 µmol, 7.568 mL), buffer solution (0.640 mL of 0.5 M phosphate buffer pH 6.0) and a solution of DBCO-PEG₄-NH₂ (17 mg in 1000 µL DMSO; 32 µmol, 0.61 mol eq.) were added. The reaction mixture was stirred at 25° C. for 30 min, after which time 200 µL of a sodium cyanoborohydride solution (2.86 mg in 200 µL of 0.5 M phosphate buffer, pH 6.0; 104.4 µmol, 2 mol eq.) was added. The reaction mixture was wrapped in aluminum foil and kept stirring in a water bath set to 25° C. for 2 days. The reaction was halted on the second day by the addition of 163 µL of a sodium borohydride solution (3.95 mg; 104.4 µmol, 2 mol eq.). After stirring for 30 minutes, the reaction mixture was extracted with dichloromethane (3×15 mL). The extract was bubbled with N₂ for 20 minutes to remove residual dichloromethane and was then transferred to three AMICON® Ultra-15 centrifugal filter devices (50 kDa MWCO; 15 mL). Dialysis was performed by conducting four exchanges with a 3% DMSO solution (15 mL each), one exchange with a 20% ethanol solution (15 mL), two exchanges with a 0.9% sodium chloride solution (15 mL each), and two exchanges with HPLC-grade water (15 mL each) to give the PS6B-DBCO derivative. To this solution (5.509 mL, 41.39 mg) was added a solution of sucrose (413.9 mg 4.139 mL water). This combined solution was divided into four fractions (2×10 mg and 2×5.7 mg) and each lyophilized to give a fine, white powder. All fractions were stored at 4° C. after lyophilized to dryness until needed for the conjugation reaction.

| Oxidized PS 6B (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 36.83 | 5.509 | 3680.16 | 1.465 | 139.27 | 3.8 | 117 | 510 |

3. Conjugation of PS6B-DBCO Derivative with CRM-12
PS6B-DBCO: 10 mg (with 100 mg of sucrose) white powder
% DBCO: 3.8%
CRM concentration: 6.755 mg/mL solution
PS:CRM (input ratio): 2:1
Reaction Procedure:
PS6B-DBCO derivative (10.0 mg white powder with 100 mg of sucrose) was dissolved in 0.9% sodium chloride solution (0.914 mL), phosphate buffer pH 7 (0.077 mL, 0.5 M) and DMSO (0.192 mL). Azido-functionalized CRM-12 solution (0.740 mL solution) was added providing a PS6B:CRM mass ratio of 2:1 (w/w). The reaction mixture was gently mixed on an orbital shaker at room temperature (20° C.) for 18 hours then for a further 2 hours at 37° C. The conjugation reaction was terminated with the addition of 100 µL of a sodium azide (1 mg; 15.38 µmol). The reaction mixture was then diluted with 0.9% sodium chloride solution to a final volume of 7 mL and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 µm, 33 mm polyethersulfone) to give the PS6B-CRM conjugate solution.

| PS 6B-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS (MDa) |
|---|---|---|---|---|---|---|---|---|---|
| 10 | 5 | 8.63 | 0.771 | 67 | 0.431 | 74 | 1.79:1 | 6.74 | 0.932 |

Example 45: Preparation of Pneumococcal PS Serotype 23F Conjugate with an eCRM (from Table 3)

1. Oxidation

PS Serotype 23F lot #: P129773 (Pfizer)

Purity PS 23F: 85% (Anthrone)

Mol. wt: 792.62

NaIO₄ solution in water (5.86 mg/mL) kDa (Repeat Unit=706.18 g/mol)

Reaction Procedure:

PS23F (25.03 mg corrected to 85%, 21.28 mg, 26.8 µmol) powder was dissolved in 12.5 mL of aqueous solution (9.37 mL of water and 3.13 mL of 0.2 M acetate buffer; pH=5.5). To this solution was added 309 µL of NaIO₄ solution (0.919 mg, 4.3 µmol, 0.16 eq). The mixture was stirred at 25° C. for 18 hours. The oxidized sample was then purified using an AMICON ultra centrifuge filter (30 kDa MWCO 6-12 mL) 6 exchanges (12 mL) of HPLC grade water to give oxidized PS23F solution.

| Mol eq of NaIO₄ | PS 23F (mg) | Vol. after purification (mL) | Anthrone (µM) | % Oxidation (BCA) | PS yield (%) |
|---|---|---|---|---|---|
| 0.16 | 25.03 | 2.61 | 11980 | 5.64 | 116 |

2. DBCO Derivatization

Reaction Procedure:

To a solution of oxidized Type 23F PS (23.26 mg, 29.3 µmol, 2.45 mL water; assumed 10% oxidation level) was added buffer solution (1.5 mL of 200 mM phosphate buffer, pH=6.01), DMSO (220 µL) and a solution of DBCO-PEG₄-NH₂ (15.36 mg in 191 µL of DMSO; 29.30 µcool, 10 equivalent) all at 25° C. The reaction mixture was then stirred at 25° C. for 30 min, after which time 91 µL of a sodium cyanoborohydride solution (8.16 mg in 200 µL of water; 58.6 µmol, 20 equivalent) was added and kept stirring for 2 days at 25° C. The reaction was halted on the second day by the addition of 111 µL of a sodium borohydride solution (2.12 mg in 212 µL of water; 29.3 µmol, 1.0 eq.). After stirring for 30 minutes, the reaction mixture was extracted with ethyl acetate (3×20 mL ethyl acetate) and then transferred to an AMICON ultra centrifuge filter (30 kDa MWCO 6-12 mL) and then dialyzed using 6 exchanges with 20% ethanol (12 ml each) in water followed by 3 exchanges with water (12 mL each) to give type 23F DBCO derivative. To this solution (3.73 mL, 16.83 mg) was added a solution of sucrose (168 mg in 1 mL water). The combined solutions were divided into three equal portions and each lyophilized to give three samples of white powder. Each sample contained 5.61 mg of PS23F-DBCO and 56 mg of sucrose for use in the next conjugation reaction.

| Oxidized PS 23F (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 23.26 | 3.73 | 7090 | 1.112 × 3 | 339 | 4.8 | 90 | 345 |

3. Conjugation of PS 23F-DBCO Derivative with CRM-12

PS 23F-DBCO: 5.61 mg white powder (with 100 mg of sucrose)

% DBCO: 4.8%

CRM concentration: 5.0 mg/mL solution

PS:CRM (input ratio): 1:1

Reaction Procedure:

Azido-functionalized CRM solution (SRS-2-159-CRM-12 in 0.78 mL solution) was added to PS23F-DBCO derivative (5.61 mg white powder with 56 mg of sucrose) providing a PS23F:CRM mass ratio of 1:1 (w/w). The reaction mixture was gently mixed by hand before gently mixing on an orbital shaker at room temperature (20° C.) for 17 hours. The click reaction was quenched by the addition of sodium azide solution (10 mg/mL, 50 µL). The conjugated PS-CRM mixture was then transferred to a prewashed dialysis filter (SpectrumLab Float-A-Lyzer G2, Cat. No. G235071, 300K MWCO) and then dialyzed with 0.9% sodium chloride solution for 24 hours (5 exchanges, 800 ml each). The dialyzed solution was filtered through a Millex-GP filter (0.22 µm) to give PS23F-CRM conjugate solution.

| PS 23F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS (MDa) |
|---|---|---|---|---|---|---|---|---|---|
| 5.61 | 5.61 | 4.50 | 0.531 | 62 | 0.351 | 41 | 1.51:1 | 9.93 | 5.91 |

Example 46: Evaluation of DBCO PEG$_4$-Amine and DBCO-Amine Incorporation into Pneumococcal Polysaccharides A variety of pneumococcal polysaccharides were oxidized as described above and reacted with DBCO-PEG$_4$-amine (DBCO or DB) or DBCO-amine (DBCA or DA) under the same conditions to determine the effect of the linker on incorporation efficiency. The below table shows that in all but one of the serotypes tested, DBCO-amine incorporates at a higher efficiency as compared to DBCO-PEG$_4$-amine per 100 polysaccharide repeating units.

| Oxidized PS Sample | PS DB/DA Sample | DB/DA Reaction Conditions | DBCO/DBCA % incorporation | DB/DA-PS Yield % | DB/DA-PS Size, kDa |
|---|---|---|---|---|---|
| 5-OX | 5-DB (15.5 mg) | 5 mg/mL, 1 eq of DBCO, 10% DMSO, Phos. Buffer 50 mM, pH 6.7, 25 C., 3 d | 4.9 | 89 | |
| | 5-DA (15.5 mg) | 5 mg/mL, 1 eq of DBCA, 10% DMSO, Phos. Buffer 50 mM, pH 6.7, 25 C., 3 d | 8.3 | 83 | |
| 9V-OX | 9V-DB (17.1 mg) | 5.0 mg/mL, 2 d, 50 mM phos buff, pH 6.0, 1 mol eq. DBCO, 15% DMSO, 25° C. | 3.9 | 56 | |
| | 9V-DA (17.1 mg) | 5.0 mg/mL, 2 d, 50 mM phos buff, pH 6.0, 1 mol eq. DBCA, 15% DMSO, 25° C. | 6 | 80 | |
| 14-OX | 14-DB (15.65 mg) | 5.0 mg/mL, 50 mM phos buffer pH 6.7, 1.0 mol. eq. DBCO, 15% DMSO, 25° C., 48 h | 8 | 80 | |
| | 14-DA (15.65 mg) | 5.0 mg/mL, 50 mM phos buffer pH 6.7, 1.0 mol. eq. DBCA, 15% DMSO, 25° C., 48 h | 4.6 | 67 | |
| 23F-OX | 23F-DB (22.3 mg) | 4 mg/ml, 48 h, 100 mM pH 6.0, 0.8 eq DBCO, 15% DMSO, 25° C. | 5.5 | 68 | |
| | 23F-DA (22.3 mg) | 4 mg/ml, 48 h, 100 mM pH 6.0, 0.8 eq DBCA, 15% DMSO, 25° C. | 7.5 | 63 | |
| 22F-OX | 22F-DB (7.0 mg) | 2 mg/mL, 1 eq of DBCO, 15% DMSO, pH 6, 25° C. 48 h. | 0.8 | 101 | |
| | 22F-DA (7.0 mg) | 2 mg/mL, 1 eq of DBCA, 15% DMSO, pH 6, 25° C. 48 h. Ppt purification. | 4.3 | 104 | |
| 22F-OX | 22F-DB (7.0 mg) | 4 mg/mL, 1 eq of DBCO, 15% DMSO, pH 6, 25° C. 48 h. | 1.2 | 80 | 838 |
| | 22F-DA (14.0 mg) | 4 mg/mL, 1 eq of DBCA, 15% DMSO, pH 6, 25° C. 48 h. Ppt purification. | 4.3 | 73 | 790 |
| 10A-OX | 10A-DB (14.60 mg) | 7 mg/mL, 10% DMSO, 50 mM phos buff, pH 6.0, 1 mol eq. DBCO, 4° C., 2 d | 1.5 | 88 | |
| | 10A-DA (14.60 mg) | 7 mg/mL, 10% DMSO, 50 mM phos buff, pH 6.0, 1 mol eq. DBCA, 4° C., 2 d | 3.8 | 82 | |
| 7F-OX | 7F-DB (12 mg) | 2.9 mg/mL 1 eq DBCO(lot#1730), 99 mM phosphate pH 6.3, 21 h @ RT, 10% DMSO | 1.9 | 78 | 160 |
| | 7F-DA (12 mg) | 2.9 mg/mL 1 eq DBCA(lot#1818), 99 mM phosphate pH 6.3, 21 h @ RT, 10% DMSO | 4.5 | 76 | 177 |

Example 47: Comparison of DBCO PEG$_4$-Amine and DBCO-Amine Conjugation to eCRM Pneumococcal polysaccharides linked to DBCO-PEG$_4$-amine (DB) or DBCO-amine (DA) were conjugated to the same eCRM from Table 3 under identical reaction conditions along the lines of the above examples to assess the effect of the linker on conjugation efficiency. The below table shows that conjugates formed with polysaccharide linked to DBCO-amine generally result in less free polysaccharide and larger conjugate size.

| DBCO PS | PS Scale (mg) | PS conc. mg/mL | Prot. Conc., mg/mL | Input Ratio | Conjugation Reaction Conditions | Yield % (PS) | PS:Prot Ratio | Free PS % | Conjugate Size MDa |
|---|---|---|---|---|---|---|---|---|---|
| 22F-DB | 2.4 | 3.2 | 2.3 | 1.4 | 3.2 mg/mL, 10% DMSO, 48 h, rt, 300 KDa dialysis, filter Millex-GP | 53 | 1.5 | 20.5 | 3.6 |
| 22F-DA | 2 | 3.2 | 2.3 | 1.4 | 3.2 mg/mL, 10% DMSO, 48 h, rt, 300 KDa dialysis, filter Millex-GP | 37 | 1.7 | LLOQ <9.2% | 6.2 |
| 7F-DB | 4 | 2.6 | 1.6 | 1.6 | 2.6 mg/mL, 18 h, RT, 300 kDa dialysis, filter Millex-MP | 94 | 2 | 31 | 1.3 |
| 7F-DA | 4 | 2.6 | 1.6 | 1.6 | 2.6 mg/mL, 18 h, RT, 300 kDa dialysis, filter Millex-MP | 84 | 2 | 14 | 1.8 |

Example 48: Immunogenicity of Pneumococcal PS Serotype-eCRM Conjugates

Figure 3:
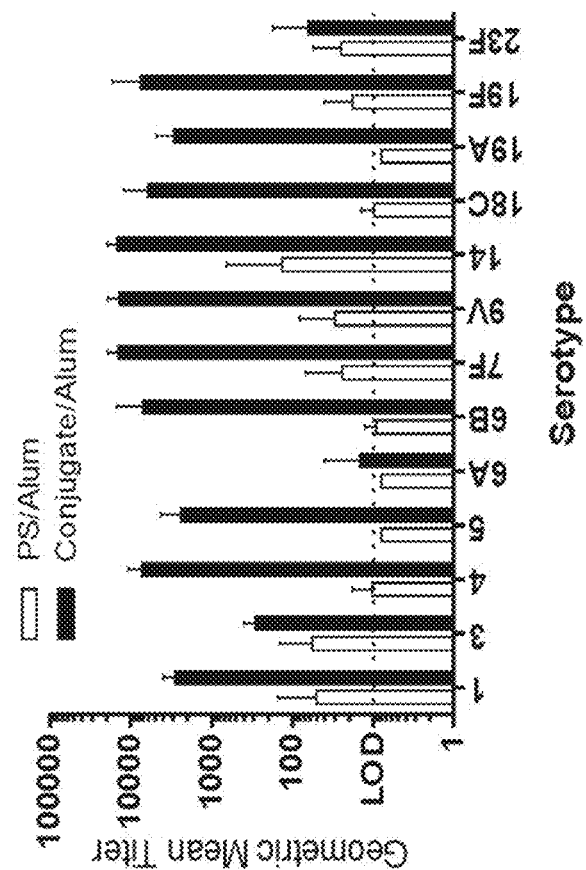
FIG. 3 shows opsonophagocytic (OPA) activity (GMT) following administration of monovalent pneumococcal polysaccharide-eCRM conjugates in mice. Serotypes are shown on the X-axis. White bars are adjuvanted polysaccharides, whereas black bars are adjuvanted conjugates.
Figure 4:
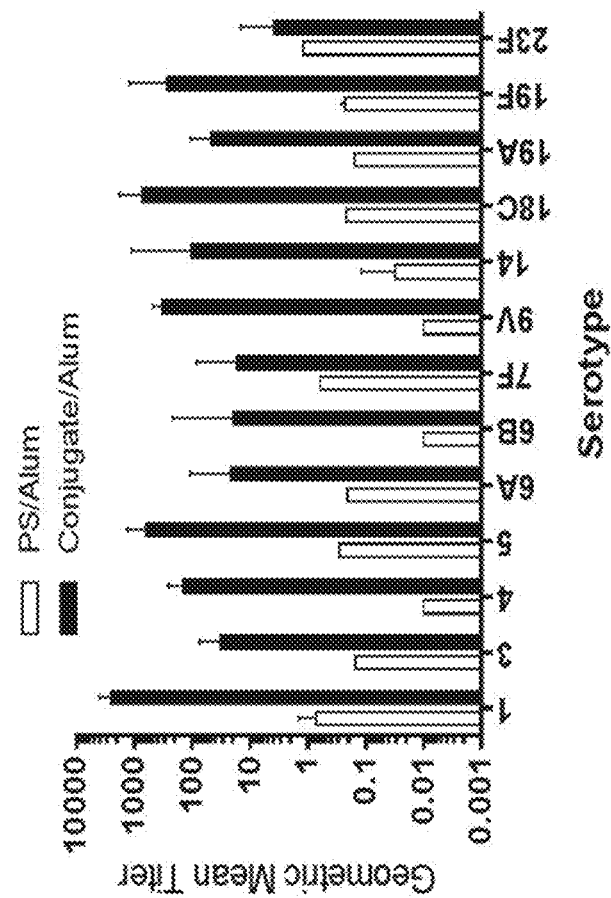
FIG. 4 shows IgG responses (GMT) following administration of monovalent pneumococcal polysaccharide-eCRM conjugates in mice. Serotypes are shown on the X-axis. White bars are adjuvanted but unconjugated polysaccharides; black bars are adjuvanted conjugates.

Experiments were conducted to determine the total IgG and functional OPA antibody responses in mice or rabbits following administration of a variety of monovalent pneumococcal polysaccharide-eCRM conjugates produced according to the present disclosure. Opsono-phagocytic activity (OPA) assays were used to measure functional antibodies in murine sera specific for various *S. pneumonia* serotypes. OPA measurements were based on Moon H. Nahm & Robert L. Burton, "Protocol for opsonophagocytic killing assay for antibodies against Group B *Streptococcus* (UAB GBS OPA)," Version B.04, March 2016 (Original Version A.01 posted September 2011) (www.vaccine.uab.edu/uploads/mdocs/UAB-GBS-OPA.pdf) and "Protocol for multiplexed opsonophagocytic killing assay (UAB-MOPA) for antibodies against *Streptococcus pneumoniae*" Version E.02, December 2014 (www.vaccine.uab.edu/uploads/mdocs/UAB-MOPA.pdj). FIG. 3 shows opsonophagocytic (OPA) activity following administration of monovalent pneumococcal polysaccharide-eCRM conjugates in mice. The total polysaccharide binding antibody (IgG) specific to each pneumococcal polysaccharide was also measured according to the methods described in Yu et al., "Development of an Automated and Multiplexed Serotyping Assay for *Streptococcus pneumoniae*," *Clin Vaccine Immunol.* 2011, 18(11): 1900-7. FIG. 4 shows IgG responses following administration of monovalent pneumococcal polysaccharide-eCRM conjugates in mice.

As summarized in the below tables, every conjugate tested elicited IgG and functional antibody responses in mice or rabbits that were comparable or superior to the OPA and IgG results shown in FIG. 3 and FIG. 4.

| PS Types | Immunogenicity in Mice IgG | Immunogenicity in Mice OPA | PS Types | Immunogenicity in Mice or Rabbits IgG | Immunogenicity in Mice or Rabbits OPA |
|---|---|---|---|---|---|
| 1 | ✓ | ✓ | 22F | ✓ | ✓ |
| 3 | ✓ | ✓ | 33F | ✓ | ✓ |
| 4 | ✓ | ✓ | 15B | ✓ | ✓ |
| 5 | ✓ | ✓ | 2 | ✓ | ✓ |
| 6A | ✓ | ✓ | 9N | ✓ | ✓ |
| 6B | ✓ | ✓ | 11A | ✓ | ✓ |
| 7F | ✓ | ✓ | 12F | ✓ | ✓ |
| 9V | ✓ | ✓ | 20 | ✓ | ✓ |
| 14 | ✓ | ✓ | 10A | ✓ | ✓ |
| 18C | ✓ | ✓ | 8 | ✓ | ✓ |
| 19A | ✓ | ✓ | 17F | ✓ | ✓ |
| 19F | ✓ | ✓ | | | |
| 23F | ✓ | ✓ | | | |

A combination of conjugates for each of 24 pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F was prepared using CRM197 derivative SEQ ID NO:9 as the carrier in each conjugate. The immunogenicity of this composition was tested using a 3-dose schedule in groups of 7 rabbits. It was also compared to the conjugated 13-valent Prevnar™ vaccine and to the unconjugated 23-valent Pneumovax™ vaccine, to which unconjugated serotype 6A polysaccharide had been added to assist the comparison. The three compositions had equivalent polysaccharide doses per serotype (except for 6B, where Prevnar™ includes a double dosage), which involved diluting the Prevnar™ and Pneumovax™. All three compositions included 6014 aluminum phosphate adjuvant per dose, which involved adding the adjuvant to Pneumovax™.

The conjugation techniques disclosed herein led to a composition with a lower amount of CRM197 carrier than in the approved Prevnar-13™ vaccine, while also including capsular polysaccharides from 11 additional serotypes. The overall weight ratio of capsular polysaccharide to CRM197 in the conjugated 24-valent composition was about double that seen in 13-valent Prevnar™.

Figure 5:
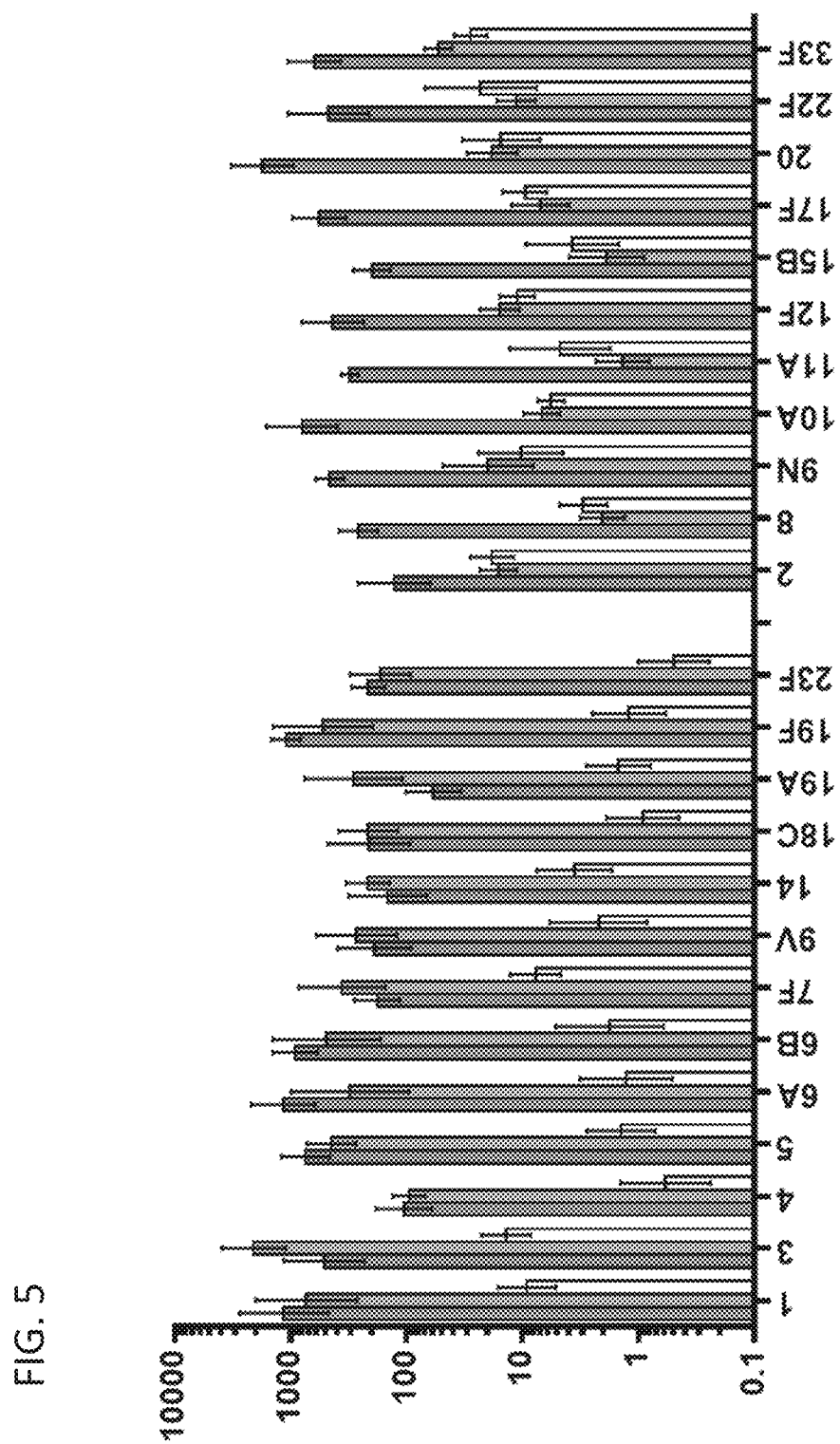
FIG. 5 shows IgG responses (GMT) following administration of multivalent pneumococcal vaccines in rabbits. Each serotype (X-axis) has data for a 24-valent conjugate vaccine of the invention (left), Prevnar-13™ (middle), and a 24-valent unconjugated vaccine (right). The data are means +/−95% confidence interval.
Figure 6:
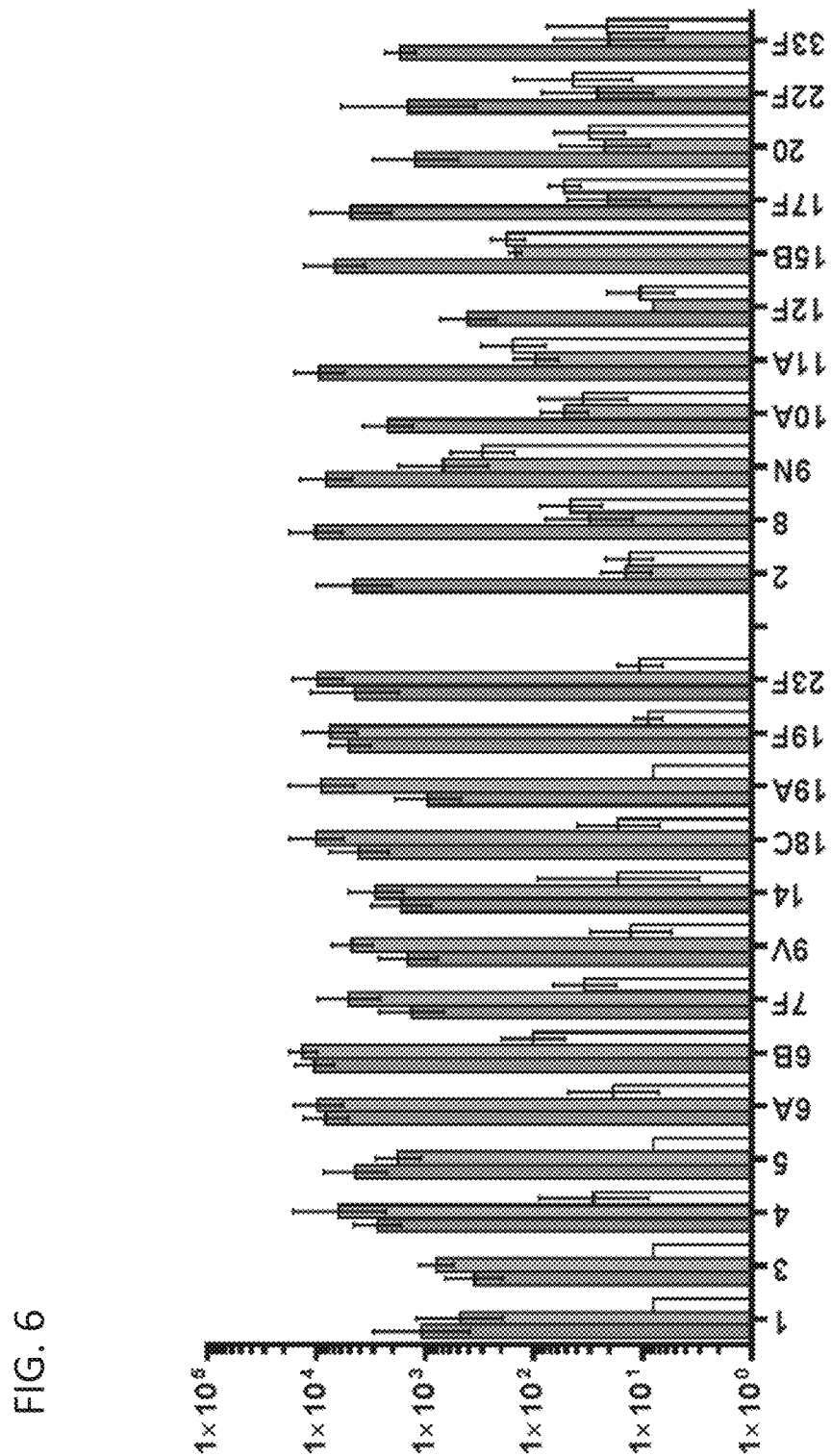
FIG. 6 is similar to FIG. 5 but shows OPA responses (GMT).

Responses after the third dose are shown in FIG. 5 (IgG responses) and FIG. 6 (OPA responses). As expected, responses using the two conjugated vaccines were much greater than with the unconjugated vaccine. Moreover, IgG and OPA responses using the 24-valent vaccine were comparable to those achieved using Prevnar-13™ in the serotypes covered by the approved vaccine, but in addition were superior against the 11 serotypes which are not included in Prevnar-13. Surprisingly, there was no evidence of carrier induced epitopic suppression.

Example 49: Pneumococcal Serotype PS3—HiD Conjugates

Figure 7:
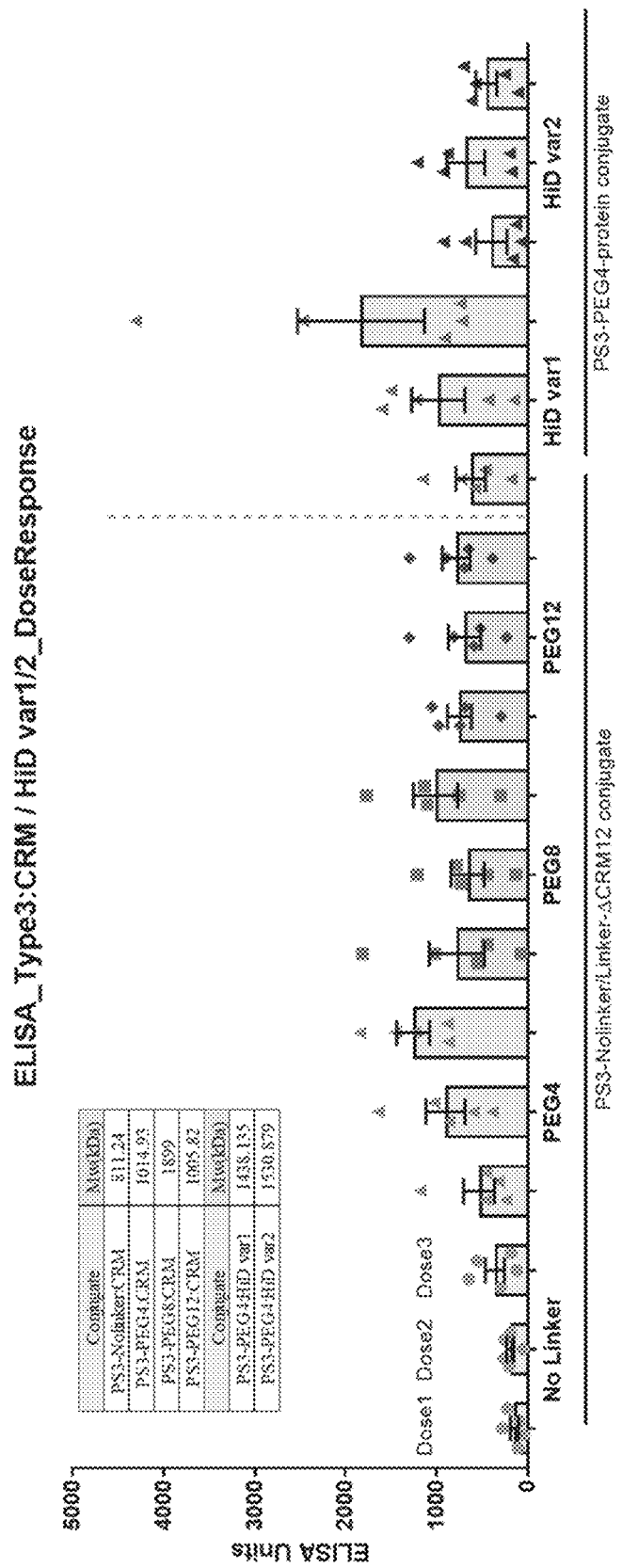
FIG. 7 shows the ELISA results of immunogenicity assays obtained comparing CRM197 and *Haemophilus influenzae* protein D conjugates of Pneumococcal polysaccharide Serotype 3.

The procedure of Example 48 was followed to prepare and evaluate conjugates of native pneumococcal polysaccharide Serotype 3 (as in Example 10, PS3 dry weight purity approximately 86%, assayed via the anthrone test; mol. wt. 360 g/mol) and H. influenza protein D (HiD). Identical conjugates were prepared, for purposes of comparison, with eCRM. The use of linkers was also evaluated (PEG4, PEG8, PEG12, or no linker). The results of an ELISA used to measure antibody response are set forth in FIG. 7.

Example 50: Preparation of a Conjugate Vaccine for Periodontitis

A vaccine against *Porphyromonas gingivalis* is prepared by conjugating capsular polysaccharides (CPS) from *P. gingivalis* serotypes K1, K2, K3, K4, K5 and/or K6 to an eCRM carrier protein as follows.

*P. gingivalis* is grown and handled by any suitable method. See, e.g., Huang et al., *Mol Oral Microbiol.* 30:438-50 (2015). CPS are purified by any method of choice. See, e.g., Gonzalez et al., *Infect. Immun.* 71:2283-2287 (2003); Schifferle et al., *J. Immunol.* 143:3035-3042 (1989); Pantosti et al., *Infect. Immun.* 59:2075-2082 (1991). Briefly, *P. gingivalis* is collected by centrifugation, rinsed with saline, suspended in water, and subjected to hot phenol-water extraction. The aqueous phase is collected, extracted with ether, and dialyzed against sterile filtered water. The aqueous material is adjusted to pH 5.5 and digested overnight with a nuclease cocktail consisting of DNase I and RNase A (Sigma). The pH is adjusted to neutrality and proteinase K (1 mg/ml; Sigma) is added to the sample and incubated overnight at 37° C. with gentle shaking. Then a second proteinase K digestion is performed and the resulting carbohydrate concentrated using a 10,000-molecular-weight cutoff membrane. CPS is precipitated with cold ethanol, suspended in deoxycholate buffer, and isolated using an S-400 gel filtration column (Pharmacia, Uppsala, Sweden). Fractions containing high-molecular-mass CPS (via SEC-MALS) are pooled, and fractions that contain LPS are discarded. The pooled fractions are concentrated, precipitated, dialyzed, and lyophilized.

To a buffered polysaccharide solution is added X molar equivalents (to polysaccharide repeating unit; X determined by screening) of 1-cyano-4-dimethylaminopyridinium tetrafluoroborate (CDAP; from 100 mg/mL solution in acetonitrile) with vigorous stirring. Five minutes after addition of CDAP, 0.5 molar equivalents of the dibenzocyclooctyne-amine linker (from DMSO stock solution) is added. After an additional, hour glycine is added to quench any unreacted cyanate esters. Alternatively, CPS may be modified using periodate or TEMPO/NCS chemistry. The derivatized polysaccharide is then purified via dialysis or UF/DF. The polysaccharide concentration is measured using an anthrone colorimetric assay, and dibenzocyclooctyne concentration is measured using absorbance at 309 nm. These two values can be combined to give an estimate of the percentage of polysaccharide derivatized with a dibenzycyclooctyne functional group.

The conjugate is prepared by mixing the derivatized polysaccharide with an eCRM protein of choice, such as those in Table 3. After 18 h incubation, one molar equivalent of sodium azide is added to quench any unreacted dibenzocyclooctyne functional groups. The conjugate is then purified via dialysis or UF/DF to remove unreacted eCRM protein. The conjugate is then analyzed to determine polysaccharide concentration (colorimetric), protein concentration (colorimetric) and the free/unconjugated saccharide percentage calculated. The molecular weight is measured using SEC-MALS.

Polysaccharide:protein conjugates are precipitated by the addition of 1% deoxycholate solution (pH 6.8) and incubation on ice for 30 minutes. Following incubation, 1M HCl is added and the mixture is centrifuged for 20 minutes at 10,000 rpm. The remaining supernatant contains unconjugated polysaccharide. To determine the polysaccharide concentration, anthrone dissolved in sulfuric acid is added to the samples and heated to 95° C. for 10 minutes. The mixture is cooled and the absorbance at 620 nm is measured. The concentration is calculated using a standard curve of the monosaccharide components of the polysaccharide.

Example 51: Periodate Activation of Pneumococcal Polysaccharide Serotypes 7F and 14

Table 4 provides information regarding the activation conditions and product obtained upon activation of Pneumococcal Polysaccharide Serotypes 7F and 14 with sodium periodate (protocol as described above unless modified as indicated in the table):

TABLE 4

| Serotype: | 7F | 14 |
| --- | --- | --- |
| Activation type | Periodate/reductive amination | Periodate/reductive amination |
| Mechanical sizing | No | No |
| Scale | 140 mg | 143 mg |
| Mol. eq. NaIO$_4$ | 0.1 eq | 0.15 eq |
| Oxidation % (determined via BCA assay) | 8.75% | 12.1% |
| Oxidation yield | 99% | 97% |
| DBCO reaction conditions | 3.0 mg/mL; 100 mM sodium phosphate buffer, pH 5.7; 3 eq. DBCO; 8 eq. NaCNBH$_3$; 10% DMSO; 16 hr | 2.0 mg/mL; 100 mM sodium phosphate buffer, pH 6.4; 2 eq. DBCO; 6 eq. NaCNBH$_3$; 10% DMSO; 15 hr |
| DBCO% | 4.1% | 5.1% |
| DBCO-PS yield | 85% | 86% |
| DBCO-PS size | 443 kD | 820 kD |

TABLE 4-continued

| Serotype: | 7F | 14 |
|---|---|---|
| Purification conditions | Tangential flow filtration (TFF), 100 kDa PES membrane, slice 50 | Tangential flow filtration (TFF), 100 kDa PES membrane, slice 50 |
| Filtration after purification | Yes, 0.22 μm after TFF | No |
| Buffer for purification | 1) 10 DV saline; 2) 10 DV H$_2$O | 1) 10 DV saline; 2) 10 DV H$_2$O |
| Storage matrix/condition | H$_2$O | H$_2$O |

Example 52: CDAP Activation of Pneumococcal Serotypes 3, 4, 17F, 22F, 6B, and 9N Table 54 provides information regarding the conditions and product obtained upon CDAP activation of the Pneumococcal serotypes activated. The CDAP protocol set forth above was followed unless modified as indicated in the table.

TABLE 5

| Serotype | Size | CDAP eq | DBCO eq | Buffer pH | ACT Time (min) | PS Conc (mg/mL) | Calib. PS-DB % | Yield % | % PS-DB | % free DB | PS-DB Peak Area | Mw (kDa) |
|---|---|---|---|---|---|---|---|---|---|---|---|---|
| 3 | Low | 0.5 | 0.25 | 9.2 | 3 | 0.73 | 1.2 | 101% | 85.4% | 0.0% | 543 | 210 |
| 3 | High | 0.5 | 1.5 | 10 | 3 | 0.81 | 2.1 | 112% | 94.9% | 0.0% | 520 | 731.65 |
| 3 | High | 5 | 0.75 | 8 | 3 | 0.73 | 2.9 | 101% | 100.0% | 0.0% | 93 | 805 |
| 3 | Low | 5 | 1.5 | 10 | 3 | 0.08 | 0.0 | 11% | 0.0% | 30.6% | 0 | 231.7 |
| 3 | Low | 2.3 | 1.25 | 8.4 | 5 | 0.44 | 7.2 | 61% | 78.5% | 0.0% | 186 | 283 |
| 3 | Low | 2.3 | 1.25 | 8.4 | 7 | 0.48 | 5.9 | 67% | 76.5% | 0.0% | 189 | 276 |
| 3 | High | 1.4 | 0.25 | 8.8 | 9 | 0.66 | 4.0 | 92% | 100.0% | 0.0% | 403 | 763.2 |
| 3 | High | 4.1 | 0.5 | 10 | 9 | 0.34 | 0.0 | 47% | 0.0% | 100.0% | 0 | 1046.1 |
| 3 | High | 0.5 | 1.50 | 8 | 13 | 0.58 | 1.5 | 80% | 67.7% | 11.4% | 315 | 730.95 |
| 3 | Low | 0.5 | 1.00 | 10 | 13 | 0.81 | 1.2 | 113% | 95.8% | 0.0% | 550 | 209.25 |
| 3 | Low | 5 | 0.25 | 8 | 13 | 0.31 | 4.9 | 42% | 82.0% | 0.0% | 306 | 239 |
| 3 | High | 5 | 1.5 | 9.2 | 13 | 0.06 | 0.0 | 8% | 0.0% | 67.3% | 0 | 1177.65 |
| 4 | Low | 2.3 | 1.00 | 8.8 | 3 | 0.70 | 8.9 | 41% | 97.4% | 0.0% | 1252 | 243 |
| 4 | Low | 2.3 | 1.00 | 8.8 | 3 | 1.08 | 6.0 | 64% | 95.7% | 1.3% | 1541 | 272.5 |
| 4 | High | 3.2 | 0.75 | 10 | 3 | 0.57 | 14.8 | 34% | 94.6% | 0.0% | 1525 | 692 |
| 4 | Low | 5 | 0.25 | 9.6 | 3 | 1.05 | 10.9 | 62% | 95.8% | 0.0% | 2471 | 324 |
| 4 | Low | 0.5 | 0.25 | 10 | 5 | 1.22 | 0.9 | 72% | 85.7% | 0.0% | 336 | 206 |
| 4 | High | 0.5 | 1.50 | 8 | 7 | 0.98 | 1.4 | 58% | 95.4% | 0.0% | 291 | 606.65 |
| 4 | High | 5 | 0.25 | 8 | 7 | 1.06 | 2.4 | 63% | 80.9% | 0.0% | 533 | 655.05 |
| 4 | Low | 4.1 | 1.50 | 10 | 11 | 1.20 | 11.9 | 71% | 93.0% | 0.8% | 3309 | 285 |
| 4 | High | 1.4 | 0.50 | 9.2 | 13 | 0.42 | 4.9 | 25% | 100.0% | 0.0% | 473 | 633 |
| 4 | Low | 3.2 | 0.75 | 8 | 13 | 0.90 | 4.5 | 53% | 94.6% | 0.0% | 967 | 231 |
| 4 | High | 5 | 1.50 | 9.2 | 13 | 0.95 | 14.1 | 56% | 99.3% | 0.0% | 3337 | 584 |
| 17F | High | 0.5 | 0.25 | 8 | 3 | 1.45 | 0.3 | 60% | 91.0% | 0.0% | 213 | 1100.15 |
| 17F | Low | 0.5 | 1.25 | 8 | 3 | 1.64 | 0.8 | 68% | 100.0% | 0.0% | 230 | 290 |
| 17F | Low | 2.3 | 0.25 | 10 | 3 | 1.63 | 3.3 | 68% | 96.7% | 0.0% | 1007 | 306.05 |
| 17F | High | 5 | 1.25 | 9.2 | 3 | 1.59 | 9.7 | 66% | 100.0% | 0.0% | 2047 | 1215.3 |
| 17F | Low | 5 | 0.25 | 8 | 5 | 1.50 | 2.7 | 62% | 94.5% | 0.0% | 599 | 289 |
| 17F | High | 0.5 | 1.50 | 10 | 9 | 1.50 | 0.3 | 62% | 78.5% | 0.0% | 135 | 1106.55 |
| 17F | Low | 0.5 | 0.50 | 8.8 | 13 | 1.49 | 0.4 | 62% | 63.6% | 0.0% | 166 | 298.8 |
| 17F | High | 3.2 | 1.50 | 8 | 13 | 1.56 | 3.8 | 65% | 100.0% | 0.0% | 1239 | 1150 |
| 17F | High | 5 | 0.25 | 10 | 13 | 1.46 | 6.2 | 61% | 98.9% | 0.0% | 1317 | 1154.8 |
| 17F | Low | 5 | 1.50 | 10 | 13 | 1.43 | 9.5 | 60% | 77.0% | 0.8% | 2399 | 319.15 |
| 22F | High | 0.5 | 0.25 | 10 | 3 | 1.24 | 0.8 | 62% | 100.0% | 0.0% | 273 | 1014 |
| 22F | Low | 3.2 | 0.25 | 8 | 3 | 1.74 | 0.8 | 87% | 63.8% | 0.0% | 496 | 165.6 |
| 22F | High | 4.1 | 1.50 | 8.4 | 3 | 1.05 | 5.4 | 53% | 93.2% | 0.0% | 1038 | 1132 |
| 22F | High | 4.1 | 1.50 | 8.4 | 3 | 1.28 | 5.3 | 64% | 95.2% | 0.0% | 1317 | 1173.65 |
| 22F | Low | 5 | 1.50 | 9.2 | 5 | 1.31 | 14.5 | 66% | 97.2% | 0.0% | 3374 | 187 |
| 22F | Low | 5 | 0.75 | 10 | 5 | 1.11 | 13.7 | 56% | 93.5% | 0.0% | 2437 | 189 |
| 22F | High | 0.5 | 1.00 | 8 | 11 | 1.36 | 0.7 | 68% | 80.9% | 0.0% | 195 | 1096.2 |
| 22F | High | 5 | 0.25 | 8.8 | 11 | 1.31 | 3.3 | 66% | 98.4% | 0.0% | 791 | 1219 |
| 22F | Low | 1.4 | 0.25 | 9.6 | 13 | 1.62 | 2.1 | 81% | 94.5% | 0.0% | 650 | 169 |
| 22F | High | 2.3 | 1.50 | 10 | 13 | 1.19 | 7.5 | 60% | 97.1% | 0.0% | 1615 | 1096 |
| 22F | Low | 5 | 1.50 | 8 | 13 | 0.24 | 101.9 | 12% | 93.0% | 0.0% | 3483 | 304 |
| 6B | Low | 0.5 | 0.25 | 8 | 3 | 1.10 | 0.0 | 78% | 83.2% | 0.0% | 168 | 387.1 |
| 6B | Low | 4.1 | 1.50 | 10 | 3 | 0.78 | 5.1 | 55% | 98.3% | 0.0% | 743 | 363 |
| 6B | High | 5 | 0.25 | 10 | 3 | 0.80 | 3.5 | 57% | 84.6% | 0.0% | 467 | 1497.2 |
| 6B | High | 0.5 | 1.00 | 9.2 | 5 | 0.84 | 0.3 | 59% | 89.7% | 0.0% | 209 | 1517 |
| 6B | Low | 2.3 | 0.50 | 10 | 5 | 0.67 | 1.7 | 48% | 100.0% | 0.0% | 563 | 362 |
| 6B | High | 3.2 | 1.50 | 8 | 5 | 0.75 | 1.0 | 53% | 7.6% | 62.2% | 212 | 1673.9 |

TABLE 5-continued

| Serotype | Size | CDAP eq | DBCO eq | Buffer pH | ACT Time (min) | PS Conc (mg/mL) | Calib. PS-DB % | Yield % | % PS-DB | % free DB | PS-DB Peak Area | Mw (kDa) |
|---|---|---|---|---|---|---|---|---|---|---|---|---|
| 6B | Low | 2.3 | 0.50 | 10 | 9 | 0.87 | 1.9 | 62% | 96.4% | 0.0% | 399 | 357.1 |
| 6B | Low | 5 | 0.75 | 8.4 | 11 | 0.87 | 2.2 | 62% | 93.7% | 0.0% | 476 | 378.6 |
| 6B | Low | 5 | 0.75 | 8.4 | 11 | 0.80 | 2.3 | 57% | 93.2% | 0.0% | 412 | 388.7 |
| 6B | Low | 0.5 | 1.50 | 8 | 13 | 0.94 | 0.8 | 67% | 73.3% | 26.7% | 362 | 400.1 |
| 6B | High | 2.3 | 0.25 | 8 | 13 | 0.68 | 0.4 | 48% | 88.3% | 0.0% | 219 | 1737 |
| 6B | High | 5 | 1.50 | 10 | 13 | 0.80 | 5.3 | 57% | 100.0% | 0.0% | 919 | 1549 |
| 9N | High | 0.5 | 1.5 | 8 | 3 | 1.96 | 2.0 | 105% | 95.4% | 4.6% | 835 | 1039.8 |
| 9N | Low | 0.5 | 1.00 | 10 | 3 | 1.76 | 1.5 | 95% | 84.2% | 0.0% | 640 | 254.35 |
| 9N | High | 3.2 | 0.25 | 8.8 | 3 | 1.75 | 4.5 | 94% | 64.4% | 0.0% | 882 | 1150 |
| 9N | Low | 5 | 1.50 | 8 | 3 | 1.83 | 4.8 | 99% | 100.0% | 0.0% | 2072 | 293 |
| 9N | Low | 5 | 1.5 | 8 | 3 | 1.44 | 6.8 | 78% | 94.4% | 0.0% | 1604 | 283.1 |
| 9N | High | 5 | 1.50 | 10 | 7 | 1.75 | 2.7 | 94% | 12.9% | 4.6% | 287 | 830.4 |
| 9N | Low | 0.5 | 0.25 | 8 | 9 | 2.52 | 0.8 | 136% | 94.0% | 0.0% | 551 | 249.2 |
| 9N | Low | 3.2 | 1.00 | 9.2 | 9 | 1.06 | 23.9 | 57% | 98.7% | 0.0% | 4969 | 281 |
| 9N | Low | 3.2 | 1.00 | 9.2 | 9 | 1.71 | 14.4 | 92% | 95.4% | 0.9% | 4708 | 290.6 |
| 9N | High | 0.5 | 0.25 | 10 | 13 | 1.38 | 0.9 | 74% | 94.8% | 0.0% | 457 | 1001 |
| 9N | Low | 1.4 | 1.50 | 9.2 | 13 | 0.99 | 9.4 | 53% | 90.0% | 0.0% | 1783 | 270 |
| 9N | Low | 1.4 | 1.50 | 9.2 | 13 | 2.41 | 5.2 | 130% | 100.0% | 0.0% | 2428 | 268 |
| 9N | High | 5 | 0.75 | 8 | 13 | 2.16 | 4.4 | 116% | 98.4% | 0.0% | 2166 | 1149 |
| 9N | Low | 5 | 0.25 | 10 | 13 | 5.03 | 1.2 | 271% | 77.8% | 2.1% | 1275 | 166 |

Sizing for the activated serotypes is given in Table 6, for both periodate and CDAP:

TABLE 6

| | | Periodate Sizing | | CDAP Sizing | | Periodate Sizing | | CDAP Sizing | |
|---|---|---|---|---|---|---|---|---|---|
| Serotype | Native ATCC Mw (kDa) | +1 Target Size (kDa) | −1 Target Size (kDa) | +1 Target Size (kDa) | −1 Target Size (kDa) | +1 Actual Size (kDa) | −1 Actual Size (kDa) | +1 Actual Size (kDa) | −1 Actual Size (kDa) |
| 1 | 699 | | | | | | | | |
| 2 | 1893 | 1000 | 500 | 500 | 250 | 803 | 518 | 518 | 316 |
| 3 | 926 | | | | | | | | |
| 4 | 802 | | | | | | | | |
| 5 | 404 | | | | | | | | |
| 6A | 583 | Native | 250 | Native | 250 | | | | |
| 6B | 1826 | 1000 | 500 | 500 | 250 | 1025 | 543 | 543 | 288 |
| 7F | 956 | | | | | | | | |
| 8 | 764 | Native | 350 | 350 | 180 | | | | |
| 9N | 1114 | Native | 500 | 500 | 250 | 1090 | 473 | 473 | 314 |
| 9V | 750 | Native | 400 | 400 | 200 | Native | 369 | 369 | 171 |
| 10A | 676 | Native | 250 | Native | 250 | | | | |
| 11A | 1959 | 500 | 250 | 500 | 250 | | | | |
| 12F | 497 | Native | 200 | Native | 200 | Native | 189 | Native | 189 |
| 14 | 669 | | | | | | | | |
| 15B | 1192 | 500 | 250 | 500 | 250 | 596 | 283 | 596 | 283 |
| 17F | 1106 | Native | 500 | Native | 500 | | | | |
| 18C | 847 | 400 | 200 | 400 | 200 | 345 | 251 | 345 | 251 |
| 19A | 269 | Native | 125 | Native | 125 | 270 | 175 | 270 | 175 |
| 19F | 334 | Native | 150 | Native | 150 | 330 | 186 | 330 | 186 |
| 20 | 700 | Native | 400 | 400 | 200 | | | | |
| 22F | 1264 | Native | 500 | 500 | 200 | Native | 431 | 431 | 242 |
| 23F | 1058 | Native | 500 | 500 | 200 | 1060 | 501 | 501 | 248 |
| 33F | 1705 | 1000 | 500 | 500 | 250 | 651 | 355 | 355 | 217 |

Example 53: Conjugation of Activated Antigens to the Polypeptide Carrier

The general conjugation protocol set forth above is used to prepare conjugates of activated antigens to a polypeptide carrier. The factors varied during conjugate preparation are identified in Table 7, with additional detail regarding the experiments set forth in Table 8:

TABLE 7

| Serotype | PS Conc Low | PS Conc High | Input ratio Low | Input ratio High | PS Size Low | PS Size High | NaCl Low | NaCl High | DMSO Low | DMSO High |
|---|---|---|---|---|---|---|---|---|---|---|
| 2 | 0.5 | 3.5 | 1 | 2 | −1 | 1 | 0 | 300 | 0 | 15 |
| 6A | 0.5 | 3.5 | 1 | 2 | −1 | 1 | 0 | 300 | 0 | 15 |
| 6B | 0.5 | 3.5 | 1 | 2 | −1 | 1 | 0 | 300 | 0 | 15 |
| 8 | 0.5 | 2 | 1 | 2 | −1 | 1 | 0 | 300 | 0 | 15 |
| 9N | 0.5 | 3.5 | 1 | 2 | −1 | 1 | 0 | 300 | 0 | 15 |
| 9V | 0.5 | 3.5 | 1 | 2 | −1 | 1 | 0 | 300 | 0 | 15 |
| 10A | 0.5 | 2.5 | 1 | 2 | −1 | 1 | 0 | 300 | 0 | 15 |
| 11A | 0.5 | 3.5 | 1 | 2 | −1 | 1 | 0 | 300 | 0 | 15 |
| 12F | 0.25 | 2 | 1 | 2 | −1 | 1 | 0 | 300 | 0 | 15 |
| 15B | 0.5 | 3.5 | 1 | 2 | −1 | 1 | 0 | 300 | 0 | 15 |
| 17F | 0.25 | 1.5 | 1 | 2 | −1 | 1 | 0 | 300 | 0 | 15 |
| 18C | 0.5 | 2.5 | 1 | 2 | −1 | 1 | 0 | 300 | 0 | 15 |
| 19A | 1 | 4 | 1 | 2 | −1 | 1 | 0 | 300 | 0 | 15 |
| 19F | 1 | 4 | 1 | 2 | −1 | 1 | 0 | 300 | 0 | 15 |
| 20 | 0.5 | 3.5 | 1 | 2 | −1 | 1 | 0 | 300 | 0 | 15 |
| 22F | 0.5 | 3.5 | 1 | 2.5 | −1 | 1 | 0 | 300 | 0 | 15 |
| 23F | 0.5 | 3.5 | 1 | 2 | −1 | 1 | 0 | 300 | 0 | 15 |
| 33F | 0.5 | 3.5 | 1 | 2 | −1 | 1 | 0 | 300 | 0 | 15 |
| Factor | Units | | | | | | | | | |
| PS Conc | mg/mL | | | | | | | | | |
| Input ratio | PS conc/CRM conc | | | | | | | | | |
| PS size | Hi/Lo | | | | | | | | | |
| NaCl | mM | | | | | | | | | |
| DMSO | v/v % | | | | | | | | | |

TABLE 8

| Factor Serotype | PS Conc (mg/mL) | Input ratio (PS:CRM, w:w) | Factor PS Size (High or Low) | Factor NaCl (mM) | Factor DMSO (v/v %) |
|---|---|---|---|---|---|
| 2 | 2.4 | 1.6 | −1 | 240 | 15 |
| 2 | 0.5 | 2.0 | −1 | 300 | 15 |
| 2 | 0.5 | 1.3 | 1 | 60 | 0 |
| 2 | 2.2 | 1.0 | 1 | 300 | 0 |
| 2 | 2.4 | 2.0 | 1 | 0 | 3 |
| 2 | 1.5 | 1.9 | −1 | 240 | 3 |
| 2 | 1.5 | 1.9 | −1 | 240 | 3 |
| 2 | 2.3 | 1.0 | −1 | 0 | 3 |
| 2 | 2.4 | 1.6 | −1 | 240 | 15 |
| 2 | 1.5 | 1.1 | 1 | 60 | 15 |
| 6A | 1.5 | 1.9 | −1 | 60 | 3 |
| 6A | 1.5 | 2.0 | 1 | 300 | 15 |
| 6A | 2.5 | 2.0 | −1 | 0 | 15 |
| 6A | 2.5 | 1.0 | −1 | 0 | 0 |
| 6A | 2.1 | 1.6 | 1 | 180 | 6 |
| 6A | 1.5 | 1.0 | 1 | 300 | 0 |
| 6A | 1.5 | 1.0 | 1 | 0 | 15 |
| 6A | 2.5 | 2.0 | −1 | 300 | 0 |
| 6A | 2.0 | 1.2 | −1 | 240 | 12 |
| 6A | 3.5 | 1.2 | 1 | 240 | 12 |
| 6B | 2.5 | 1.5 | 1 | 0 | 0 |
| 6B | 2.5 | 1.0 | −1 | 60 | 15 |
| 6B | 2.4 | 2.0 | −1 | 240 | 3 |
| 6B | 2.1 | 1.0 | 1 | 300 | 9 |
| 6B | 2.5 | 1.5 | 1 | 0 | 0 |
| 6B | 0.5 | 1.9 | 1 | 120 | 6 |
| 6B | 1.5 | 1.0 | −1 | 60 | 0 |
| 6B | 1.5 | 1.6 | −1 | 300 | 15 |
| 6B | 1.7 | 2.0 | 1 | 60 | 12 |
| 6B | 3.5 | 2.0 | 1 | 180 | 12 |
| 8 | 1.5 | 1.0 | −1 | 240 | 12 |
| 8 | 1.3 | 1.7 | 0 | 0 | 0 |
| 8 | 0.5 | 1.7 | −1 | 120 | 3 |
| 8 | 1.1 | 1.3 | 1 | 240 | 0 |
| 8 | 2.0 | 1.6 | 1 | 180 | 3 |
| 8 | 1.0 | 2.0 | −1 | 240 | 12 |
| 8 | 1.0 | 1.0 | 1 | 0 | 15 |
| 8 | 1.5 | 2.0 | 1 | 120 | 12 |
| 8 | 2.0 | 1.5 | −1 | 180 | 6 |
| 8 | 2.0 | 1.5 | 1 | 180 | 6 |
| 9N | 2.5 | 2.0 | −1 | 300 | 6 |
| 9N | 1.9 | 1.5 | 1 | 300 | 0 |
| 9N | 0.5 | 2.0 | −1 | 240 | 15 |
| 9N | 1.5 | 1.0 | −1 | 300 | 12 |
| 9N | 1.5 | 2.0 | 1 | 0 | 9 |
| 9N | 1.5 | 1.6 | −1 | 120 | 0 |
| 9N | 2.5 | 1.0 | 1 | 0 | 3 |
| 9N | 2.1 | 1.4 | −1 | 0 | 15 |
| 9N | 2.5 | 1.5 | 1 | 180 | 15 |
| 9N | 0.5 | 1.0 | 1 | 0 | 3 |
| 9V | 2.5 | 1.0 | −1 | 0 | 9 |
| 9V | 2.5 | 2.0 | 1 | 60 | 0 |
| 9V | 1.5 | 2.0 | −1 | 0 | 9 |
| 9V | 1.9 | 1.5 | 1 | 300 | 6 |
| 9V | 3.5 | 1.3 | 1 | 180 | 6 |
| 9V | 0.5 | 1.6 | 1 | 180 | 6 |
| 9V | 1.6 | 1.0 | −1 | 240 | 0 |
| 9V | 2.5 | 2.0 | −1 | 300 | 15 |
| 9V | 1.5 | 1.0 | 1 | 60 | 15 |
| 9V | 2.5 | 1.0 | −1 | 0 | 9 |
| 10A | 3.5 | 1.7 | 1 | 180 | 6 |
| 10A | 2.5 | 1.0 | −1 | 180 | 6 |
| 10A | 1.5 | 1.0 | 1 | 0 | 0 |
| 10A | 1.9 | 1.8 | −1 | 0 | 15 |
| 10A | 1.5 | 2.0 | 1 | 180 | 9 |
| 10A | 2.5 | 2.0 | 1 | 0 | 0 |
| 10A | 1.9 | 1.8 | −1 | 300 | 0 |
| 10A | 2.2 | 1.2 | 1 | 300 | 15 |
| 10A | 0.5 | 1.4 | −1 | 240 | 12 |
| 10A | 1.5 | 1.0 | 1 | 0 | 0 |
| 11A | 0.5 | 1.1 | −1 | 0 | 3 |
| 11A | 3.5 | 2.0 | 1 | 300 | 15 |
| 11A | 1.5 | 1.6 | −1 | 180 | 12 |
| 11A | 1.5 | 1.0 | 1 | 300 | 15 |
| 11A | 2.5 | 2.0 | −1 | 0 | 0 |
| 11A | 2.5 | 1.5 | 1 | 180 | 6 |
| 11A | 2.2 | 1.0 | −1 | 300 | 0 |
| 11A | 1.5 | 2.0 | 1 | 300 | 0 |
| 11A | 1.5 | 1.0 | 1 | 0 | 0 |
| 11A | 2.5 | 1.0 | −1 | 0 | 15 |
| 11A | 1.9 | 2.0 | 1 | 0 | 15 |
| 12F | 1.1 | 1.6 | 1 | 300 | 9 |
| 12F | 1.4 | 2.0 | 1 | 0 | 0 |
| 12F | 1.4 | 1.0 | −1 | 300 | 0 |

TABLE 8-continued

| Factor Serotype | PS Conc (mg/mL) | Input ratio (PS:CRM, w:w) | Factor PS Size (High or Low) | Factor NaCl (mM) | Factor DMSO (v/v %) |
|---|---|---|---|---|---|
| 12F | 1.0 | 1.5 | −1 | 0 | 9 |
| 12F | 0.3 | 1.9 | 1 | 0 | 15 |
| 12F | 0.8 | 1.0 | 1 | 120 | 0 |
| 12F | 1.4 | 2.0 | −1 | 180 | 15 |
| 12F | 0.8 | 1.0 | −1 | 300 | 15 |
| 12F | 1.4 | 1.0 | 1 | 0 | 15 |
| 12F | 0.8 | 2.0 | −1 | 300 | 0 |
| 15B | 2.5 | 1.2 | −1 | 300 | 0 |
| 15B | 2.5 | 2.0 | 1 | 300 | 0 |
| 15B | 2.5 | 1.7 | 1 | 0 | 15 |
| 15B | 2.1 | 1.0 | 1 | 180 | 9 |
| 15B | 0.5 | 1.9 | −1 | 300 | 0 |
| 15B | 1.5 | 1.5 | 1 | 0 | 0 |
| 15B | 2.0 | 2.0 | −1 | 120 | 6 |
| 15B | 3.5 | 1.1 | 1 | 0 | 15 |
| 15B | 1.5 | 1.7 | 1 | 300 | 15 |
| 15B | 1.5 | 1.0 | −1 | 0 | 15 |
| 17F | 0.7 | 2.0 | 1 | 0 | 0 |
| 17F | 0.7 | 1.0 | −1 | 60 | 6 |
| 17F | 0.3 | 1.1 | −1 | 180 | 15 |
| 17F | 1.1 | 2.0 | −1 | 120 | 0 |
| 17F | 1.5 | 1.7 | 1 | 60 | 3 |
| 17F | 0.7 | 1.9 | 1 | 240 | 12 |
| 17F | 0.9 | 1.0 | 1 | 300 | 0 |
| 17F | 1.1 | 1.0 | −1 | 300 | 15 |
| 17F | 0.7 | 1.9 | 1 | 240 | 12 |
| 17F | 1.1 | 1.4 | 1 | 0 | 15 |
| 18C | 2.5 | 2.0 | −1 | 300 | 0 |
| 18C | 1.8 | 1.3 | −1 | 60 | 0 |
| 18C | 1.3 | 2.0 | 1 | 300 | 0 |
| 18C | 1.3 | 2.0 | 1 | 300 | 0 |
| 18C | 1.2 | 1.2 | −1 | 240 | 15 |
| 18C | 1.2 | 1.0 | 1 | 0 | 3 |
| 18C | 1.6 | 2.0 | 1 | 0 | 15 |
| 18C | 1.8 | 1.1 | 1 | 300 | 12 |
| 18C | 2.5 | 1.4 | 1 | 60 | 15 |
| 18C | 0.5 | 1.9 | 1 | 0 | 15 |
| 19A | 2.0 | 1.0 | −1 | 0 | 0 |
| 19A | 2.0 | 1.4 | −1 | 240 | 15 |
| 19A | 2.5 | 1.1 | 1 | 240 | 0 |
| 19A | 2.5 | 1.1 | 1 | 240 | 0 |
| 19A | 2.9 | 2.0 | −1 | 180 | 0 |
| 19A | 1.0 | 1.7 | 1 | 300 | 6 |
| 19A | 3.0 | 2.0 | 1 | 300 | 15 |
| 19A | 3.0 | 1.0 | −1 | 0 | 15 |
| 19A | 4.0 | 1.4 | −1 | 300 | 6 |
| 19A | 2.1 | 1.9 | 1 | 60 | 9 |
| 19F | 2.4 | 1.2 | 1 | 0 | 15 |
| 19F | 3.0 | 2.0 | −1 | 180 | 15 |
| 19F | 4.0 | 1.0 | −1 | 300 | 12 |
| 19F | 2.0 | 2.0 | −1 | 60 | 3 |
| 19F | 1.0 | 2.0 | 1 | 180 | 9 |
| 19F | 2.0 | 1.0 | −1 | 300 | 12 |
| 19F | 3.0 | 1.0 | −1 | 0 | 0 |
| 19F | 4.0 | 2.0 | 1 | 0 | 6 |
| 19F | 2.8 | 1.5 | 1 | 300 | 3 |
| 19F | 2.8 | 1.5 | 1 | 300 | 3 |
| 20 | 3.5 | 1.8 | −1 | 0 | 15 |
| 20 | 2.5 | 1.0 | 1 | 0 | 0 |
| 20 | 3.5 | 1.0 | 1 | 300 | 0 |
| 20 | 1.5 | 2.0 | 1 | 300 | 0 |
| 20 | 0.5 | 1.0 | 1 | 300 | 0 |
| 20 | 1.7 | 1.2 | −1 | 180 | 6 |
| 20 | 2.5 | 2.0 | 1 | 240 | 3 |
| 20 | 2.2 | 1.8 | 1 | 60 | 12 |
| 20 | 2.5 | 1.0 | 1 | 300 | 15 |
| 20 | 1.5 | 2.0 | −1 | 0 | 15 |
| 22F | 2.5 | 2.5 | 1 | 0 | 9 |
| 22F | 2.4 | 1.0 | −1 | 0 | 15 |
| 22F | 2.0 | 2.5 | −1 | 300 | 15 |
| 22F | 1.5 | 2.5 | −1 | 0 | 0 |
| 22F | 1.5 | 1.8 | 1 | 180 | 15 |
| 22F | 1.5 | 1.0 | −1 | 300 | 3 |
| 22F | 2.5 | 1.9 | −1 | 240 | 0 |
| 22F | 3.5 | 2.1 | 1 | 300 | 0 |
| 22F | 2.5 | 1.0 | 1 | 300 | 15 |
| 22F | 0.5 | 2.1 | 1 | 300 | 3 |
| 22F | 2.0 | 1.0 | 1 | 0 | 0 |
| 23F | 3.5 | 1.6 | 1 | 120 | 9 |
| 23F | 2.5 | 1.0 | 1 | 300 | 0 |
| 23F | 2.0 | 1.9 | 1 | 300 | 15 |
| 23F | 2.4 | 2.0 | −1 | 180 | 0 |
| 23F | 1.5 | 2.0 | −1 | 0 | 15 |
| 23F | 1.6 | 1.4 | 1 | 0 | 0 |
| 23F | 0.5 | 1.5 | 1 | 180 | 6 |
| 23F | 2.5 | 1.1 | −1 | 0 | 15 |
| 23F | 1.5 | 1.0 | −1 | 300 | 9 |
| 33F | 1.5 | 1.1 | 1 | 0 | 6 |
| 33F | 2.3 | 2.0 | 1 | 60 | 15 |
| 33F | 1.5 | 2.0 | −1 | 0 | 6 |
| 33F | 2.5 | 1.6 | −1 | 300 | 9 |
| 33F | 0.5 | 1.6 | −1 | 240 | 6 |
| 33F | 1.7 | 2.0 | 1 | 240 | 0 |
| 33F | 1.6 | 1.0 | −1 | 240 | 15 |
| 33F | 2.4 | 1.0 | −1 | 60 | 0 |
| 33F | 2.5 | 1.6 | −1 | 300 | 9 |

Example 54: Multivalent Immunogenic Composition

A combination of conjugates for each of 24 pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F was prepared using CRM197 derivative SEQ ID NO:14 (with X=pAMF) as the carrier polypeptide in each conjugate. The immunogenicity of this multivalent composition was confirmed using a 3-dose schedule in groups of 7 rabbits, by intramuscular injection of 0.25 mL vaccine. Each dose included 2414 saccharide (11.1 g per serotype), giving a concentration of 961.1 g/mL.

A combination of conjugates for each of 32 pneumococcal serotypes 1, 2, 3, 4, 5, 6A, 6B, 6C, 7C, 7F, 8, 9N, 9V, 10A, 11A, 12F, 14, 15A, 15B, 16F, 17F, 18C, 19A, 19F, 20, 22F, 23A, 23B, 23F, 31, 33F, and 35B was then prepared and immunogenicity confirmed in a similar manner.

For comparison purposes, the 13-valent Prevnar™ conjugate vaccine was also tested, along with a 24-valent unconjugated vaccine made of the 23-valent Pneumovax™ vaccine supplemented by unconjugated serotype 6A polysaccharide. These four compositions had equivalent polysaccharide doses per serotype (except for 6B, where Prevnar™ includes a double dosage), which involved diluting the Prevnar™ and Pneumovax™. All three compositions included aluminum phosphate adjuvant (6014 Al$^{+++}$ per dose), which involved adding the adjuvant to Pneumovax™. The compositions were preservative-free.

The 24-valent conjugate composition included a lower amount of carrier polypeptide than in the approved Prevnar-13™ vaccine, even though it also includes capsular saccharides from 11 additional serotypes. The overall weight ratio of capsular saccharide to carrier polypeptide in the 24-valent conjugate composition was about double that seen in Prevnar™.

IgG and OPA responses were measured in the rabbits. After the third dose both of these responses were much greater in rabbits which received the two conjugated vaccines than in those which received the unconjugated vaccine. Moreover, IgG and OPA responses using the 24-valent composition were comparable to those achieved using Prevnar™ in the 13 serotypes covered by the approved vaccine, but were in addition superior against the 11 serotypes which are not included in Prevnar™. Surprisingly, there was no evidence of carrier induced epitopic suppression using the 24-valent composition.

Figure 8:
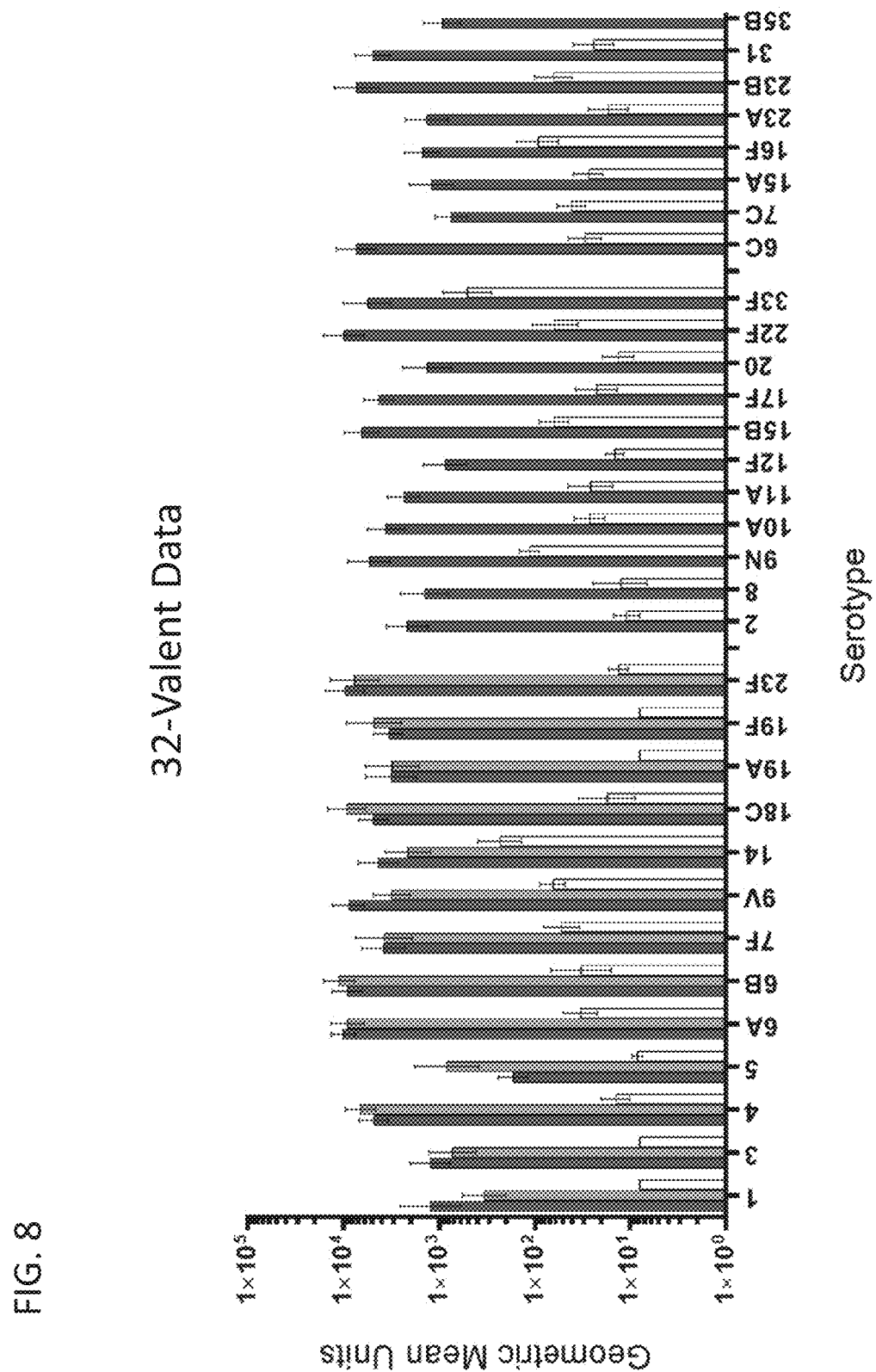
FIG. 8 provides the geometric mean titer for each of the 32 indicated serotypes in a 32-valent vaccine of the present invention, relative to a polysaccharide/alum formulation and Prevnar-13™, as described in the examples.

FIG. 8 provides the geometric mean titer for each of the 32 serotypes in the 32-valent conjugate composition relative to the polysaccharide/alum formulation and Prevnar-13™.

The multivalent conjugate composition can usefully be packaged into a pre-filled sterile syringe so that it can be easily distributed in unit dose form, and can then be administered at the point of use without needing to transfer the contents of a vial into a syringe for injection etc.

Example 55: Substitutable Positions in CRM197

A variety of Asp, Asn, Glu, Gln, Lys, Arg, Ser and Thr residues within the native CRM197 sequence (SEQ ID NO: 1) were individually replaced with pAMF by mutating their codons to TAG and expressing the protein at 25° C. in a cell-free system in which this codon is recognized by a tRNA which incorporates the nnAA. The mutant polypeptides were expressed with an N-terminal methionine and with a downstream hexahistidine tag attached via a Gly-Ser-Gly tripeptide linker.

Expression efficiency was assessed by checking 14C-Leu incorporation into the mutant proteins, looking both at total protein and soluble protein. In general, mutations in the catalytic domain of CRM197 led to reduced expression levels relative to the unmodified CRM197 sequence, and the mutants with the best expression levels generally involved substitutions downstream of Arg-193, which can be used to delineate the end of the catalytic domain.

The best 72 mutants showed increased expression levels of both total and soluble proteins and had substitutions at the following residues, numbered according to SEQ ID NO: 11: Ser-198, Ser-200, Asp-211, Lys-212, Lys-218, Lys-221, Lys-229, Ser-231, Ser-233, Lys-236, Ser-239, Glu-240, Glu-248, Glu-249, Gln-252, Thr-253, Glu-256, Glu-259, Ser-261, Lys-264, Thr-265, Thr-267, Thr-269, Gln-287, Glu-292, Thr-293, Asp-295, Asn-296, Ser-297, Lys-299, Asp-352, Asn-359, Glu-362, Ser-374, Arg-377, Ser-381, Lys-385, Thr-386, Asp-392, Ser-397, Asn-399, Thr-400, Arg-407, Thr-408, Ser-451, Arg-455, Lys-456, Arg-460, Arg-462, Asp-465, Asp-467, Thr-469, Arg-472, Lys-474, Ser-475, Asn-481, Asn-486, Arg-493, Ser-494, Ser-495, Ser-496, Lys-498, Ser-501, Asn-502, Ser-505, Asp-507, Lys-516, Thr-517, Asp-519, Lys-522, Asn-524, and Lys-534.

```
Native CRM 197 plus N-terminus Met:
                                                                SEQ ID NO: 1
MGADDVVDSSKSFVMENFSSYHGTKPGYVDSIQKGIQKPKSGTQGNYDDDWKEFYSTDNKYDAAGYSVDNENPLSGKAGG

VVKVTYPGLTKVLALKVDNAETIKKELGLSLTEPLMEQVGTEEFIKRFGDGASRVVLSLPFAEGSSSVEYINNWEQAKAL

SVELEINFETRGKRGQDAMYEYMAQACAGNRVRRSVGSSLSCINLDWDVIRDKTKTKIESLKEHGPIKNKMSESPNKTVS

EEKAKQYLEEFHQTALEHPELSELKTVTGTNPVFAGANYAAWAVNVAQVIDSETADNLEKTTAALSILPGIGSVMGIADG

AVHHNTEEIVAQSIALSSLMVAQAIPLVGELVDIGFAAYNFVESIINLFQVVHNSYNRPAYSPGHKTQPFLHDGYAVSWN

TVEDSIIRTGFQGESGHDIKITAENTPLPIAGVLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSKLSLFFEIKS

Nucleic acid pUC57-CRM197:
                                                                SEQ ID NO: 2
ATGGGCGCAGACGATGTTGTGGACTCAAGTAAATCATTTGTCATGGAAAACTTCTCCTCATATCACGGCACGAAACCGGG

CTACGTTGATAGCATTCAGAAAGGTATCCAAAAACCGAAATCTGGCACGCAGGGTAACTACGATGACGATTGGAAAGAAT

TCTACAGCACCGACAACAAATATGATGCGGCCGGTTACTCAGTCGACAACGAAAATCCGCTGTCGGGCAAAGCCGGCGGT

GTGGTTAAAGTGACGTATCCGGGCCTGACCAAAGTCCTGGCCCTGAAAGTGGATAATGCAGAAACCATCAAAAAGAACT

GGGTCTGAGCCTGACGGAACCGCTGATGGAACAGGTTGGCACCGAAGAATTTATCAAACGCTTCGGCGATGGTGCCAGTC

GTGTCGTGCTGTCCCTGCCGTTCGCAGAAGGTAGCTCTAGTGTGGAATATATTAACAATTGGGAACAAGCGAAAGCCCTG

TCCGTTGAACTGGAAATCAACTTTGAAACCCGCGGCAAACGTGGTCAGGATGCGATGTATGAATACATGGCACAAGCTTG

CGCGGGTAATCGCGTTCGTCGCAGCGTCGGCTCCTCACTGTCTTGTATCAACCTGGACTGGGATGTTATCCGTGATAAAA

CCAAAACGAAAATCGAAAGTCTGAAAGAACATGGCCCGATCAAAAACAAAATGAGCGAATCTCCGAATAAAACGGTGTCC

GAAGAAAAAGCTAAACAGTATCTGGAAGAATTCCACCAAACCGCACTGGAACATCCGGAACTGTCAGAACTGAAAACCGT

GACGGGTACCAACCCGGTTTTTGCCGGCGCAAATTACGCAGCTTGGGCTGTGAACGTTGCGCAAGTGATTGACTCGGAAA

CGGCCGATAATCTGGAAAAAACCACGCGGCCCTGAGTATTCTGCCGGGCATCGGTTCCGTTATGGGTATTGCCGACGGC

GCAGTCCATCACAACACCGAAGAAATTGTGGCCCAGTCTATCGCACTGTCGAGCCTGATGGTTGCTCAAGCGATTCCGCT

GGTTGGCGAACTGGTTGATATCGGCTTTGCAGCTTACAACTTCGTGGAAAGTATTATCAACCTGTTTCAGGTTGTCCACA

ACTCATATAATCGCCCGGCCTACTCGCCGGGTCACAAAACCCAACCGTTCCTGCATGACGGCTACGCGGTTAGCTGGAAT

ACGGTCGAAGATTCTATTATCCGTACCGGCTTTCAGGGTGAATCTGGCCACGACATTAAAATCACGGCTGAAAACACCCC
```

-continued

```
GCTGCCGATTGCAGGTGTTCTGCTGCCGACGATCCCGGGTAAACTGGATGTTAACAAATCAAAAACCCATATCTCGGTCA

ACGGTCGCAAAATTCGTATGCGCTGCCGTGCGATCGACGGCGATGTGACCTTCTGTCGTCCGAAAAGCCCGGTCTATGTG

GGCAACGGTGTCCATGCTAATCTGCACGTGGCGTTTCATCGCTCTAGTTCCGAAAAAATCCATAGTAACGAAATCTCATC

GGATTCCATTGGTGTGCTGGGCTACCAGAAAACCGTGGACCATACCAAAGTGAATAGCAAACTGAGCCTGTTCTTCGAAA

TCAAATCGTAA
```

Binding epitope for human CD4+ cells on tetanus toxin at H176-195:
SEQ ID NO: 3
IDKISDVSTIVPYIGPALNI Binding epitope for human CD4+ cells on tetanus toxin at H491-510:
SEQ ID NO: 4
NNFTVSFWLRVPKVSASHLE Binding epitope for human CD4+ cells on BB (from G protein of Strep G148 at AA 25-40):
SEQ ID NO: 5
VSDYYKNLINNAKTVE Binding epitope for human CD4+ cells on BB (from G protein of Strep G148 at AA 63-78):
SEQ ID NO: 6
DGLSDFLKSQTPAEDT Binding epitope for human CD4+ cells on BB (from G protein of Strep G148 at AA 74-89):
SEQ ID NO: 7
AEDTVKSIELAEAKVL H. influenzae Protein D (HiD):
SEQ ID NO: 8
CSSHSSNMANTQMKSDKIIIAHRGASGYLPEHTLESKALAFAQQADYLEQDLAMTKDGRLVVIHDHFLDGLTDVAKKFPH

RHRKDGRYYVIDFTLKEIQSLEMTENFETKDGKQAQVYPNRFPLWKSHFRIHTFEDEIEFIQGLEKSTGKKVGIYPEIKA

PWFHHQNGKDIAAETLKVLKKYGYDKKTDMVYLQTFDFNELKRIKTELLPQMGMDLKLVQLIAYTDWKETQEKDPKGYWV

NYNYDWMFKPGAMAEVVKYADGVGPGWYMLVNKEESKPDNIVYTPLVKELAQYNVEVHPYTVRKDALPEFFTDVNQMYDA

LLNKSGATGVFTDEPDTGVEFLKGIK

CRM197 with 6 preferred nnAA sites ("X") and N-terminal Met:
SEQ ID NO: 9
MGADDVVDSSKSFVMENFSSYHGTKPGYVDSIQXGIQKPKSGTQGNYDDDWKEFYSTDNKYDAAGYSVDNENPLSGKAGG

VVKVTYPGLTKVLALKVDNAETIKKELGLSLTEPLMEQVGTEEFIKRFGDGASRVVLSLPFAEGSSSVEYINNWEQAKAL

SVELEINFETRGKRGQDAMYEYMAQACAGNRVRRSVGSSLSCINLDWDVIRDXTKTKIESLKEHGPIKNKMSESPNKTVS

EEKAXQYLEEFHQTALEHPELSELXTVTGTNPVFAGANYAAWAVNVAQVIDSETADNLEKTTAALSILPGIGSVMGIADG

AVHHNTEEIVAQSIALSSLMVAQAIPLVGELVDIGFAAYNFVESIINLFQVVHNSYNRPAYSPGHXTQPFLHDGYAVSWN

TVEDSIIRTGFQGESGHDIKITAENTPLPIAGVLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSXLSLFFEIKS

Histidine tag:
SEQ ID NO: 10
GSGHHHHHH

Native CRM 197:
SEQ ID NO: 11
GADDVVDSSKSFVMENFSSYHGTKPGYVDSIQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDGASRVVLSLPFAEGSSSVEYINNWEQAKALS

VELEINFETRGKRGQDAMYEYMAQACAGNRVRRSVGSSLSCINLDWDVIRDKTKTKIESLKEHGPIKNKMSESPNKTVSE

EKAKQYLEEFHQTALEHPELSELKTVTGTNPVFAGANYAAWAVNVAQVIDSETADNLEKTTAALSILPGIGSVMGIADGA

VHHNTEEIVAQSIALSSLMVAQAIPLVGELVDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHISVNGRKIRMRCRAIDGDVTFCRPKSPVYVG

NGVHANLHVAFHRSSSEKIHSNEISSDSIGVLGYQKTVDHTKVNSKLSLFFEIKS

CRM197 with Arg-Asn substitution:

SEQ ID NO: 12

GADDVVDSSKSFVMENFSSYHGTKPGYVDSIQKGIQKPKSGTQGNYDDDWKEFYSTDNKYDAAGYSVDNENPLSGKAGGV

VKVTYPGLTKVLALKVDNAETIKKELGLSLTEPLMEQVGTEEFIKRFGDGASRVVLSLPFAEGSSSVEYINNWEQAKALS

VELEINFETRGKRGQDAMYEYMAQACAGNRVRNSVGSSLSCINLDWDVIRDKIKTKIESLKEHGPIKNKMSESPNKTVSE

EKAKQYLEEFHQTALEHPELSELKTVTGINPVFAGANYAAWAVNVAQVIDSETADNLEKTTAALSILPGIGSVMGIADGA

VHHNTEEIVAQSIALSSLMVAQAIPLVGELVDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHISVNGRKIRMRCRAIDGDVTFCRPKSPVYVG

NGVHANLHVAFHRSSSEKIHSNEISSDSIGVLGYQKTVDHTKVNSKLSLFFEIKS

CRM197 with Arg-Asn substitution and N-terminus Met:

SEQ ID NO: 13

MGADDVVDSSKSFVMENESSYHGTKPGYVDSIQKGIQKPKSGTQGNYDDDWKEFYSTDNKYDAAGYSVDNENPLSGKAGG

VVKVTYPGLIKVLALKVDNAETIKKELGLSLTEPLMEQVGTEEFIKREGDGASRVVLSLPFAEGSSSVEYINNWEQAKAL

SVELEINFETRGKRGQDAMYEYMAQACAGNRVRNSVGSSLSCINLDWDVIRDKIKTKIESLKEHGPIKNKMSESPNKTVS

EEKAKQYLEEFHQTALEHPELSELKTVTGINPVFAGANYAAWAVNVAQVIDSETADNLEKTTAALSILPGIGSVMGIADG

AVHHNTEEIVAQSIALSSLMVAQAIPLVGELVDIGFAAYNFVESIINLFQVVHNSYNRPAYSPGHKTQPFLHDGYAVSWN

TVEDSIIRTGFQGESGHDIKITAENTPLPIAGVLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSKLSLFFEIKS

CRM197 with Arg-Asn substitution, 6 preferred nnAA sites ("X") and N-terminus Met:

SEQ ID NO: 14

MGADDVVDSSKSFVMENESSYHGTKPGYVDSIQXGIQKPKSGTQGNYDDDWKEFYSTDNKYDAAGYSVDNENPLSGKAGG

VVKVTYPGLIKVLALKVDNAETIKKELGLSLTEPLMEQVGTEEFIKREGDGASRVVLSLPFAEGSSSVEYINNWEQAKAL

SVELEINFETRGKRGQDAMYEYMAQACAGNRVRNSVGSSLSCINLDWDVIRDXTKTKIESLKEHGPIKNKMSESPNKTVS

EEKAXQYLEEFHQTALEHPELSELXTVTGINPVFAGANYAAWAVNVAQVIDSETADNLEKTTAALSILPGIGSVMGIADG

AVHHNTEEIVAQSIALSSLMVAQAIPLVGELVDIGFAAYNFVESIINLFQVVHNSYNRPAYSPGHXTQPFLHDGYAVSWN

TVEDSIIRTGFQGESGHDIKITAENTPLPIAGVLLPTIPGKLDVNKSKTHISVNGRKIRMRCRAIDGDVTFCRPKSPVYV

GNGVHANLHVAFHRSSSEKIHSNEISSDSIGVLGYQKTVDHTKVNSXLSLFFEIKS

Tetanus toxin:

SEQ ID NO: 15

MPITINNFRYSDPVNNDTIIMMEPPYCKGLDIYYKAFKITDRIWIVPERYEFGTKPEDENPPSSLIEGASEYYDPNYLRT

DSDKDRELQTMVKLENRIKNNVAGEALLDKIINAIPYLGNSYSLLDKEDINSNSVSFNLLEQDPSGATTKSAMLINLIIF

GPGPVLNKNEVRGIVLRVDNKNYFPCRDGEGSIMQMAFCPEYVPTEDNVIENITSLTIGKSKYFQDPALLLMHELIHVLH

GLYGMQVSSHEIIPSKQEIYMQHTYPISAEELFTFGGQDANLISIDIKNDLYEKTLNDYKAIANKLSQVTSCNDPNIDID

SYKQIYQQKYQFDKDSNGQYIVNEDKFQILYNSIMYGETEIELGKKENIKTRLSYFSMNHDPVKIPNLLDDTIYNDTEGF

NIESKDLKSEYKGQNMRVNTNAFRNVDGSGLVSKLIGLCKKIIPPTNIRENLYNRTASLTDLGGELCIKIKNEDLTFIAE

KNSFSEEPFQDEIVSYNTKNKPLNFNYSLDKIIVDYNLQSKITLPNDRTTPVTKGIPYAPEYKSNAASTIEIHNIDDNTI

YQYLYAQKSPTTLQRITMINSVDDALINSTKIYSYFPSVISKVNQGAQGILFLQWVRDIIDDETNESSQKTTIDKISDVS

TIVPYIGPALNIVKQGYEGNFIGALETTGVVLLLEYIPEITLPVIAALSIAESSTQKEKIIKTIDNFLEKRYEKWIEVYK

LVKAKWLGTVNTQFQKRSYQMYRSLEYQVDAIKKIIDYEYKIYSGPDKEQIADEINNLKNKLEEKANKAMININIFMRES

SRSELVNQMINEAKKQLLEFDTQSKNILMQYIKANSKFIGITELKKLESKINKVESTPIPFSYSKNLDCWVDNEEDIDVI

LKKSTILNLDINNDIISDISGFNSSVITYPDAQLVPGINGKAIHLVNNESSEVIVHKAMDIEYNDMENNFTVSEWLRVPK

VSASHLEQYGTNEYSIISSMKKHSLSIGSGWSVSLKGNNLIWILKDSAGEVRQITFRDLPDKENAYLANKWVFITITNDR

LSSANLYINGVLMGSAEITGLGAIREDNNITLKLDRCNNNNQYVSIDKFRIFCKALNPKEIEKLYTSYLSITFLRDFWGN

PLRYDTEYYLIPVASSSKDVQLKNITDYMYLTNAPSYTNGKLNIYYRRLYNGLKFIIKRYTPNNEIDSFVKSGDFIKLYV

SYNNNEHIVGYPKDGNAFNNLDRILRVGYNAPGIPLYKKMEAVKLRDLKTYSVQLKLYDDKNASLGLVGTHNGQIGNDPN

RDILIASNWYENHLKDKILGCDWYFVPTDEGWTND

---

The invention claimed is:

1. A carrier protein for use in a crosslinked protein-antigen conjugate vaccine comprising at least 98% sequence identity to SEQ ID NO:9, wherein:
   a 2-amino-3-(4-(azidomethyl)phenyl)propanoic acid (pAMF) non-natural amino acid (nnAA) is present at residues 34, 213, 245, 265, 386, and 527 numbered according to SEQ ID NO:9.

2. The carrier protein according to claim 1, that does not contain an Arg-Arg dipeptide.

3. The carrier protein according to claim 1, wherein the carrier protein comprises the sequence of SEQ ID NO:14.

4. A carrier protein for use in a crosslinked protein-antigen conjugate vaccine comprising at least 98% sequence identity to SEQ ID NO:14, wherein:
   a 2-amino-3-(4-(azidomethyl)phenyl)propanoic acid (pAMF) non-natural amino acid (nnAA) is present at residues 34, 213, 245, 265, 386, and 527 numbered according to SEQ ID NO:14.

* * * * *

SEQUENCE LISTING

<160> NUMBER OF SEQ ID NOS: 15

<210> SEQ ID NO 1
<211> LENGTH: 536
<212> TYPE: PRT
<213> ORGANISM: Corynebacterium diphtheriae

<400> SEQUENCE: 1

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp

```
             325                 330                 335
Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
            435                 440                 445

Thr His Ile Ser Val Asn Gly Arg Lys Ile Arg Met Arg Cys Arg Ala
        450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
            515                 520                 525

Ser Leu Phe Phe Glu Ile Lys Ser
            530                 535

<210> SEQ ID NO 2
<211> LENGTH: 1611
<212> TYPE: DNA
<213> ORGANISM: Artificial Sequence
<220> FEATURE:
<223> OTHER INFORMATION: pUC57-CRM197

<400> SEQUENCE: 2
atgggcgcag acgatgttgt ggactcaagt aaatcatttg tcatggaaaa cttctcctca      60
tatcacggca cgaaaccggg ctacgttgat agcattcaga aagtatcca  aaaaccgaaa     120 tctggcacgc agggtaacta cgatgacgat tggaaagaat ctacagcac cgacaacaaa      180 tatgatgcgc ccgttactc agtcgacaac gaaaatccgc tgtcgggcaa agccggcggt      240
gtggttaaag tgacgtatcc gggcctgacc aaagtcctgg ccctgaaagt ggataatgca     300
gaaaccatca aaaagaact gggtctgagc ctgacggaac cgctgatgga acaggttggc      360
accgaagaat ttatcaaacg cttcggcgat ggtgccagtc gtgtcgtgct gtccctgccg     420
ttcgcagaag gtagctctag tgtggaatat attaacaatt gggaacaagc gaaagccctg     480
tccgttgaac tggaaatcaa ctttgaaacc cgcggcaaac gtggtcagga tgcgatgtat     540
gaatacatgg cacaagcttg cgcgggtaat cgcgttcgtc gcagcgtcgg ctcctcactg     600
tcttgtatca acctggactg ggatgttatc cgtgataaaa ccaaaacgaa atcgaaagt      660 ctgaaagaac atgcccgat caaaaacaaa atgagcgaat ctccgaataa acggtgtcc      720 gaagaaaaag ctaaacagta tctggaagaa ttccaccaaa ccgcactgga acatccggaa     780
ctgtcagaac tgaaaaccgt gacgggtacc aacccggttt tgccggcgc aaattacgca     840
```

```
gcttgggctg tgaacgttgc gcaagtgatt gactcggaaa cggccgataa tctggaaaaa      900
accacggcgg ccctgagtat tctgccgggc atcggttccg ttatgggtat tgccgacggc      960
gcagtccatc acaacaccga agaaattgtg gcccagtcta tcgcactgtc gagcctgatg     1020
gttgctcaag cgattccgct ggttggcgaa ctggttgata tcggctttgc agcttacaac     1080
ttcgtggaaa gtattatcaa cctgtttcag gttgtccaca actcatataa tcgcccggcc     1140
tactcgccgg gtcacaaaac ccaaccgttc ctgcatgacg gctacgcggt tagctggaat     1200
acggtcgaag attctattat ccgtaccggc tttcagggtg aatctggcca cgacattaaa     1260
atcacggctg aaaacacccc gctgccgatt gcaggtgttc tgctgccgac gatcccgggt     1320
aaactggatg ttaacaaatc aaaaacccat atctcggtca acggtcgcaa aattcgtatg     1380
cgctgccgtg cgatcgacgg cgatgtgacc ttctgtcgtc cgaaaagccc ggtctatgtg     1440
ggcaacggtg tccatgctaa tctgcacgtg gcgtttcatc gctctagttc cgaaaaaatc     1500
catagtaacg aaatctcatc ggattccatt ggtgtgctgg gctaccagaa aaccgtggac     1560
cataccaaag tgaatagcaa actgagcctg ttcttcgaaa tcaaatcgta a              1611
```

```
<210> SEQ ID NO 3
<211> LENGTH: 20
<212> TYPE: PRT
<213> ORGANISM: Artificial Sequence
<220> FEATURE:
<223> OTHER INFORMATION: Binding epitope for human CD4+ cells on tetanus
      toxin at H176-195

<400> SEQUENCE: 3

Ile Asp Lys Ile Ser Asp Val Ser Thr Ile Val Pro Tyr Ile Gly Pro
1               5                   10                  15

Ala Leu Asn Ile
            20

<210> SEQ ID NO 4
<211> LENGTH: 20
<212> TYPE: PRT
<213> ORGANISM: Artificial Sequence
<220> FEATURE:
<223> OTHER INFORMATION: Binding epitope for human CD4+ cells on tetanus
      toxin at H491-510

<400> SEQUENCE: 4

Asn Asn Phe Thr Val Ser Phe Trp Leu Arg Val Pro Lys Val Ser Ala
1               5                   10                  15

Ser His Leu Glu
            20

<210> SEQ ID NO 5
<211> LENGTH: 16
<212> TYPE: PRT
<213> ORGANISM: Artificial Sequence
<220> FEATURE:
<223> OTHER INFORMATION: Binding epitope for human CD4+ cells on BB
      (from G protein of Strep G148 at AA 25-40)

<400> SEQUENCE: 5

Val Ser Asp Tyr Tyr Lys Asn Leu Ile Asn Asn Ala Lys Thr Val Glu
1               5                   10                  15

<210> SEQ ID NO 6
<211> LENGTH: 16
<212> TYPE: PRT
<213> ORGANISM: Artificial Sequence
```

```
<220> FEATURE:
<223> OTHER INFORMATION: Binding epitope for human CD4+ cells on BB
      (from G protein of Strep G148 at AA 63-78)

<400> SEQUENCE: 6

Asp Gly Leu Ser Asp Phe Leu Lys Ser Gln Thr Pro Ala Glu Asp Thr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Binding epitope for human CD4+ cells on BB
      (from G protein of Strep G148 at AA 74-89)

<400> SEQUENCE: 7

Ala Glu Asp Thr Val Lys Ser Ile Glu Leu Ala Glu Ala Lys Val Leu
1               5                   10                  15

<210> SEQ ID NO 8
<211> LENGTH: 346
<212> TYPE: PRT
<213> ORGANISM: Haemophilus influenzae

<400> SEQUENCE: 8

Cys Ser Ser His Ser Ser Asn Met Ala Asn Thr Gln Met Lys Ser Asp
1               5                   10                  15

Lys Ile Ile Ile Ala His Arg Gly Ala Ser Gly Tyr Leu Pro Glu His
            20                  25                  30

Thr Leu Glu Ser Lys Ala Leu Ala Phe Ala Gln Gln Ala Asp Tyr Leu
        35                  40                  45

Glu Gln Asp Leu Ala Met Thr Lys Asp Gly Arg Leu Val Val Ile His
    50                  55                  60

Asp His Phe Leu Asp Gly Leu Thr Asp Val Ala Lys Lys Phe Pro His
65                  70                  75                  80

Arg His Arg Lys Asp Gly Arg Tyr Tyr Val Ile Asp Phe Thr Leu Lys
                85                  90                  95

Glu Ile Gln Ser Leu Glu Met Thr Glu Asn Phe Glu Thr Lys Asp Gly
            100                 105                 110

Lys Gln Ala Gln Val Tyr Pro Asn Arg Phe Pro Leu Trp Lys Ser His
        115                 120                 125

Phe Arg Ile His Thr Phe Glu Asp Glu Ile Glu Phe Ile Gln Gly Leu
    130                 135                 140

Glu Lys Ser Thr Gly Lys Lys Val Gly Ile Tyr Pro Glu Ile Lys Ala
145                 150                 155                 160

Pro Trp Phe His His Gln Asn Gly Lys Asp Ile Ala Ala Glu Thr Leu
                165                 170                 175

Lys Val Leu Lys Lys Tyr Gly Tyr Asp Lys Lys Thr Asp Met Val Tyr
            180                 185                 190

Leu Gln Thr Phe Asp Phe Asn Glu Leu Lys Arg Ile Lys Thr Glu Leu
        195                 200                 205

Leu Pro Gln Met Gly Met Asp Leu Lys Leu Val Gln Leu Ile Ala Tyr
    210                 215                 220

Thr Asp Trp Lys Glu Thr Gln Glu Lys Asp Pro Lys Gly Tyr Trp Val
225                 230                 235                 240

Asn Tyr Asn Tyr Asp Trp Met Phe Lys Pro Gly Ala Met Ala Glu Val
                245                 250                 255
```

```
Val Lys Tyr Ala Asp Gly Val Gly Pro Gly Trp Tyr Met Leu Val Asn
                260                 265                 270

Lys Glu Glu Ser Lys Pro Asp Asn Ile Val Tyr Thr Pro Leu Val Lys
            275                 280                 285

Glu Leu Ala Gln Tyr Asn Val Glu Val His Pro Tyr Thr Val Arg Lys
        290                 295                 300

Asp Ala Leu Pro Glu Phe Phe Thr Asp Val Asn Gln Met Tyr Asp Ala
305                 310                 315                 320

Leu Leu Asn Lys Ser Gly Ala Thr Gly Val Phe Thr Asp Phe Pro Asp
                325                 330                 335

Thr Gly Val Glu Phe Leu Lys Gly Ile Lys
            340                 345

<210> SEQ ID NO 9
<211> LENGTH: 536
<212> TYPE: PRT
<213> ORGANISM: Artificial Sequence
<220> FEATURE:
<223> OTHER INFORMATION: CRM197 with 6 preferred nnAA sites and
      N-terminus Met
<220> FEATURE:
<221> NAME/KEY: misc_feature
<222> LOCATION: (34)..(34)
<223> OTHER INFORMATION: Xaa can be any non-naturally occurring amino
      acid
<220> FEATURE:
<221> NAME/KEY: misc_feature
<222> LOCATION: (213)..(213)
<223> OTHER INFORMATION: Xaa can be any non-naturally occurring amino
      acid
<220> FEATURE:
<221> NAME/KEY: misc_feature
<222> LOCATION: (245)..(245)
<223> OTHER INFORMATION: Xaa can be any non-naturally occurring amino
      acid
<220> FEATURE:
<221> NAME/KEY: misc_feature
<222> LOCATION: (265)..(265)
<223> OTHER INFORMATION: Xaa can be any non-naturally occurring amino
      acid
<220> FEATURE:
<221> NAME/KEY: misc_feature
<222> LOCATION: (386)..(386)
<223> OTHER INFORMATION: Xaa can be any non-naturally occurring amino
      acid
<220> FEATURE:
<221> NAME/KEY: misc_feature
<222> LOCATION: (527)..(527)
<223> OTHER INFORMATION: Xaa can be any non-naturally occurring amino
      acid

<400> SEQUENCE: 9

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Xaa Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110
```

```
Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Xaa Thr Lys Thr Lys Ile Glu Ser Leu Lys Glu His
        210                 215                 220

Gly Pro Ile Lys Asn Lys Met Ser Glu Ser Pro Asn Lys Thr Val Ser
225                 230                 235                 240

Glu Glu Lys Ala Xaa Gln Tyr Leu Glu Phe His Gln Thr Ala Leu
                245                 250                 255

Glu His Pro Glu Leu Ser Glu Leu Xaa Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Xaa Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
        450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Xaa Leu
        515                 520                 525
```

```
Ser Leu Phe Phe Glu Ile Lys Ser
    530                 535

<210> SEQ ID NO 10
<211> LENGTH: 9
<212> TYPE: PRT
<213> ORGANISM: Artificial Sequence
<220> FEATURE:
<223> OTHER INFORMATION: Histidine tag

<400> SEQUENCE: 10

Gly Ser Gly His His His His His His
1               5

<210> SEQ ID NO 11
<211> LENGTH: 535
<212> TYPE: PRT
<213> ORGANISM: Corynebacterium diphtheriae

<400> SEQUENCE: 11

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys G

```
              290                 295                 300
Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 12
<211> LENGTH: 535
<212> TYPE: PRT
<213> ORGANISM: Artificial Sequence
<220> FEATURE:
<223> OTHER INFORMATION: CRM197 with Arg-Asn substitution

<400> SEQUENCE: 12

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
```

-continued

```
            115                 120                 125
Asp Gly Ala Ser Arg Val Val Leu Ser Leu Pro Phe Ala Glu Gly Ser
            130                 135                 140
Ser Ser Val Glu Tyr Ile Asn Asn Trp Glu Gln Ala Lys Ala Leu Ser
145                 150                 155                 160
Val Glu Leu Glu Ile Asn Phe Glu Thr Arg Gly Lys Arg Gly Gln Asp
                    165                 170                 175
Ala Met Tyr Glu Tyr Met Ala Gln Ala Cys Ala Gly Asn Arg Val Arg
                    180                 185                 190
Asn Ser Val Gly Ser Ser Leu Ser Cys Ile Asn Leu Asp Trp Asp Val
                    195                 200                 205
Ile Arg Asp Lys Thr Lys Thr Lys Ile Glu Ser Leu Lys Glu His Gly
            210                 215                 220
Pro Ile Lys Asn Lys Met Ser Glu Ser Pro Asn Lys Thr Val Ser Glu
225                 230                 235                 240
Glu Lys Ala Lys Gln Tyr Leu Glu Glu Phe His Gln Thr Ala Leu Glu
                    245                 250                 255
His Pro Glu Leu Ser Glu Leu Lys Thr Val Thr Gly Thr Asn Pro Val
                    260                 265                 270
Phe Ala Gly Ala Asn Tyr Ala Ala Trp Ala Val Asn Val Ala Gln Val
                    275                 280                 285
Ile Asp Ser Glu Thr Ala Asp Asn Leu Glu Lys Thr Thr Ala Ala Leu
            290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                    325                 330                 335
Ser Leu Met Val Ala Gln Ala Ile Pro Leu Val Gly Glu Leu Val Asp
                    340                 345                 350
Ile Gly Phe Ala Ala Tyr Asn Phe Val Glu Ser Ile Ile Asn Leu Phe
                    355                 360                 365
Gln Val Val His Asn Ser Tyr Asn Arg Pro Ala Tyr Ser Pro Gly His
            370                 375                 380
Lys Thr Gln Pro Phe Leu His Asp Gly Tyr Ala Val Ser Trp Asn Thr
385                 390                 395                 400
Val Glu Asp Ser Ile Ile Arg Thr Gly Phe Gln Gly Glu Ser Gly His
                    405                 410                 415
Asp Ile Lys Ile Thr Ala Glu Asn Thr Pro Leu Pro Ile Ala Gly Val
                    420                 425                 430
Leu Leu Pro Thr Ile Pro Gly Lys Leu Asp Val Asn Lys Ser Lys Thr
                    435                 440                 445
His Ile Ser Val Asn Gly Arg Lys Ile Arg Met Arg Cys Arg Ala Ile
            450                 455                 460
Asp Gly Asp Val Thr Phe Cys Arg Pro Lys Ser Pro Val Tyr Val Gly
465                 470                 475                 480
Asn Gly Val His Ala Asn Leu His Val Ala Phe His Arg Ser Ser Ser
                    485                 490                 495
Glu Lys Ile His Ser Asn Glu Ile Ser Ser Asp Ser Ile Gly Val Leu
                    500                 505                 510
Gly Tyr Gln Lys Thr Val Asp His Thr Lys Val Asn Ser Lys Leu Ser
                    515                 520                 525
Leu Phe Phe Glu Ile Lys Ser
            530                 535
```

<210> SEQ ID NO 13
<211> LENGTH: 536
<212> TYPE: PRT
<213> ORGANISM: Artificial Sequence
<220> FEATURE:
<223> OTHER INFORMATION: CRM197 with Arg-Asn substitution and N-terminus Met

<400> SEQUENCE: 13

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Asn Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
```

```
                    355                 360                 365
Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser
    530                 535

<210> SEQ ID NO 14
<211> LENGTH: 536
<212> TYPE: PRT
<213> ORGANISM: Artificial Sequence
<220> FEATURE:
<223> OTHER INFORMATION: CRM197 with Arg-Asn substitution, 6 preferred
      nnAA sites and N-terminus Met
<220> FEATURE:
<221> NAME/KEY: misc_feature
<222> LOCATION: (34)..(34)
<223> OTHER INFORMATION: Xaa can be any non-naturally occurring amino
      acid
<220> FEATURE:
<221> NAME/KEY: misc_feature
<222> LOCATION: (213)..(213)
<223> OTHER INFORMATION: Xaa can be any non-naturally occurring amino
      acid
<220> FEATURE:
<221> NAME/KEY: misc_feature
<222> LOCATION: (245)..(245)
<223> OTHER INFORMATION: Xaa can be any non-naturally occurring amino
      acid
<220> FEATURE:
<221> NAME/KEY: misc_feature
<222> LOCATION: (265)..(265)
<223> OTHER INFORMATION: Xaa can be any non-naturally occurring amino
      acid
<220> FEATURE:
<221> NAME/KEY: misc_feature
<222> LOCATION: (386)..(386)
<223> OTHER INFORMATION: Xaa can be any non-naturally occurring amino
      acid
<220> FEATURE:
<221> NAME/KEY: misc_feature
<222> LOCATION: (527)..(527)
<223> OTHER INFORMATION: Xaa can be any non-naturally occurring amino
      acid

<400> SEQUENCE: 14

Met Gly Ala Asp Asp Val Val Asp Ser Ser Lys Ser Phe Val Met Glu
1               5                   10                  15
```

```
Asn Phe Ser Ser Tyr His Gly Thr Lys Pro Gly Tyr Val Asp Ser Ile
            20                  25                  30

Gln Xaa Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
                115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Asn Ser Val Gly Ser Ser Leu Ser Cys Ile Asn Leu Asp Trp Asp
        195                 200                 205

Val Ile Arg Asp Xaa Thr Lys Thr Lys Ile Glu Ser Leu Lys Glu His
        210                 215                 220

Gly Pro Ile Lys Asn Lys Met Ser Glu Ser Pro Asn Lys Thr Val Ser
225                 230                 235                 240

Glu Glu Lys Ala Xaa Gln Tyr Leu Glu Glu Phe His Gln Thr Ala Leu
                245                 250                 255

Glu His Pro Glu Leu Ser Glu Leu Xaa Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Xaa Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
```

```
                     435                 440                 445
Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Xaa Leu
        515                 520                 525

Ser Leu Phe Phe Glu Ile Lys Ser
    530                 535
```

<210> SEQ ID NO 15
<211> LENGTH: 1315
<212> TYPE: PRT
<213> ORGANISM: Clostridium tetani

<400> SEQUENCE: 15

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270
```

```
Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
```

```
            690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
                    740                 745                 750

Lys Lys Ile Ile Asp Tyr Glu Tyr Lys Ile Tyr Ser Gly Pro Asp Lys
                755                 760                 765

Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
                835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
        930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110
```

-continued

```
Leu Arg Asp Phe Trp Gly Asn Pro Leu Arg Tyr Asp Thr Glu Tyr
    1115            1120                1125

Tyr Leu Ile Pro Val Ala Ser Ser Ser Lys Asp Val Gln Leu Lys
    1130            1135                1140

Asn Ile Thr Asp Tyr Met Tyr Leu Thr Asn Ala Pro Ser Tyr Thr
    1145            1150                1155

Asn Gly Lys Leu Asn Ile Tyr Tyr Arg Arg Leu Tyr Asn Gly Leu
    1160            1165                1170

Lys Phe Ile Ile Lys Arg Tyr Thr Pro Asn Asn Glu Ile Asp Ser
    1175            1180                1185

Phe Val Lys Ser Gly Asp Phe Ile Lys Leu Tyr Val Ser Tyr Asn
    1190            1195                1200

Asn Asn Glu His Ile Val Gly Tyr Pro Lys Asp Gly Asn Ala Phe
    1205            1210                1215

Asn Asn Leu Asp Arg Ile Leu Arg Val Gly Tyr Asn Ala Pro Gly
    1220            1225                1230

Ile Pro Leu Tyr Lys Lys Met Glu Ala Val Lys Leu Arg Asp Leu
    1235            1240                1245

Lys Thr Tyr Ser Val Gln Leu Lys Leu Tyr Asp Asp Lys Asn Ala
    1250            1255                1260

Ser Leu Gly Leu Val Gly Thr His Asn Gly Gln Ile Gly Asn Asp
    1265            1270                1275

Pro Asn Arg Asp Ile Leu Ile Ala Ser Asn Trp Tyr Phe Asn His
    1280            1285                1290

Leu Lys Asp Lys Ile Leu Gly Cys Asp Trp Tyr Phe Val Pro Thr
    1295            1300                1305

Asp Glu Gly Trp Thr Asn Asp
    1310            1315
```